(12) United States Patent
Heyer et al.

(10) Patent No.: US 7,649,093 B2
(45) Date of Patent: Jan. 19, 2010

(54) NAPHTHALENE COMPOUNDS AS SELECTIVE ESTROGEN RECEPTOR MODULATORS

(75) Inventors: Dennis Heyer, Durham, NC (US); Jing Fang, Durham, NC (US); Frank Navas, III, Durham, NC (US); Subba Reddy Katamreddy, Durham, NC (US); Jennifer Poole Peckham, Durham, NC (US); Philip Stewart Turnbull, Durham, NC (US); Aaron Bayne Miller, Durham, NC (US); Adwoa Akwabi-Ameyaw, Durham, NC (US)

(73) Assignee: Glaxo Smith Kline LLC, Wilmington, DE (US)

( * ) Notice: Subject to any disclaimer, the term of this patent is extended or adjusted under 35 U.S.C. 154(b) by 0 days.

(21) Appl. No.: 11/570,838

(22) PCT Filed: Jun. 21, 2005

(86) PCT No.: PCT/US2005/021963

§ 371 (c)(1),
(2), (4) Date: Dec. 18, 2006

(87) PCT Pub. No.: WO2006/002185

PCT Pub. Date: Jan. 5, 2006

(65) Prior Publication Data

US 2007/0276000 A1      Nov. 29, 2007

Related U.S. Application Data

(60) Provisional application No. 60/581,913, filed on Jun. 22, 2004.

(51) Int. Cl.
*C07D 471/00* (2006.01)
*C07D 295/00* (2006.01)
*A61K 31/445* (2006.01)

(52) U.S. Cl. .................... 546/86; 514/319; 544/386
(58) Field of Classification Search .............. 546/86; 514/319; 544/386
See application file for complete search history.

(56) References Cited

U.S. PATENT DOCUMENTS

| 5,916,916 A | 6/1999 | Hauser et al. |
| 5,929,090 A | 7/1999 | Hauser et al. |
| 6,355,632 B1 * | 3/2002 | Palkowitz .............. 514/212.01 |
| 2007/0203180 A1 * | 8/2007 | Hoekstra et al. ............ 514/311 |

FOREIGN PATENT DOCUMENTS

| EP | 0 826 679 | 3/1998 |
| EP | 0 835 867 | 4/1998 |
| EP | 0 835 868 | 4/1998 |
| WO | 2004/009086 | 1/2004 |

OTHER PUBLICATIONS

F. Z. Dorwald "Side Reactions in Organic Synthesis: A Guide to Successful Synthesis Design" 2005, Wiley-VCH Verlag GmbH & Co. KGaA Wienheim.*
N. Miyaura and A. Suzuki Chem. Rev. 1995, 95, 2457-2483.*
J. Matthews and J.-A. Gustafsson Molecular Interventions 2003, 3(5), 281-292.*

* cited by examiner

*Primary Examiner*—Rita J Desai
*Assistant Examiner*—John Mabry
(74) *Attorney, Agent, or Firm*—J. Scott Young

(57) ABSTRACT

The present invention relates to cycloalkylidene compounds with a variety of therapeutic uses, more particularly novel naphthalene compounds that are particularly useful for selective estrogen receptor modulation.

17 Claims, No Drawings

NAPHTHALENE COMPOUNDS AS SELECTIVE ESTROGEN RECEPTOR MODULATORS

CROSS REFERENCE TO RELATED APPLICATIONS

This application is filed pursuant to 35 USC 371 as a United States National Phase Application of International Patent Application Serial No. PCT/US2005/021963 filed on Jun. 21, 2005, which claims priority from provisional application No. 60/581,913 filed Jun. 22, 2004 in the United States.

FIELD OF THE INVENTION

The present invention relates to novel compounds with a variety of therapeutic uses, more particularly novel substituted naphthalene compounds that are particularly useful for selective estrogen receptor modulation.

BACKGROUND OF THE INVENTION

Estrogens are well-known endocrine regulators in the cellular processes involved in the development and maintenance of the reproductive system. Estrogens have also been shown to have important effects in many non-reproductive tissues such as bone, liver, the cardiovascular system, and the central nervous system. The most widely accepted hypothesis of how estrogens exert their effects is by binding to an intracellular steroid hormone receptor. After the receptor and bound ligand are transferred to the nucleus of the cell, the complex binds to recognition sites in DNA, which allows for the modulation of certain genes. Additionally, it is now becoming apparent that estrogens may mediate their effects via membrane-initiated signaling cascade, though much of this work is still experimental. Kousteni et al., *Journal of Clinical Investigation*, (2003), 111, 1651-1664, herein incorporated by reference with regard to such teaching.

Certain substances have demonstrated the ability to exhibit their biological activity in a "tissue-selective" manner. In other words, tissue selectivity allows functionality as estrogen agonists in certain tissues, while acting as estrogen antagonists in other tissues. The term "selective estrogen receptor modulators" (SERMs) has been given to these molecules. Examples of SERMs include tamoxifen, raloxifene, lasofoxifene, clomiphene, and nafoxidine. The molecular basis for this tissue-selective activity is not completely understood. Without being limited to any particular theory, the ability of the ligand to place the estrogen receptor into different conformational states and allowing for differential capabilities in recruiting coactivator and corepressor proteins, as well as other important proteins involved in transcriptional regulation, is believed to play a role. See, McDonnell, D. P., *The Molecular Pharmacology of SERMs*, Trends Endocrinol. Metab. 1999, 301-311, herein incorporated by reference with regard to such description.

Historically estrogens were believed to manifest their biological activity through a single estrogen receptor, now termed estrogen receptor alpha (ERα). More recently, however, there was the discovery of second subtype of estrogen receptor, termed estrogen receptor beta (ERβ). See, Kuiper et al., WO 97/09348 and Kuiper et al., *Cloning of a Novel Estrogen Receptor Expressed in Rat Prostate and Ovary*, Proc. Natl. Acad. Sci. U.S.A., 1996, pp. 5925-5930, herein incorporated by reference with regard to such subtype. ERβ is expressed in humans. See, Mosselman et al., *ERβ: Identification and Characterization of a Novel Human Estrogen Receptor*, FEBR S Lett., 1996, pp. 49-53, herein incorporated by reference with regard to such expression. The discovery of this second subtype of estrogen receptor significantly increased the biological complexity of estrogen signaling and may be responsible for some of the tissue-selective actions of the currently available SERMs.

As noted above, estrogens have important effects in many non-reproductive tissues. Thus, estrogen modulation is believed useful in the treatment or prophylaxis of diseases and conditions associated with such tissues, including bone, liver, and the central nervous system. For example, osteoporosis is characterized by the net loss of bone mass per unit volume. Such bone loss results in a failure of the skeleton to provide adequate structural support for the body, thereby creating an increased risk of fracture. One of the most common types of osteoporosis is postmenopausal osteoporosis, which is associated with accelerated bone loss subsequent to cessation of menses and declining levels of endogenous estrogen in women. There is an inverse relationship between densitometric measures of bone mass and fracture risk, for per- and postmenopausal women in the process of rapid bone loss due to declining levels of estrogen. See, Slemenda, et al., *Predictors of Bone Mass in Perimenopausal Women, A Prospective Study of Clinical Data Using Photon Abr sorptiometry*, Ann. Intern. Med., 1990, pp. 96-101 and Marshall, et al., *Meta-Analysis of How Well Measures of Bone Mineral Density Predict Occurrence of Osteoporotic Fractures*, Br Med. J., 1996, pp. 1254-1259, each of which is herein incorporated by reference with regard to such relationship. Elderly women currently have a lifetime risk of fractures of about 75%. In addition there is an approximate 40% risk of hip fracture for Caucasian women over age 50 in the United States. The economic burden from osteoporotic fractures is considerable because of the necessity of hospitalization. In addition, although osteoporosis is generally not thought of as lifethreatening, the mortality within 4 months of hip fracture is currently approximately 20 to 30%. Current therapies for postmenopausal osteoporosis include hormone replacement therapy or treatment with other antiresorptive agents such as bisphosphonates or calcitonin. Similarly, SERMS have been shown to be effective in the treatment of postmenopausal osteoporosis (see, Lindsay, R.: *Sex steroids in the pathogenesis and prevention of osteoporosis*. In: Osteoporosis 1988. Etiology, Diagnosis and Management. Riggs B L (ed) I, Raven Press, New York, USA (1988):333-358; Barzel U S: *Estrogens in the prevention and treatment of postmenopausal osteoporosis*: a review. Am J. Med (1988) 85:847-850; and Ettinger, B., Black, D. M., et al., *Reduction of Vertebral Fracture Risk in Postmenopausal Women with Osteoporosis Treated with Raloxifene, JAMA,* 1999, 282, 637-645, each of which is incorporated by reference with regard to such teaching).

As another example, the effects of estrogens on breast tissue, particularly breast cancer, have been well documented. For example, a previously identified SERM, tamoxifen, decreases the risk of recurrent breast cancer, contralateral breast cancer, and mortality as well as increases the diseasefree survival rate of patients with breast cancer at multiple stages of the disease. See, Cosman, F., Lindsay, R. *Selective Estrogen Receptor Modulators: Clinical Spectrum*, Endocrine Rev., 1999, pp. 418-434, herein incorporated by reference with regard to such teaching. The profile of tamoxifen, however, is not ideal due to potential interactive properties on reproductive tissues, such as uterine tissues. There is room for an improved therapy for the treatment of such cancers, namely a SERM with no agonist properties on any reproductive tissues.

Cardiovascular disease is the leading cause of death among postmenopausal women. Until recently, the preponderance of data suggested that estrogen replacement therapy in postmenopausal women reduced the risk of cardiovascular disease, although some studies reported no beneficial effect on overall mortality. See, Barrett-Connor, E. et al., *The Potential of SERMs for Reducing the Risk of Coronary Heart Disease*, Trends Endocrinol. Metab., 1999, pp. 320-325, herein incorporated by reference. The mechanism(s) by which estrogens were believed to exert their beneficial effects on the cardiovascular system are not entirely clear. Potentially estrogen's effects on serum cholesterol and lipoproteins, antioxidant properties, vascular smooth muscle proliferation, and inhibition of arterial cholesterol accumulation were believed to play a role. Id. See also, Cosman, F., Lindsay, R. *Selective Estrogen Receptor Modulators: Clinical Spectrum*, Endocrine Rev., 1999, pp. 418-434, herein incorporated by reference. In light of the recent reports of the HERS II and WHI studies, however, continuous combined Hormone Therapy, namely, CEE+MPA [Conjugated Equine Estrogen+Medroxy Progesterone Acetate], confers no cardiovascular benefit in menopausal women. See, Hulley S., Grady, D., Bush, T., et al., *Randomized trial of estrogen plus progestin for secondary prevention of coronary heart disease in postmenopausal women*. Heart and Estrogen/progestin Replacement Study (HERS) Research Group. *J. Am. Med. Assoc.* (1998) 280:605-613 and Wassertheil-Smoller S., Hendrix, S. L., Limacher, M., et al., for the WHI Investigators. *Effect of estrogen plus progestin on stroke in postmenopausal women: the Women's Health Initiative: a randomized trial. JAMA* (2003) 289, 2673-2684, each herein incorporated by reference with regard to such teaching). To what extent these findings may be extrapolated to SERMs is an issue that remains to be determined.

Other therapeutic alternatives include estrogen replacement therapy and/or hormone replacement therapy, which may be useful in the treatment of vasomotor symptoms, genitourinary atrophy, depression, and diabetes. Over 75% of women experience vasomotor symptoms during the climacteric years. Clinical signs, such as vasomotor symptoms and genitourinary atrophy, abate upon treatment with estrogen replacement therapy. Sagraves, R., *J. Clin. Pharmacol.* (1995), 35(9 *Suppl*):2S-10S, herein incorporated by reference with regard to such teaching. Preliminary data suggest that estradiol may alleviate depression during perimenopause and that the combination of estrogens and selective serotonin reuptake inhibitors may alleviate depression during the postmenopausal period. Soares, C. N., Poitras, J. R., and Prouty, J., *Drugs Aging*, (2003), 20(2), 85-100, herein incorporated by reference with regard to such teaching. Furthermore, hormone replacement therapy may improve glycemic control among women with diabetes. Palin, S. L. et al., *Diabetes Research and Clinical Practice*, (2001), 54, 67-77; Ferrara, A. et al., *Diabetes Care*, (2001), 24(7), 1144-1150, each incorporated herein by reference with regard to such teaching. There is a need, however, for improved therapies that present better side effect profiles.

The present inventors discovered a novel group of cycloalkylidene compounds, which bind to and modulate estrogen receptor alpha and estrogen receptor beta. As SERMS, these compounds are believed to be useful for the treatment and/or prophylaxis of menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, and the treatment and/or prevention of osteoporosis.

SUMMARY OF THE INVENTION

The present invention includes compounds of formula (I):

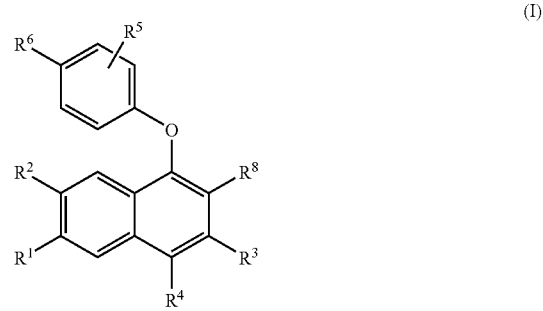

(I)

including salts, solvates, and pharmacologically functional derivatives thereof wherein:

$R^1$ is H, OH, alkoxy, or halogen;

$R^2$ is H, OH, or halogen;

$R^3$ is alkyl, haloalkyl, cycloalkyl, alkoxy, or alkoxyalkyl;

$R^4$ is H or alkoxy;

$R^5$ is H, halogen, or haloalkyl;

$R^6$ is $—(Y)_z—R^7$;

z is 0 or 1;

Y is $—C{\equiv}C—$ or $—CR^e{=}CR^f—$;

when z is 0, then $R^7$ is alkyl, alkoxy, aryl, heteroaryl, heterocyclyl, cyano, $—CO_2H$, $—(CH_2)_tCO_2H$, $—O(CH_2)_tCO_2H$, $—O(CH_2)_tCN$, $—(CH_2)_tOH$, $—O(CH_2)_tOH$, $—O(CH_2)_t—O—(CH_2)_tOH$, $—CONR^aR^b$, $—NR^aSO_2R^d$, or $—NR^aC(O)R^c$;

when z is 1, then $R^7$ is $—CO_2H$, $—(CH_2)_tCO_2H$, $—(CH_2)_tOH$, $—CONR^aR^b$, or $—PO_3HR^a$;

t is 1 to 8;

$R^8$ is aryl or heteroaryl;

$R^a$ is alkyl, cycloalkyl, aryl, heteroaryl, or heterocyclyl;

$R^b$ is alkyl, cycloalkyl, aryl, heteroaryl, or heterocyclyl;

$R^c$ is alkyl, cycloalkyl, aryl, heteroaryl, or heterocyclyl;

$R^d$ is alkyl, cycloalkyl, aryl, heteroaryl, or heterocyclyl;

or $R^a$ and $R^b$, $R^a$ and $R^c$, or $R^a$ and $R^c$ may combine with the atoms to which they are bound to form a heteroaryl or heterocyclyl group; and $R^e$ and $R^f$ each independently are selected from H, alkyl, halogen, and haloalkyl, wherein for each occurrence of alkyl, alkoxy, cycloalkyl, aryl, heteroaryl, or heterocyclyl, each may be optionally substituted.

Another aspect of the present invention includes a compound of formula (I):

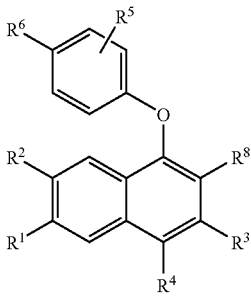

(I)

including salts, solvates, and pharmacologically functional derivatives thereof wherein:

$R^1$ is H, OH, alkoxy, or halogen;

$R^2$ is H, OH, or halogen;

$R^3$ is alkyl, haloalkyl, cycloalkyl, alkoxy, or alkoxyalkyl;

$R^4$ is H or alkoxy;

$R^5$ is H, halogen, or haloalkyl;

$R^6$ is —$(Y)_z$—$R^7$;

z is 0 or 1;

Y is —C≡C— or $CR^e$=$CR^f$—;

when z is 0, then $R^7$ is alkyl, alkoxy, aryl, heteroaryl, heterocyclyl, cyano, —$CO_2R^a$, —$(CH_2)_tCO_2R^a$, —$O(CH_2)_tCO_2R^a$, —$O(CH_2)CN$, —$(CH_2)_tOH$, —$O(CH_2)_tOH$, —$O(CH_2)_t$—O—$(CH_2)_tOH$, —$CONR^aR^b$, —$NR^aSO_2R^d$, or —$NR^aC(O)R^c$;

when z is 1, then $R^7$ is —$CO_2R^a$, —$(CH_2)_tCO_2R^a$, —$(CH_2)_tOH$, —$CONR^aR^b$, or —$PO_3HR^a$;

t is 1 to 8;

$R^8$ is aryl or heteroaryl;

$R^a$ is H, alkyl, haloalkyl, cycloalkyl, aryl, heteroaryl, or heterocyclyl;

$R^b$ is H, alkyl, haloalkyl, cycloalkyl, aryl, heteroaryl, or heterocyclyl;

$R^c$ is H, alkyl, haloalkyl, cycloalkyl, aryl, heteroaryl, or heterocyclyl;

$R^d$ is H, alkyl, haloalkyl, cycloalkyl, aryl, heteroaryl, or heterocyclyl;

or $R^a$ and $R^b$, $R^a$ and $R^c$, or $R^a$ and $R^c$ may combine with the atoms to which they are bound to form a heteroaryl or heterocyclyl group; and $R^e$ and $R^f$ each independently are selected from H, alkyl, halogen, and haloalkyl, wherein for each occurrence of alkyl, alkoxy, cycloalkyl, aryl, heteroaryl, or heterocyclyl, each may be optionally substituted.

In embodiments of the present invention alkyl is $C_{1-9}$alkyl, alkoxy is $C_{1-8}$alkoxy, alkenyl is $C_{2-8}$alkenyl, and alkynyl is $C_{2-8}$alkynyl.

In an embodiment of the present invention $R^1$ is H or OH. Particularly $R^1$ is OH.

In an embodiment of the present invention $R^2$ is H, OH, or F.

In an embodiment of the present invention $R^3$ is alkyl or haloalkyl.

In an embodiment of the present invention $R^4$ is H.

In an embodiment of the present invention $R^5$ is H or haloalkyl. Particularly $R^5$ is haloalkyl.

In an embodiment of the present invention z is 1, Y is —$CR^e$=$CR^f$—, $R^e$ and $R^f$ each are H, and $R^7$ is —$CO_2H$.

In an embodiment of the present invention z is O and $R^7$ is —$CO_2H$.

In an embodiment of the present invention $R^8$ is phenyl; phenyl substituted with OH, halogen, or haloalkyl; thienyl, furyl, or pyridyl. Particularly $R^8$ is phenyl or phenyl monosubstituted with halogen. Particularly $R^8$ is phenyl, 3-fluorophenyl, or 4-fluorophenyl.

The present invention includes embodiments in which each variable in Formula (I) is selected from the group(s) herein identified.

Another aspect of the present invention includes a compound selected from:

1-({4-[(6-Hydroxy-3-methyl-2-phenyl-1-naphthalenyl)oxy]phenyl}carbonyl)-4-piperidinecarboxylic acid;

1-({4-[(6-Hydroxy-3-methyl-2-phenyl-1-naphthalenyl)oxy]phenyl}carbonyl)-4-piperidinecarboxylic acid;

4-[(6-Hydroxy-3-methyl-2-phenyl-1-naphthalenyl)oxy]benzoic acid;

(2E)-3-{4-[(6-hydroxy-3-methyl-2-phenyl-1-naphthalenyl)oxy]-2-(trifluoromethyl)phenyl]-2-propenoic acid;

(2E)-3-{3-fluoro-4-[(6-hydroxy-3-methyl-2-phenyl-1-naphthalenyl)oxy]phenyl}-2-propenoic acid;

1,1,1-trifluoro-N-{4-[(6-hydroxy-3-methyl-2-phenyl-1-naphthalenyl)oxy]phenyl}methanesulfonamide;

(2E)-3-{4-[(6-hydroxy-3-methyl-2-phenyl-1-naphthalenyl)oxy}-3-(trifluoromethyl)phenyl]-2-propenoic acid;

N-{4-[(6-hydroxy-3-methyl-2-phenyl-1-naphthalenyl)oxy]phenyl}-4-methylbenzenesulfonamide;

3-({4-[(6-hydroxy-3-methyl-2-phenyl-1-naphthalenyl)oxy]phenyl}amino)-3-oxopropanoic acid;

(2E)-3-(4-{[6-Hydroxy-2-(4-hydroxyphenyl)-3-methyl-1-naphthalenyl]oxy}phenyl)-2-propenoic acid;

(2E)-3-{4-[(3-Ethyl-6-hydroxy-2-phenyl-1-naphthalenyl)oxy]phenyl}-2-propenoic acid;

7-Ethyl-5-({4-[(1E)-3-(4-methyl-1-piperazinyl)-3-oxo-1-propen-1-yl]phenyl}oxy)-6-phenyl-2-naphthalenol;

(2E)-3-(4-{[6-Hydroxy-3-(1-methylethyl)-2-phenyl-1-naphthalenyl]oxy}phenyl)-2-propenoic acid;

(2E)-3-{4-[(3-Butyl-6-hydroxy-2-phenyl-1-naphthalenyl)oxy]phenyl}-2-propenoic acid;

(2E)-3-{4-[(3-Methyl-2-phenyl-1-naphthalenyl)oxy]phenyl}-2-propenoic acid;

(2E)-3-{4-[(6-Hydroxy-2-phenyl-3-propyl-1-naphthalenyl]oxy}phenyl)-2-propenoic acid;

(2E)-3-(4-{[6-Hydroxy-3-(2-methylpropyl)-2-phenyl-1-naphthalenyl]oxy}phenyl)-2-propenoic acid;

(2E)-3-{4-[(6-Hydroxy-3-pentyl-2-phenyl-1-naphthalenyl)oxy]phenyl}-2-propenoic acid;

(2E)-3-(4-{[6-Hydroxy-2-phenyl-3-(3,3,3-trifluoropropyl)-1-naphthalenyl]oxy}phenyl)-2-propenoic acid;

(2E)-3-{4-[(7-Fluoro-6-hydroxy-2-phenyl-3-propyl-1-naphthalenyl)oxy]phenyl}-2-propenoic acid;

(2E)-3-[4-({3-[(Methyloxy)methyl]-2-phenyl-1-naphthalenyl}oxy)phenyl]-2-propenoic acid;

(2E)-3-{4-[(3-Cyclopropyl-6-hydroxy-2-phenyl-1-naphthalenyl)oxy]phenyl}-2-propenoic acid;

(2E)-3-{4-[(3-Cyclopropyl-6-hydroxy-2-phenyl-1-naphthalenyl)oxy]phenyl}-2-propenoic acid;

(2E)-3-(4-{[3-Butyl-2-(4-fluorophenyl)-1-naphthalenyl]oxy}phenyl)-2-propenoic acid;

(2E)-3-(4-{[3-Butyl-2-(4-hydroxyphenyl)-1-naphthalenyl]oxy}phenyl)-2-propenoic acid;
(2E)-3-{4-[(7-Fluoro-6-hydroxy-2-phenyl-3-propyl-1-naphthalenyl)oxy]phenyl}-2-propenamide;
(2E)-3-{4-[(3-Butyl-2-phenyl-1-naphthalenyl)oxy]phenyl}-2-propenoic acid;
(2E)-3-(4-{[2-Phenyl-3-(trifluoromethyl)-1-naphthalenyl]oxy}phenyl)-2-propenoic acid;
4-{[2-(4-Hydroxyphenyl)-3-(trifluoromethyl)-1-naphthalenyl]oxy}benzoic acid;
(2E)-3-{4-[(6-Hydroxy-3-octyl-2-phenyl-1-naphthalenyl)oxy]phenyl}-2-propenoic acid;
{2-[4-(6-Hydroxy-3-methyl-2-phenyl-naphthalen-1-yloxy)-phenyl]-vinyl}-phosphonic acid;
3-[4-(6-Hydroxy-3-methyl-2-thiophen-3-yl-naphthalen-1-yloxy)-phenyl]-acrylic acid;
3-{4-[2-(4-Fluoro-phenyl)-6-hydroxy-3-methyl-naphthalen-1-yloxy]-phenyl}-acrylic acid;
3-{4-[6-Hydroxy-3-methyl-2-(3-trifluoromethyl-phenyl)-naphthalen-1-yloxy]-phenyl}-acrylic acid;
3-[4-(2-Furan-2-yl-6-methoxy-3-methyl-naphthalen-1-yloxy)-phenyl]-acrylic acid;
3-[4-(6-Methoxy-3-methyl-2-pyridin-4-yl-naphthalen-1-yloxy)-phenyl]-acrylic acid;
3-[4-(6-Hydroxy-3-methyl-2-phenyl-naphthalen-1-yloxy)-phenyl]-2-methyl-acrylic acid;
2-[4-(6-Hydroxy-3-methyl-2-phenyl-naphthalen-1-yloxy)-benzylidene]-3-methyl-butyric acid;
3-{4-[2-(4-Fluoro-phenyl)-6-hydroxy-3-propyl-naphthalen-1-yloxy]-2-trifluoromethyl-phenyl}-2-methyl-acrylic acid;
3-{4-[2-(4-Fluoro-phenyl)-6-hydroxy-3-propyl-naphthalen-1-yloxy]-2-trifluoromethyl-phenyl}-2-methyl-acrylamide;
2-Chloro-3-[4-(6-hydroxy-3-methyl-2-phenyl-naphthalen-1-yloxy)-phenyl]-acrylic acid;
({4-[(6-hydroxy-3-methyl-2-phenyl-1-naphthalenyl)oxy]phenyl}oxy) acetic acid;
4-[(6-hydroxy-3-methyl-2-phenyl-1 naphthalenyl)oxy]benzonitrile;
(2E)-3-[4-[(3-methyl-2-phenyl-1-naphthalenyl)oxy]-2-(trifluoromethyl)phenyl]-2-propenoic acid;
7-methyl-5-({4-[(1E)-3-oxo-3-(1-piperidinyl)-1-propen-1-yl]phenyl}oxy)-6-phenyl-2-naphthalenol;
(2E)-3-(4-{[6-Hydroxy-2-(3-hydroxyphenyl)-3-methyl-1-naphthalenyl]oxy}phenyl)-2-propenoic acid;
3-(4-{[6-Hydroxy-2-(3-hydroxyphenyl)-3-methyl-1-naphthalenyl]oxy}phenyl)propanoic acid;
3-(4-{[6-Hydroxy-2-(4-hydroxyphenyl)-3-methyl-4-(methyloxy)-1-naphthalenyl]oxy}phenyl)propanoic acid;
(2E)-3-(4-{[7-Hydroxy-2-(4-hydroxyphenyl)-3-methyl-1-naphthalenyl]oxy}phenyl)-2-propenoic acid;
3-(4-{[7-Hydroxy-2-(4-hydroxyphenyl)-3-methyl-1-naphthalenyl]oxy}phenyl)propanoic acid;
N-{4-[(6-hydroxy-3-methyl-2-phenyl-1-naphthalenyl)oxy]phenyl}methanesulfonamide;
N-{4-[(6-hydroxy-3-methyl-2-phenyl-1-naphthalenyl)oxy]phenyl}ethanesulfonamide;
2,2,2-trifluoro-N-{4-[(6-hydroxy-3-methyl-2-phenyl-1-naphthalenyl)oxy]phenyl}ethanesulfonamide;
N-[4-[(6-hydroxy-3-methyl-2-phenyl-1-naphthalenyl)oxy]-2-(trifluoromethyl)phenyl]methanesulfonamide;
N-{4-[(6-hydroxy-3-methyl-2-phenyl-1-naphthalenyl)oxy]-2-methylphenyl}methanesulfonamide;
4-{[2-(4-fluorophenyl)-6-hydroxy-3-methyl-1-naphthalenyl]oxy}-2-(trifluoromethyl)benzoic acid;
(2E)-3-[4-{[2-(3-fluorophenyl)-6-hydroxy-3-methyl-1-naphthalenyl]oxy}-2-(trifluoromethyl)phenyl]-2-propenoic acid;
4-{[2-(4-fluorophenyl)-6-hydroxy-3-methyl-1-naphthalenyl]oxy}benzoic acid;
(2E)-3-[4-{[2-(4-fluorophenyl)-6-hydroxy-3-propyl-1-naphthalenyl]oxy}-2-(trifluoromethyl)phenyl]-2-propenoic acid;
(2E)-3-[4-{[2-(4-fluorophenyl)-6-hydroxy-3-propyl-1-naphthalenyl]oxy}-2-(trifluoromethyl)phenyl]-2-propenamide;
4-{[2-(4-fluorophenyl)-6-hydroxy-3-methyl-1-naphthalenyl]oxy}-2-(trifluoromethyl)benzamide;
Methyl 4-{[2-(3-fluorophenyl)-6-hydroxy-3-methyl-1-naphthalenyl]oxy}-2-(trifluoromethyl)benzoate;
4-[(4-{[3-Methyl-6-(methyloxy)-2-phenyl-1-naphthalenyl]oxy}phenyl)oxy]butanoic acid;
2-({2-[(4-{[3-Methyl-6-(methyloxy)-2-phenyl-1-naphthalenyl]oxy}phenyl)oxy]ethyl}oxy)ethanol;
5-{[4-({2-[(2-hydroxyethyl)oxy]ethyl}oxy)phenyl]oxy}-7-methyl-6-phenyl-2-naphthalenol;
6-(3-fluorophenyl)-5-{[4-({2-[(2-hydroxyethyl)oxy]ethyl}oxy)-3-(trifluoromethyl)phenyl]oxy}-7-methyl-2-naphthalenol;
{[4-{[2-(3-fluorophenyl)-6-hydroxy-3-methyl-1-naphthalenyl]oxy}-2-(trifluoromethyl)phenyl]oxy}acetic acid; and
6-(3-fluorophenyl)-5-{[4-[(2-hydroxyethyl)oxy]-3-(trifluoromethyl)phenyl]oxy}-7-methyl-2-naphthalenol, including salts, solvates, and pharmaceutically acceptable derivatives thereof.

Another aspect of the present invention includes (2E)-3-[4-{[2-(3-fluorophenyl)-6-hydroxy-3-methyl-1-naphthalenyl]oxy}-2-(trifluoromethyl)phenyl]-2-propenoic acid, salts, solvates, or pharmaceutically acceptable derivatives.

Another aspect of the present invention includes pharmaceutical compositions that include a compound of the present invention, preferably along with a pharmaceutically acceptable carrier. Thus, another aspect of the present invention includes a compound of the present invention for use as an active therapeutic substance.

Another aspect of the present invention includes a compound of the present invention for use in the treatment or prophylaxis of conditions or disorders affected by selective estrogen receptor modulation. More particularly the treatment or prophylaxis may relate to osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, polycystic ovary syndrome, counteracting preeclampsia, premenstral syndrome, contraception, uterine fibroid disease, and/or aortic smooth muscle cell proliferation, vaginal dryness, pruritus, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain, dysmenorrhea, menopausal or postmenopausal disorders, vasomotor symptoms, urogenital or vulvar vaginal atrophy, atrophic vaginitis, endometriosis, female sexual dysfunction, for enhancing libido, for the treatment of hypoactive sexual disorder, sexual arousal disorder, for increasing the frequency and intensity of orgasms, vaginismus, osteopenia, BPH (benign prostatic hypertrophy), autoimmune diseases, Hashimoto's thyroiditis, SLE (systemic lupus erythematosus), myasthenia gravis, or reperfusion damage of ischemic myocardium. Preferably the condition or disorder is menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, or osteoporosis.

Another aspect of the present invention includes the use of a compound of the present invention in the manufacture of a medicament for use in the treatment or prophylaxis of conditions or disorders associated with selective estrogen receptor modulation. More particularly such a medicament is believed useful in the treatment or prophylaxis of osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, polycystic ovary syndrome, counteracting preeclampsia, premenstral syndrome, contraception, uterine fibroid disease, and/or aortic smooth muscle cell proliferation, vaginal dryness, pruritus, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain, dysmenorrhea, menopausal or postmenopausal disorders, vasomotor symptoms, urogenital or vulvar vaginal atrophy, atrophic vaginitis, endometriosis, female sexual dysfunction, for enhancing libido, for the treatment of hypoactive sexual disorder, sexual arousal disorder, for increasing the frequency and intensity of orgasms, vaginismus, osteopenia, BPH (benign prostatic hypertrophy), autoimmune diseases, Hashimoto's thyroiditis, SLE (systemic lupus erythematosus), myasthenia gravis, or reperfusion damage of ischemic myocardium. Preferably the condition or disorder is menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, or osteoporosis.

Another aspect of the present invention includes a method for the treatment or prophylaxis of conditions or disorders associated with selective estrogen receptor modulation comprising the administration of a compound of the present invention. More particularly the condition or disorder is osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, polycystic ovary syndrome, counteracting preeclampsia, premenstral syndrome, contraception, uterine fibroid disease, and/or aortic smooth muscle cell proliferation, vaginal dryness, pruritus, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain, dysmenorrhea, menopausal or postmenopausal disorders, vasomotor symptoms, urogenital or vulvar vaginal atrophy, atrophic vaginitis, endometriosis, female sexual dysfunction, for enhancing libido, for the treatment of hypoactive sexual disorder, sexual arousal disorder, for increasing the frequency and intensity of orgasms, vaginismus, osteopenia, BPH (benign prostatic hypertrophy), autoimmune diseases, Hashimoto's thyroiditis, SLE (systemic lupus erythematosus), myasthenia gravis, or reperfusion damage of ischemic myocardium. Preferably the condition or disorder is menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, or osteoporosis.

DETAILED DESCRIPTION OF THE PREFERRED EMBODIMENT

The present invention is described in terms known and appreciated by those skilled in the art. For ease of reference certain terms hereafter are defined. The fact that certain terms are defined, however, should not be considered as indicative that any term that is undefined is indefinite. Rather, all terms used herein are believed to describe the invention in terms such that one of ordinary skill can appreciate the scope of the present invention.

As used herein the term "alkyl" refers to a straight or branched chain hydrocarbon, preferably having from one to twelve carbon atoms, which may be optionally substituted. Examples of "alkyl" as used herein include, but are not limited to, methyl, ethyl, propyl, isopropyl, isobutyl, n-butyl, tert-butyl, isopentyl, n-pentyl, and the like.

As used herein the term "alkenyl" refers to a straight or branched chain hydrocarbon that contains one or more carbon-to-carbon double bond, preferably having from two to twelve carbon atoms, which may be optionally substituted. Examples of "alkenyl" as used herein include, but are not limited to, vinyl, 1-propenyl, allyl, and the like.

As used herein the term "alkynyl" refers to a straight or branched chain hydrocarbon that contains one or more carbon-to-carbon triple bonds, preferably having from two to twelve carbon atoms, which may be optionally substituted. Examples of "alkynyl" as used herein include, but are not limited to, ethynyl, 1-propynyl, 2-propynyl, and the like.

As used herein, the term "alkylene" refers to a straight or branched chain divalent hydrocarbon radical, preferably having from one to ten carbon atoms. Multiple degrees of substitution are allowed. Examples of "alkylene" as used herein include, but are not limited to, methylene, ethylene, n-propylene, n-butylene, and the like.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups and the like.

As used herein the term "alkoxy" refers to the group —OR, where R is alkyl as defined above.

As used herein the term "alkoxyalkyl" refers to an ether group —ROR, where each R independently is alkyl as defined above.

As used herein the term "acyl" refers to the group —C(O)R, where R is alkyl, aryl, heteroaryl, or heterocyclyl, as each is defined herein.

As used herein the term "hydroxy" refers to the group —OH.

As used herein the term "carboxy" refers to the group —C(O)OH.

As used herein the term "nitro" refers to the group —NO$_2$.

As used herein the term "amino" refers to the group —NH$_2$, or when referred to as substituted amino defines such groups substituted with alkyl.

As used herein, the term "cycloalkyl" refers to a non-aromatic cyclic hydrocarbon ring, preferably having from three to ten carbon atoms, which may be optionally substituted. Exemplary "cycloalkyl" groups include, but are not limited to, cyclopropyl, cyclobutyl, cyclopentyl, cyclohexyl, and cycloheptyl.

As used herein, the term "aryl" refers to an optionally substituted benzene ring or to an optionally substituted benzene ring system fused to one or more optionally substituted benzene rings to form, for example, anthracene, phenanthrene, or naphthalene ring systems. Examples of "aryl" groups include, but are not limited to, phenyl, 2-naphthyl, 1-naphthyl, and biphenyl, as well as substituted derivatives thereof.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen atoms, where N-oxides, sulfur oxides, and dioxides are permissible heteroatom substitutions. The heteroaryl rings may be optionally substituted and multiple degrees of substitution should be considered within the scope of the present invention. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "heterocycle" or "heterocyclyl" refers to a mono- or poly-cyclic ring system containing optionally one or more degrees of unsaturation and also containing one or more heteroatoms. Preferred heteroatoms include N, O, and/or S, including N-oxides, sulfur oxides, and dioxides. Preferably the ring is three to ten-membered and is either saturated or has one or more degrees of unsaturation. Optionally, as used herein, the heterocycle may be substituted, with multiple degrees of substitution being allowed. Such rings may be optionally fused to one or more of another "heterocyclic" ring(s), heteroaryl ring(s), aryl ring(s), or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein throughout the present specification, the phrase "optionally substituted" or variations thereof denote an optional substitution, including multiple degrees of substitution, with one or more substituent group. The phrase should not be interpreted so as to be imprecise or duplicative of substitution patterns herein described or depicted. Rather, those of ordinary skill in the art will appreciate that the phrase is included to provide for obvious modifications, which are encompassed within the scope of the appended claims.

Exemplary optional substituent groups include acyl; alkyl; alkenyl; alkynyl; alkylsulfonyl; alkoxy; cyano; halogen; haloalkyl; hydroxy; nitro; cycloalkyl, which may be further substituted with acyl, alkoxy, alkyl, alkenyl, alkynyl, alkylsulfonyl, cyano, halogen, haloalkyl, hydroxy, or nitro; heterocyclyl, which may be further substituted with acyl, alkoxy, alkyl, alkenyl, alkynyl, alkylsulfonyl, cyano, halogen, haloalkyl, hydroxy, or nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; —$CO_2H$; —$CONR^aR^b$; —$NR^aSO_2R^d$; —$NR^aCOR^c$; —$SO_2{}_NR^aR^b$; —$SO_2{}_NR^aCOR^c$; and —$CONR^aSO_2R^d$, where each of $R^a$, $R^b$, $R^c$, and $R^d$ independently are as herein defined.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5$^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts, solvates, and physiological functional derivatives thereof, may be administered as the raw chemical. Additionally, the active ingredient may be presented as a pharmaceutical composition. Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as described above. The carrier(s), diluent(s) or excipient(s) must be acceptable, in the sense of being compatible with the other ingredients of the formulation and not deleterious to the recipient of the pharmaceutical composition. In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the age and weight of the animal, the precise condition requiring treatment and its severity, the nature of the formulation, and the route of administration are all factors to be considered. The therapeutically effective amount ultimately should be at the discretion of the attendant physician or veterinarian. For example, an effective amount of a compound of formula (I) for the treatment of humans suffering from osteoporosis, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein that are mediated by estrogen.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders, such as carboxymethylcellulose, aliginates, gelatins, or polyvinyl pyrrolidone, solution retardants, such as paraffin, resorption accelerators such as a quaternary salt and/or abr sorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone (PVP), pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent. Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring agents.

The compounds of the present invention and their salts, solvates, and physiologically functional derivatives thereof, may be employed alone or in combination with other therapeutic agents for the treatment of the conditions herein described. For example, in osteoporosis therapy, combination with other osteoporosis therapeutic agents is envisaged. Osteoporosis combination therapies according to the present invention thus comprise the administration of at least one compound of formula (I) or a salt, solvate, or physiologically functional derivative thereof, and the use of at least one other osteoporosis treatment method. Preferably, combination therapies according to the present invention comprise the administration of at least one compound of formula (I) or a salt, solvate, or physiologically functional derivative thereof, and at least one other osteoporosis treatment agent, for example, a bone building agent. The compound(s) of formula (I) and the other pharmaceutically active agent(s) may be administered together or separately and, when administered separately, administration may occur simultaneously or sequentially in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other osteoporosis treatment agents may be in combination by administration concomitantly in: (1) a unitary pharmaceutical composition including each compound; or (2) separate pharmaceutical compositions each including one of the compounds. Alternatively, the combination may be administered separately in a sequential manner wherein one treatment agent is administered first and the other(s) subsequently or vice versa. Such sequential administration may be close in time or remote in time.

The compounds of the present invention and their salts, solvates, and physiologically functional derivatives thereof, may be employed alone or in combination with other therapeutic agents for the treatment of the conditions herein described. For example, regarding the use of the compounds of the present invention in the prevention of reduced bone mass, density, or growth, combination may be had with other anabolic or osteoporosis therapeutic agents. As one example, osteoporosis combination therapies according to the present invention would thus comprise the administration of at least one compound of the present invention or a salt, solvate, or physiologically functional derivative thereof, and the use of at least one other osteoporosis therapy. As a further example, combination therapies according to the present invention include the administration of at least one compound of the present invention or a salt, solvate, or physiologically functional derivative thereof, and at least one other osteoporosis treatment agent, for example, an anti-bone resorption agent. The compound(s) of the present invention and the other pharmaceutically active agent(s) may be administered together or separately and, when administered separately, administration may occur simultaneously or sequentially, in any order. The amounts of the compound(s) and the agent(s) and the relative timings of administration will be selected in order to achieve the desired combined therapeutic effect. The administration in combination of a compound of the present invention including salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

As noted, one potential additional osteoporosis treatment agent is a bone building (anabolic) agent. Bone building agents can lead to increases in parameters such as bone mineral density that are greater than those than can be achieved with anti-resorptive agents. In some cases, such anabolic agents can increase trabecular connectivity leading to greater structural integrity of the bone.

Other potential therapeutic combinations include the compounds of the present invention combined with other compounds of the present invention, growth promoting agents, growth hormone secretagogues, growth hormone releasing factor and its analogs, growth hormone and its analogs, somatomedins, alpha-ardenergic agonists, serotonin 5-$HT_D$ agonists, selective serotonin reuptake inhibitors, agents that inhibit somatostatin or its release, 5-α-reductase inhibitors, aromatase inhibitors, GnRH inhibitors, parathyroid hormone, bisphosphonates, estrogen, testosterone, SERMs, progesterone receptor agonists, and/or with other modulators of nuclear hormone receptors.

The compounds of the present invention may be used in the treatment of a variety of disorders and conditions and, as such, the compounds of the present invention may be used in combination with a variety of other suitable therapeutic agents useful in the treatment or prophylaxis of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins, minerals, creatine, piloic acid, carnitine, or coenzyme Q10.

An aspect of the present invention is the use of the compounds of the present invention for the treatment or prophylaxis of a variety of disorders including, but not limited to, osteoporosis, bone demineralization and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain, dysmenorrhea, menopausal or postmenopausal disorders, vasomotor symptoms, urogenital or vulvar vaginal atrophy, atrophic vaginitis, endometriosis, female sexual dysfunction, for enhancing libido, for the treatment of hypoactive sexual disorder, sexual arousal disorder, for increasing the frequency and intensity of orgasms, vaginismus, osteopenia, BPH (benign prostatic hypertrophy), autoimmune diseases, Hashimoto's thyroiditis, SLE (systemic lupus erythematosus), myasthenia gravis, reperfusion damage of ischemic myocardium, In particular, the compounds of the present invention are believed useful, either alone or in combination with other agents, in the treatment of menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, and the treatment and/or prevention of osteoporosis.

The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

EXPERIMENTAL SECTION

Abbreviations:

As used herein the symbols and conventions used in these processes, schemes and examples are consistent with those used in the contemporary scientific literature, for example, the *Journal of the American Chemical Society or the Journal* of *Biological Chemistry*. Specifically, the following abbreviations may be used in the examples and throughout the specification:

g (grams); mg (milligrams);
L (liters); mL (milliliters);
µL (microliters); psi (pounds per square inch);
M (molar); mM (millimolar);
Hz (Hertz); MHz (megahertz);
mol (moles); mmol (millimoles);
RT (room temperature); h (hours);
d (days); EI (electron impact);
min (minutes); TLC (thin layer chromatography);
mp (melting point); RP (reverse phase);
$T_r$ (retention time); TFA (trifluoroacetic acid);
TEA (triethylamine); THF (tetrahydrofuran);
TFAA (trifluoroacetic anhydride); $CD_3OD$ (deuterated methanol);
$CDCl_3$ (deuterated chloroform); DMSO (dimethylsulfoxide);
$SiO_2$ (silica); atm (atmosphere);
EtOAc (EtOAc); $CHCl_3$ (chloroform);
HCl (hydrochloric acid); Ac (acetyl);
DMF (N,N-dimethylformamide); Me (methyl);
$Cs_2CO_3$ (cesium carbonate); EtOH (ethanol);
Et (ethyl); tBu (tert-butyl);
MeOH (methanol); $CH_2Cl_2$ (dichloromethane);
$MgSO_4$ (magnesium sulfate); $CH_3CN$ (acetonitrile);
$K_2CO_3$ (potassium carbonate); $TiCl_4$ (titanium tetrachloride);
EtOAc (EtOAc); $CO_2$ (carbon dioxide);
$Pd(OAc)_2$ (palladium acetate); $Et_2O$ (diethyl ether);
$P(o-tolyl)_3$ (tri-o-tolylphosphine); $Na_2SO_4$ (sodium sulfate);
NaH (sodium hydride); DME (1,2-dimethoxyethane);
NaI (sodium iodide); NaOH (sodium hydroxide);
$NH_4Cl$ (ammonium chloride); $NaHCO_3$ (sodium bicarbonate);
$AlCl_3$ (aluminum chloride); $(C_2H_5O)_2P(O)H$ (diethyl phosphite);
$NaN_3$ (sodium azide); $CBr_4$ (carbon tetrabromide);
PPh (triphenylphosphine); CuI (copper (I) iodide);
$Pd(Ph_3P)_4$ (tetrakis(triphenylphosphine)palladium (0));
$(iPrO)_3B$ (triisopropyl borate); nBuLi (butyllithium);
$Na_2CO_3$ (sodium carbonate); DMAP (4-(dimethylamino)pyridine);
eq (equivalents);
HRMS (high resolution mass spectrometry);
LCMS (liquid chromatography mass spectrometry);
LRMS (low resolution mass spectrometry);
APCI (Atmospheric Pressure Chemical Ionization);
LiHMDS (lithium bis(trimethylsilyl)amide);
KHMDS (potassium bis(trimethylsilyl)amide);
$Pd(Ph_3P)_2Cl_2$ (dichlorobis(triphenylphosphine)palladium(II));
EDC (N-(3-dimethylaminopropyl)-N'-ethyl-carbodimide;
dpppe (1,5-bis(diphenylphosphanyl)pentane;
DMAc (N,N-dimethylacetamide);
HPLC (high performance liquid chromatography);
tmeda (N,N,N',N',-tetramethylethylenediamine);
$Pd_2(dba)_3$ (dipalladiumtris(dibenzylidene acetone)).

Unless otherwise noted, reagents and solvents were obtained from commercial suppliers and were used without further purification. Unless otherwise indicated, all reactions were conducted at room temperature and all temperatures are expressed in ° C. (degrees Centigrade).

Thin-layer chromatography (TLC) was performed on silica gel 60 $F_{254}$ precoated plates. Detection was effected by exposure to UV light (254 nm). Flash and flush column chromatography was performed using Silica Gel 60. Reverse phase preparative and analytical HPLC were performed using C18 columns and acetonitrile:water gradients with 0.05% TFA as a modifier.

Compound purity and characterization were determined by $^1$H-NMR, liquid chromatography-mass spectrometry (LCMS), high resolution mass spectrometry (HRMS), combustion (elemental) analysis, HPLC, and melting point. Compounds of general formula (I) were typically found to have purities of >90%.

$^1$H NMR spectra were recorded on Varian INOVA-300 and Varian INOVA-400 instruments. Chemical shifts are expressed in parts per million (ppm, δ units). Coupling constants are in units of hertz (Hz). Splitting patterns describe apparent multiplicities and are designated as s (singlet), d (doublet), dd (doublet of doublet), t (triplet), q (quartet), m (multiplet), or br (broad).

Low resolution mass spectra were obtained on Micromass ZQ, Micromass ZMD, Micromass QuattroMicro, and Micromass GCT instruments from Micromass Ltd., Altricham, UK, using either Atmospheric Pressure Chemical Ionization (APCI) or ESI Ionization (ESI).

High resolution mass spectral data (HRMS) were recorded with Micromass LCT and Micromass GCT instruments.

Combustion analyses were performed by Atlantic Microlab, Inc. (Norcross, Ga.).

Melting points were recorded in open capillary tubes and are uncorrected.

The bolded numerals reference the compounds as depicted in the following schemes.

As illustrated below, compounds of formula (I) can be prepared using the routes described in Schemes 1-6. Several routes to the substituted naphthol VI are described in Schemes 1-5. Reaction of aryl acetic acids (I) with a phenethylbromide (II) in the presence of nBuLi affords the carboxylic acid III. Friedel-Crafts cyclization of III via the intermediate acid chloride yields the tetralone IV. For Friedel-Crafts reaction conditions, see *Friedel-Crafts and Related Reactions*, G. A. Olah, ed., Vol 3, Pt 1, pp 1-382, J. Wiley and Sons, New York (1964); G. A. Olah, *Friedel-Crafts Chemistry*, Wiley Interscience, New York, (1973); and Larock, R. C., *Comprehensive Organic Transformations*, VCH Publishers, New York, 1989, each herein incorporated by reference with regard to such teaching. Conversion of IV to the intermediate naphthol VI was effected in 2 steps.

Further elaboration of the R3 substituent of VI can be carried out. For example, when R3 is an ester, saponification will yield the carboxylic acid VII and treatment with a reducing agent such as LAH yields the corresponding alcohol VIII. Acid VII can also be converted to a carboxamide IX. Treatment of acid (VII) with an amine in the presence of a coupling agent such as EDC and DMAP in dichloromethane followed by deprotection (if R* is not hydrogen) provides amide IX. Alternatively, acid VII can be converted to the acid chloride using oxalyl chloride and DMF in toluene followed by treatment of the crude acid chloride with an amine and deprotection (if R* is not hydrogen) to give amide IX. For conversion of carboxylic acids to amides, see Larock, R. C., *Comprehensive Organic Transformations*, VCH Publishers, New York, 1989.

Similarly, preparation of analogues of compounds VI-IX from a benzophenone related to compound III in which the methoxy group is meta to the carbonyl group can be accomplished using identical procedures (See Example 68).

Scheme 1
Dianion Route to Naphthalene-Based ER Ligands

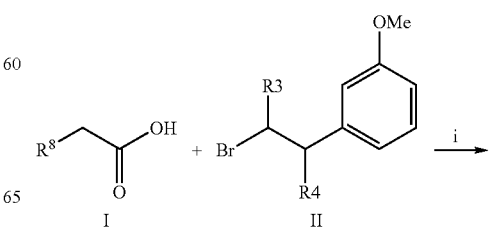

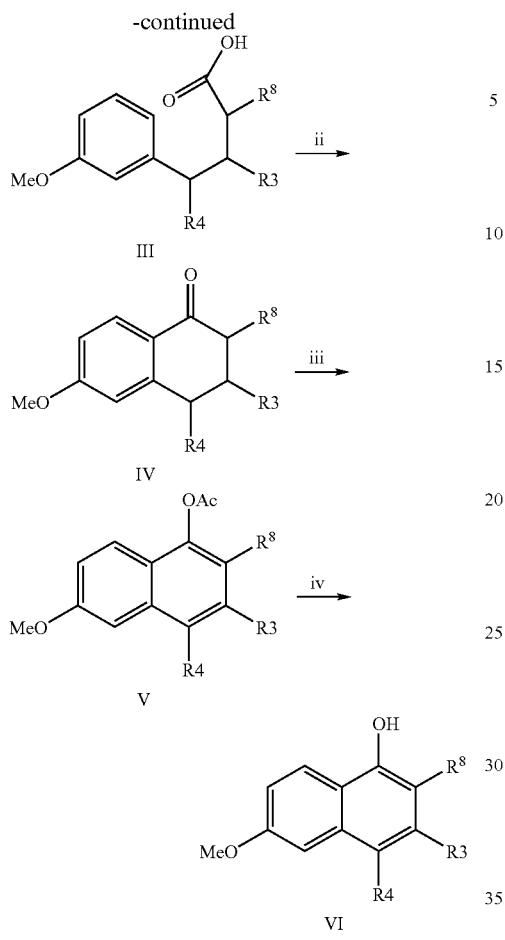

(i) nBuLi, THF, -78° C.; (ii) a. (COCl)$_2$, CH$_2$Cl$_2$, RT; b. AlCl$_3$, CH$_2$Cl$_2$, 0° C.;
(iii) a. isopropenyl acetate, pTsOH, reflux; b. DDQ, toluene, reflux;
(iv) NaOMe, MeOH, THF Alternatively, naphthol VI can be prepared via intermediate XII, the synthesis of which is described in Scheme 2. Condensation of carbonyl compound A with an aryl Grignard reagent such as VII yields the acid VIII. A procedure for preparing acid VII (R3=Me, R4=H) has been described by D. L. Vander Jagt et. al. *J. Med. Chem.*, 1998, 41, 3879-3887. Intramolecular Fridel-Crafts acylation affords the tetralone IX. Naphthols such as XI can be prepared using a modification of the procedure reported by G. R. Green et. al. *Tetrahedron*, 1998 54, 9875-9894. Treatment of 1x with bromine in chloroform gave the dibromide X which can be dehydrohalogenaetd by exposure to a base such as DBU. The moderately unstable naphthol XI was protected as a MOM-ether. Conversion of XII to VI is described in Scheme 3.

Scheme 2
MOM Bromide Route to Naphthalene-Based ER Ligands

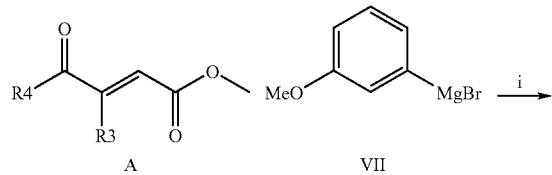

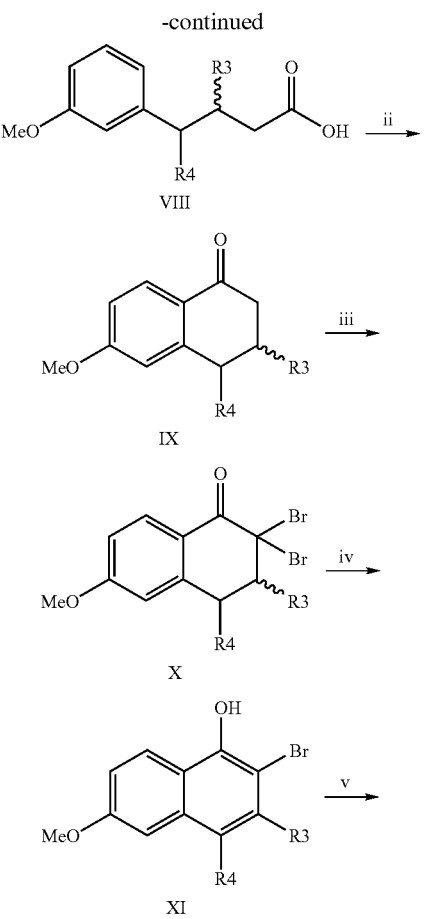

(i) a. aldehyde A; b. EtOH, KOH, reflux; c. H$_2$, Pd/C, HOAc, 60° C.;
(ii) a. (COCl)$_2$, CH$_2$Cl$_2$; b. AlCl$_3$, RT;
(iii) Br$_2$, CHCl$_3$, RT; (iv) DBU, 40° C.; (v) MOMCl, Hunig's base, THF Another route to preparation of naphthol VI was effected using the Peterson olefination protocol described in Scheme 3. Treatment of aryl ketone XIII with ethyl (trimethylsilyl) acetate affords acrylate ester XIV as a mixture of E and Z-isomers. For Peterson Olefination reaction conditions, see Ager, *Organic Reactions* 1990, 38, pp 1-223, herein incorporated by reference with regard to such teaching. Ester XIV was hydrogenated followed by Friedel-Crafts cyclization to tetralone IX using conditions previously described. Compound IX to the MOM-protected naphthol XII was carried using the conditions described for Scheme 2. Suzuki coupling of aryl boronic acids to the aryl bromide XII followed by removal of the MOM group yielded naphthol VI. For a review of the Suzuki boronic acid coupling reaction, see Miyaura, N. and Suzuki, A., *Chem. Rev.* 1995, 95, pp 2457-2483, herein incorporated by reference with regard to such teaching.

Scheme 3
Peterson Olefination Route to Naphthalene-Based ER Ligands

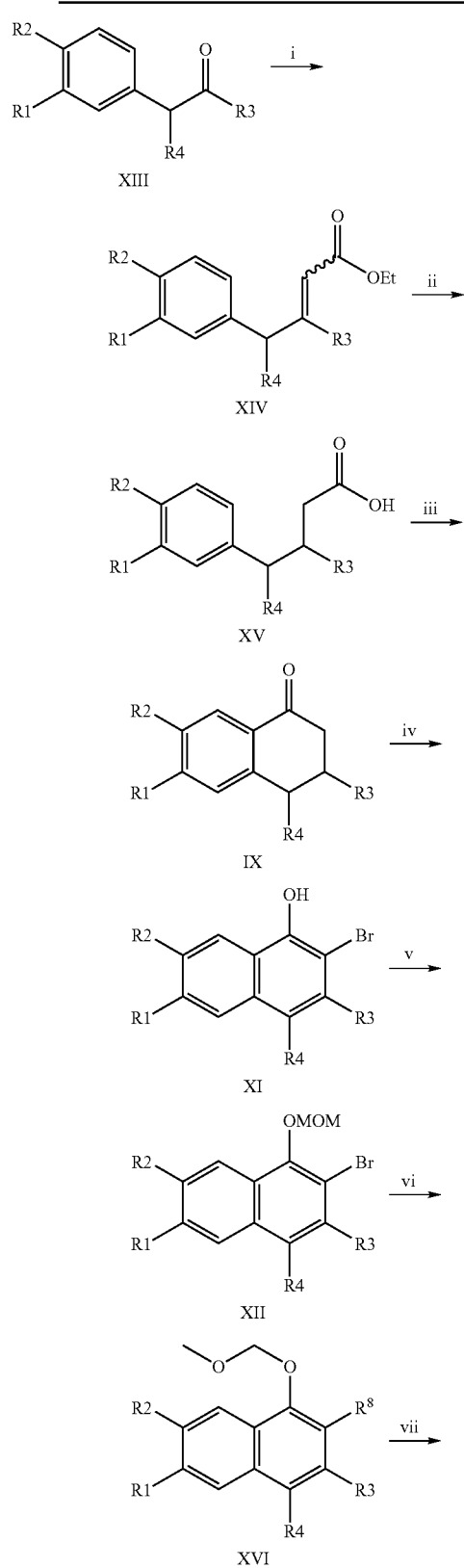

(i) DCHA, nBuLi, TMSCH$_2$CO$_2$Et, -40° C.; (ii) a, H$_2$, Pd/C; b, NaOH;
(iii) (COCl)$_2$, CH$_2$Cl$_2$, then AlCl$_3$; (iv) a, Br$_2$, CHCl$_3$; b, DBU, CH$_3$CN;
(v) MOMCl, iPr$_2$NEt; (vi) ArB(OH)$_2$, Pd(PPh$_3$)$_4$, Na$_2$CO$_3$, DME, 160° C.;
or; a, nBuLi, B(OMe)$_3$; b, Pinacol, MgSO$_4$; c, ArBr, Pd(PPh$_3$)$_4$, Na$_2$CO$_3$, DME, 160° C. (vii) HCl, dioxane Naphthol VI can also be prepared using an acetylene cyclization approach based on the methodology reported by Makra, F. et al., *Tetrahedron Lett.*, 1995, 36, 6815-6818, herein incorporated by reference with regard to such teaching. Sonagashira coupling of terminal acetylenes to ortho-substituted aryl halide or triflate XVII in the presence of CuI and a palladium catalyst yields alkyne XVIII. The synthesis of compound XVIII used the procedure described by Zhang, Q, et. al, *J. Org. Chem.*, 2000, 7977-7983, herein incorporated by reference with regard to such teaching. Preparation of the Weinreb amide followed by coupling to a benzylsubstituted grignard reagent provided ketone XIX, which can be cyclized to naphthol VI in the presence of a base such as potassium bis(trimethylsilyl)amide (KHMDS).

Scheme 4
Alkyne Cyclization Route to Naphthalene-Based ER Ligands

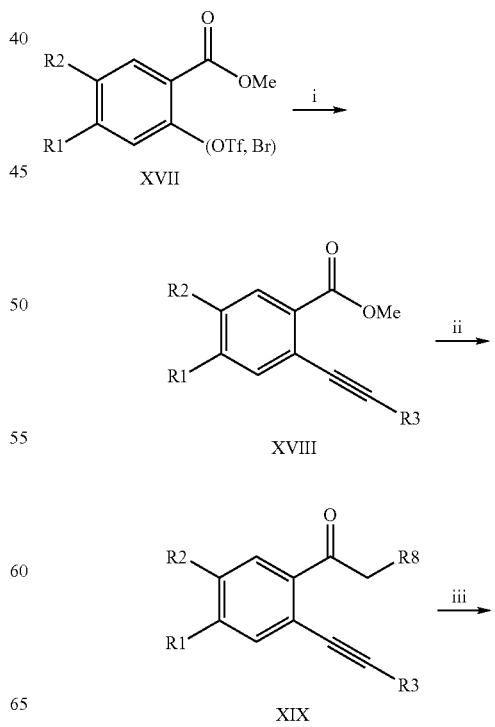

-continued

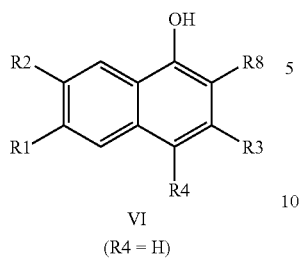

VI
(R4 = H)

(i) HCCR3, Pd(PPh₃)₂Cl₂, CuI, DIPEA, DMF; (ii) a. N,O-dimethylhydroxylamine HCl salt, nBuLi, -20° C.; b. ArCH₂MgCl; (iii) KHMDS, toluene, 80° C.

Compounds of formula (I) can also be prepared starting from cyclobutenones (Scheme 5). The requisite cyclobutenones are made from the treatment of dialkylsquarates such as dimethylsquarate XX with organometallic reagents such as methyllithium to afford β-alkoxy enol ethers. Acylation with trifluoroacetic anhydride (TFAA) activates carbinol intermediates for further derivatization. Methanol treatment of the trifluoroacetate intermediate affords dimethyl ketal protected cyclobutenediones XXI (Gayo, L. M.; Winters, M. P.; Moore, H. W. *J. Org. Chem.* 1992, 57, 6896). Addition of a second organometallic reagent such as (3-methoxy phenyl)lithium to the protected cyclobutenediones XXI gives cyclobutenediones XXII after TFAA promoted hydrolysis of the corresponding β-hydroxy enol ether. Addition of another organolithium reagent such as (3-methoxy phenyl)lithium to XXII is followed by trapping of the resulting lithium alkoxide with reagents such as methyltriflate. Hydrolysis of the ketal moiety or direct hydrolysis with aqueous acid provides highly substituted 4-alkoxy or 4-hydroxycyclobutenones XXIII. Hydroxycyclobutenones are treated with Lewis acids such as BF₃/Et₂O and silanes such as triethylsilane to provide 4-protiocyclobutenones XXIV. Finally, thermolysis of the 4-protio XXIV) or 4-alkoxy XXIII substituted cyclobutenones by heating in a higher boiling solvent such as toluene proceeds through a dienyl ketene to afford highly substituted naphthols VI. This method of naphthol synthesis provides a variety of substitution patterns that are not easily accessed through traditional methods (Turnbull, P.; Moore H. W. *J. Org. Chem.* 1995, 60, 644).

Scheme 5
Cyclobutenone Route to Naphthalene-Based ER Ligands

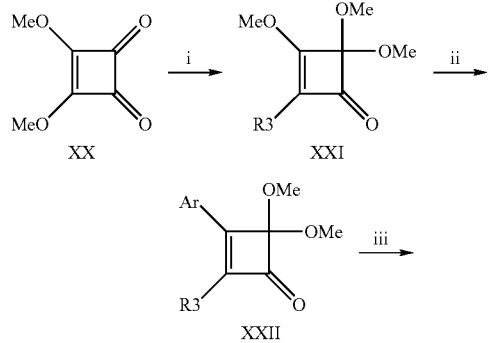

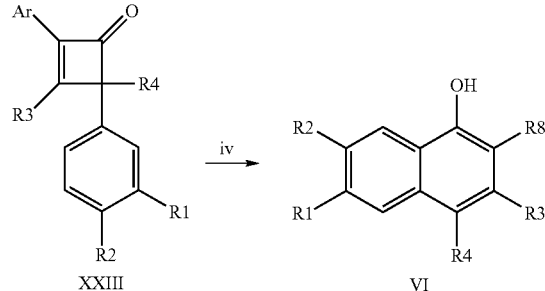

(i) a. R³Li; b. TFAA; c. MeOH; (ii) a. R⁸Br, nBuLi; b. TFAA; c. H₂O;
(iii) a. R¹PhBr, nBuLi; b. H₃O⁺; or R⁴OTf, H₃O⁺; (iv) Toleune, reflux;
(v) Trialkylsilane, BF₃/Et₂O The 1-position of the substituted naphthol VI prepared by the methods described in Schemes 1-5 can be functionalized further to provide compounds that are active on the estrogen receptor (ER). As depicted in Scheme 6, O-arylation with appropriately substituted aryl flourides (such as, 4-fluorobenzaldehyde) and a base such as cesium carbonate or sodium hydride, provides the substituted naphthalene XXV. The substituted benzaldehyde XXV, may be further functionalized by Wittig olefination with a reagent such as an ylide generated from triethylphosphonoacetate derivatives. Saponification of the resulting acrylate esters with aqueous lithium hydroxide or aqueous sodium hydroxide provides acrylic acids. Deprotection with BBr₃ (R1 or R2=OMe) or H₂/Pd (R1 or R2=O-benzyl) affords naphthols (XXVI). Reduction of the acrylic acid olefin (XXVI) with H₂/Pd provides propanoic acids (XXVII). Additionally, the acrylic acids can be converted to the corresponding carboxamides (prior to treatment with BBr₃), via the intermediate acid chlorides, with an amine in the presence of Et₃N (see Example 45 below).

Alternatively, aldehyde XXV can be subjected to Baeyer-Villiger oxidation to provide phenol XXVIII. For a review of the Baeyer-Villiger reaction see, *Oxidations in Organic Chemistry*, Hudlicky, T., pp. 186-195, American Chemical Society: Washington, 1990, herein incorporated by reference with regard to such teaching. Phenol XXVIII can be alkylated with an haloacetic acid ester followed by saponification to afford acid XXIX or with an appropriate alkyl halide to afford alcohol derivatives such as XXX. For examples of related phenol alkylation reactions see Rubin, V. et al., *Bioorganic & Med. Chem.* (2001), 9, 1579-1586, herein incorporated by reference with regard to such teaching. The aldehyde intermediate XXV in Scheme 6 can also be converted to the corresponding carboxylic acid or methyl ester XXXI. Phenol XXVIII may be used to prepare aryl (Ar) or heteroaryl (Het) substituted analogues XXXII via Suzuki reaction of an intermediate aryl triflate. For a review of the Suzuki boronic acid coupling reaction, see Miyaura, N. and Suzuki, A., *Chem. Rev.* 1995, 95, pp 2457-2483 and Ritter, K., Synthesis 1993, pp 735-762, herein incorporated by reference with regard to such teaching.

Scheme 6
Preparation of Naphthalene-Based ER Ligands from Intermediate

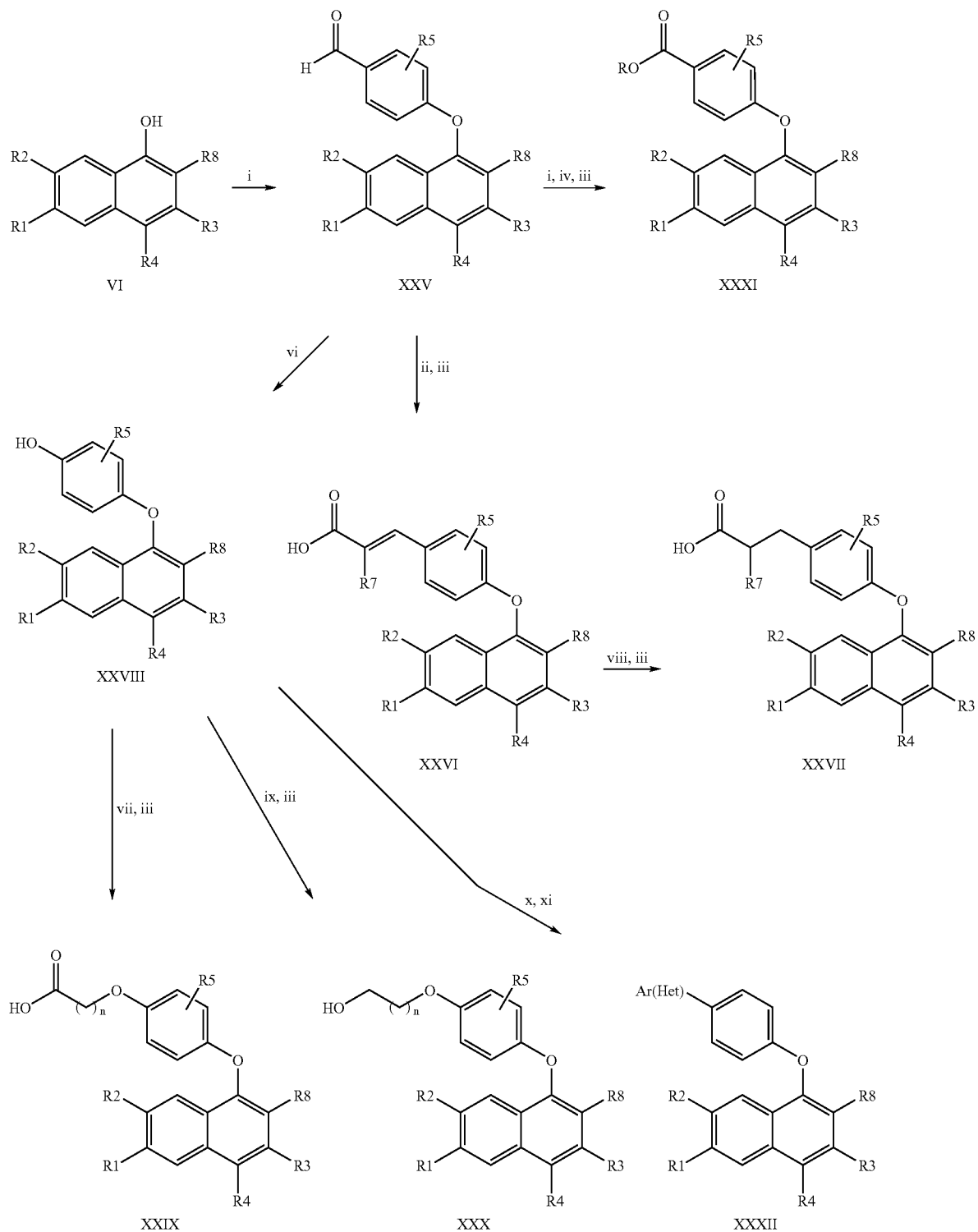

(i) 4-F-benzaldehyde, NaH or Cs₂CO₃, DMF; (ii) a. nBuLi, (EtO)₂PO(CHR₇) CO₂Et; b. NaOH; or malonic acid, piperidine, pyridine; (iii) BBr₃, CH₂Cl₂; (iv) MnO₂, NaCN, MeOH,CH₂Cl₂, or, H₂NSO₃H, NaClO₂, dioxane/H₂O
(vi) aqueous H₂O₂, H⁺; (vii) a. Br(CH₂)nCO₂Et, Cs₂CO₃, DMF; b. NaOH, EtOH/THF, Δ; (viii) 5% Pd/C, EtOH/EtOAc;
(ix) HO(CH₂)₂O(CH₂)₂Cl or HO(CH₂)Cl, Cs₂CO₃, DMF; (x) (CF₃SO₂)₂O, Et₃N, CH₂Cl₂; (xi) HetB(OH)₂ or ArB(OH)₂, Pd(PPh₃)₄, Na₂CO₃, DME, Δ.

Scheme 7 describes additional synthetic transformations of naphthol VI that yield compounds active at the estrogen receptor. Reaction of VI with appropriately substituted aryl flourides (such as, 4-fluoronitrobenzene) and a base such as cesium carbonate or sodium hydride, provides the substituted naphthalene XXXIII. Nitroaryl intermediate XXXIII can be treated with a reducing agent such as $PtO_2$ to yield an aniline that can be subsequently acylated with a sulfonyl chloride to afford sulfonamide XXXIV (see Examples 6 and 8 below).

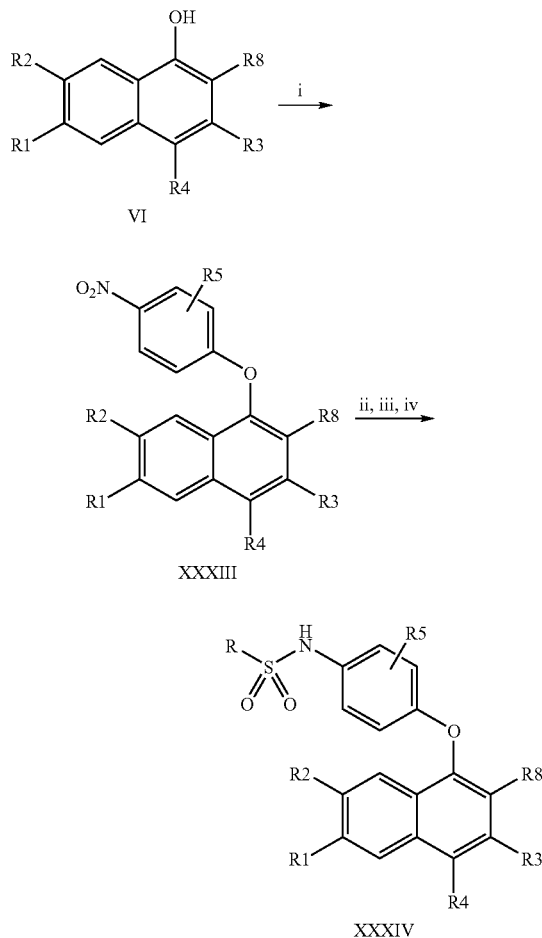

(i) 4-F-nitrobenzene, base; (ii) $H_2$, $PtO_2$, EtOH; (iii) $RSO_2Cl$, pyridine; (iv) $BBr_3$, $CH_2Cl_2$.

EXAMPLES

The following specific examples are included as illustrations and are not to be construed as limiting the scope of the present invention. For ease of reference the compounds are given reference numbers and referred to herein using this shorthand. The reference to any given compound should not be interpreted as the actual compound generated by any particular example, but rather as a general reference to a compound.

Example 1 (11)

Prepared Using Scheme 1

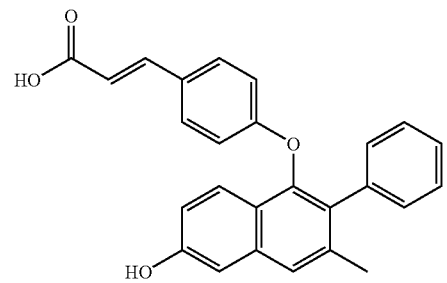

Step 1: 1-[3-(methyloxy)phenyl]-2-propanol (1)

To a cold solution (5° C.) of 1-[3-(methyloxy)phenyl]-2-propanone (75 g, 0.457 mol) in MeOH (500 mL) was added $NaBH_4$ (19 g, 0.502 mol) portion-wise over a period of 0.5 h. The resultant mixture was stirred at that temperature for 1 h. Reaction mixture was quenched with 1 N aqueous HCl (250 mL) and concentrated under reduced pressure to remove most of the methanol. The reaction mixture was extracted with EtOAc (3×150 mL). The combined organic layer was washed with water (1×100 mL), brine (1×100 mL), dried ($Na_2SO_4$) and concentrated under reduced pressure to afford the crude product. The reaction mixture was just passed through a pad of silica gel and washed with 1:1 hexanes:EtOAc to afford 75 g (99%) of the title compound. $^1$H NMR (400 MHz, $CDCl_3$): δ 7.24-7.20 (m, 1H), 6.80-6.75 (m, 3H), 4.02-3.97 (m, 1H), 3.79 (s, 3H), 2.78-2.63 (m, 2H), 1.25-1.19 (m, 3H).

Step 2: 1-methyl-2-[3-(methyloxy)phenyl]ethyl methanesulfonate (2)

To a cold solution (5° C.) of 1-[3-(methyloxy)phenyl]-2-propanol (1) (75 g, 0.45 mol) in $CH_2Cl_2$ (500 mL) were added $Et_3N$ (100 mL, 0.72 mol) and DMAP (2.75 g, 22.5 mmol). Methanesulfonic acid (52 mL, 0.675 mol) was added slowly (drop-wise) to the above reaction mixture at that temperature over a period of 40 min. The resultant mixture was stirred between 5° C. and 10° C. for 8 h under $N_2$. The reaction mixture was washed with $H_2O$ (3×150 mL), brine (1×100 mL), dried ($Na_2SO_4$) and concentrated under reduced pressure to afford the crude product which was passed through a pad of silica to afford 108 g (98%) of the title compound. $^1$H NMR (400 MHz, $CDCl_3$): δ 7.24 and 7.20 (dd, $J_1$=15.2 Hz, $J_2$=3.8 Hz, 1H), 6.81-6.76 (m, 3H), 4.87 (sextet, J=6.00 Hz, 1H), 3.77 (s, 3H), 2.96 and 2.92 (dd, $J_1$=14.0 Hz, $J_2$=8.0 Hz, 1H), 2.87 and 2.84 (dd, $J_1$=14.0 Hz, $J_2$=5.6, Hz, 1H), 2.54 (s, 3H), 1.44 (d, J=6.4 Hz, 3H).

Step 3: 1-(2-bromopropyl)-3-(methyloxy) benzene (3)

A round-bottomed flask was charged with 1-methyl-2-[3-(methyloxy)phenyl]ethyl methanesulfonate (2) (90 g, 0.368 mol), LiBr (80 g, 0.92 mol), and acetone (650 mL). The reaction mixture was refluxed for 24 h under $N_2$ and then cooled to room temperature. The reaction mixture was filtered and concentrated under reduced pressure to afford the crude product. The product was passed through a pad of silica gel to remove inorganic impurities. The product was distilled under reduced pressure (2-3 mm Hg) at 130-135° C. to afford ~85 g (100%) of the title compound. $^1$H NMR (400 MHz, CDCl$_3$): δ 7.25 (dd, J$_1$=8.00 Hz, J$_2$=8.00 Hz, 1H), 6.84-6.78 (m, 3H), 4.32 (sextet, J=4.00 Hz, 1H), 3.82 (s, 3H), 3.25 and 3.21 (dd, J$_1$=16.00 Hz, J$_2$=8.00 Hz, 1H), 3.07 and 3.04 (dd, J$_1$=16.00 Hz, J$_2$=8.00 Hz, 1H), 1.71 (d, J=8.00 Hz, 1H).

Step 4:
3-methyl-4-[3-(methyloxy)phenyl]-2-phenylbutanoic acid (4)

To a cold (−78° C.) solution of phenylacetic acid (7.08 g, 52 mmol) in anhydrous THF (300 mL) was added slowly n-BuLi (2.5 M solution in n-hexanes) over a period of 0.5 h. The 1-(2-bromopropyl)-3-(methyloxy)benzene (3) (18 g, 78.6 mmol) was added slowly and the reaction mixture stirred at −78° C. for 1 h and 23 h at room temperature. The reaction mixture was quenched with 1 N NaOH (200 mL) and the resulting mixture heated to 50° C. for 2 h. The reaction mixture was cooled to room temperature and washed with Et$_2$O (2×150 mL). The ethereal layer was washed with brine, dried (Na$_2$SO$_4$) and then concentrated to afford the excess 1-(2-bromopropyl)-3-(methyloxy)benzene. The aqueous phase was acidified with 20% aqueous HCl and then extracted with EtOAc (4×200 mL). The combined organic layer was washed with brine, dried (Na$_2$SO$_4$) and concentrated under reduced pressure to afford 13 g (88%, crude yield) of compound 4 as an oil. This crude product was taken on to the next step without further purification or characterization.

Step 5: 3-methyl-6-(methyloxy)-2-phenyl-3,4-dihydro-1(2H)-naphthalenone (5)

To a solution of 3-methyl-4-[3-(methyloxy)phenyl]-2-phenylbutanoic acid (4) (13 g, 45.7 mmol) in CH$_2$Cl$_2$ (300 mL) was added oxalyl chloride (12 mL, 137.1 mmol) at room temperature. The reaction mixture was stirred for 10 h and concentrated under reduced pressure to afford the crude acid chloride. The acid chloride was redissolved in CH$_2$Cl$_2$ (300 mL) and cooled to 5° C. Anhydrous aluminum chloride (9.2 g, 68.6 mmol) was added, portion-wise, over a period of 15 min. The resulting brown colored reaction mixture was stirred at 5° C. for 3 h under $N_2$. The reaction mixture was poured onto 2 N HCl (400 mL), stirred for 15 min and the layers were separated. The aqueous phase was further extracted with CH$_2$Cl$_2$ (3×200 mL). The combined organic solution was washed with sat. NaHCO$_3$ (1×150 mL), brine (1×100 mL), dried (Na$_2$SO$_4$) and then concentrated under reduced pressure to afford the crude product. The product was purified by SiO$_2$ flash column chromatography using hexanes:EtOAc (9:1 to 4:1) as an eluent to afford 5.62 g (46% over 3 steps) of the title compound. $^1$H NMR (400 MHz, CDCl$_3$): δ 8.03 (d, J$_1$=8.00 Hz, 1H), 7.35-7.20 (m, 3H), 7.12 (d, J=8.00 Hz, 1H), 6.86 and 6.84 (dd, J$_1$=12.0 Hz, J$_2$=4.00 Hz, 1H), 6.73 (br.s, 1H), 3.87 (s, 3H), 3.34 (d, J=12.0 Hz, 1H), 3.03 and 3.0 (dd, J$_1$=16.0 Hz, J$_2$=4.0 Hz, 1H), 2.85 and 2.81 (dd, J$_1$=16.0 Hz, J$_2$=8.0 Hz, 1H), 2.53 (m, 1H), 0.95 (d, J=4.0 Hz, 3H). 6.84-6.78 (m, 3H), 4.32 (sextet, J=4.0 Hz, 1H), 3.82 (s, 3H), 3.25 and 3.21 (dd, J$_1$=16.0 Hz, J$_2$=8.0 Hz, 1H), 3.07 and 3.04 (dd, J$_1$=16.0 Hz, J$_2$=8.0 Hz, 1H), 1.71 (d, J=8.00 Hz, 1H).

Step 6: 3-methyl-6-(methyloxy)-2-phenyl-1-naphthalenyl acetate (6)

A round-bottomed flask was charged with 3-methyl-6-(methyloxy)-2-phenyl-3,4-dihydro-1(2H)-naphthalenone (5) (3.8 g, 14.3 mmol), Isopropyl acetate (70 mL), and p-toluene sulfonic acid (1.4 g, 7.14 mmol). The reaction mixture was refluxed for 16 h under $N_2$. Reaction mixture was cooled to room temperature and DDQ (9.74 g, 43 mmol) was introduced to the reaction mixture and refluxed for an additional 3 h. Reaction mixture was concentrated under reduced pressure to afford the crude product. The product was purified by SiO$_2$ column chromatography using hexanes:EtOAc (19:1 to 9:1) as an eluent to afford 4.10 g (94%) of the title compound (6). $^1$H NMR (400 MHz, CDCl$_3$): δ 7.64 (d, J=12.0 Hz, 1H), 7.55 (br s, 1H), 7.43 and 7.39 (dd, J$_1$=16.0 Hz, J$_2$=8.0 Hz, 2H), 7.38 and 7.34 (m, 1H), 7.26-7.24 (m, 2H), 7.14-7.11 (m, 2H), 3.92 (s, 3H), 2.22 (s, 3H), 2.00 (s, 3H).

Step 7: 6-methoxy-3-methyl-2-phenyl-1-naphthol (7)

To a solution of 3-methyl-6-(methyloxy)-2-phenyl-1-naphthalenyl acetate (6) (4.00 g, 13.1 mmol) in THF and MeOH (200 mL, 1:1) was added sodium methoxide (26 mL, 0.5 M solution in MeOH) at room temperature. The reaction mixture was stirred for 3 h under $N_2$. The reaction mixture was concentrated under reduced pressure to afford the crude product, which was purified by SiO$_2$ column chromatography to afford 3.4 g (99%) of compound 7 as a white solid. $^1$H NMR (400 MHz, CDCl$_3$): δ 8.10 (d, J=8.0 Hz, 1H), 7.54 (dd, J$_1$=12.0 Hz, J$_2$=8.0 Hz, 2H), 7.45 (dd, J$_1$=8.0 Hz, J$_2$=8.0 Hz, 1H), 7.36 (d, J$_1$=4.0 Hz, 2H), 7.23 (s, 1H), 7.10 and 7.08 (dd, J$_1$=8.0 Hz, J$_2$=4.0 Hz, 1H), 7.05 (d, J$_1$=4.0 Hz, 1H), 5.21 (s, 1H), 3.93 (s, 3H), 2.18 (s, 3H).

Step 8: 4-[(6-methoxy-3-methyl-2-phenyl-1-naphthyl)oxy]benzaldehyde (8)

A round-bottomed flask was charged with 3-methyl-6-(methyloxy)-2-phenyl-1-naphthalenol (7) (2.5 g, 9.5 mmol), 4-fluorobenzaldehyde (1.22 mL, 11.4 mmol), Cs$_2$CO$_3$ (4.04 g, 12.4 mmol), and anhydrous DMF (25 mL) under $N_2$. The reaction mixture was refluxed for 3 h. Reaction mixture was cooled at room temperature and purified by SiO$_2$ column chromatography using hexanes:EtOAc (19:1 to 4:1) as an eluent to afford 3.41 g (98%) of the title compound as a white foam. $^1$H NMR (400 MHz, CDCl$_3$): δ 9.80 (s, 1H), 7.68 (d, J=9.2 Hz, 1H), 7.62 (d, J=8.4 Hz, 2H), 7.61 (d, J=5.2 Hz, 1H), 7.25 (d, J=7.6 Hz, 2H), 7.22 (d, J=5.2 Hz, 1H), 7.15 (d, J=2.4 Hz, 1H), 7.14 (d, J=1.6 Hz, 1H), 7.11 (s, 1H), 7.07 and 7.04 (dd, J$_1$=9.2 Hz, J$_2$=2.4 Hz, 1H), 6.71 (d, J=8.8 Hz, 2H), 3.94 (s, 3H), 2.26 (s, 3H). LCMS (ESI) m/z, 368.92 (M+H)$^+$.

Step 9: ethyl (2E)-3-(4-{[3-methyl-6-(methyloxy)-2-phenyl-1-naphthalenyl]oxy}phenyl)-2-propenoate (9)

To a cold (−78° C.) solution of triethyl phosphonoacetate (2.43 mL, 12.23 mmol) in anhydrous THF (100 mL) was added n-BuLi (5.2 mL, 13.04 mmol, 2.5 M solution in hexanes). The reaction mixture was stirred for 0.5 h under $N_2$. A solution of 4-{[3-methyl-6-(methyloxy)-2-phenyl-1-naphthalenyl]oxy}benzaldehyde (8) in THF (100 mL) was added to the above reaction mixture and stirred for 0.5 h at −78° C. The reaction mixture was allowed to warm to room temperature and then stirred for 3.5 h. Reaction mixture was quenched with 1 N HCl (100 mL) and then extracted with EtOAc. The combined organic layer was washed with brine, dried (Na$_2$SO$_4$) and then concentrated under reduced pressure to afford the crude product. The product was purified by SiO$_2$ column chromatography to afford 2.65 g (74%) of compound (9) as a white foam. IR (film) 2978, 1708, 1634, 1601, 1505, 1232, 1165 cm$^{-1}$. $^1$H NMR (400 MHz, CDCl$_3$): δ 7.71 (d, J=9.2 Hz, 1H), 7.57 (s, 1H), 7.54 (d, J=16.0 Hz, 1H), 7.27-7.22 (m, 6H), 7.15-7.11 (m, 3H), 7.05 and 7.03 (dd, J$_1$=9.1 Hz, J$_2$=2.4 Hz, 1H), 6.58 (d, J=8.8 Hz, 2H), 6.22 (d, J=16.0 Hz, 1H). 4.22 (q, J=7.2 Hz, 2H), 3.93 (s, 3H), 2.24 (s, 3H), 1.30 (t, J=7.2 Hz, 3H). $^{13}$C NMR (100 MHz, CDCl$_3$): δ 167.2, 161.0, 158.3, 147.1, 144.1, 136.4, 136.4, 135.5, 130.83, 129.6 (2C), 129.4 (2C), 127.0 (2C), 127.6, 126.9, 124.4, 124.2, 121.4, 118.5, 115.9, 115.9 (2C), 105.32, 60.3, 55.3, 21.24, 14.30. HRMS Calcd for C$_{29}$H$_{26}$O$_4$: 439.1909. Found: 439.1904.

Step 10: (2E)-3-(4-{[3-methyl-6-(methyloxy)-2-phenyl-1-naphthalenyl]oxy}phenyl)-2-propenoic acid (10)

Ethyl (2E)-3-(4-{[3-methyl-6-(methyloxy)-2-phenyl-1-naphthalenyl]oxy}phenyl)-2-propenoate (9) (2.20 g, 5.02 mmol) was dissolved in THF and EtOH (1:1, 50 mL). To this mixture was added 1 N NaOH (50 mL, excess) at room temperature and the stirred reaction heated to 70° C. for 0.5 h. After cooling to RT, the reaction mixture was acidified with 20% aqueous HCl, and then extracted with EtOAc. The organic layer was washed with brine, dried (Na$_2$SO$_4$), and concentrated under reduced pressure to afford the crude product. The product was purified by flash column chromatography with CHCl$_3$:MeOH (9:1 to 4:1) as an eluent to give 2.02 g (98%) of compound (10) as a white solid. $^1$H NMR (400 MHz, CDCl$_3$): δ 7.70 (d, J=8.0 Hz, 1H), 7.64 (d, J=16.0 Hz, 1H), 7.57 (s, 1H), 7.26 (dd, J$_1$=12.0 Hz, J$_2$=12.0 Hz, 4H), 7.22 (d, J=4.0 Hz, 1H), 7.14 (d, J=1.8 Hz, 2H), 7.12 (s, 1H), 7.06 and 7.04 (dd, J=12.0 Hz, J$_2$=6.8 Hz, 1H), 6.60 (d, J=8.0 Hz, 2H), 6.22 (d, J=16.0 Hz, 1H), 3.92 (s, 3H), 2.24 (s, 3H). LCMS (ESI) m/z 439.07 (M+H)$^+$.

Step 11: (2E)-3-{4-[(6-hydroxy-3-methyl-2-phenyl-1-naphthalenyl)oxy]phenyl}-2-propenoic acid (11)

To a cold (5° C.) solution of (2E)-3-(4-{[3-methyl-6-(methyloxy)-2-phenyl-1-naphthalenyl]oxy}phenyl)-2-propenoic acid (10) (1.10 g, 2.68 mmol) in CH$_2$Cl$_2$ (60 mL) was added BBr$_3$ (0.8 mL, 8 mmol) slowly. The reaction mixture was stirred between 5° C. and 20° C. for 1 h and poured into water (150 mL) slowly. The layers were separated and the aqueous layer was further extracted with EtOAc (3×150 mL). The combined organic layer was washed with brine (1×100 mL) dried (Na$_2$SO$_4$) and concentrated to afford the crude product. Purification by flash column chromatography on silica gel using CHCl$_3$:MeOH as an eluent, gave 0.88 g (83%) of the title compound as an off-white solid. IR (film): 30.58, 1682, 1632, 1599, 1504, 1227, 1165 cm$^{-1}$. $^1$H NMR (400 MHz, MeOH-d$_4$): δ 7.60 (d, J=8.8 Hz, 1H), 7.51 (s, 1H), 7.52 (d, J=16.0 Hz, 1H), 7.33 (d, J=8.8 Hz, 2H), 7.27-7.20 (m, 3H), 7.14-11 (m, 3H), 6.96 and 6.94 (dd, J$_1$=9.2 Hz, J$_2$=2.4 Hz, 1H), 6.57 (d, J=8.4 Hz, 2H), 6.75 (d, J=16.0 Hz, 1H), 2.19 (s, 3H). $^{13}$C NMR (100 MHz, MeOH-d$_4$): δ 169.5, 161.3, 156.1, 147.1, 144.78, 136.82, 136.3, 135.9, 130.3, 129.8, 129.5, 127.8, 126.83, 124.0, 123.9, 120.9, 118.1, 115.8, 115.7, 108.6, 20.32. HRMS Calcd for C$_{26}$H$_{20}$O$_4$: 397.1440. Found: 397.1439.

Example 2 (18)

Prepared Using Scheme 2

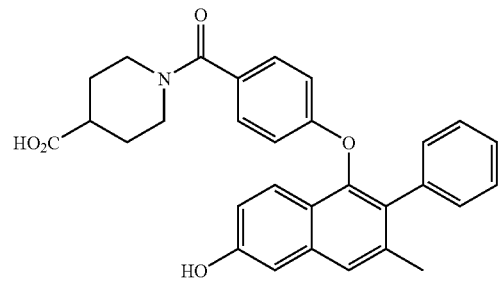

Step 1: 3-Methyl-6-(methyloxy)-3,4-dihydro-1(2H)-naphthalenone (12)

The Grignard, hydrolysis, and catalytic hydrogenation procedures described herein are analogous to those described for the preparation of similar compounds as reported by D. L. Vander Jagt et. al. (*J. Med. Chem.*, 1998, 41, 3879-3887), with modification. To a stirred ice-water cooled solution of ethyl-3-methyl-4-oxocrotonate (50.1 g, 0.352 mol) in anhydrous THF (200 mL) was slowly added dropwise 3-methoxyphenylmagnesium bromide (1 M in THF) (352 mL, 0.352 mol, 1.0 eq) between 0-10° C. under a N$_2$. The ice-water bath was removed and the reaction mixture was stirred at RT for 1.5 h. The reaction mixture was poured slowly into a mixture of ice (650 g) and 6 N HCl (170 mL) and then extracted with Et$_2$O. The organic phase was separated, washed with H$_2$O followed by brine, dried over MgSO$_4$, filtered, and the filtrate was concentrated to give 98.4 g of crude ethyl (2E)-4-hydroxy-3-methyl-4-[3-(methyloxy)phenyl]-2-butenoate. The crude intermediate ester was dissolved in EtOH (900 mL) and KOH (44.2 g, 0.788 mol) was added followed by H$_2$O (200 mL). The reaction mixture was heated at reflux for 3 h and allowed to cool at RT. The EtOH was removed in vacuo and the basic aqueous mixture was diluted with H$_2$O (500 mL) and then washed with Et$_2$O. The basic aqueous mixture was cooled in an ice-water bath and the pH was adjusted to ~2 (litmus paper) via the slow dropwise addition of 6 N HCl. The acidic aqueous mixture was extracted with EtOAc (2×). The organic extracts were combined, washed with H$_2$O followed by brine, dried over MgSO$_4$, filtered, and the filtrate was concentrated to give 74.14 g of crude (2E)-4-hydroxy-3-methyl-4-[3-(methyloxy)phenyl]-2-butenoic acid as a dark orange oil. The crude butenoic acid was reduced by catalytic hydrogenation in three batches as described below. To a parr hydrogenation bottle containing 10% palladium on carbon (1.0 g) was added a solution of the crude butenoic acid (24.13 g) in acetic acid (160 mL). The reaction mixture was hydrogenated at 25-30 psi over a 1 h period as the reaction mixture was warmed to 60° C. Once the temperature reached 60° C., the pressure of H$_2$ was increased to 55 psi for 7 h. The reaction mixture was allowed to stand overnight at RT between 40-45 psi. The reaction mixture was filtered through a pad of celite. The pad was washed with EtOH (2×) and the filtrate was concentrated to give 18.61 g of crude 3-methyl-4-[3-(methyloxy)phenyl]

butanoic acid as an oil. The remaining crude (2E)-4-hydroxy-3-methyl-4-[3-(methyloxy)phenyl]-2-butenoic acid was hydrogenated in a similar manner to give a total of 61.9 g of crude 3-methyl-4-[3-(methyloxy)phenyl]butanoic acid. To a solution of crude 3-methyl-4-[3-(methyloxy)phenyl]butanoic acid (18.6 g) in $CH_2Cl_2$ (400 mL) was slowly added oxalyl chloride (24 mL) with stirring at RT under $N_2$. The reaction mixture was allowed to stir at RT overnight. The reaction mixture was concentrated in vacuo to give crude 4-[3-(methyloxy)phenyl]butanoyl chloride as an oil. The crude acid chloride was dissolved in $CH_2Cl_2$ (400 mL) and the solution was cooled in an ice-water bath. To the cold acid chloride solution was added $AlCl_3$ (22.4 g, 0.168 mol) portionwise between 0-5° C. over a 1 h period. The reaction mixture was stirred for an additional 3 h and then slowly poured into 400 mL of cold 6 N HCl (cooled in an ice-water bath). The mixture was transferred to a separatory funnel and the organic phase was separated. The aqueous phase was extracted with $CH_2Cl_2$. The organic extracts were combined, carefully washed with saturated $NaHCO_3$ followed by brine, dried over $MgSO_4$, filtered, and the filtrate was concentrated to give 15.6 g of the crude title compound as a brown-orange oil. The remaining crude 3-methyl-4-[3-(methyloxy)phenyl]butanoic acid was treated in a similar manner to provide an additional 32.8 g of the crude title compound. The crude title compound (48.4 g) was purified by chromatography over $SiO_2$ with hexanes:EtOAc (9:1) to give 19.2 g (29% from 3-methoxyphenylmagnesium bromide) of the title compound 12 as a pale yellow solid. $^1H$ NMR (400 MHz; $CDCl_3$): δ 1.13 (d, J=6.2 Hz, 3H), 2.22-2.38 (m, 2H), 2.65 (m, 2H), 2.93 (m, 1H), 3.85 (s, 3H), 6.69 (d, J=2.4 Hz, 1H), 6.82 (dd, J=2.5 Hz, 8.7 Hz, 1H), 7.99 (d, J=8.6 Hz, 1H). HRMS (ESI) Calcd for $C_{12}H_{15}O_2$: 191.1072 $(M+H)^+$. Found: 191.1064.

Step 2: 2-Bromo-3-methyl-6-(methyloxy)-1-naphthalenol (13)

This compound was prepared according to procedures described for similar compounds (i.e. 2-bromo-1-naphthols) as reported by G. R. Green et. al. (*Tetrahedron*, (1998), 54, 9875-9894), with modification. To a stirred solution of 3-methyl-6-(methyloxy)-3,4-dihydro-1(2H)-naphthalenone (12) (4.80 g, 25.2 mmol) in $CHCl_3$ (130 mL) was slowly added dropwise a solution of $Br_2$ (8.12 g, 50.81 mmol, 2.02 eq) in $CHCl_3$ (60 mL) over a period of 4 h at RT under $N_2$. The reaction mixture was stirred overnight. The reaction mixture was concentrated to give 9.82 g of crude 2,2-dibromo-3-methyl-6-(methyloxy)-3,4-dihydro-1(2H)-naphthalenone as a dark brown-orange oil [$^1H$ NMR (400 MHz; $CDCl_3$): δ 1.49 (d, J=6.3 Hz, 3H), 2.56 (m, 1H), 2.91 (m, 2H), 3.86 (s, 3H), 6.67 (d, J=2.2 Hz, 1H), 6.90 (dd, J=2.5 Hz, 8.9 Hz, 1H), 8.14 (d, J=8.8 Hz, 1H)]. A solution of 2,2-dibromo-3-methyl-6-(methyloxy)-3,4-dihydro-1(2H)-naphthalenone (9.8 g, 25.2 mmol) in $CH_3CN$ (160 mL) was cooled in an ice-water bath to 0-5° C. and 1,8-diazabicyclo[5.4.0]undec-7-ene (DBU) (6 mL, 6.11 g, 39.6 mmol, 1.57 eq) was added slowly dropwise under $N_2$. The ice-water bath was removed and the reaction mixture was allowed to stir at RT under $N_2$ for 40 min. To the reaction mixture was added 1 N HCl (160 mL) and the aqueous mixture was extracted with $CH_2Cl_2$ (2x). The organic extracts were combined, washed with $H_2O$ (2x), dried over $MgSO_4$, filtered, and the filtrate was concentrated to give 6.8 g (100%) of the title compound 13 as a solid. $^1H$ NMR (400 MHz; $d_6$-DMSO-$d_6$): δ 2.43 (s, 3H), 3.83 (s, 3H), 7.07 (dd, J=2.2 Hz, 9.2 Hz, 1H), 7.16 (d, J=2.2 Hz, 1H), 7.29 (s, 1H), 8.04 (d, J=9.1 Hz, 1H), 9.66 (s, 1H).

Step 3: 2-bromo-6-methoxy-1-(methoxymethoxy)-3-methylnaphthalene (14)

To an ice-water cooled solution of 2-bromo-3-methyl-6-(methyloxy)-1-naphthalenol (13) (6.8 g, 25.5 mmol) in THF (70 mL) was slowly added N,N-diisopropylethylamine (7 mL, 5.19 g, 40 mmol, 1.58 eq) followed by the slow addition of chloromethylmethyl ether (3.2 mL, 3.39 g, 42.1 mmol, 1.65 eq) between 0-5° C. with stirring under $N_2$. The ice-water bath was removed and the reaction mixture was allowed to stir at RT overnight. The reaction mixture was diluted with $Et_2O$ (400 mL), washed with $H_2O$ (2x250 mL) followed by 1 N HCl (2x250 mL), dried over $MgSO_4$, filtered, and the filtrate was concentrated to give the crude product as a dark orange oil. The crude product was partially purified by flash chromatography over $SiO_2$ with hexanes:EtOAc (12:1 to 9:1) to give 6.32 g of the impure title compound. The impure compound was purified by flash chromatography over $SiO_2$ with hexanes:EtOAc (15:1) to give 4.8 g (60%) of compound 14 as a pale yellow oil. $^1H$ NMR (400 MHz; DMSO-$d_6$): δ 3.59 (s, 3H), 3.85 (s, 3H), 5.18 (s, 2H), 7.17 (dd, J=2.5 Hz, 9.3 Hz, 1H), 7.26 (d, J=2.4 Hz, 1H), 7.60 (s, 1H), 7.95 (d, J=9.2 Hz, 1H). $^1H$ NMR (400 MHz; $CDCl_3$): δ 2.54 (s, 3H), 3.72 (s, 3H), 3.90 (s, 3H), 5.24 (s, 2H), 7.02 (d, J=2.4 Hz, 1H), 7.12 (dd, J=2.6 Hz, 9.2 Hz, 1H), 7.42 (s, 1H), 8.03 (d, J=9.1 Hz, 1H). (Note: In DMSO-$d_6$, the 3-methyl group is coincident with the DMSO peak.) HRMS (EI+) calcd for $C_{14}H_{15}BrO_3$: 310.0205 $(M^{·+})$. Found: 310.0196.

Step 4: 3-Methyl-6-(methyloxy)-1-{[(methyloxy)methyl]oxy}-2-phenylnaphthalene (15)

2-Bromo-3-methyl-6-(methyloxy)-1-{[(methyloxy)methyl]oxy}naphthalene (14) (2.32 g, 7.46 mmol), phenylboronic acid (1.83 g, 15.0 mmol, 2.0 eq), tetrakistriphenylphosphine palladium (0) (0.869 g, 0.752 mmol, 10 mol %), 2 M sodium carbonate (65 mL), and ethylene glycol dimethyl ether (65 mL) were combined in a glass pressure bottle. The bottle was sealed with a screw cap and the reaction mixture was heated at 160° C. with stirring for 25 min. The reaction mixture was allowed to cool at RT. The reaction mixture was transferred to a separatory funnel and extracted with $Et_2O$. The organic phase was separated, dried over $MgSO_4$, filtered, and the filtrate was concentrated to give 4.96 g of the crude product. The crude product was combined with an additional 4.43 g of crude product (from a second Suzuki coupling reaction) and purified the crude product by chromatography over $SiO_2$ with hexanes:$CH_2Cl_2$ (2:3) to give 4.2 g (91%) of the title compound (15) as a yellow oil. $^1H$ NMR (400 MHz; DMSO-$d_6$): δ 2.13 (s, 3H), 2.98 (s, 3H), 3.86 (s, 3H), 4.64 (s, 2H), 7.13 (dd, J=2.4 Hz, 9.1 Hz, 1H), 7.25 (d, J=2.4 Hz, 1H), 7.29 (d, J=7.0 Hz, 2H), 7.36 (t, J=7.5 Hz, 1H), 7.45 (t, J=7.5 Hz, 2H), 7.51 (s, 1H), 7.94 (d, J=9.1 Hz, 1H).

Step 5: 6-Methoxy-3-methyl-2-phenyl-1-naphthol (7)

3-Methyl-6-(methyloxy)-1-{[(methyloxy)methyl]oxy}-2-phenylnaphthalene (15) (1.31 g, 4.25 mmol) was dissolved in HCl (4 N in 1,4-dioxane) (10 mL) and the solution was stirred at RT under $N_2$ for 30 min. The reaction mixture was concentrated to give 1.83 g of crude 3-methyl-6-(methyloxy)-2-phenyl-1-naphthalenol (7) as a gold-yellow oil. Compound (7) was previously characterized and used directly in the following reaction without additional purification.

Step 5: 4-{[3-Methyl-6-(methyloxy)-2-phenyl-1-naphthalenyl]oxy}benzaldehyde (8)

A solution of crude 3-methyl-6-(methyloxy)-2-phenyl-1-naphthalenol (7) (1.83 g) in DMF (8 mL) was slowly added dropwise to an ice-water cooled suspension of NaH (60% dispersion in oil) (0.179 g, 4.48 mmol) in DMF (8 mL) with stirring under $N_2$. The ice-water bath was removed and the reaction mixture was allowed to stir at RT for 10 min. To the reaction mixture was added a solution of 4-fluorobenzaldehyde (0.9 mL, 1.04 g, 8.39 mmol) in DMF (3 mL). The reaction mixture was heated at 70° C. for 18 h. The reaction mixture was partially concentrated and the crude product was partitioned between $CH_2Cl_2$ and $H_2O$. The organic phase was separated, dried over $MgSO_4$, filtered, and the filtrate was concentrated to give the crude title compound. The crude product was purified by flash chromatography over $SiO_2$ with hexanes:EtOAc (9:1) to give 1.04 g (66%) of compound (8) as a yellow amorphous solid. $^1$H NMR (400 MHz; DMSO-$d_6$): δ 2.19 (s, 3H), 3.88 (s, 3H), 6.78 (d, J=8.6 Hz, 2H), 7.09 (dd, J=2.6 Hz, 9.1 Hz, 1H), 7.19 (m, 2H), 7.24 (m, 1H), 7.30 (m, 2H), 7.38 (d, J=2.4 Hz, 1H), 7.53 (d, J=7.2 Hz, 1H), 7.70 (d, J=8.7 Hz, 2H), 7.75 (s, 1H), 9.78 (s, 1H). AP LRMS m/z 369 (M+H)$^+$.

Step 6: 4-{[3-Methyl-6-(methyloxy)-2-phenyl-1-naphthalenyl]oxy}benzoic acid (16)

To 4-{[3-methyl-6-(methyloxy)-2-phenyl-1-naphthalenyl]oxy}benzaldehyde (8) (0.565 g, 1.53 mmol) was added a 2:1 acetone:$H_2O$ solution (21 mL). The turbid solution was cooled in an ice-water bath and sulfamic acid (0.158 g, 1.63 mmol, 1.06 eq) was added portionwise over several minutes. The reaction mixture was stirred for 5 min and sodium chlorite (80% tech. Grade) (0.185 g, 1.64 mmol, 1.07 eq) was added portionwise. The reaction mixture was stirred for 30 min. The acetone was removed in vacuo and the reaction mixture was partitioned between $H_2O$ and $CH_2Cl_2$. The organic phase was separated and the aqueous phase was extracted with $CH_2Cl_2$. The organic extracts were combined, dried over $MgSO_4$, filtered, and the filtrate was concentrated to give the crude product. The crude product was purified by flash chromatography over $SiO_2$ with $CH_2Cl_2$:MeOH (94:6) to give 0.47 g (80%) of the compound 16 as a gold-yellow amorphous solid. $^1$H NMR (400 MHz; DMSO-$d_6$): δ 2.17 (s, 3H), 3.86 (s, 3H), 6.64 (d, J=8.7 Hz, 2H), 7.07 (dd, J=2.6 Hz, 9.2 Hz, 1H), 7.16 (m, 2H), 7.21-7.30 (m, 3H), 7.35 (d, J=2.4 Hz, 1H), 7.52 (d, J=9.1 Hz, 1H), 7.70 (m, 3H), 12.63 (br s, 1H). AP LRMS m/z 385 (M+H)$^+$.

Step 7: 1-[(4-{[3-Methyl-6-(methyloxy)-2-phenyl-1-naphthalenyl]oxy}phenyl)carbonyl]-4-piperidinecarboxylic acid (17)

To a suspension of 4-{[3-methyl-6-(methyloxy)-1-naphthalenyl]oxy}benzoic acid (16) (0.149 g, 0.388 mmol) in toluene (3 mL) was added oxalyl chloride (0.06 mL, 0.087 g, 0.687 mmol, 1.8 eq) followed by DMF (1 drop). The reaction mixture was stirred at RT under $N_2$ for 45 min. The reaction mixture was concentrated to give crude 4-{[3-methyl-6-(methyloxy)-2-phenyl-1-naphthalenyl]oxy}benzoyl chloride as a yellow oil. Isonipecotic acid (0.051 g, 0.39 mmol), triethylamine (0.12 mL, 0.087 g, 0.86 mmol) and $H_2O$ (2 mL) were combined and the solution was cooled in an ice-water bath under $N_2$. To the cold isonipecotic acid solution was slowly added dropwise a solution of 4-{[3-methyl-6-(methyloxy)-2-phenyl-1-naphthalenyl]oxy}benzoyl chloride in THF (2 mL) with stirring under $N_2$. The ice-water bath was removed and the reaction mixture was allowed to stir for 5 d. The pH of the reaction mixture was adjusted to ~1 (litmus paper) with 1 N HCl and the acidic reaction mixture was partitioned between EtOAc and $H_2O$. The organic phase was separated, washed with $H_2O$ (2×), dried over $MgSO_4$, filtered, and the filtrate was concentrated to give the crude title compound. The crude product was purified by flash chromatography over $SiO_2$ with $CH_2Cl_2$:MeOH (94:6) to give 0.133 g (69%) of compound 17 as an amorphous solid. $^1$H NMR (400 MHz; DMSO-$d_6$): δ 1.42 (m, 2H), 1.80 (m, 2H), 2.17 (s, 3H), 2.93 (br s, 2H), 3.87 (s, 3H), 6.59 (d, J=8.6 Hz, 2H), 7.09 (dd, J=2.5 Hz, 9.2 Hz, 1H), 7.15 (m, 4H), 7.25 (m, 3H), 7.35 (d, J=2.4 Hz, 1H), 7.61 (d, J=9.1 Hz, 1H), 7.70 (s, 1H), 12.25 (br s, 1H). AP LRMS m/z 494 (M-H)$^-$.

Step 8: 1-({4-[(6-Hydroxy-3-methyl-2-phenyl-1-naphthalenyl)oxy]phenyl}carbonyl)-4-piperidinecarboxylic acid (18)

To an ice-water cooled solution of 1-[(4-{[3-methyl-6-(methyloxy)-2-phenyl-1-naphthalenyl]oxy}phenyl)carbonyl]-4-piperidinecarboxylic acid (17) (0.13 g, 0.26 mmol) in $CH_2Cl_2$ (8 mL) was slowly added $BBr_3$ (1 M in $CH_2Cl_2$) (1.0 mL, 1 mmol, 3.8 eq) dropwise with stirring under $N_2$. The reaction mixture was stirred with cooling for 3.5 h. The reaction mixture was partitioned between $H_2O$ and $CH_2Cl_2$. The organic phase was separated, washed with brine, dried over $MgSO_4$, filtered, and the filtrate was concentrated to give 0.060 g of the crude product. The crude product was purified by reverse phase preparative HPLC with an $CH_3CN$:$H_2O$ gradient (50:50 to 100:0) with 0.05% TFA as modifier to give 0.019 g (15%) of the title compound (18) as a white solid. $^1$H NMR (400 MHz; $CD_3OD$): δ 1.60 (br s, 2H), 1.92 (br s, 2H), 2.18 (s, 3H), 2.59 (m, 1H), 3.06 (br s 2H), 3.65 (br s, 1H), 4.36 (br s, 1H), 6.60 (d, J=8.7 Hz, 2H), 6.96 (dd, J=2.4 Hz, 9.2 Hz, 1H), 7.13 (m, 5H), 7.22 (m, 3H), 7.51 (s, 1H), 7.64 (d, J=9.0 Hz, 1H). HRMS (ESI) Calcd for $C_{30}H_{28}NO_5$: 482.1967 (M+H)$^+$. Found: 482.1956.

Example 3 (19)

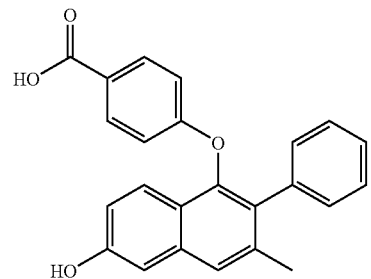

Step 1: 4-[(6-Hydroxy-3-methyl-2-phenyl-1-naphthalenyl)oxy]benzoic acid

To a round-bottomed flask containing 4-{[3-methyl-6-(methyloxy)-2-phenyl-1-naphthalenyl]oxy}benzaldehyde (8) (0.157 g, 0.426 mmol) was added 6 mL of an acetone:water (2:1) solution. The slightly turbid solution was cooled in an ice-water bath and sulfamic acid (0.097 g, 0.999 mmol, 2.3 eq) was added portionwise over five minutes. The reaction mixture was stirred for 5 min and sodium chlorite (80% tech.

Grade) (0.059 g, 0.52 mmol, 1.23 eq) was added portionwise. The reaction mixture was stirred for 40 min. The acetone was removed in vacuo and the crude product was partitioned between water and $CH_2Cl_2$. The organic phase was separated, washed with brine, dried over $MgSO_4$, filtered, and the filtrate was concentrated to give 0.155 g of crude 4-{[3-methyl-6-(methyloxy)-2-phenyl-1-naphthalenyl]oxy}benzoic acid as an amorphous solid. Flash chromatography over $SiO_2$ with $CH_2Cl_2$:MeOH (96:4) gave the impure 4-{[3-methyl-6-(methyloxy)-2-phenyl-1-naphthalenyl]oxy}benzoic acid. Attempted precipitation of the impurity from a solution of 4-{[3-methyl-6-(methyloxy)-2-phenyl-1-naphthalenyl]oxy}benzoic acid in MeOH had failed to purify the compound. Therefore, the impure 4-{[3-methyl-6-(methyloxy)-2-phenyl-1-naphthalenyl]oxy}benzoic acid (0.105 g) was dissolved in $CH_2Cl_2$ (6 mL) and the stirred solution was cooled in an ice-water bath. To the cold solution was slowly added $BBr_3$ (1 M in $CH_2Cl_2$) (0.82 mL, 0.82 mmol) and the reaction mixture was stirred under $N_2$ with cooling for 3 h. The reaction mixture was partitioned between $CH_2Cl_2$ and water. The organic phase was separated, washed with brine, dried over $MgSO_4$, filtered, and the filtrate was concentrated to give 0.115 g of the crude title compound. The crude title compound was purified by reverse phase preparative HPLC using an $CH_3CN:H_2O$ gradient (25:75 to 100:0) with 0.05% TFA as a modifier to give 0.013 g (8% from FN1, Step 5) of the title compound (19) as an off-white solid. $^1$H NMR (400 MHz; DMSO-$d_6$): δ 2.14 (s, 3H), 6.64 (d, J=8.8 Hz, 2H), 6.98 (dd, J=2.2 Hz, 8.9 Hz, 1H), 7.15 (m, 3H), 7.21 (m, 1H), 7.27 (m, 2H), 7.48 (d, J=9.1 Hz, 1H), 7.58 (s, 1H), 7.70 (d, J=8.8 Hz, 2H), 9.86 (s, 1H), 12.58 (br s, 1H). HRMS (ESI) Calcd for $C_{24}H_{17}O_4$: 369.1127 (M−H)$^-$. Found: 369.1148.

Example 4 (23)

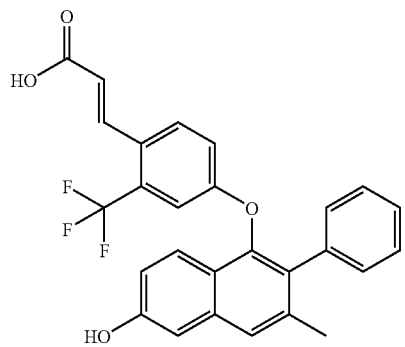

Step 1: 6-Methoxy-3-methyl-2-phenyl-1-naphthol (13)

6-methoxy-1-(methoxymethyl)-3-methyl-2-phenyl-naphthalene (15) (500 mg, 1.62 mmol, 1 equiv) was dissolved in 4 N HCl in dioxane (5 mL) and the mixture was stirred at RT for 1 h. The reaction was then concentrated to dryness to provide 7 (428 mg, 100%) as a tan oil. $^1$H NMR (400 MHz, DMSO-$d_6$): δ 8.59 (s, 1H), 8.04 (m, 1H), 7.38 (m, 3H), 7.21 (m, 4H), 7.03 (m, 1H), 3.84 (s, 3H), 2.06 (m, 3H). LRMS m/z 265.1 (M+H)$^+$.

Step 2: 4-[(6-hydroxy-3-methyl-2-phenyl-1-naphthalenyl)oxy]-2-(trifluoromethyl)benzaldehyde (20)

Compound 7 (215 mg, 0.81 mmol, 1 equiv) was dissolved in DMF (5 mL) and cooled to 0° C. under $N_2$. Sodium hydride, 60% dispersion (36 mg, 0.89 mmol, 1.1 equiv), followed by 4-fluoro-2-(trifluoromethyl)benzaldehyde (312 mg, 1.63 mmol, 2 equiv) were added and the entire reaction mixture was heated to 70° C. for 3 days. The mixture was then partitioned between EtOAc (50 mL) and $H_2O$ (50 mL). The organic layer was washed with saturated aqueous NaCl (100 mL), dried over $Na_2SO_4$, filtered and concentrated to dryness. The residue was purified by silica gel flash column chomatography (10% EtOAc in hexanes) to provide 20 (308 mg, 87%) as a clear oil. $^1$HNMR (400 MHz, DMSO-$d_6$): δ 10.01 (s, 1H), 7.89 (d, J=8.8 Hz, 1H), 7.78 (s, 1H), 7.60 (d, J=9.1 Hz, 1H), 7.39 (d, J=2.4 Hz, 1H), 7.32-7.10 (m, 7H), 6.95 (dd, J=8.6, 2.4 Hz, 1H), 3.88 (s, 3H), 2.20 (s, 3H). MS m/z 473.3 (M+H)$^+$.

Step 3: ethyl (2E)-3-[4-[(6-hydroxy-3-methyl-2-phenyl-1-naphthalenyl)oxy]-2-(trifluoromethyl)phenyl]-2-propenoate (21)

n-Butyl lithium (0.7 mL, 1.13 mmol, 1.6 equiv) was added to a solution of triethyl phosphonacetate (0.2 mL, 1.05 mmol, 1.5 equiv) in THF (15 mL) at −78° C. The mixture was stirred at −78° C. before the slow addition of a solution of compound 20 (308 mg, 0.71 mmol, 1 equiv) in THF (7 mL) via a dropping funnel. The entire reaction mixture was stirred at this temperature for 15 min and then at RT for 18 h. The reaction was quenched with 1 N HCl (5 mL) and extracted with EtOAc (100 mL). The organics were washed with saturated aqueous NaCl (50 mL), dried over $Na_2SO_4$, filtered and concentrated to dryness. The residue was purified by silica gel flash column chromatography (10% EtOAc in hexanes) to provide compound 21 (216 mg, 60%) as a clear oil. $^1$HNMR (400 MHz, DMSO-$d_6$): δ 7.85 (m, 1H), 7.75 (m, 1H), 7.66 (m, 1H), 7.59 (m, 1H), 7.36 (m, 1H), 7.32-7.21 (m, 3H), 7.17-7.10 (m, 3H), 6.96 (m, 1H), 6.80 (m, 1H), 6.54 (m, 1H), 4.15 (m, 2H), 3.87 (s, 3H), 2.19 (s, 3H), 1.21 (m, 3H). MS m/z 505.5 (M−H)$^-$.

Step 4: (2E)-3-[4-{[3-methyl-6-(methyloxy)-2-phenyl-1-naphthalenyl]oxy}-2-(trifluoromethyl)phenyl]-2-propenoic acid (23)

Compound 21 (216 mg, 0.43 mmol, 1 equiv) was dissolved in EtOH (5 mL) and THF (5 mL). 1 N NaOH (4.3 mL, 4.26 mmol, 10 equiv)) was added and the solution was refluxed for 1.5 h. The reaction was cooled to RT and then acidified to pH 2 with 1 N HCl. The product was extracted with EtOAc (100 mL) and the organic layer was washed with saturated aqueous NaCl (50 mL), dried over $Na_2SO_4$, filtered and concentrated to provide the title compound (22) (204 mg, 100%), as a pale yellow solid. $^1$HNMR (400 MHz, DMSO-$d_6$): δ 7.81 (m, 1H), 7.75 (s, 1H), 7.60 (m, 2H), 7.37 (m, 1H), 7.31-7.22 (m, 3H), 7.16 (m, 2H), 7.11 (m, 1H), 6.95 (m, 1H), 6.80 (m, 1H), 6.42 (m, 1H), 3.87 (s, 3H), 2.19 (s, 3H). MS m/z 477.5 (M−H)$^-$.

Step 5: (2E)-3-[4-[(6-hydroxy-3-methyl-2-phenyl-1-naphthalenyl)oxy]-2-(trifluoromethyl)phenyl]-2-propenoic acid (23)

Compound 22 (204 mg, 0.43 mmol, 1 equiv) was dissolved in $CH_2Cl_2$ (20 mL) and cooled to 0° C. under $N_2$. $BBr_3$ (0.2 mL, 2.15 mmol, 5 equiv) was added dropwise and the resulting solution was allowed to stir at 0° C. for 2 h. The reaction mixture was then poured into ice and the product extracted into EtOAc (250 mL). The organics were washed with saturated aqueous NaCl (100 mL), dried over $Na_2SO_4$, filtered and concentrated to dryness. The residue was purified by silica gel flash column chomatography (50% EtOAc in hexanes) to provide the title compound (23) (122 mg, 66%) as a yellow solid. $^1$HNMR (400 MHz, DMSO-$d_6$): δ 10.81 (s, 1H), 7.81 (m, 1H), 7.63 (m, 2H), 7.54 (m, 1H), 7.31-7.14 (m, 6H), 7.02 (m, 1H), 6.95 (m, 1H), 6.82 (m, 1H), 6.44 (m, 1H), 2.16 (s, 3H). MS m/z 463.3 (M−H)⁻.

Example 5 (27)

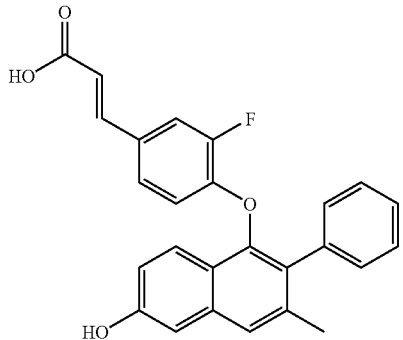

Step 1: 3-fluoro-4-{[3-methyl-6-(methyloxy)-2-phenyl-1-naphthalenyl]oxy}benzaldehyde (24)

Compound 7 (204 mg, 0.77 mmol, 1 equiv) was dissolved in DMF (5 mL) and cooled to 0° C. under $N_2$. Sodium hydride, 60% dispersion (34 mg, 0.85 mmol, 1.1 equiv), followed by 3,4-difluorobenzaldehyde (170 μL, 1.54 mmol, 2 equiv) were added and the entire reaction mixture was heated to 70° C. for 2 days. The mixture was then partitioned between EtOAc (50 mL) and $H_2O$ (50 mL). The organic layer was washed with saturated aqueous NaCl (100 mL), dried over $Na_2SO_4$, filtered and concentrated to dryness. The residue was purified by silica gel flash column chomatography (5% EtOAc in hexanes) to provide 24 (103 mg, 44%) as a clear oil. ¹HNMR (400 MHz, DMSO-$d_6$): δ 9.75 (s, 1H), 7.77 (s, 1H), 7.63 (m, 1H), 7.58 (d, J=9.2 Hz, 1H), 7.47 (m, 1H), 7.38 (m, 1H), 7.31-7.17 (m, 5H), 7.12 (dd, J=2.3, 8.9 Hz, 1H), 6.58 (t, J=7.3, 8.9 Hz, 1H), 3.87 (s, 3H), 2.19 (s, 3H). MS m/z 463.3 (M−H)⁻.

Step 2: ethyl (2E)-3-(3-fluoro-4-{[3-methyl-6-(methyloxy)-2-phenyl-1-naphthalenyl]oxy}phenyl)-2-propenoate (25)

n-Butyl lithium (960 μL, 1.54 mmol, 4.6 equiv) was added to a solution of triethyl phosphonoacetate (0.3 mL, 1.51 mmol, 4.5 equiv) in THF (8 mL) at −78° C. The mixture was stirred at −78° C. for 30 min before the slow addition of a solution of 24 (308 mg, 0.71 mmol, 1 equiv) in THF (4 mL) via a dropping funnel. The entire reaction mixture was stirred at this temperature for 15 min and then at RT for 18 h. The reaction was quenched with 1 N HCl (5 mL) and extracted with EtOAc (100 mL). The organics were washed with saturated aqueous NaCl (50 mL), dried over $Na_2SO_4$, filtered and concentrated to dryness. The residue was purified by silica gel flash column chomatography (10% EtOAc in hexanes) to provide 25 (130 mg, 85%) as a clear oil. ¹HNMR (400 MHz, DMSO-$d_6$): δ 7.74 (m, 1H), 7.65-7.56 (m, 2H), 7.46 (m, 1H), 7.37 (m, 1H), 7.32-7.18 (m, 6), 7.11 (m, 1H), 6.48 (m, 1H), 6.36 (m, 1H), 4.13 (m, 2H), 3.87 (s, 3H), 2.18 (s, 3H), 1.23 (m, 3H). MS m/z 457.4 (M+H)⁺.

Step 3: (2E)-3-(3-fluoro-4-{[3-methyl-6-(methyloxy)-2-phenyl-1-naphthalenyl]oxy}phenyl)-2-propenoic acid (26)

Compound 25 (130 mg, 0.29 mmol, 1 equiv) was dissolved in EtOH (5 mL) and THF (5 mL). A solution of 1 N NaOH (2.9 mL, 2.85 mmol, 10 equiv)) was added and the solution refluxed for 1.5 h. The reaction was cooled to RT and then acidified to pH 2 with 1 N HCl. The product was extracted with EtOAc (100 mL) and the organic layer was washed with saturated aqueous NaCl (50 mL), dried over $Na_2SO_4$, filtered and concentrated to provide the title compound (26) (204 mg, 100%), as a pale yellow solid. ¹HNMR (400 MHz, DMSO-$d_6$): δ 7.74 (s, 1H), 7.58 (m, 2), 7.38 (m, 2H), 7.32-7.16 (m, 6H), 7.11 (m, 1H), 6.36 (m, 2H), 3.87 (s, 3H), 2.18 (s, 3H). LRMS m/z 429.4 (M+H)⁺.

Step 4: (2E)-3-{3-fluoro-4-[(6-hydroxy-3-methyl-2-phenyl-1-naphthalenyl)oxy]phenyl}-2-propenoic acid (27)

Compound 26 (122 mg, 0.29 mmol, 1 equiv) was dissolved in $CH_2Cl_2$ (25 mL) and cooled to 0° C. under $N_2$. $BBr_3$ (135 μL, 1.42 mmol, 5 equiv) was added dropwise and the resulting solution was allowed to stir at 0° C. for 3 h. The reaction mixture was then poured into ice and the product extracted into EtOAc (250 mL). The organics were washed with saturated aqueous NaCl (100 mL), dried over $Na_2SO_4$, filtered and concentrated to dryness. The residue was purified by silica gel flash column chromatography (50% EtOAc in hexanes) to provide the title compound (27) (122 mg, 66%) as a yellow solid. ¹HNMR (400 MHz, DMSO-$d_6$): δ 9.89 (s, 1H), 7.61-7.51 (m, 3H), 7.39 (m, 1H), 7.31-7.15 (m, 7H), 7.01 (m, 1H), 6.38 (m, 2H), 2.15 (s, 3H). MS m/z 413.4 (M−H)⁻.

Example 6 (32)

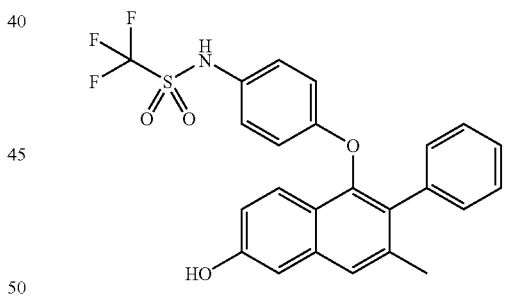

Step 1: 3-methyl-6-(methyloxy)-1-[(4-nitrophenyl)oxy]-2-phenylnaphthalene (28)

Compound 7 (428 mg, 1.62 mmol, 1 equiv) was dissolved in DMF (5 mL) and cooled to 0° C. under $N_2$. Sodium hydride, 60% dispersion (71 mg, 1.78 mmol, 1.1 equiv), followed by 1-fluoro-4-nitrobenzene (457 mg, 3.24 mmol, 2 equiv) were added and the entire reaction mixture was heated to 70° C. for 18 h. The mixture was then partitioned between EtOAc (50 mL) and $H_2O$ (50 mL). The organic layer was washed with saturated aqueous NaCl (100 mL), dried over $Na_2SO_4$, filtered and concentrated to dryness. The residue was purified by silica gel flash column chomatography (5% EtOAc in hexanes) to provide 28 (490 mg, 78%) as a clear oil. ¹HNMR (400 MHz, DMSO-$d_6$): δ 8.03 (m, 2H), 7.76 (s, 1H), 7.53 (m, 1H), 7.38-7.08 (m, 7H), 6.78 (m, 2H), 3.87 (s, 3H), 2.18 (s, 3H). MS m/z 473.3 (M+H)+.

Step 2: 4-{[3-methyl-6-(methyloxy)-2-phenyl-1-naphthalenyl]oxy}aniline (29)

PtO₂ (10 mg) was added to a solution of 28 (490 mg, 1.27 mmol, 1 equiv) in EtOH (5 mL). The reaction mixture was stirred under an atmosphere of H₂ (50 psi) for 1.5 h. The mixture was then filtered thru a pad of celite and concentration down to provide compound 29 (452 mg, 100%) as a clear oil. ¹HNMR (400 MHz, DMSO-d₆): δ 7.61 (m, 2H), 7.32-7.23 (m, 4H), 7.16 (m, 2H), 7.02 (m, 1H), 6.32-6.26 (m, 4H), 5.74 (br s, 2H), 3.85 (s, 3H), 2.14 (s, 3H). MS m/z 356.2 (M+H)+.

Step 3: 1,1,1-trifluoro-N-(4-{[3-methyl-6-(methyloxy)-2-phenyl-1-naphthalenyl]oxy}phenyl)-N-[(trifluoromethyl)sulfonyl]methanesulfonamide (30)

Triethylamine (55 μL, 0.40 mmol, 2 equiv) was added to a solution of 29 (70 mg, 0.20 mmol, 1 equiv) in CH₂Cl₂ (5 mL) at 0° C. After 10 min, trifluoromethanesulfonic anhydride (37 μL, 0.22 mmol, 1.1 equiv) was added and the reaction was stirred at 0° C. for 30 min. The reaction mixture was concentrated to dryness and the residue purified by silica gel flash column chomatography (10% EtOAc in hexanes) to afford the title compound (30) (94 mg, 78%) as a yellow oil. ¹HNMR (400 MHz, DMSO-d₆): δ 7.74 (m, 1H), 7.66 (m, 1H), 7.38 (m, 3H), 7.22 (m, 3H), 7.14-7.08 (m, 3H), 6.70 (m, 2H), 3.88 (s, 3H), 2.16 (s, 3H). MS m/z 618.1 (M−H)−.

Step 4: 1,1,1-trifluoro-N-(4-{[3-methyl-6-(methyloxy)-2-phenyl-1-naphthalenyl]oxy}phenyl)methanesulfonamide (31)

1 N Sodium Hydroxide (2 mL) was added to a solution of 30 (94 mg, 0.15 mmol, 1 equiv) in CH₂Cl₂ (2 mL) and the reaction mixture was stirred at RT for 3 days. The reaction was then acidified to pH 2 with 1 N HCl and the product extracted into CH₂Cl₂ (100 mL). The organic layer was washed with saturated aqueous NaHCO₃ (2×50 mL), dried over MgSO₄, filtered and concentrated to dryness. The residue was purified by silica gel flash column chomatography (20% EtOAc in hexanes) to provide 31 (47 mg, 64%) as a yellow oil. ¹HNMR (400 MHz, DMSO-d₆): δ 11.52 (br s, 1H), 7.69 (m, 1H), 7.57 (m, 1H), 7.34-7.21 (m, 4H), 7.15 (m, 2H), 7.07 (m, 1H), 6.99 (m, 2H), 6.59 (m, 2H), 3.86 (s, 3H), 2.16 (s, 3H). MS m/z 486.1 (M−H)−.

Step 5: 1,1,1-trifluoro-N-{4-[(6-hydroxy-3-methyl-2-phenyl-1-naphthalenyl)oxy]phenyl}methanesulfonamide (32)

Compound 31 (47 mg, 0.10 mmol, 1 equiv) was dissolved in CH₂Cl₂ (5 mL) and cooled to 0° C. under N₂. BBr₃ (46 μL, 0.49 mmol, 5 equiv) was added dropwise and the resulting solution was allowed to stir at 0° C. for 4 h. The reaction mixture was then poured into ice and product extracted into EtOAc (250 mL). The organics were washed with saturated aqueous NaCl (100 mL), dried over Na₂SO₄, filtered and concentrated to dryness. The residue was purified by silica gel flash column chomatography (1:1 EtOAc:hexanes) to provide the title compound (32) (30 mg, 66%) as a yellow solid. ¹HNMR (400 MHz, DMSO-d₆): δ 11.53 (br s, 1H), 10.69

(br s, 1H), 7.88 (m, 1H), 7.60 (m, 1H), 7.27-7.14 (m, 7H), 6.98 (m, 2H), 6.59 (m, 2H), 2.20 (s, 3H). MS m/z 472.3 (M−H)−.

Example 7 (36)

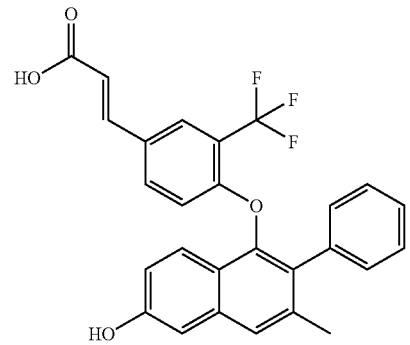

Step 1: 4-{[3-Methyl-6-(methyloxy)-2-phenyl-1-naphthalenyl]oxy}-3-(trifluoromethyl)benzaldehyde (33)

Compound 7 (215 mg, 0.81 mmol, 1 equiv) was dissolved in DMF (5 mL) and cooled to 0° C. under N₂. Sodium hydride, 60% dispersion (36 mg, 0.89 mmol, 1.1 equiv), followed by 4-fluoro-3-(trifluoromethyl)benzaldehyde (311 mg, 1.62 mmol, 2 equiv) were added and the entire reaction mixture was heated to 70° C. for 3 days. The mixture was then partitioned between EtOAc (50 mL) and H₂O (50 mL). The organic layer was washed with saturated aqueous NaCl (100 mL), dried over Na₂SO₄, filtered and concentrated to dryness. The residue was purified by silica gel flash column chromatography (10% EtOAc in hexanes) to provide compound 33 (216 mg, 61%) as a clear oil. ¹HNMR (400 MHz, DMSO-d₆): δ 9.84 (s, 1H), 8.10 (m, 1H), 7.87 (m, 1H), 7.81 (s, 1H), 7.48-7.13 (m, 8H), 6.64 (m, 1H), 3.88 (s, 3H), 2.22 (s, 3H). MS m/z 437.4 (M+H)+.

Step 2: Ethyl (2E)-3-[4-{[3-methyl-6-(methyloxy)-2-phenyl-1-naphthalenyl]oxy}-3-(trifluoromethyl)phenyl]-2-propenoate (24)

n-Butyl lithium (0.5 mL, 0.79 mmol, 1.6 equiv) was added to a solution of triethyl phosphonacetate (0.15 mL, 0.742 mmol, 1.5 equiv) in THF (10 mL) at −78° C. The mixture was stirred at −78° C. before the slow addition of a solution of 33 (216 mg, 0.5 mmol, 1 equiv) in THF (5 mL) via a dropping funnel. The entire reaction mixture was stirred at this temperature for 15 min and then at RT for 18 h. The reaction was quenched with 1 N HCl (5 mL) and extracted with EtOAc (100 mL). The organics were washed with saturated aqueous NaCl (50 mL), dried over Na₂SO₄, filtered and concentrated to dryness. The residue was purified by silica gel flash column chromatography (10% EtOAc in hexanes) to provide 34 (90 mg, 36%) as a clear oil. ¹HNMR (400 MHz, DMSO-d₆): δ 7.93 (m, 1H), 7.78 (m, 1H), 7.70 (m, 1H), 7.56 (m, 1H), 7.46 (m, 1H), 7.39-7.10 (m, 7H), 6.53 (m, 1H), 6.40 (m, 1H), 4.13 (m, 2H), 3.87 (s, 3H), 3.30 (s, 3H), 2.20 (s, 3H), 1.20 (m, 3H). MS m/z 507.42 (M+H)+.

Step 3: (2E)-3-[4-{[3-methyl-6-(methyloxy)-2-phenyl-1-naphthalenyl]oxy}-3-(trifluoromethyl)phenyl]-2-propenoic acid (35)

Compound 34 (90 mg, 0.18 mmol, 1 equiv) was dissolved in EtOH (5 mL) and THF (5 mL). 1 M aqueous NaOH (1.8 mL, 1.8 mmol, 10 equiv)) was added and the solution was refluxed for 1.5 h. The reaction was cooled to RT and then acidified to pH 2 with 1 N HCl. The product was extracted with EtOAc (100 mL) and the organic layer was washed with saturated aqueous NaCl (50 mL), dried over $Na_2SO_4$, filtered and concentrated to provide the title compound (35) (85 mg, 100%), as a pale yellow solid. $^1$HNMR (400 MHz, DMSO-$d_6$): δ 7.88 (m, 1H), 7.78 (s, 1H), 7.67 (m, 1H), 7.52-7.11 (m, 9H), 6.44-6.40 (m, 2H), 3.87 (s, 3H), 2.21 (s, 3H). MS m/z 477.03 (M−H)⁻.

Step 4: (2E)-3-[4-[(6-hydroxy-3-methyl-2-phenyl-1-naphthalenyl)oxy]-3-(trifluoromethyl)phenyl]-2-propenoic acid (36)

Compound 35 (85 mg, 0.18 mmol, 1 equiv) was dissolved in $CH_2Cl_2$ (10 mL) and cooled to 0° C. under $N_2$. $BBr_3$ (84 μL, 0.89 mmol, 5 equiv) was added dropwise and the resulting solution was allowed to stir at 0° C. for 2 h. The reaction mixture was then poured into ice and the product extracted into EtOAc (250 mL). The organics were washed with saturated aqueous NaCl (100 mL), dried over $Na_2SO_4$, filtered and concentrated to dryness. The residue was purified by silica gel flash column chromatography (50% EtOAc in hexanes) to provide the title compound (36) (44 mg, 53%) as a yellow solid. $^1$HNMR (400 MHz, DMSO-$d_6$): δ 12.30 (s, 1H), 7.87 (m, 1H), 7.69-7.65 (m, 2H), 7.51-7.01 (m, 9H), 6.43-6.40 (m, 2H), 2.17 (s, 3H). MS m/z 463.5 (M−H)⁻.

Example 8 (40)

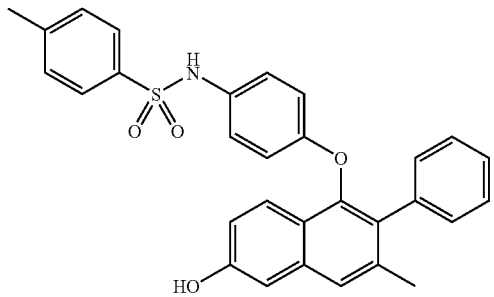

Step 1: 3-methyl-6-(methyloxy)-1-[(4-nitrophenyl)oxy]-2-phenylnaphthalene (37)

Compound 7 (428 mg, 1.62 mmol, 1 equiv) was dissolved in DMF (5 mL) and cooled to 0° C. under $N_2$. Sodium hydride, 60% dispersion (71 mg, 1.78 mmol, 1.1 equiv), followed by 1-fluoro-4-nitrobenzene (457 mg, 3.24 mmol, 2 equiv) were added and the entire reaction mixture was heated to 70° C. for 18 h. The mixture was then partitioned between EtOAc (50 mL) and $H_2O$ (50 mL). The organic layer was washed with saturated aqueous NaCl (100 mL), dried over $Na_2SO_4$, filtered and concentrated to dryness. The residue was purified by silica gel flash column chromatography (5% EtOAc in hexanes) to provide 37 (490 mg, 78%) as a clear oil. $^1$HNMR (400 MHz, DMSO-$d_6$): δ 8.03 (m, 2H), 7.76 (s, 1H), 7.53 (m, 1H), 7.38-7.08 (m, 7H), 6.78 (m, 2H), 3.87 (s, 3H), 2.18 (s, 3H). MS m/z 473.3 (M+H)⁺.

Step 2: 4-{[3-methyl-6-(methyloxy)-2-phenyl-1-naphthalenyl]oxy}aniline (38)

$PtO_2$ (10 mg) was added to a solution of 37 (490 mg, 1.27 mmol, 1 equiv) in EtOH (5 mL). The reaction mixture was stirred under an atmosphere of $H_2$ (50 psi) for 1.5 h. The mixture was then filtered thru a pad of celite and concentration down to provide 38 (452 mg, 100%) as a clear oil. $^1$HNMR (400 MHz, DMSO-$d_6$): δ 7.61 (m, 2H), 7.32-7.23 (m, 4H), 7.16 (m, 2H), 7.02 (m, 1H), 6.32-6.26 (m, 4H), 5.74 (br s, 2H), 3.85 (s, 3H), 2.14 (s, 3H). MS m/z 356.2 (M+H)⁺.

Step 3: 4-methyl-A-(4-{[3-methyl-6-(methyloxy)-2-phenyl-1-naphthalenyl]oxy}phenyl)benzenesulfonamide (39)

Pyridine (82 μL, 1.02 mmol, 3 equiv) was added to a solution of 38 (120 mg, 0.34 mmol, 1 equiv) in $CH_2Cl_2$ (5 mL) at RT. After 10 min, p-toluenesulfonyl chloride (130 mg, 0.68 mmol, 2 equiv) was added and the reaction was stirred at RT for 1 h. The reaction mixture was diluted with $CH_2Cl_2$ (50 mL) and washed with saturated aqueous $NaHCO_3$ (100 mL). The organic layer was dried over $MgSO_4$, filtered, concentrated and the residue purified by silica gel flash column chromatography (20% EtOAc in hexanes) to provide 39 (121 mg, 70%) as a yellow oil. $^1$HNMR (400 MHz, DMSO-$d_6$): δ 9.76 (s, 1H), 7.65 (m, 1H), 7.52-7.45 (m, 3H), 7.31-7.22 (m, 6H), 7.11-7.02 (m, 3H), 6.76 (m, 2H), 6.42 (m, 2H), 3.85 (s, 3H), 2.33 (s, 3H), 2.14 (s, 3H). MS m/z 510.64 (M+H)⁺.

Step 4: N-{4-[(6-hydroxy-3-methyl-2-phenyl-1-naphthalenyl)oxy]phenyl}-4-methylbenzenesulfonamide (40)

Compound 39 (121 mg, 0.24 mmol, 1 equiv) was dissolved in $CH_2Cl_2$ (5 mL) and cooled to 0° C. under $N_2$. $BBr_3$ (112 μL, 1.19 mmol, 5 equiv) was added dropwise and the resulting solution was allowed to stir at 0° C. for 4 h. The reaction mixture was then poured into ice and product extracted into EtOAc (250 mL). The organics were washed with saturated aqueous NaCl (100 mL), dried over $Na_2SO_4$, filtered and concentrated to dryness. The residue was purified by reverse phase HPLC (0 to 100% $CH_3CN$ in water w/0.1% TFA) to provide the title compound (40) (35 mg, 30%) as a yellow solid. $^1$HNMR (400 MHz, DMSO-$d_6$): δ 9.81 (s, 1H), 9.74 (s, 1H), 7.51-7.44 (m, 4H), 7.29-7.21 (m, 5H), 7.09-7.06 (m, 3H), 6.95-6.92 (m, 1H), 6.75 (m, 2H), 6.41 (m, 2H), 2.32 (s, 3H), 2.10 (s, 3H). MS m/z 494.4 (M−H)⁻.

Example 9 (43)

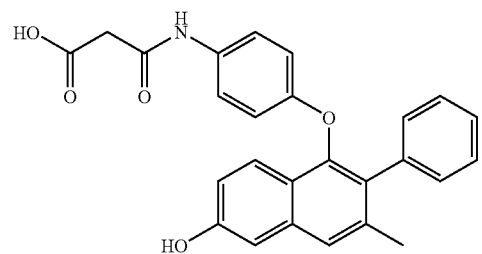

Step 1: methyl 3-[(4-{[3-methyl-6-(methyloxy)-2-phenyl-1-naphthalenyl]oxy}phenyl)amino]-3-oxopropanoate (41)

N-ethyldiisopropylamine (147 μL, 0.84 mmol, 3 equiv) was added to a solution of 38 (100 mg, 0.28 mmol, 1 equiv) in CH$_2$Cl$_2$ (5 mL) at 0° C. After 10 min, methyl 3-chloro-3-oxopropionate (60 μL, 0.56 mmol, 2 equiv) was added and the reaction was stirred at 0° C. for 3 h. The reaction mixture was diluted with CH$_2$Cl$_2$ (50 mL) and washed with saturated aqueous NaHCO$_3$ (100 mL). The organic layer was dried over MgSO$_4$, filtered, concentrated and the residue purified by silica gel flash column chromatography (30% EtOAc:hexanes) to provide 41 (87 mg, 68%) as a yellow oil. $^1$HNMR (400 MHz, DMSO-d$_6$): δ 10.00 (s, 1H), 7.68 (s, 1H), 7.56 (m, 1H), 7.33-7.17 (m, 8H), 7.06-7.03 (m, 1H), 6.53 (m, 2H), 3.86 (s, 3H), 3.61 (s, 3H), 3.37 (s, 2H), 2.17 (s, 3H). MS m/z 455.87 (M+H)$^+$.

Step 2: 3-[(4-{[3-methyl-6-(methyloxy)-2-phenyl-1-naphthalenyl]oxy}phenyl)amino]-3-oxopropanoic acid (42)

Compound 11 (87 mg, 0.2 mmol, 1 equiv) was dissolved in THF (4 mL). 1 M aqueous NaOH (1.0 mL, 1.0 mmol, 5 equiv)) was added and the solution was stirred at RT for 1.5 h. The reaction was acidified to pH 2 with 1 N HCl. The product was extracted with EtOAc (100 mL) and the organic layer was washed with saturated aqueous NaCl (50 mL), dried over Na$_2$SO$_4$, filtered and concentrated to provide the title compound (42) (75 mg, 85%), as a pale yellow solid. $^1$HNMR (400 MHz, DMSO-d$_6$): δ 9.94 (s, 1H), 7.67 (s, 1H), 7.55 (s, 1H), 7.32-7.16 (m, 9H), 7.06-7.03 (m, 1H), 6.67-6.51 (m, 2H), 3.85 (s, 3H), 2.48 (m, 2H), 2.16 (s, 3H). MS m/z 442.50 (M−H)$^-$.

Step 3: 3-({4-[(6-hydroxy-3-methyl-2-phenyl-1-naphthalenyl)oxy]phenyl}amino)-3-oxopropanoic acid (43)

Compound 42 (75 mg, 0.17 mmol, 1 equiv) was dissolved in CH$_2$Cl$_2$ (5 mL) and cooled to 0° C. under N$_2$. BBr$_3$ (80 μL, 0.85 mmol, 5 equiv) was added dropwise and the resulting solution was allowed to stir at 0° C. for 2 h. The reaction mixture was then poured into ice and product extracted into EtOAc (250 mL). The organics were washed with saturated aqueous NaCl (100 mL), dried over Na$_2$SO$_4$, filtered and concentrated to dryness. The residue was purified by reverse phase HPLC (0 to 100% CH$_3$CN in water w/0.1% TFA) to provide the title compound (43) (22 mg, 30%) as a tan solid. $^1$HNMR (400 MHz, DMSO-d$_6$): δ 10.66 (br s, 1H) 10.36 (br s, 1H), 7.87 (s, 1H), 7.57 (m, 1H), 7.32-7.15 (m, 9H), 6.56 (m, 2H), 2.52 (s, 2H), 2.21 (s, 3H). MS m/z 428.5 (M+H)$^+$.

Example 10 (50)

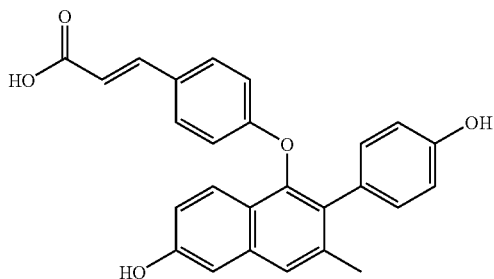

Step 1: 3-Methyl-6-(methyloxy)-1-{[(methyloxy)methyl]oxy}-2-[4-(methyloxy)phenyl] naphthalene (44)

Suzuki coupling of 2-bromo-3-methyl-6-(methyloxy)-1{[(methyloxy)methyl]oxy}naphthalene (14) (0.35 g, 1.12 mmol) with 4-methoxyphenyl boronic acid (0.34 g, 2.24 mmol) in the presence of Pd(PPh$_3$)$_4$ in DME using a sealed tube at 160° C. gave 0.41 g (~100%) of compound 44 as an off-white solid. $^1$H NMR (400 MHz, CDCl$_3$): δ 2.22 (s, 3H), 3.16 (s, 3H), 3.86 (s, 3H), 3.92 (s, 3H), 4.72 (s, 2H), 6.98 (d, J=8.7 Hz, 2H), 7.07 (d, J=2.4 Hz, 1H), 7.10 (dd, J$_1$=9.1 Hz, J$_2$=2.5 Hz, 1H), 7.26 (d, J=8.6 Hz, 2H), 7.42 (s, 1H), 8.04 (d, J=9.1 Hz, 1H).

Step 2: 3-Methyl-6-(methyloxy)-2-[4-(methyloxy) phenyl]-1-naphthalenol (45)

As described for Example 2 (Step 5), treatment of 3-Methyl-6-(methyloxy)-1-{[(methyloxy)methyl]oxy}-2-[4-(methyloxy)phenyl]naphthalene (44) (0.41 g, 1.21 mmol) with 4 M HCl in dioxane at room temperature yielded 0.30 g (89%) of the title compound (45) as a light yellow solid. $^1$H NMR (400 MHz, CDCl$_3$): δ 2.16 (s, 3H), 3.88 (s, 3H), 3.92 (s, 3H), 5.23 (s, 1H), 7.02-7.10 (m, 4H), 7.20 (s, 1H), 7.26 (d, J=8.6 Hz, 2H), 8.07 (d, J=9.2 Hz, 1H). LCMS (APCI): m/z 295 (M+H)$^+$, m/z 291 (M−H)$^-$.

Step 3: 4-({3-Methyl-6-(methyloxy)-2-[4-(methyloxy)phenyl]-1-naphthalenyl}oxy)benzaldehyde (46)

3-Methyl-6-(methyloxy)-2-[4-(methyloxy)phenyl]-1-naphthalenol (45) (0.30 g, 1.00 mmol) was treated with NaH in DMF followed by addition of 4-fluorobenzaldehyde to give 0.32 g (81%) of the title compound (46) as a light yellow foam. $^1$H NMR (400 MHz, CDCl$_3$): δ 2.26 (s, 3H), 3.76 (s, 3H), 3.93 (s, 3H), 6.71 (d, J=8.8 Hz, 2H), 6.79 (d, J=8.7 Hz, 2H), 7.02-7.07 (m, 3H), 7.14 (d, J=2.6 Hz, 1H), 7.58 (s, 1H), 7.63 (d, J=8.8 Hz, 2H), 7.66 (d, J=9.1 Hz, 1H), 9.80 (s, 1H). LCMS (APCI): m/z 399 (M+H)$^+$.

Step 4: Ethyl (2E)-3-[4-({3-methyl-6-(methyloxy)-2-[4-(methyloxy)phenyl]-1-naphthalenyl}oxy)phenyl]-2-propenoate (47)

Using the procedure described in Example 1 (Step 9), 4-({3-Methyl-6-(methyloxy)-2-[4-(methyloxy)phenyl]-1-naphthalenyl}oxy)benzaldehyde (46) (0.32 g, 0.81 mmol) was treated with a mixture of triethylphosphonoacetate and nBuLi to give 0.33 g (86%) of the title compound (47) as a light yellow foam. $^1$H NMR (400 MHz, CDCl$_3$): δ 1.30 (t, J=7.1 Hz, 3H), 2.24 (s, 3H), 3.77 (s, 3H), 3.92 (s, 3H), 4.22 (q, J=7.1 Hz, 2H), 6.22 (d, J=15.9 Hz, 1H), 6.59 (d, J=8.6 Hz, 2H), 6.79 (d, J=8.6 Hz, 2H), 7.00-7.07 (m, 3H), 7.12 (d, J=2.5 Hz, 1H), 7.26 (d, J=8.6 Hz, 2H), 7.54 (d, J=15.9 Hz, 1H), 7.55 (s, 1H), 7.69 (d, J=9.2 Hz, 1H). LCMS (APCI): m/z 469 (M+H)$^+$.

Step 5: (2E)-3-[4-({3-Methyl-6-(methyloxy)-2-[4-(methyloxy)phenyl]-1-naphthalenyl}oxy)phenyl]-2-propenoic acid (48)

Using the procedure described in Example 1 (Step 10), ethyl ester (47) (0.33 g, 0.69 mmol) was saponified with 1 N NaOH in THF and EtOH to give 0.26 g (85%) of compound (48) as an off-white foam. $^1$H NMR (400 MHz, CDCl$_3$): δ 2.25 (s, 3H), 3.77 (s, 3H), 3.92 (s, 3H), 6.22 (d, J=16.0 Hz, 1H), 6.61 (d, J=8.8 Hz, 2H), 6.79 (d, J=8.6 Hz, 2H), 7.00-7.07 (m, 3H), 7.12 (d, J=2.5 Hz, 1H), 7.28 (d, J=8.7 Hz, 2H), 7.56 (s, 1H), 7.63 (d, J=15.9 Hz, 1H), 7.68 (d, J=9.2 Hz, 1H). LCMS (APCI): m/z 441 (M+H)$^+$.

Step 6: (2E)-3-(4-{[6-Hydroxy-2-(4-hydroxyphenyl)-3-methyl-1-naphthalenyl]oxy}phenyl)-2-propenoic acid (50)

Using the procedure described in Example 1 (Step 11), methyl ether 49 (0.16 g, 0.36 mmol) was treated with BBr$_3$ in CH$_2$Cl$_2$ to give the crude product as a red viscous oil. The crude product was purified by flash chromatography over SiO$_2$ with CHCl$_3$:MeOH (100:1 to 3:1) to give 0.12 g (79%) of the title compound (50) as an orange solid. mp 162-164° C. $^1$H NMR (400 MHz, CH$_3$OH-d$_4$): δ 2.20 (s, 3H), 6.26 (d, J=15.9 Hz, 1H), 6.58 (d, J=8.6 Hz, 2H), 6.67 (d, J=8.6 Hz, 2H), 6.90-6.98 (m, 3H), 7.10 (d, J=2.2 Hz, 1H), 7.35 (d, J=8.8 Hz, 2H), 7.48 (s, 1H), 7.53 (d, J=15.9 Hz, 1H), 7.59 (d, J=9.2 Hz, 1H). LCMS (ESI): m/z 411 (M–H)$^-$. HRMS (EI) Calc for C$_{26}$H$_{20}$O$_5$: 413.1389 (M$^+$). Found: 413.1367.

Example 11 (61)

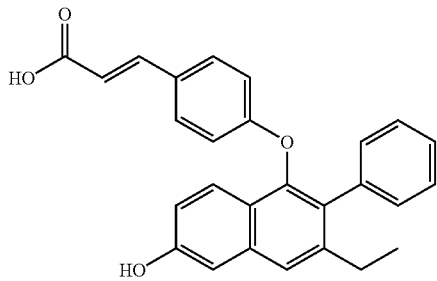

Step 1: 1-[3-(Methyloxy)phenyl]-2-butanol (51)

To a stirred suspension of CuI (0.40 g, 2.08 mmol) in 3-methoxyphenylmagnesium bromide in THF (31.2 mL, 1.0M THF solution, 31.2 mmol) at −20° C. was slowly added a solution of 1,2-epoxybutane (1.50 g, 20.8 mmol) in THF (1 mL). The mixture was allowed to warm up to room temperature and stirred at room temperature overnight. The reaction mixture was cooled in an ice bath and quenched with saturated aqueous NH$_4$Cl. The mixture was extracted with ethyl acetate (3×70 mL). The combined organic phase was washed with 1 N NaOH, brine, dried (Na$_2$SO$_4$) filtered, and the filtrate was concentrated to give the crude product as a brown oil. The crude product was purified by flash chromatography over SiO$_2$ with hexanes:EtOAc (4:1) to give 3.50 g (94%) of compound (51) as a colorless oil. $^1$H NMR (400 MHz, CDCl$_3$): δ 1.00 (t, J=7.4 Hz, 3H), 1.50-1.65 (m, 2H), 2.62 (dd, J$_1$=13.5 Hz, J$_2$=8.6 Hz, 1H), 2.82 (dd, J$_1$=13.5 Hz, J$_2$=4.1 Hz, 1H), 3.74-3.79 (m, 1H), 3.80 (s, 3H), 6.75-6.85 (m, 3H), 7.20-7.25 (m, 1H).

Step 2: 1-{[3-(Methyloxy)phenyl]methyl}propyl methanesulfonate (52)

1-[3-(Methyloxy)phenyl]-2-butanol (51) (3.50 g, 19.4 mmol) was dissolved in CH$_2$Cl$_2$ (90 mL). To this solution was added Et$_3$N (5.4 mL, 38.8 mmol) followed by catalytic amount of N,N-dimethylaminopyridine (DMAP). The mixture was cooled in an ice bath, methanesulfonyl chloride (2.3 mL, 29.1 mmol) was added dropwise. The reaction mixture was allowed to warm up to room temperature and stirred at room temperature overnight. Water was added to the mixture, CH$_2$Cl$_2$ layer was separated. The aqueous layer was further extracted with CH$_2$Cl$_2$ (50 mL). The extracts were combined and washed with brine, (Na$_2$SO$_4$), filtered, and the filtrate was concentrated to give the crude product as a brown oil. The crude product was purified by flash chromatography over SiO$_2$ with hexanes:EtOAc (4:1) to give 4.66 g (94%) of the title compound (52) as a yellow oil, which solidified upon freezing. $^1$H NMR (400 MHz, CDCl$_3$): δ 1.03 (t, J=7.5 Hz, 3H), 1.70-1.85 (m, 2H), 2.53 (s, 3H), 2.94 (d, J=6.7 Hz, 2H), 3.80 (s, 3H), 4.70-4.80 (m, 1H), 6.75-6.85 (m, 3H), 7.20-7.25 (m, 1H).

Step 3: 3-(2-Bromobutyl)phenyl methyl ether (53)

To a solution of 1-{[3-(methyloxy)phenyl]methyl}propyl methanesulfonate (52) (4.66 g, 18.0 mmol) in acetone (60 mL) was added LiBr (3.13 g, 36.1 mmol). The reaction mixture was refluxed under nitrogen for 8 h. Another 0.80 g of LiBr was added, and the reflux was continued for 1 h. Cooled to room temperature, the solid was filtered off and washed with acetone. The filtrate was concentrated to give the crude product as a brown oil. The crude product was purified by flash chromatography over SiO$_2$ with hexanes:EtOAc (100:1) to give 2.07 g (47%) of the title compound (53) as a yellow oil. $^1$H NMR (400 MHz, CDCl$_3$): δ 1.06 (t, J=7.2 Hz, 3H), 1.70-1.82 (m, 1H), 1.83-1.95 (m, 1H), 3.10-3.20 (m, 2H), 3.80 (s, 3H), 4.10-4.20 (m, 1H), 6.75-6.85 (m, 3H), 7.22 (t, J=7.9 Hz, 1H).

Step 4: 3-{[3-(Methyloxy)phenyl]methyl}-2-phenylpentanoic acid (54)

Phenylacetic acid (0.84 g, 6.07 mmol) was dissolved in THF (50 mL) and cooled in an ice bath. nBuLi (2.5 M in hexanes, 5.4 mL, 13.4 mmol) was added dropwise. The mixture was stirred at 0° C. for 1 h, then at room temperature for 5 h. HMPA (0.25 mL) was added, and the stirring was continued for another 30 min. Cooled in an ice bath, a solution of 3-(2-bromobutyl)phenyl methyl ether (53) (1.77 g, 7.28 mmol) in THF (10 mL) was added dropwise. The resulting mixture was allowed to warm up to room temperature and stir at room temperature overnight, then heated at 50° C. for 1 h. Cooled and quenched with 0.5 N NaOH (25 mL), the mixture was again heated at 50° C. for 1 h. After cooled to room temperature and extracted with ether, the aqueous layer was acidified with 5 N HCl and extracted with CHCl$_3$. The extracts were combined and washed with brine, dried (Na$_2$SO$_4$), filtered, and the filtrate was concentrated to give the crude product as a yellow oil. The crude product was purified by flash chromatography over SiO$_2$ with CH$_2$Cl$_2$: Acetone (8:1) to give 0.81 g (45%) of the title compound (54) as a colorless viscous oil. $^1$HNMR indicated it was a mixture of two diastereomers with a ratio of 2:1.

Step 5: 3-Ethyl-6-(methyloxy)-2-phenyl-3,4-dihydro-1(2H)-naphthalenone (55)

To a solution of 3-{[3-(methyloxy)phenyl]methyl}-2-phenylpentanoic acid (54) (0.98 g, 3.28 mmol) in CH$_2$Cl$_2$ (20 mL) at room temperature was added oxalyl chloride (0.88 mL, 9.85 mmol) followed by one drop of DMF. The mixture was stirred at room temperature overnight. CH$_2$Cl$_2$ and excess of oxalyl chloride were removed under vacuum. The residue was dissolved in CH$_2$Cl$_2$ (30 mL), cooled in an ice bath, AlCl$_3$ (0.67 g, 4.93 mmol) was added. The resulting brown solution was stirred at 0° C. for 5 h. Poured into 1 N HCl (35 mL) with ice, and the mixture was extracted with CH$_2$Cl$_2$. The extracts were combined and washed with brine, dried over Na₂SO₄, filtered, and the filtrate was concentrated to give the crude product as a yellow oil. The crude product was purified by flash chromatography over SiO₂ with hexanes:EtOAc (6.5:1) to give 0.84 g (91%) of the title compound (55) as a greenish-yellow oil. ¹HNMR indicated it was a mixture of two diastereomers with a ratio of 2:1.

Step 6: 3-Ethyl-6-(methyloxy)-2-phenyl-1-naphthalenyl acetate (56)

3-Ethyl-6-(methyloxy)-2-phenyl-3,4-dihydro-1(2H)-naphthalenone (55) (0.84 g, 3.00 mmol) was dissolved in isopropenyl acetate (30 mL). pTsOH monohydrate (100 mg) was added. The mixture was refluxed under nitrogen for 3 days. Cooled to room temperature, 2,3-dichloro-5,6-dicyano-1,4-benzoquinone (1.74 g, 7.50 mmol) was added. The resulting mixture was refluxed under nitrogen overnight. Cooled to room temperature and diluted with CH₂Cl₂ (150 mL). The mixture was washed with 0.2 N NaOH (4×20 mL), water (2×20 mL), brine (30 mL), dried over Na₂SO₄, filtered, and the filtrate was concentrated to give the crude product as a dark brown tar. The crude product was purified by flash chromatography over SiO₂ with hexanes:acetone (50:1) to give 0.61 g (64%) of the title compound (56) as a white solid. ¹H NMR (400 MHz, CDCl₃): δ 1.11 (t, J=7.5 Hz, 3H), 1.97 (s, 3H), 2.55 (q, J=7.5 Hz, 2H), 3.93 (s, 3H), 7.10-7.16 (m, 2H), 7.20-7.25 (m, 2H), 7.30-7.45 (m, 3H), 7.57 (s, 1H), 7.62 (d, J=8.9 Hz, 1H).

Step 7: 3-Ethyl-6-(methyloxy)-2-phenyl-1-naphthalenol (57)

To a solution of 3-ethyl-6-(methyloxy)-2-phenyl-1-naphthalenyl acetate (56) (0.61 g, 1.90 mmol) in MeOH (20 mL) and THF (20 mL) was added NaOMe (0.5M in MeOH, 10 mL). The mixture was stirred at room temperature for 3 h. Cooled to room temperature, 2,3-dichloro-5,6-dicyano-1,4-benzoquinone (1.74 g, 7.50 mmol) was added. Most of the solvent was removed and the residue was diluted with water (20 mL) and acidified with 5 N HCl. The mixture was extracted with CH₂Cl₂. The extracts were combined and washed with brine, dried over Na₂SO₄, filtered, and the filtrate was concentrated to give the crude product as a brown oil. The crude product was purified by flash chromatography over SiO₂ with hexanes:EtOAc (10:1) to give 0.52 g (98%) of compound 57 as a light yellow oil. ¹H NMR (400 MHz, CDCl₃): δ 1.08 (t, J=7.5 Hz, 3H), 2.49 (q, J=7.5 Hz, 2H), 3.93 (s, 3H), 5.14 (s, 1H), 7.05-7.10 (m, 2H), 7.24 (s, 1H), 7.32-7.38 (m, 2H), 7.42-7.48 (m, 1H), 7.50-7.56 (m, 2H), 8.05-8.10 (m, 1H).

Step 8: 4-{[3-Ethyl-6-(methyloxy)-2-phenyl-1-naphthalenyl]oxy}benzaldehyde (58)

To a suspension of NaH (60% in mineral oil, 78 mg, 1.95 mmol) in DMF (15 mL) at 0° C. was added a solution of 3-ethyl-6-(methyloxy)-2-phenyl-1-naphthalenol (57) (0.52 g, 1.86 mmol) in DMF (5 mL). The mixture was stirred at room temperature for 10 min. 4-Fluorobenzaldehyde (0.47 g, 3.72 mmol) in DMF (3 mL) was added and the resulting mixture was heated at 70° C. for 36 h. Cooled to room temperature, the mixture was poured into water (50 mL) and extracted with EtOAc. The extracts were combined and washed with brine, dried over Na₂SO₄, filtered, and the filtrate was concentrated to give the crude product as a dark brown oil. The crude product was purified by flash chromatography over SiO₂ with hexanes:EtOAc (25:1) to give 0.61 g (86%) of compound 58 as a light yellow foam. ¹H NMR (400 MHz, CDCl₃): δ 1.13 (t, J=7.5 Hz, 3H), 2.57 (q, J=7.5 Hz, 2H), 3.94 (s, 3H), 6.68 (d, J=8.6 Hz, 2H), 7.06 (dd, J₁=9.2 Hz, J₂=2.4 Hz, 1H), 7.08-7.15 (m, 2H), 7.17-7.27 (m, 4H), 7.58-7.64 (m, 3H), 7.67 (d, J=9.2 Hz, 1H), 9.79 (s, 1H). LCMS (APCI): m/z 383 (M+H)⁺.

Step 9: Ethyl (2E)-3-(4-{[3-ethyl-6-(methyloxy)-2-phenyl-1-naphthalenyl]oxy}phenyl)-2-propenoate (59)

Triethylphosphonoacetate (0.44 g, 1.89 mmol) was dissolved in THF (12 mL). Cooled to −78° C., nBuLi (1.6 M in hexanes, 1.20 mL, 1.89 mmoL) was added dropwise. The mixture was stirred at −78° C. for 30 min. To this solution was added 4-{[3-ethyl-6-(methyloxy)-2-phenyl-1-naphthalenyl]oxy}benzaldehyde (58) (0.60 g, 1.58 mmol) in THF (12 mL) slowly. The resulting mixture was allowed to warm up to room temperature and stirred at room temperature (3 h in total). The mixture was poured into water (50 mL) and extracted with EtOAc (2×50 mL). The extracts were combined and washed with brine, dried over Na₂SO₄, filtered, and the filtrate was concentrated to give the crude product as a light yellow oil. The crude product was purified by flash chromatography over SiO₂ with hexanes:EtOAc (25:1) to give 0.67 g (94%) of the title compound (59) as a white foam. ¹H NMR (400 MHz, CDCl₃): δ 1.12 (t, J=7.5 Hz, 3H), 1.30 (t, J=7.2 Hz, 3H), 2.56 (q, J=7.5 Hz, 2H), 3.93 (s, 3H), 4.22 (q, J=7.2 Hz, 2H), 6.21 (d, J=16.0 Hz, 1H), 6.56 (d, J=8.6 Hz, 2H), 7.04 (dd, J₁=8.6 Hz, J₂=2.4 Hz, 1H), 7.10-7.20 (m, 3H), 7.20-7.27 (m, 5H), 7.54 (d, J=16.0 Hz, 1H), 7.59 (s, 1H), 7.72 (d, J=9.2 Hz, 1H). LCMS (APCI): m/z 453 (M+H)⁺.

Step 10: (2E)-3-(4-{[3-Ethyl-6-(methyloxy)-2-phenyl-1-naphthalenyl]oxy}phenyl)-2-propenoic acid (60)

To a solution of ethyl (2E)-3-(4-{[3-ethyl-6-(methyloxy)-2-phenyl-1-naphthalenyl]oxy}phenyl)-2-propenoate (59) (0.67 g, 1.49 mmol) in THF (10 mL) and EtOH (10 mL) was added 1 N NaOH (12 mL). The resulting mixture was heated at 60° C. for 2 h. Cooled in an ice bath, the mixture was acidified with 2 N HCl and extracted with EtOAc (3×50 mL). The extracts were combined and washed with brine, dried over Na₂SO₄, filtered, and the filtrate was concentrated to give the crude product, which was triturated with hot hexanes (containing a small amount of CHCl₃ and MeOH) to give 0.62 g (98%) of the title compound (60) as a white solid. ¹H NMR (400 MHz, CDCl₃): δ 1.13 (t, J=7.5 Hz, 3H), 2.56 (q, J=7.5 Hz, 2H), 3.94 (s, 3H), 6.23 (d, J=15.9 Hz, 1H), 6.59 (d, J=8.8 Hz, 2H), 7.04 (dd, J₁=9.1 Hz, J₂=2.4 Hz, 1H), 7.10-7.16 (m, 2H), 7.19 (d, J=2.5 Hz, 1H), 7.20-7.30 (m, 5H), 7.60 (s, 1H), 7.63 (d, J=15.8 Hz, 1H), 7.70 (d, J=9.2 Hz, 1H). LCMS (ESI): m/z 423 (M−H)⁻.

Step 11: (2E)-3-{4-[(3-Ethyl-6-hydroxy-2-phenyl-1-naphthalenyl)oxy]phenyl}-2-propenoic acid (61)

To a solution of (2E)-3-(4-{[3-ethyl-6-(methyloxy)-2-phenyl-1-naphthalenyl]oxy}phenyl)-2-propenoic acid (60) (104 mg, 0.25 mmol) in reagent grade CH₂Cl₂ (10 mL) at −10° C. was added BBr₃ (1 M in CH₂Cl₂, 0.74 mL, 0.74 mmol) dropwise. The mixture was then stirred at −5° C. to 0° C. for 2 h, poured into ice water and extracted with EtOAc. The combined organic extract was washed with brine, dried over Na₂SO₄, filtered, and the filtrate was concentrated to give the crude product as reddish brown oil. The crude product was purified by reverse phase preparation HPLC on Agilent 1100 (30% CH$_3$CN in H$_2$O to 100% CH$_3$CN) to give 64 mg (64%) of the title compound (61) as light beige solid. mp 188-190° C. $^1$H NMR (400 MHz, CH$_3$CN-d$_4$): δ 1.07 (t, J=7.5 Hz, 3H), 2.55 (q, J=7.5 Hz, 2H), 6.26 (d, J=16.0 Hz, 1H), 6.56 (d, J=8.8 Hz, 2H), 6.96 (dd, J$_1$=9.2 Hz, J$_2$=2.4 Hz, 1H), 7.10-7.16 (m, 3H), 7.18-7.28 (m, 3H), 7.34 (d, J=8.8 Hz, 2H), 7.52 (d, J=16.0 Hz, 1H), 7.53 (s, 1H), 7.59 (d, J=8.9 Hz, 1H). LCMS (ESI): m/z 411 (M+H)$^+$, m/z 409 (M−H)$^−$. HRMS (EI) Calcd for C$_{27}$H$_{22}$O$_4$: 411.1596 (M$^{+•}$). Found: 411.1596.

Example 12 (63)

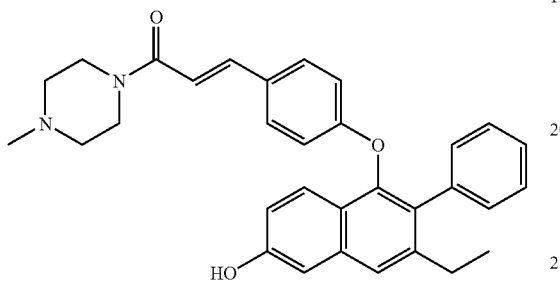

Step 1: 1-[(2E)-3-(4-{[3-Ethyl-6-(methyloxy)-2-phenyl-1-naphthalenyl]oxy}phenyl)-2-propenoyl]-4-methylpiperazine (62)

To a solution of (2E)-3-(4-{[3-Ethyl-6-(methyloxy)-2-phenyl-1-naphthalenyl]oxy}phenyl)-2-propenoic acid (60) (0.10 g, 0.24 mmol) in CH$_2$Cl$_2$ (3 mL) at room temperature was added oxalyl chloride (63 μL, 0.71 mmol). The mixture was stirred at room temperature overnight. CH$_2$Cl$_2$ and excess of oxalyl chloride were removed under vacuum. The residue was dissolved in CH$_2$Cl$_2$ (4 mL), cooled in an ice bath, 1-methyl piperazine (40 μL, 0.35 mmol) was added. The resulting mixture was allowed to stir at room temperature overnight. Diluted with CH$_2$Cl$_2$ (50 mL), the mixture was washed with saturated aqueous NaHCO$_3$, 0.5 N NaOH and brine, dried over Na$_2$SO$_4$, filtered, and the filtrate was concentrated to give the crude product as a yellow oil. The crude product was purified by flash chromatography over SiO$_2$ with CHCl$_3$:MeOH (75:1 to 50:1) to give 84 mg (70%) of compound 62 as a white foam. $^1$H NMR (400 MHz, CH$_3$OH-d$_4$): δ 1.09 (t, J=7.5 Hz, 3H), 2.32 (s, 3H), 2.47 (br s, 4H), 2.58 (q, J=7.5 Hz, 2H), 3.71 (br s, 4H), 3.92 (s, 3H), 6.54 (d, J=8.7 Hz, 2H), 6.91 (d, J=15.4 Hz, 1H), 7.02 (dd, J$_1$=9.2 Hz, J$_2$=2.4 Hz, 1H), 7.10-7.16 (m, 2H), 7.18-7.28 (m, 3H), 7.30 (d, J=2.4 Hz, 1H), 7.37 (d, J=8.8 Hz, 2H), 7.44 (d, J=15.4 Hz, 1H), 7.63 (d, J=9.3 Hz, 1H), 7.66 (s, 1H). LCMS (APCI): m/z 507 (M+H)$^+$.

Step 2: 7-Ethyl-5-({4-[(1E)-3-(4-methyl-1-piperazinyl)-3-oxo-1-propen-1-yl]phenyl}oxy)-6-phenyl-2-naphthalenol (63)

To a solution of 1-[(2E)-3-(4-{[3-ethyl-6-(methyloxy)-2-phenyl-1-naphthalenyl]oxy}phenyl)-2-propenoyl]-4-methylpiperazine (61) (83 mg, 0.17 mmol) in reagent grade CH$_2$Cl$_2$ (8 mL) at −10° C. was added BBr$_3$ (97 μL, 1.03 mmol) dropwise. The mixture was then stirred at 0° C. to 5° C. for 6 h, poured into saturated aqueous NaHCO$_3$ (30 mL) and extracted with CH$_2$Cl$_2$. The combined extract was washed with brine, dried over Na$_2$SO$_4$, filtered, and the filtrate was concentrated to give the crude product as a brown solid. The crude product was triturated with hot hexanes (containing small amount of CH$_2$Cl$_2$ and MeOH) to give 44 mg (55%) of the title compound (63) as an off-white solid. mp 195-196° C. $^1$H NMR (400 MHz, CH$_3$OH-d$_4$): δ 1.07 (t, J=7.5 Hz, 3H), 2.31 (s, 3H), 2.47 (br s, 4H), 2.54 (q, J=7.5 Hz, 2H), 3.70 (br s, 4H), 6.54 (d, J=8.8 Hz, 2H), 6.91 (d, J=15.4 Hz, 1H), 6.96 (dd, J$_1$=9.1 Hz, J$_2$=2.4 Hz, 1H), 7.10-7.17 (m, 3H), 7.18-7.28 (m, 3H), 7.37 (d, J=8.6 Hz, 2H), 7.44 (d, J=15.4 Hz, 1H), 7.52 (s, 1H), 7.60 (d, J=9.1 Hz, 1H). LCMS (ESI): m/z 493 (M+H)$^+$, m/z 491 (M−H)$^−$. HRMS (EI) Calc for C$_{32}$H$_{32}$N$_2$O$_3$: 493.2491 (M$^{+•}$). Found: 493.2500.

Example 13 (76)

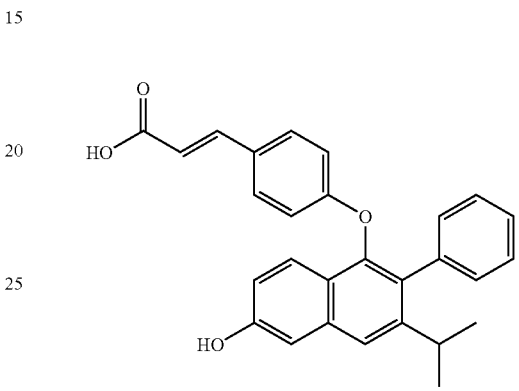

Step 1: 3-Methyl-1-[3-(methyloxy)phenyl]-2-butanone (64)

To a stirred suspension of Pd(PPh$_3$)$_2$Cl$_2$ (0.86 g, 1.22 mmol) and zinc powder (3.19 g, 48.8 mmol) in 1,2-dimethoxyethane (DME, 100 mL) at room temperature was slowly added a solution of 3-methoxybenzyl bromide (5.0 g, 24.4 mmol) and isobutyryl chloride in DME (25 mL). The mixture was stirred at room temperature for 1 h. Water was added, and the mixture was extracted with ether. The combined ether extract was washed with brine, dried over Na$_2$SO$_4$, filtered, and the filtrate was concentrated to give the crude product as a brown oil. The crude product was purified by flash chromatography over SiO$_2$ with hexanes:EtOAc (20:1) to give 3.03 g (64) of compound (§4 as a colorless oil. $^1$H NMR (400 MHz, CDCl$_3$): δ 1.09 (d, J=7.0 Hz, 6H), 2.70-2.75 (m, 1H), 3.70 (s, 2H), 3.79 (s, 3H), 6.70-6.85 (m, 3H), 7.23 (t, J=8.0 Hz, 1H).

Step 2: Ethyl 4-methyl-3-{[3-(methyloxy)phenyl]methyl}pentanoate (66)

Dicyclohexylamine (5.80 g, 31.5 mmol) was dissolved in THF (50 mL). The solution was cooled to −78° C., nBuLi (1.6 M in hexanes, 19.7 mL, 31.5 mmol) was added dropwise. After 20 min, a solution of ethyl (trimethylsilyl) acetate (5.1 g, 31.5 mmol) in THF (25 mL) was added. The mixture was stirred at −78° C. for additional 15 min, then, 3-methyl-1-[3-(methyloxy)phenyl]-2-butanone (64) (3.03 g, 15.8 mmol) in THF (25 mL) was added. The resulting mixture was allowed to warm up to −40° C., then stirred between −40° C. and −20° C. for 7 h. The reaction was quenched with saturated aqueous NH$_4$Cl (25 mL), the white solid was filtered off and washed with ether. To the filtrate was added water (50 mL), the ether layer was separated and the aqueous layer was further extracted with ether (2×50 mL). The combined ether extract was washed with water, brine, dried over $Na_2SO_4$, filtered, and the filtrate was concentrated to give the crude product as a yellow oil. The crude product was purified by flash chromatography over $SiO_2$ with hexanes:EtOAc (30:1 to 15:1) to give 2.02 g of ethyl-4-methyl-3-{[3-(methyloxy)phenyl]methyl}-2-pentenoate (65) contaminated with ethyl (trimethylsilyl) acetate as a colorless oil.

The oily mixture containing (65) was dissolved in ethanol (50 mL) and 10% Pd/C (200 mg) was added. The mixture was hydrogenated at room temperature using a hydrogen balloon overnight. Filtered through celite, the filtrate was concentrated to give 1.72 g of compound (66) (41% from the ketone) of the title compound as a colorless oil. $^1$H NMR (400 MHz, $CDCl_3$): δ 0.89 (d, J=7.4 Hz, 3H), 0.91 (d, J=7.6 Hz, 3H), 1.21 (t, J=7.2 Hz, 3H), 1.70-1.80 (m, 1H), 2.10-2.20 (m, 2H), 2.20-2.30 (m, 1H), 2.44 (dd, $J_1$=13.6 Hz, $J_2$=7.4 Hz, 1H), 2.64 (dd, $J_1$=13.7 Hz, $J_2$=6.2 Hz, 1H), 3.79 (s, 3H), 4.04 (q, J=7.2 Hz, 2H), 6.70-6.80 (m, 3H), 7.15-7.20 (m, 1H).

Step 3: 4-Methyl-3-{[3-(methyloxy)phenyl]methyl}pentanoic acid (67)

Ethyl 4-methyl-3-{[3-(methyloxy)phenyl]methyl}pentanoate (66) (1.72 g, 6.51 mmol) was dissolved in THF (30 mL) and EtOH (30 mL). To this solution was added 1 N NaOH (35 mL). The reaction mixture was heated at 60° C. for 1.5 h. Cooled, the mixture was extracted with EtOAc. The combined extract was washed with brine, dried over $Na_2SO_4$, filtered, and the filtrate was concentrated to give 1.54 g (100%) of the crude product 67 as a yellow oil. The crude product was used without further purification. $^1$H NMR (400 MHz, $CDCl_3$): δ 0.91 (d, J=6.9 Hz, 3H), 0.94 (d, J=6.7 Hz, 3H), 1.70-1.80 (m, 1H), 2.10-2.25 (m, 2H), 2.32 (dd, $J_1$=15.3 Hz, $J_2$=6.5 Hz, 1H), 2.46 (dd, $J_1$=13.7 Hz, $J_2$=8.2 Hz, 1H), 2.67 (dd, $J_1$=13.7 Hz, $J_2$=6.4 Hz, 1H), 3.79 (s, 3H), 6.70-6.80 (m, 3H), 7.15-7.25 (m, 1H).

Step 4: 3-(1-Methylethyl)-6-(methyloxy)-3,4-dihydro-1(2H)-naphthalenone (68)

To a solution of 4-methyl-3-{[3-(methyloxy)phenyl]methyl}pentanoic acid (67) (0.15 g, 0.63 mmol) in $CH_2Cl_2$ (5 mL) was added oxalyl chloride (0.17 mL, 1.90 mmol) followed by one drop of DMF. The mixture was stirred at room temperature overnight. $CH_2Cl_2$ and excess of oxalyl chloride were removed under vacuum. The residue was dissolved in $CH_2Cl_2$ (10 mL), cooled in an ice bath, $AlCl_3$ (0.13 g, 0.95 mmol) was added. The resulting mixture was stirred at 0° C. for 4 h. Poured into 1 N HCl (7 mL) with ice, and the mixture was extracted with $CH_2Cl_2$. The extracts were combined and washed with brine, dried over $Na_2SO_4$, filtered, and the filtrate was concentrated to give the crude product as a brown oil. The crude product was purified by flash chromatography over $SiO_2$ with hexanes:EtOAc (8:1) to give 0.112 g (81%) of the title compound (68) as a light yellow viscous oil, which solidified after standing. $^1$H NMR (400 MHz, $CDCl_3$): δ 0.97 (d, J=6.8 Hz, 3H), 0.98 (d, J=6.7 Hz, 3H), 1.60-1.70 (m, 1H), 1.90-2.05 (m, 1H), 2.30 (dd, $J_1$=16.5 Hz, $J_2$=2.8 Hz, 1H), 2.65-2.80 (m, 1H), 2.85-2.95 (m, 1H), 3.85 (s, 3H), 6.71 (d, J=2.2 Hz, 1H), 6.81 (dd, $J_1$=8.8 Hz, $J_2$=2.4 Hz, 1H), 7.98 (d, J=8.8 Hz, 1H).

Step 5: 2-Bromo-3-(1-methylethyl)-6-(methyloxy)-1-naphthalenol (69)

To a solution of 3-(1-methylethyl)-6-(methyloxy)-3,4-dihydro-1(2H)-naphthalenone (68) (0.40 g, 1.83 mmol) in $CH_2CO_2$ (15 mL) was added a solution of bromine (0.59 g, 3.68 mmol) in $CH_2Cl_2$ (5 mL). The mixture was stirred at room temperature overnight. Volatiles were removed under vacuum at room temperature. The residue was dissolved in $CH_3CN$ (15 mL), cooled in an acetone-ice bath, DBU (0.44 g, 2.75 mmol) in $CH_3CN$ (2 mL) was added dropwise. The resulting mixture was allowed to warm up to room temperature and stirred for 1 h. 5 N HCl (1 mL) was added followed by brine (50 mL), and the mixture was extracted with $CH_2Cl_2$. The extracts were combined and washed with brine, dried over $Na_2SO_4$, filtered, and the filtrate was concentrated to give the crude product as a brown oil. The crude product was purified by flash chromatography over $SiO_2$ with hexanes:EtOAc (25:1) to give 0.43 g (79% from tetralone) of the title compound (69) as a colorless viscous oil. $^1$H NMR (400 MHz, $CDCl_3$): δ 1.32 (d, J=6.8 Hz, 6H), 3.35 (sept, J=6.8 Hz, 1H), 3.91 (s, 3H), 6.11 (s, 1H), 7.04 (d, J=2.4 Hz, 1H), 7.08 (dd, $J_1$=9.1 Hz, $J_2$=2.5 Hz, 1H), 7.21 (s, 1H), 8.08 (d, J=9.1 Hz, 1H).

Step 6: 2-Bromo-3-(1-methylethyl)-6-(methyloxy)-1-{[(methyloxy) methyl]oxy}naphthalene (70)

2-Bromo-3-(1-methylethyl)-6-(methyloxy)-1-naphthalenol (69) (0.43 g, 1.45 mmol) was dissolved in THF (6 mL) followed by addition of diisopropylethylamine (1.02 mL, 5.78 mmol). Cooled in an ice bath, chloromethyl methyl ether (0.34 mL, 4.32 mmol) was added. The mixture was stirred at room temperature overnight. Diluted with $CH_2Cl_2$ (50 mL) and water (20 mL), and $CH_2Cl_2$ layer was separated. The aqueous layer was further extracted with $CH_2Cl_2$ (2×25 mL). The organic extracts were combined and washed with brine, dried over $Na_2SO_4$, filtered, and the filtrate was concentrated to give the crude product as a yellow oil. The crude product was purified by flash chromatography over $SiO_2$ with hexanes:EtOAc (25:1) to give 0.43 g (79% from tetralone) of compound (70) as a light brown oil. $^1$H NMR (400 MHz, $CDCl_3$): δ 1.32 (d, J=6.8 Hz, 6H), 3.49 (sept, J=6.8 Hz, 1H), 3.73 (s, 3H), 3.91 (s, 3H), 5.23 (s, 2H), 7.08 (d, J=2.4 Hz, 1H), 7.12 (dd, $J_1$=9.1 Hz, $J_2$=2.4 Hz, 1H), 7.43 (s, 1H), 8.02 (d, J=9.1 Hz, 1H).

Step 7: 3-(1-Methylethyl)-6-(methyloxy)-1-{[(methyloxy)methyl]oxy}-2-phenyl naphthalene (71)

A sealed tube containing 2-bromo-3-(1-methylethyl)-6-(methyloxy)-1-{[(methyloxy)methyl]oxy}naphthalene (70) (0.24 g, 0.71 mmol), phenyl boronic acid (0.18 g, 1.41 mmol), $Pd(PPh_3)_4$ (82 mg, 0.07 mmol), 2 M $Na_2CO_3$ (5 mL) and DME (5 mL) was heated at 160° C. for 20 min. Cooled to room temperature, the mixture was extracted with ether (2×50 mL). The organic extracts were combined and washed with brine, dried over $Na_2SO_4$, filtered, and the filtrate was concentrated to give the crude product as a yellow oil. The crude product was purified by flash chromatography over $SiO_2$ with hexanes:EtOAc (25:1) to give 0.23 g (97%) of compound 71 as a colorless oil. $^1$H NMR (400 MHz, $CDCl_3$): δ 1.16 (d, J=6.8 Hz, 6H), 2.92 (sept, J=6.8 Hz, 1H), 3.06 (s, 3H), 3.93 (s, 3H), 4.71 (s, 2H), 7.08-7.15 (m, 2H), 7.30-7.40 (m, 3H), 7.40-7.46 (m, 2H), 7.52 (s, 1H), 8.01 (d, J=9.0 Hz, 1H).

Step 8: 3-(1-Methylethyl)-6-(methyloxy)-2-phenyl-1-naphthalenol (72)

3-(1-Methylethyl)-6-(methyloxy)-1-{[(methyloxy)methyl]oxy}-2-phenyl naphthalene (71) (0.42 g, 1.24 mmol)

was dissolved in dioxane (8 mL). 4 M HCl in dioxane (8 mL) was added and the reaction mixture was stirred at room temperature for 30 min. The mixture was diluted with water (25 mL) and brine (25 mL) and extracted with EtOAc (3×50 mL). The combined organic extracts were washed with brine, dried over Na$_2$SO$_4$, filtered, and the filtrate was concentrated to give the crude product as a light yellow oil. The crude product was purified by flash chromatography over SiO$_2$ with hexanes:EtOAc (20:1) to give 0.36 g (98%) of the title compound (72) as a white solid. $^1$H NMR (400 MHz, CDCl$_3$): δ 1.16 (d, J=6.8 Hz, 6H), 2.79 (sept, J=6.8 Hz, 1H), 3.93 (s, 3H), 5.08 (s, 1H), 7.05-7.12 (m, 2H), 7.30 (s, 1H), 7.32-7.38 (m, 2H), 7.42-7.50 (m, 1H), 7.50-7.58 (m, 2H), 8.07 (d, J=9.0 Hz, 1H). LCMS (APCI): m/z 293 (M+H)$^+$.

Step 9: 4-{[3-(1-Methylethyl)-6-(methyloxy)-2-phenyl-1-naphthalenyl]oxy}benzaldehyde (73)

3-(1-Methylethyl)-6-(methyloxy)-2-phenyl-1-naphthalenol (72) (0.35 g, 1.21 mmol) was treated with NaH in DMF followed by addition of 4-fluorobenzaldehyde to give 0.44 g (91%) of the title compound (73) as a light yellow foam. $^1$H NMR (400 MHz, CDCl$_3$): δ 1.20 (d, J=6.8 Hz, 6H), 2.91 (sept, J=6.8 Hz, 1H), 3.94 (s, 3H), 6.67 (d, J=8.8 Hz, 2H), 7.05 (dd, J$_1$=9.0 Hz, J$_2$=2.4 Hz, 1H), 7.08-7.13 (m, 2H), 7.18-7.26 (m, 4H), 7.61 (d, J=8.6 Hz, 2H), 7.64-7.70 (m, 1H), 9.79 (s, 1H). LCMS (ESI): m/z 397 (M+H)$^+$.

Step 10: Ethyl (2E)-3-(4-{[3-(1-methylethyl)-6-(methyloxy)-2-phenyl-1-naphthalenyl]oxy}phenyl)-2-propenoate (74)

4-{[3-(1-Methylethyl)-6-(methyloxy)-2-phenyl-1-naphthalenyl]oxy}benzaldehyde (73) (0.44 g, 1.10 mmol) was treated with a mixture of triethylphosphonoacetate and nBuLi to give 0.45 g (88%) of the title compound (74) as a light yellow foam. $^1$H NMR (400 MHz, CDCl$_3$): δ 1.19 (d, J=6.8 Hz, 6H), 1.30 (t, J=7.0 Hz, 3H), 2.90 (sept, J=6.8 Hz, 1H), 3.94 (s, 3H), 4.22 (q, J=7.0 Hz, 2H), 6.21 (d, J=16.0 Hz, 1H), 6.54 (d, J=8.6 Hz, 2H), 7.04 (dd, J$_1$=9.2 Hz, J$_2$=2.4 Hz, 1H), 7.07-7.15 (m, 2H), 7.18-7.28 (m, 6H), 7.54 (d, J=16.0 Hz, 1H), 7.65 (s, 1H), 7.70 (d, J=9.2 Hz, 1H). LCMS (ESI): m/z 467 (M+H)$^+$.

Step 11: (2E)-3-(4-{[3-(1-Methylethyl)-6-(methyloxy)-2-phenyl-1-naphthalenyl]oxy}phenyl)-2-propenoic acid (75)

Ethyl ester 74 (0.45 g, 0.97 mmol) was saponified with 1 N NaOH in THF and EtOH to give 0.33 g (78%) of the title compound (75) as a light yellow solid. $^1$H NMR (400 MHz, CDCl$_3$): δ 1.19 (d, J=6.8 Hz, 6H), 2.90 (sept, J=6.8 Hz, 1H), 3.94 (s, 3H), 6.22 (d, J=15.9 Hz, 1H), 6.56 (d, J=8.8 Hz, 2H), 7.04 (dd, J$_1$=9.1 Hz, J$_2$=2.4 Hz, 1H), 7.06-7.15 (m, 2H), 7.18-7.30 (m, 6H), 7.62 (d, J=16.0 Hz, 1H), 7.65 (s, 1H), 7.69 (d, J=9.1 Hz, 1H). LCMS (ESI): m/z 439 (M+H)$^+$.

Step 12: (2E)-3-(4-{[6-Hydroxy-3-(1-methylethyl)-2-phenyl-1-naphthalenyl]oxy}phenyl)-2-propenoic acid (76)

The methyl ether (75) (0.15 g, 0.34 mmol) was treated with BBr$_3$ in CH$_2$Cl$_2$ to give the crude product as a yellow viscous oil, which was purified by reverse phase preparation HPLC on Agilent 1100 to afford 102 mg (70%) of the title compound (76) as a light yellow solid. mp 198-199° C. $^1$H NMR (400 MHz, CH$_3$OH-d$_4$): δ 1.18 (d, J=6.8 Hz, 6H), 2.88 (sept, J=6.8 Hz, 1H), 6.26 (d, J=15.9 Hz, 1H), 6.54 (d, J=8.6 Hz, 2H), 6.96 (dd, J$_1$=9.2 Hz, J$_2$=2.4 Hz, 1H), 7.08-7.15 (m, 2H), 7.17 (d, J=2.2 Hz, 1H), 7.18-7.30 (m, 3H), 7.33 (d, J=8.6 Hz, 2H), 7.52 (d, J=15.9 Hz, 1H), 7.56-7.64 (m, 2H). LCMS (ESI): m/z 425 (M+H)$^+$, m/z 423 (M−H)$^-$. HRMS (EI) Calc for C$_{28}$H$_{24}$O$_4$: 425.1753 (M$^{+\cdot}$). Found: 425.1742.

Example 14 (85)

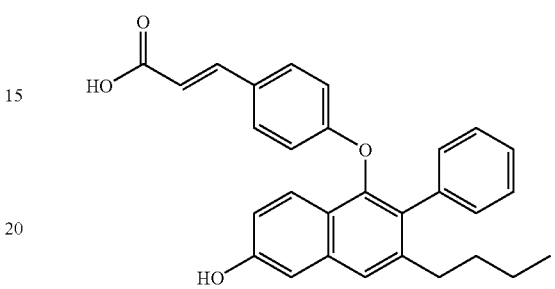

Step 1: Methyl 4-(methyloxy)-2-{[(trifluoromethyl)sulfonyl]oxy}benzoate (77)

To a stirred solution of methyl 4-methoxysalicylate (2.0 g, 10.8 mmol) in pyridine (6 mL) at 0° C. was slowly added trifluoromethanesulfonic anhydride (2.13 mL, 12.4 mmol). The mixture was allowed to warm up to room temperature, stirred at room temperature for 2 h, then heated at 40° C. overnight. Cooled and diluted with water (50 mL), the mixture was extracted with ether (3×50 mL). The combined ether extracts were washed with water (50 mL), 10% HCl (50 mL), water (50 mL) and brine, dried over Na$_2$SO$_4$, filtered, and the filtrate was concentrated to give the crude product as a yellow oil. The crude product was purified by flash chromatography over SiO$_2$ eluted with a gradient from hexanes to 20% EtOAc in hexanes to give 3.40 g (~100%) of compound 77 as a colorless oil. $^1$H NMR (400 MHz, CDCl$_3$): δ 3.88 (s, 3H), 3.93 (s, 3H), 6.77 (d, J=2.4 Hz, 1H), 6.95 (dd, J$_1$=8.9 Hz, J$_2$=2.5 Hz, 1H), 8.06 (d, J=8.8 Hz, 1H).

Step 2: Methyl 2-(1-hexyn-1-yl)-4-(methyloxy)benzoate (78)

To a degassed solution of methyl 4-(methyloxy)-2-{[(trifluoromethyl)sulfonyl]oxy}benzoate (77) (0.72 g, 2.30 mmol), Pd(PPh$_3$)$_2$Cl$_2$ (0.16 g, 0.23 mmol), CuI (44 mg, 0.23 mmol), diisopropylethylamine (1.41 mL, 8.02 mmol) in DMF (10 mL) at room temperature was added 1-hexyne (0.55 mL, 4.60 mmol). The mixture was stirred at room temperature overnight. Poured into saturated aqueous NH$_4$Cl (15 mL), the mixture was extracted with EtOAc. The combined organic extract was washed with water, brine, dried over Na$_2$SO$_4$, filtered, and the filtrate was concentrated to give the crude product as a dark brown oil. The crude product was purified by flash chromatography over SiO$_2$ eluted with a gradient from hexanes to 5% EtOAc in hexanes to give 0.55 g (98%) of 78 as a light brown oil. $^1$H NMR (400 MHz, CDCl$_3$): δ 0.95 (t, J=7.2 Hz, 3H), 1.45-1.58 (m, 2H), 1.60-1.70 (m, 2H), 2.48 (t, J=7.2 Hz, 2H), 3.83 (s, 3H), 3.87 (s, 3H), 6.82 (dd, J$_1$=8.9 Hz, J$_2$=2.6 Hz, 1H), 6.98 (d, J=2.5 Hz, 1H), 7.88 (d, J=8.8 Hz, 1H).

Step 3: 2-(1-Hexyn-1-yl)-N-methyl-N,4-bis(methyloxy)benzamide (79)

A suspension of N,O-dimethylhydroxylamine hydrochloride (1.11 g, 11.2 mmol), in THF (35 mL) was cooled to −20° C. in a dry ice-acetonitrile bath. To this solution was added nBuLi (1.6 M in hexanes, 14.0 mL, 22.3 mmol). The mixture was stirred until all the salt had dissolved. A solution of methyl 2-(1-hexyn-1-yl)-4-(methyloxy)benzoate (78) (0.55 g, 2.23 mmol) in THF (2 mL) was added slowly. The mixture was allowed to warm up to room temperature and stirred at room temperature for 3 h, quenched with water and extracted with ether (3×50 mL). The combined ether extract was washed with brine, dried over $Na_2SO_4$, filtered, and the filtrate was concentrated to give the crude product as a brown oil. The crude product was purified by flash chromatography over $SiO_2$ with hexanes:EtOAc (2.5:1) to yield 0.42 g (68%) of 79 as a light brown oil. $^1$H NMR (400 MHz, $CDCl_3$): δ 0.92 (t, J=7.2 Hz, 3H), 1.40-1.55 (m, 2H), 1.55-1.65 (m, 2H), 2.39 (t, J=7.0 Hz, 2H), 3.28 (br s, 3H), 3.61 (br s, 3H), 3.80 (s, 3H), 6.83 (dd, $J_1$=8.5 Hz, $J_2$=2.5 Hz, 1H), 6.92 (d, J=2.5 Hz, 1H), 7.24 (d, J=8.6 Hz, 1H). LCMS (ESI): m/z 276 (M+H)$^+$.

Step 4: 1-[2-(1-Hexyn-1-yl)-4-(methyloxy)phenyl]-2-phenylethanone (80)

2-(1-Hexyn-1-yl)-N-methyl-N,4-bis(methyloxy)benzamide (79) (0.42 g, 1.51 mmol) was dissolved in THF (10 mL). Cooled to 0° C. in an ice bath, benzylmagnesium chloride (2 M in THF, 1.50 mL, 3.0 mmol) was added. The mixture was stirred at 0° C. for 3 h, quenched with saturated aqueous $NH_4Cl$ and extracted with EtOAc (2×50 mL). The combined organic extract was washed with brine, dried over $Na_2SO_4$, filtered, and the filtrate was concentrated to give the crude product as a yellow oil. The crude product was purified by flash chromatography over $SiO_2$ eluted with a gradient from hexanes to 15% EtOAc in hexanes to give 0.37 g (80%) of the title compound (80) as a colorless oil. $^1$H NMR (400 MHz, $CDCl_3$): δ 0.93 (t, J=7.3 Hz, 3H), 1.40-1.55 (m, 2H), 1.55-1.65 (m, 2H), 2.46 (t, J=7.2 Hz, 2H), 3.83 (s, 3H), 4.44 (s, 2H), 6.82 (dd, $J_1$=8.8 Hz, $J_2$=2.7 Hz, 1H), 6.96 (d, J=2.5 Hz, 1H), 7.20-7.34 (m, 5H), 7.65 (d, J=8.7 Hz, 1H). LCMS (ESI): m/z 307 (M+H)$^+$.

Step 5: 3-Butyl-6-(methyloxy)-2-phenyl-1-naphthalenol (81)

A solution of 1-[2-(1-hexyn-1-yl)-4-(methyloxy)phenyl]-2-phenylethanone (80) (0.37 g, 1.21 mmol) in toluene (1.5 mL) was added to a KHMDS solution in toluene (0.5 M, 2.90 mL, 1.45 mmol) at −78° C. under nitrogen. Dry ice bath was removed, the mixture was stirred and allowed to warm up to 0° C., then heated at 80° C. for 1 h. Cooled in an ice bath, the mixture was acidified with 2 N HCl and extracted with ether. The combined ether extract was washed with brine, dried over $Na_2SO_4$, filtered, and the filtrate was concentrated to give the crude product as orange brown oil. The crude product was purified by flash chromatography over $SiO_2$ with hexanes:EtOAc (15:1) to give 0.25 g (68%) of 81 as a light brown oil. $^1$H NMR (400 MHz, $CDCl_3$): δ 0.75 (t, J=7.3 Hz, 3H), 1.10-1.25 (m, 2H), 1.35-1.50 (m, 2H), 2.47 (t, J=7.8 Hz, 2H), 3.92 (s, 3H), 5.15 (s, 1H), 7.05-7.10 (m, 2H), 7.22 (s, 1H), 7.34 (d, J=6.9 Hz, 2H), 7.40-7.50 (m, 1H), 7.50-7.56 (m, 2H), 8.08 (d, J=9.8 Hz, 1H). LCMS (ESI): m/z 307 (M+H)$^+$.

Step 6: 4-{[3-Butyl-6-(methyloxy)-2-phenyl-1-naphthalenyl]oxy}benzaldehyde (82)

3-Butyl-6-(methyloxy)-2-phenyl-1-naphthalenol (81) (0.25 g, 0.82 mmol) was treated with NaH in DMF followed by addition of 4-fluorobenzaldehyde to give 0.27 g (82%) of 82 as a light yellow oil. $^1$H NMR (400 MHz, $CDCl_3$): δ 0.77 (t, J=7.3 Hz, 3H), 1.10-1.25 (m, 2H), 1.40-1.50 (m, 2H), 2.55-2.60 (m, 2H), 3.94 (s, 3H), 6.68 (d, J=8.6 Hz, 2H), 7.05 (dd, $J_1$=9.1 Hz, $J_2$=2.4 Hz, 1H), 7.08-7.13 (m, 2H), 7.17 (d, J=2.6 Hz, 1H), 7.18-7.25 (m, 3H), 7.58-7.64 (m, 3H), 7.67 (d, J=9.1 Hz, 1H), 9.79 (s, 1H). LCMS (ESI): m/z 411 (M+H)$^+$.

Step 7: Ethyl (2E)-3-(4-{[3-butyl-6-(methyloxy)-2-phenyl-1-naphthalenyl]oxy}phenyl)-2-propenoate (83)

4-{[3-Butyl-6-(methyloxy)-2-phenyl-1-naphthalenyl]oxy}benzaldehyde (82) (0.27 g, 0.67 mmol) was treated with a mixture of triethylphosphonoacetate and nBuLi to give 0.30 g (94%) of the title compound (83) as a light yellow solid. $^1$H NMR (400 MHz, $CDCl_3$): δ 0.77 (t, J=7.4 Hz, 3H), 1.10-1.25 (m, 2H), 1.30 (t, J=7.1 Hz, 3H), 1.40-1.50 (m, 2H), 2.50-2.60 (m, 2H), 3.93 (s, 3H), 4.22 (q, J=7.1 Hz, 2H), 6.21 (d, J=15.9 Hz, 1H), 6.56 (d, J=8.8 Hz, 2H), 7.04 (dd, $J_1$=9.1 Hz, $J_2$=2.4 Hz, 1H), 7.08-7.15 (m, 2H), 7.16 (d, J=2.3 Hz, 1H), 7.18-7.25 (m, 5H), 7.53 (d, J=15.9 Hz, 1H), 7.57 (s, 1H), 7.70 (d, J=9.1 Hz, 1H). LCMS (ESI): m/z 481 (M+H)$^+$.

Step 8: (2E)-3-(4-{[3-Butyl-6-(methyloxy)-2-phenyl-1-naphthalenyl]oxy}phenyl)-2-propenoic acid (84)

Ethyl ester 83 (0.30 g, 0.62 mmol) was saponified with 1 N NaOH in THF and EtOH to give 0.24 g (86%) of the title compound (84) as a white solid. $^1$H NMR (400 MHz, $CDCl_3$): δ 0.77 (t, J=7.3 Hz, 3H), 1.10-1.28 (m, 2H), 1.40-1.50 (m, 2H), 2.50-2.60 (m, 2H), 3.93 (s, 3H), 6.22 (d, J=16.0 Hz, 1H), 6.58 (d, J=8.6 Hz, 2H), 7.04 (dd, $J_1$=9.1 Hz, $J_2$=2.4 Hz, 1H), 7.08-7.15 (m, 2H), 7.16 (d, J=2.4 Hz, 1H), 7.18-7.30 (m, 5H), 7.58 (s, 1H), 7.62 (d, J=15.9 Hz, 1H), 7.69 (d, J=9.2 Hz, 1H). LCMS (ESI): m/z 453 (M+H)$^+$, m/z 451 (M−H)$^-$.

Step 9: (2E)-3-{4-[(3-Butyl-6-hydroxy-2-phenyl-1-naphthalenyl)oxy]phenyl}-2-propenoic acid (85)

Methyl ether 84 (0.15 g, 0.33 mmol) was treated with $BBr_3$ in $CH_2Cl_2$ to give the crude product as a yellow viscous oil, which was purified by reverse phase preparation HPLC on Agilent 1100 to afford 95 mg (65%) of the title compound (85) as pale yellow solid. mp 128-130° C. $^1$H NMR (400 MHz, $CH_3OH-d_4$): δ 0.74 (t, J=7.3 Hz, 3H), 1.10-1.25 (m, 2H), 1.35-1.45 (m, 2H), 2.50-2.60 (m, 2H), 6.25 (d, J=16.1 Hz, 1H), 6.55 (d, J=8.6 Hz, 2H), 6.96 (dd, $J_1$=9.0 Hz, $J_2$=2.0 Hz, 1H), 7.08-7.18 (m, 3H), 7.18-7.28 (m, 3H), 7.33 (d, J=8.6 Hz, 2H), 7.46-7.58 (m, 2H), 7.59 (d, J=9.0 Hz, 1H). LCMS (ESI): m/z 439 (M+H)$^+$, m/z 437 (M−H)$^-$. Anal. Calc for $C_{29}H_{26}O_4 \cdot 0.4H_2O$: C, 78.15; H, 6.06. Found: C, 78.03; H, 6.00.

Example 15 (89)

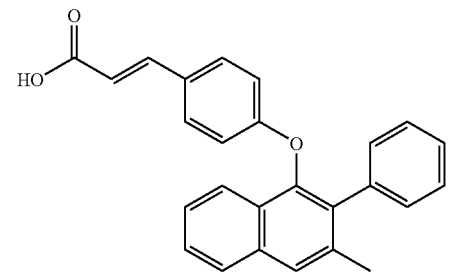

Step 1: 3-Methyl-2-phenyl-1-naphthalenol (86)

Methyl 2-bromobenzoate (1.0 g, 4.56 mmol) and methallylbenzene (0.62 g, 4.56 mmol) were dissolved in DMF (10 mL). Diisopropylethylamine (1.60 mL, 9.11 mmol) was added followed by addition of Pd(PPh$_3$)$_4$ (0.27 g, 0.23 mmol). The reaction mixture was heated to reflux and stirred overnight, cooled, poured into water (60 mL) and extracted with ether (2×75 mL). The combined ether extract was washed with water, brine, dried over Na$_2$SO$_4$, filtered, and the filtrate was concentrated to give the crude product as a brown oil. The crude product was purified by flash chromatography over SiO$_2$ with hexanes:EtOAc (50:1 to 40:1) to give 0.25 g (20%) of a mixture of methyl 2-(2-methyl-3-phenyl-1-propen-1-yl) benzoate and methyl 2-[2-(phenylmethyl)-2-propen-1-yl] benzoate ('mixture A') as a colorless oil. To THF (8 mL) at −78° C. was added LDA (2.0M in heptane/THF/ethylbenzene, 1.50 mL, 3.0 mmol). Then a solution of 'mixture A' (0.25 g, 0.96 mmol) in THF (10 mL) was added. The reaction mixture was stirred at −78° C. for 2 h, then allowed to warm up to room temperature and stirred at room temperature for 1 h. The mixture was quenched with saturated aqueous NH$_4$Cl and extracted with EtOAc. The combined organic extract was washed with brine, dried over Na$_2$SO$_4$, filtered, and the filtrate was concentrated to give the crude product as a brown oil. The crude product was purified by flash chromatography over SiO$_2$ with hexanes:EtOAc (40:1) to give 0.12 g (52%) of compound 86 as a colorless oil. $^1$H NMR (400 MHz, CDCl$_3$): δ 2.19 (s, 3H), 5.24 (s, 1H), 7.30-7.38 (m, 3H), 7.40-7.50 (m, 3H), 7.52-7.58 (m, 2H), 7.73 (d, J=7.9 Hz, 1H), 8.18 (d, J=8.3 Hz, 1H). LCMS (ESI): m/z 235 (M+H)$^+$.

Step 2: 4-[(3-Methyl-2-phenyl-1-naphthalenyl)oxy] benzaldehyde (87)

3-Methyl-2-phenyl-1-naphthalenol (86) (0.11 g, 0.48 mmol) was treated with NaH in DMF followed by addition of 4-fluorobenzaldehyde to give 0.12 g (70%) of the title compound (87) as a colorless viscous oil. $^1$H NMR (400 MHz, CDCl$_3$): δ 2.27 (s, 3H), 6.71 (d, J=8.8 Hz, 2H), 7.10-7.16 (m, 2H), 7.20-7.30 (m, 3H), 7.39 (t, J=7.4 Hz, 1H), 7.50 (t, J=7.2 Hz, 1H), 7.62 (d, J=8.6 Hz, 2H), 7.71 (s, 1H), 7.78 (d, J=8.2 Hz, 1H), 7.85 (d, J=8.2 Hz, 1H), 9.80 (s, 1H). LCMS (ESI): m/z 339 (M+H)$^+$.

Step 3: Ethyl (2E)-3-{4-[(3-methyl-2-phenyl-1-naphthalenyl)oxy]phenyl}-2 propenoate (88)

4-[(3-Methyl-2-phenyl-1-naphthalenyl)oxy]benzaldehyde (87) (112 mg, 0.33 mmol) was treated with a mixture of triethylphosphonoacetate and nBuLi to give 124 mg (92%) of the title compound (88) as a colorless viscous oil. $^1$H NMR (400 MHz, CDCl$_3$): δ 0.87 (t, J=6.9 Hz, 3H), 2.26 (s, 3H), 4.22 (q, J=7.2 Hz, 2H), 6.21 (d, J=15.9 Hz, 1H), 6.58 (d, J=8.8 Hz, 2H), 7.10-7.15 (m, 2H), 7.20-7.30 (m, 5H), 7.38 (t, J=7.1 Hz, 1H), 7.48 (t, J=7.5 Hz, 1H), 7.54 (d, J=16.0 Hz, 1H), 7.68 (s, 1H), 7.81 (d, J=8.4 Hz, 1H), 7.84 (d, J=8.3 Hz, 1H). LCMS (APCI): m/z 409 (M+H)$^+$.

Step 4: (2E)-3-{4-[(3-Methyl-2-phenyl-1-naphthalenyl)oxy]phenyl}-2-propenoic acid (89)

Ethyl ester 88 (123 mg, 0.30 mmol) was saponified with 1 N NaOH in THF and EtOH to give 90 mg (79%) of the title compound (89) as a white solid. mp 224-225° C. $^1$H NMR (400 MHz, CDCl$_3$): δ 2.26 (s, 3H), 6.22 (d, J=16.0 Hz, 1H), 6.61 (d, J=8.8 Hz, 2H), 7.10-7.16 (m, 2H), 7.20-7.30 (m, 5H), 7.38 (t, J=7.4 Hz, 1H), 7.49 (t, J=7.2 Hz, 1H), 7.62 (d, J=15.9 Hz, 1H), 7.68 (s, 1H), 7.80 (d, J=8.5 Hz, 1H), 7.84 (d, J=8.3 Hz, 1H). LCMS (ESI): m/z 381 (M+H)$^+$, m/z 379 (M−H)$^−$. Anal. Calc for C$_{26}$H$_{20}$O$_3$.0.33H$_2$O: C, 80.81; H, 5.39. Found: C, 80.73; H, 5.03.

Example 16 (101)

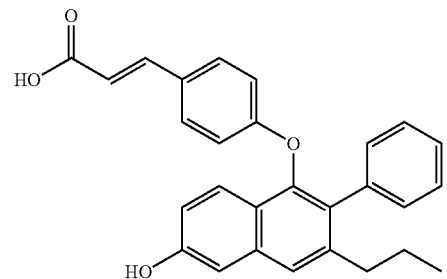

Step 1: 1-[3-(Methyloxy)phenyl]-2-pentanone (90)

Coupling of 3-methoxybenzyl bromide (5.0 g, 24.4 mmol) and butyryl chloride (2.65 g, 24.4 mmol) in DME with Pd(PPh$_3$)$_2$Cl$_2$ and Zn gave the crude product as a brown oil. The crude product was purified by flash chromatography over SiO$_2$ eluted with a gradient from hexanes to 20% EtOAc in hexanes to give 2.49 g (53%) of the title compound (90) as a colorless oil. $^1$H NMR (400 MHz, CDCl$_3$): δ 0.86 (t, J=7.4 Hz, 3H), 1.50-1.65 (m, 2H), 2.42 (t, J=7.2 Hz, 2H), 3.63 (s, 2H), 3.79 (s, 3H), 6.74 (d, J=1.8 Hz, 1H), 6.75-6.85 (m, 2H), 7.22 (d, J=7.9 Hz, 1H).

Step 2: Ethyl 3-{[3-(methyloxy)phenyl]methyl}hexanoate (91)

Peterson olefination of 1-[3-(methyloxy)phenyl]-2-pentanone (90) (2.49 g, 13.0 mmol) with ethyl (trimethylsilyl)acetate (4.20 g, 25.9 mmol) in the presence of dicyclohexylamine and nBuLi gave the α,β-unsaturated ester, which was purified and hydrogenated at room temperature with 10% Pd/C under a hydrogen balloon to yield 3.12 g (91% from the ketone) of the title compound (91) as a colorless oil. $^1$H NMR (400 MHz, CDCl$_3$): δ 0.87 (t, J=7.0 Hz, 3H), 1.23 (t, J=7.2 Hz, 3H), 1.25-1.40 (m, 4H), 2.10-2.25 (m, 3H), 2.45-2.55 (m, 1H), 2.60-2.70 (m, 1H), 3.79 (s, 3H), 4.09 (q, J=7.2 Hz, 2H), 6.70-6.80 (m, 3H), 7.18 (d, J=7.5 Hz, 1H).

Step 3: 3-{[3-(Methyloxy)phenyl]methyl}hexanoic acid (92)

Ethyl ester 91 (3.12 g, 11.8 mmol) was saponified with 1 N NaOH in THF and EtOH to give 2.76 g (99%) of the title compound (92) as a yellow oil. $^1$H NMR (400 MHz, CDCl$_3$): δ 0.87 (t, J=6.8 Hz, 3H), 1.25-1.45 (m, 4H), 2.10-2.22 (m, 1H), 2.25-2.30 (m, 2H), 2.50-2.60 (m, 1H), 2.65-2.75 (m, 1H), 3.79 (s, 3H), 6.70-6.80 (m, 3H), 7.19 (d, J=7.8 Hz, 1H).

Step 4: 6-(Methyloxy)-3-propyl-3,4-dihydro-1(2H)-naphthalenone (93)

3-{[3-(Methyloxy)phenyl]methyl}hexanoic acid (92) (2.76 g, 11.7 mmol) was treated with oxalyl chloride followed by AlCl$_3$ in CH$_2$Cl$_2$ to give 2.10 g (82%) of compound 93 as a light yellow solid. $^1$H NMR (400 MHz, CDCl$_3$): δ 0.90-1.00 (m, 3H), 1.35-1.50 (m, 4H), 2.10-2.35 (m, 2H), 2.60-2.75 (m, 2H), 2.90-3.00 (m, 1H), 3.85 (s, 3H), 6.65-6.70 (m, 1H), 6.82 (dd, $J_1$=8.7 Hz, $J_2$=1.4 Hz, 1H), 7.98 (d, J=8.8 Hz, 1H). LCMS (ESI): m/z 219 (M+H)$^+$.

Step 5: 2-Bromo-6-(methyloxy)-3-propyl-1-naphthalenol (94)

Treatment of 6-(methyloxy)-3-propyl-3,4-dihydro-1(2H)-naphthalenone (93) (0.50 g, 2.29 mmol) with bromine followed by DBU in CH$_3$CN gave 0.62 g of compound 94 as an off-white solid. $^1$H NMR (400 MHz, CDCl$_3$): δ 1.01 (t, J=7.4 Hz, 3H), 1.65-1.75 (m, 2H), 2.79 (t, J=7.7 Hz, 2H), 3.90 (s, 3H), 6.06 (s, 1H), 7.00 (d, J=2.4 Hz, 1H), 7.08 (dd, $J_1$=9.1 Hz, $J_2$=2.4 Hz, 1H), 7.17 (s, 1H), 8.07 (d, J=9.1 Hz, 1H). LCMS (ESI): m/z 295 (M+H)$^+$, m/z 293 (M−H)$^−$.

Step 6: 2-Bromo-6-(methyloxy)-1-{[(methyloxy)methyl]oxy}-3-propylnaphthalene (95)

2-Bromo-6-(methyloxy)-3-propyl-1-naphthalenol (94) (0.62 g, 2.10 mmol) was treated with chloromethyl methyl ether in the presence of diisopropylethylamine in THF to give 0.66 g (92%) of the title compound (95) as a light yellow oil. $^1$H NMR (400 MHz, CDCl$_3$): δ 1.02 (t, J=7.3 Hz, 3H), 1.65-1.75 (m, 2H), 2.84 (t, J=7.7 Hz, 2H), 3.72 (s, 3H), 3.90 (s, 3H), 5.23 (s, 2H), 7.04 (d, J=2.6 Hz, 1H), 7.12 (dd, $J_1$=9.3 Hz, $J_2$=2.5 Hz, 1H), 7.38 (s, 1H), 8.03 (d, J=9.1 Hz, 1H). LCMS (ESI): m/z 361 (M+Na)$^+$, m/z 337 (M−H)$^−$.

Step 7: 6-(Methyloxy)-1-{[(methyloxy)methyl]oxy}-2-phenyl-3-propylnaphthalene (96)

Suzuki coupling of 2-bromo-6-(methyloxy)-1-{[(methyloxy)methyl]oxy}-3-propylnaphthal (95) (0.66 g, 1.93 mmol) with phenyl boronic acid (0.49 g, 3.86 mmol) in the presence of Pd(PPh$_3$)$_4$ in DME using a sealed tube at 160° C. gave 0.65 g (~100%) of the title compound (96) as a colorless oil. $^1$H NMR (400 MHz, CDCl$_3$): δ 0.79 (t, J=7.4 Hz, 3H), 1.40-1.55 (m, 2H), 2.52 (t, J=7.8 Hz, 2H), 3.07 (s, 3H), 3.93 (s, 3H), 4.71 (s, 2H), 7.08-7.14 (m, 2H), 7.30-7.38 (m, 3H), 7.39-7.46 (m, 3H), 8.03 (d, J=8.8 Hz, 1H). LCMS (ESI): m/z 337 (M+H)$^+$.

Step 8: 6-(Methyloxy)-2-phenyl-3-propyl-1-naphthalenol (97)

6-(Methyloxy)-1-{[(methyloxy)methyl]oxy}-2-phenyl-3-propylnaphthalene (96) (0.65 g, 1.92 mmol) was treated with 4 M HCl in dioxane at room temperature to give 0.54 g (97%) of compound 97 as a light yellow oil. $^1$H NMR (400 MHz, CDCl$_3$): δ 0.79 (t, J=7.3 Hz, 3H), 1.40-1.55 (m, 2H), 2.45 (t, J=7.7 Hz, 2H), 3.92 (s, 3H), 5.15 (s, 1H), 7.05-7.10 (m, 2H), 7.22 (s, 1H), 7.35 (d, J=7.3 Hz, 2H), 7.42-7.48 (m, 1H), 7.49-7.56 (m, 2H), 8.08 (d, J=9.5 Hz, 1H). LCMS (ESI): m/z 293 (M+H)$^+$, m/z 291 (M−H)$^−$.

Step 9: 4-{[6-(Methyloxy)-2-phenyl-3-propyl-1-naphthalenyl]oxy}benzaldehyde (98)

6-(Methyloxy)-2-phenyl-3-propyl-1-naphthalenol (97) (0.54 g, 1.86 mmol) was treated with NaH in DMF followed by addition of 4-fluorobenzaldehyde to give 0.66 g (89%) of the title compound (98) as a light yellow foam. $^1$H NMR (400 MHz, CDCl$_3$): δ 0.81 (t, J=7.3 Hz, 3H), 1.40-1.55 (m, 2H), 2.53 (t, J=7.7 Hz, 2H), 3.94 (s, 3H), 6.67 (d, J=8.7 Hz, 2H), 7.05 (dd, $J_1$=9.0 Hz, $J_2$=2.5 Hz, 1H), 7.08-7.14 (m, 2H), 7.18 (d, J=2.5 Hz, 1H), 7.19-7.25 (m, 3H), 7.58-7.64 (m, 3H), 7.67 (d, J=9.2 Hz, 1H), 9.79 (s, 1H). LCMS (ESI): m/z 397 (M+H)$^+$.

Step 10: Ethyl (2E)-3-(4-{[6-(methyloxy)-2-phenyl-3-propyl-1-naphthalenyl]oxy}phenyl)-2-propenoate (99)

4-{[6-(Methyloxy)-2-phenyl-3-propyl-1-naphthalenyl]oxy}benzaldehyde (98) (0.66 g, 1.66 mmol) was treated with a mixture of triethylphosphonoacetate and nBuLi to give 0.70 g (91%) of the title compound (99) as a light yellow viscous oil. $^1$H NMR (400 MHz, CDCl$_3$): δ 0.81 (t, J=7.3 Hz, 3H), 1.30 (t, J=7.1 Hz, 3H), 1.45-1.55 (m, 2H), 2.52 (t, J=7.7 Hz, 2H), 3.93 (s, 3H), 4.22 (q, J=7.1 Hz, 2H), 6.21 (d, J=16.1 Hz, 1H), 6.56 (d, J=8.4 Hz, 2H), 7.04 (dd, $J_1$=9.2 Hz, $J_2$=2.4 Hz, 1H), 7.08-7.14 (m, 2H), 7.16 (d, J=2.4 Hz, 1H), 7.19-7.25 (m, 5H), 7.53 (s, 1H), 7.57 (d, J=15.9 Hz, 1H), 7.70 (d, J=9.2 Hz, 1H). LCMS (APCI): m/z 467 (M+H)$^+$.

Step 11: (2E)-3-(4-{[6-(Methyloxy)-2-phenyl-3-propyl-1-naphthalenyl]oxy}phenyl)-2-propenoic acid (100)

Ethyl ester (99) (0.70 g, 1.50 mmol) was saponified with 1 N NaOH in THF and EtOH to give 0.59 g (90%) of the title compound (100) as a white solid. $^1$H NMR (400 MHz, CDCl$_3$): δ 0.81 (t, J=7.3 Hz, 3H), 1.45-1.55 (m, 2H), 2.53 (t, J=7.7 Hz, 2H), 3.93 (s, 3H), 6.22 (d, J=16.0 Hz, 1H), 6.57 (d, J=8.6 Hz, 2H), 7.04 (dd, $J_1$=9.1 Hz, $J_2$=2.4 Hz, 1H), 7.08-7.14 (m, 2H), 7.16 (d, J=2.4 Hz, 1H), 7.19-7.30 (m, 5H), 7.57 (s, 1H), 7.62 (d, J=15.9 Hz, 1H), 7.69 (d, J=9.2 Hz, 1H). LCMS (APCI): m/z 439 (M+H)$^+$, m/z 437 (M−H)$^−$.

Step 12: (2E)-3-{4-[(6-Hydroxy-2-phenyl-3-propyl-1-naphthalenyl)oxy]phenyl}-2-propenoic acid (101)

Methyl ether (100) (0.15 g, 0.34 mmol) was treated with BBr$_3$ in CH$_2$Cl$_2$ to give the crude product as a yellow viscous oil, which was purified by reverse phase preparation HPLC on Agilent 1100 to afford 96 mg (66%) of the title compound (101) as pale yellow solid. mp 120-122° C. $^1$H NMR (400 MHz, CH$_3$OH-d$_4$): δ 0.77 (t, J=7.4 Hz, 3H), 1.45-1.55 (m, 2H), 2.52 (t, J=7.8 Hz, 2H), 6.25 (d, J=15.9 Hz, 1H), 6.55 (d, J=8.7 Hz, 2H), 6.96 (dd, $J_1$=9.0 Hz, $J_2$=2.4 Hz, 1H), 7.10-7.16 (m, 3H), 7.18-7.27 (m, 3H), 7.34 (d, J=8.8 Hz, 2H), 7.48-7.56 (m, 2H), 7.69 (d, J=9.0 Hz, 1H). LCMS (ESI): m/z 425 (M+H)$^+$, m/z 423 (M−H)$^−$. Anal. Calc for C$_{28}$H$_{24}$O$_4$·0.33H$_2$O: C, 78.12; H, 5.78. Found: C, 77.97; H, 5.58.

Example 17 (109)

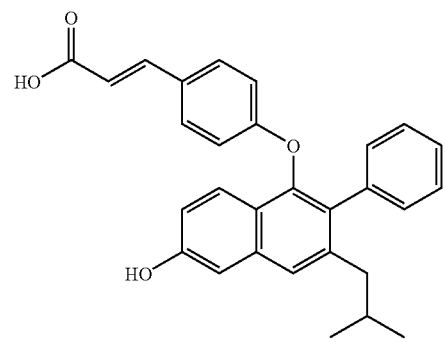

Step 1: Methyl 4-(methyloxy)-2-(4-methyl-1-pentyn-1-yl)benzoate (102)

Coupling of methyl 4-(methyloxy)-2-{[(trifluoromethyl)sulfonyl]oxy}benzoate (77) (1.0 g, 3.18 mmol) with 4-methyl pentyne (0.78 mL, 6.36 mmol) using Pd(PPh₃)₂Cl₂ and CuI gave 0.77 g (98%) of compound 102 as a brown oil. $^1$H NMR (400 MHz, CDCl₃): δ 1.06 (d, J=6.8 Hz, 6H), 1.90-2.00 (m, 1H), 2.37 (d, J=6.4 Hz, 2H), 3.83 (s, 3H), 3.87 (s, 3H), 6.82 (dd, J₁=8.8 Hz, J₂=2.8 Hz, 1H), 7.00 (d, J=2.7 Hz, 1H), 7.88 (d, J=8.8 Hz, 1H). LCMS (ESI): m/z 247 (M+H)⁺.

Step 2: N-Methyl-N,4-bis(methyloxy)-2-(4-methyl-1-pentyn-1-yl)benzamide (103)

Treatment of methyl 4-(methyloxy)-2-(4-methyl-1-pentyn-1-yl)benzoate (102) (0.76 g, 3.09 mmol) with a mixture of N,O-dimethylhydroxylamine hydrochloride and nBuLi gave 0.72 g (85%) of the title compound (103) as a yellow oil. $^1$H NMR (400 MHz, CDCl₃): δ 1.02 (d, J=6.6 Hz, 6H), 1.80-1.95 (m, 1H), 2.28 (d, J=6.6 Hz, 2H), 3.28 (br s, 3H), 3.59 (br s, 3H), 3.80 (s, 3H), 6.84 (dd, J₁=8.6 Hz, J₂=2.5 Hz, 1H), 6.94 (d, J=2.6 Hz, 1H), 7.24 (d, J=8.6 Hz, 1H). LCMS (ESI): m/z 276 (M+H)⁺.

Step 3: 1-[4-(Methyloxy)-2-(4-methyl-1-pentyn-1-yl)phenyl]-2-phenylethanone (104)

N-Methyl-N,4-bis(methyloxy)-2-(4-methyl-1-pentyn-1-yl)benzamide (103) (0.72 g, 2.62 mmol) was treated with benzylmagnesium chloride in THF to give 0.73 g (91%) of the title compound (104) as a light yellow oil. $^1$H NMR (400 MHz, CDCl₃): δ 1.04 (d, J=6.6 Hz, 6H), 1.85-2.00 (m, 1H), 2.35 (d, J=6.6 Hz, 2H), 3.83 (s, 3H), 4.44 (s, 2H), 6.82 (dd, J₁=8.8 Hz, J₂=2.5 Hz, 1H), 6.98 (d, J=2.5 Hz, 1H), 7.19-7.25 (m, 3H), 7.26-7.32 (m, 2H), 7.65 (d, J=8.8 Hz, 1H). LCMS (APCI): m/z 307 (M+H)⁺.

Step 4: 6-(Methyloxy)-3-(2-methylpropyl)-2-phenyl-1-naphthalenol (105)

A solution of 1-[4-(methyloxy)-2-(4-methyl-1-pentyn-1-yl)phenyl]-2-phenylethanone (104) (0.73 g, 2.39 mmol) in toluene was treated with a KHMDS solution in toluene to give 0.66 g (91%) of the title compound (105) as a light yellow viscous oil. $^1$H NMR (400 MHz, CDCl₃): δ 0.73 (d, J=6.8 Hz, 6H), 1.55-1.70 (m, 1H), 2.38 (d, J=7.1 Hz, 2H), 3.93 (s, 3H), 5.15 (s, 1H), 7.05-7.10 (m, 2H), 7.18 (s, 1H), 7.30-7.36 (m, 2H), 7.42-7.48 (m, 1H), 7.49-7.55 (m, 2H), 8.08 (d, J=8.8 Hz, 1H). LCMS (APCI): m/z 307 (M+H)⁺.

Step 5: 4-{[6-(Methyloxy)-3-(2-methylpropyl)-2-phenyl-1-naphthalenyl]oxy}benzaldehyde (106)

6-(Methyloxy)-3-(2-methylpropyl)-2-phenyl-1-naphthalenol (105) (0.66 g, 2.16 mmol) was treated with NaH in DMF followed by addition of 4-fluorobenzaldehyde to give 0.74 g (83%) of the title compound (106) as a light yellow foam. $^1$H NMR (400 MHz, CDCl₃): δ 0.75 (d, J=6.8 Hz, 6H), 1.60-1.70 (m, 1H), 2.47 (d, J=7.1 Hz, 2H), 3.94 (s, 3H), 6.67 (d, J=8.8 Hz, 2H), 7.05 (dd, J₁=9.1 Hz, J₂=2.4 Hz, 1H), 7.07-7.12 (m, 2H), 7.15-7.25 (m, 4H), 7.56 (s, 1H), 7.61 (d, J=8.6 Hz, 2H), 7.67 (d, J=9.1 Hz, 1H), 9.79 (s, 1H). LCMS (ESI): m/z 411 (M+H)⁺.

Step 6: Ethyl (2E)-3-(4-{[6-(methyloxy)-3-(2-methylpropyl)-2-phenyl-1-naphthalenyl]oxy}phenyl)-2-propenoate (107)

4-{[6-(Methyloxy)-3-(2-methylpropyl)-2-phenyl-1-naphthalenyl]oxy}benzaldehyde (106) (0.74 g, 1.79 mmol) was treated with a mixture of triethylphosphonoacetate and nBuLi to give 0.82 g (95%) of the title compound (107) as a yellow viscous oil. $^1$H NMR (400 MHz, CDCl₃): δ 0.74 (d, J=6.6 Hz, 6H), 1.30 (t, J=7.1 Hz, 3H), 1.60-1.70 (m, 1H), 2.46 (d, J=7.1 Hz, 2H), 3.93 (s, 3H), 4.22 (q, J=7.1 Hz, 2H), 6.21 (d, J=16.0 Hz, 1H), 6.55 (d, J=8.8 Hz, 2H), 7.04 (dd, J₁=9.2 Hz, J₂=2.4 Hz, 1H), 7.06-7.12 (m, 2H), 7.16 (d, J=2.4 Hz, 1H), 7.18-7.25 (m, 5H), 7.53 (d, J=16.0 Hz, 1H), 7.54 (s, 1H), 7.70 (d, J=9.2 Hz, 1H). LCMS (ESI): m/z 481 (M+H)⁺.

Step 7: (2E)-3-(4-{[6-(Methyloxy)-3-(2-methylpropyl)-2-phenyl-1-naphthalenyl]oxy}phenyl)-2-propenoic acid (108)

Ethyl ester (107) (0.82 g, 1.70 mmol) was saponified with 1 N NaOH in THF and EtOH to give 0.77 g (~100%) of the title compound (108) as an off-white foam. $^1$H NMR (400 MHz, CDCl₃): δ 0.75 (d, J=6.4 Hz, 6H), 1.60-1.70 (m, 1H), 2.46 (d, J=7.1 Hz, 2H), 3.93 (s, 3H), 6.22 (d, J=15.9 Hz, 1H), 6.57 (d, J=8.6 Hz, 2H), 7.04 (dd, J₁=9.2 Hz, J₂=2.2 Hz, 1H), 7.06-7.14 (m, 2H), 7.16 (d, J=2.2 Hz, 1H), 7.18-7.25 (m, 5H), 7.54 (s, 1H), 7.63 (d, J=16.0 Hz, 1H), 7.70 (d, J=9.2 Hz, 1H). LCMS (ESI): m/z 453 (M+H)⁺, m/z 451 (M−H)⁻.

Step 8: (2E)-3-(4-{[6-Hydroxy-3-(2-methylpropyl)-2-phenyl-1-naphthalenyl]oxy}phenyl)-2-propenoic acid (109)

Methyl ether (108) (0.15 g, 0.33 mmol) was treated with BBr₃ in CH₂Cl₂ to give the crude product as a yellow viscous oil, which was purified by reverse phase preparation HPLC on Agilent 1100 to afford 99 mg (68%) of the title compound (109) as pale yellow solid. mp 126-128° C. $^1$H NMR (400 MHz, CH₃OH-d₄): δ 0.72 (d, J=6.6 Hz, 6H), 1.55-1.65 (m, 1H), 2.47 (d, J=7.1 Hz, 2H), 6.26 (d, J=15.9 Hz, 1H), 6.55 (d, J=8.8 Hz, 2H), 6.96 (dd, J₁=9.1 Hz, J₂=2.4 Hz, 1H), 7.10-7.16 (m, 3H), 7.17-7.27 (m, 3H), 7.34 (d, J=8.8 Hz, 2H), 7.47 (s, 1H), 7.51 (d, J=15.9 Hz, 1H), 7.60 (d, J=9.0 Hz, 1H). LCMS (ESI): m/z 439 (M+H)⁺, m/z 437 (M−H)⁻. Anal. Calc for C₂₉H₂₆O₄·0.25H₂O: C, 78.62; H, 6.03. Found: C, 78.45; H, 5.96.

Example 18 (117)

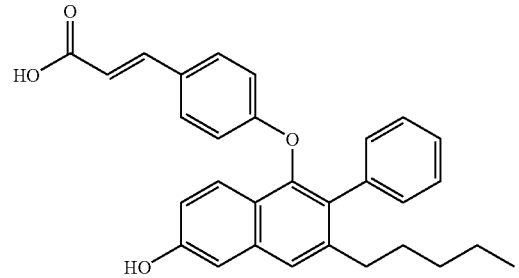

Step 1: Methyl 2-(1-heptyn-1-yl)-4-(methyloxy)benzoate (110)

Coupling of methyl 4-(methyloxy)-2-{[(trifluoromethyl)sulfonyl]oxy}benzoate (77) (0.80 g, 2.55 mmol) with 1-heptyne (0.70 mL, 5.10 mmol) using Pd(PPh₃)₂Cl₂ and CuI gave 0.67 g (~100%) of compound 110 as a brown oil. $^1$H NMR (400 MHz, CDCl₃): δ 0.92 (t, J=7.3 Hz, 3H), 1.30-1.50 (m, 4H), 1.60-1.70 (m, 2H), 2.47 (t, J=7.2 Hz, 2H), 3.83 (s, 3H), 3.87 (s, 3H), 6.82 (dd, $J_1$=8.9 Hz, $J_2$=2.7 Hz, 1H), 6.99 (d, J=2.7 Hz, 1H), 7.89 (d, J=8.8 Hz, 1H).

Step 2: 2-(1-Heptyn-1-yl)-N-methyl-N,4-bis(methyloxy)benzamide (111)

Treatment of methyl 2-(1-heptyn-1-yl)-4-(methyloxy) benzoate (110) (0.67 g, 2.57 mmol) with a mixture of N,O-dimethylhydroxylamine hydrochloride and nBuLi gave 0.58 g (78%) of the title compound (111) as a yellow oil. $^1$H NMR (300 MHz, CDCl$_3$): δ 0.93 (t, J=7.0 Hz, 3H), 1.30-1.50 (m, 4H), 1.60-1.70 (m, 2H), 2.41 (t, J=7.1 Hz, 2H), 3.31 (br s, 3H), 3.64 (br s, 3H), 3.83 (s, 3H), 6.86 (dd, $J_1$=8.5 Hz, $J_2$=2.5 Hz, 1H), 6.96 (d, J=2.6 Hz, 1H), 7.27 (d, J=8.6 Hz, 1H). LCMS (ESI): m/z 290 (M+H)$^+$.

Step 3: 1-[2-(1-Heptyn-1-yl)-4-(methyloxy)phenyl]-2-phenylethanone (112)

2-(1-Heptyn-1-yl)-N-methyl-N,4-bis(methyloxy)benzamide (111) (0.58 g, 2.00 mmol) was treated with benzylmagnesium chloride in THF to give 0.57 g (89%) of the title compound (112) as a light yellow oil. $^1$H NMR (400 MHz, CDCl$_3$): δ 0.89 (t, J=7.2 Hz, 3H), 1.30-1.50 (m, 4H), 1.60-1.70 (m, 2H), 2.45 (t, J=7.2 Hz, 2H), 3.83 (s, 3H), 4.44 (s, 2H), 6.82 (dd, $J_1$=8.8 Hz, $J_2$=2.8 Hz, 1H), 6.97 (d, J=2.7 Hz, 1H), 7.19-7.26 (m, 3H), 7.27-7.32 (m, 2H), 7.65 (d, J=8.8 Hz, 1H). LCMS (ESI): m/z 321 (M+H)$^+$, m/z 319 (M−H)$^-$.

Step 4: 6-(Methyloxy)-3-pentyl-2-phenyl-1-naphthalenol (113)

A solution of 1-[2-(1-heptyn-1-yl)-4-(methyloxy)phenyl]-2-phenylethanone (112) (0.57 g, 1.78 mmol) in toluene was treated with a KHMDS solution in toluene to give 0.42 g (74%) of compound 113 as a light brown viscous oil. $^1$H NMR (400 MHz, CDCl$_3$): δ 0.78 (t, J=6.9 Hz, 3H), 1.10-1.25 (m, 4H), 1.35-1.50 (m, 2H), 2.47 (t, J=7.9 Hz, 2H), 3.93 (s, 3H), 5.16 (s, 1H), 7.06-7.12 (m, 2H), 7.23 (s, 1H), 7.32-7.38 (m, 2H), 7.43-7.49 (m, 1H), 7.50-7.56 (m, 2H), 8.08 (d, J=10.0 Hz, 1H). LCMS (ESI): m/z 321 (M+H)$^+$, m/z 319 (M−H)$^-$.

Step 5: 4-{[6-(Methyloxy)-3-pentyl-2-phenyl-1-naphthalenyl]oxy}benzaldehyde (114)

6-(Methyloxy)-3-pentyl-2-phenyl-1-naphthalenol (113) (0.41 g, 1.28 mmol) and 4-fluorobenzaldehyde was heated with Cs$_2$CO$_3$ in DMF at 100° C. to give 0.44 g (80%) of the title compound (114) as a light yellow oil. $^1$H NMR (400 MHz, CDCl$_3$): δ 0.78 (t, J=6.8 Hz, 3H), 1.10-1.25 (m, 4H), 1.40-1.55 (m, 2H), 2.47 (t, J=7.9 Hz, 2H), 3.94 (s, 3H), 6.68 (d, J=8.6 Hz, 2H), 7.05 (dd, $J_1$=9.1 Hz, $J_2$=2.4 Hz, 1H), 7.08-7.14 (m, 2H), 7.18 (d, J=2.4 Hz, 1H), 7.19-7.25 (m, 3H), 7.58-7.64 (m, 3H), 7.67 (d, J=9.1 Hz, 1H), 9.79 (s, 1H). LCMS (ESI): m/z 425 (M+H)$^+$.

Step 6: Ethyl (2E)-3-(4-{[6-(methyloxy)-3-pentyl-2-phenyl-1-naphthalenyl]oxy}phenyl)-2-propenoate (115)

4-{[6-(Methyloxy)-3-pentyl-2-phenyl-1-naphthalenyl]oxy}benzaldehyde (114) (0.44 g, 1.02 mmol) was treated with a mixture of triethylphosphonoacetate and nBuLi to give 0.48 g (95%) of compound 115 as a light yellow viscous oil, which solidified upon standing. $^1$H NMR (400 MHz, CDCl$_3$): δ 0.78 (t, J=6.8 Hz, 3H), 1.10-1.25 (m, 4H), 1.30 (t, J=7.1 Hz, 3H), 1.40-1.55 (m, 2H), 2.53 (t, J=7.8 Hz, 2H), 3.93 (s, 3H), 4.22 (q, J=7.1 Hz, 2H), 6.21 (d, J=15.9 Hz, 1H), 6.56 (d, J=8.8 Hz, 2H), 7.04 (dd, $J_1$=9.1 Hz, $J_2$=2.4 Hz, 1H), 7.08-7.14 (m, 2H), 7.16 (d, J=2.4 Hz, 1H), 7.19-7.25 (m, 5H), 7.53 (d, J=16.1 Hz, 1H), 7.57 (s, 1H), 7.70 (d, J=9.1 Hz, 1H). LCMS (ESI): m/z 495 (M+H)$^+$.

Step 7: (2E)-3-(4-{[6-(Methyloxy)-3-pentyl-2-phenyl-1-naphthalenyl]oxy}phenyl)-2-propenoic acid (116)

Ethyl ester (115) (0.48 g, 0.97 mmol) was saponified with 1 N NaOH in THF and EtOH to give 0.42 g (93%) of the title compound (116) as a white solid. $^1$H NMR (400 MHz, CDCl$_3$): δ 0.78 (t, J=6.8 Hz, 3H), 1.10-1.25 (m, 4H), 1.40-1.55 (m, 2H), 2.53 (t, J=7.8 Hz, 2H), 3.93 (s, 3H), 6.22 (d, J=16.0 Hz, 1H), 6.58 (d, J=8.8 Hz, 2H), 7.04 (dd, $J_1$=9.1 Hz, $J_2$=2.4 Hz, 1H), 7.08-7.14 (m, 2H), 7.16 (d, J=2.4 Hz, 1H), 7.19-7.30 (m, 5H), 7.58 (s, 1H), 7.62 (d, J=15.9 Hz, 1H), 7.69 (d, J=9.2 Hz, 1H). LCMS (ESI): m/z 467 (M+H)$^+$, m/z 465 (M−H)$^-$.

Step 8: (2E)-3-{4-[(6-Hydroxy-3-pentyl-2-phenyl-1-naphthalenyl)oxy]phenyl}-2-propenoic acid (117)

Methyl ether (116) (0.15 g, 0.32 mmol) was treated with BBr$_3$ in CH$_2$Cl$_2$ to give the crude product as orange viscous oil, which was purified by reverse phase preparation HPLC on Agilent 1100 to afford 79 mg (54%) of the title compound (117) as a light yellow solid. mp 110-113° C. $^1$H NMR (400 MHz, CH$_3$OH-d$_4$): δ 0.77 (t, J=6.8 Hz, 3H), 1.05-1.20 (m, 4H), 1.35-1.50 (m, 2H), 2.54 (t, J=7.8 Hz, 2H), 6.25 (d, J=16.0 Hz, 1H), 6.55 (d, J=8.8 Hz, 2H), 6.96 (dd, $J_1$=9.0 Hz, $J_2$=2.2 Hz, 1H), 7.08-7.15 (m, 3H), 7.17-7.27 (m, 3H), 7.33 (d, J=8.8 Hz, 2H), 7.48-7.57 (m, 2H), 7.59 (d, J=9.2 Hz, 1H). LCMS (ESI): m/z 451 (M−H)$^-$. Anal. Calc for C$_{30}$H$_{28}$O$_4$·0.25H$_2$O: C, 78.84; H, 6.29. Found: C, 78.80; H, 6.14.

Example 19 (129)

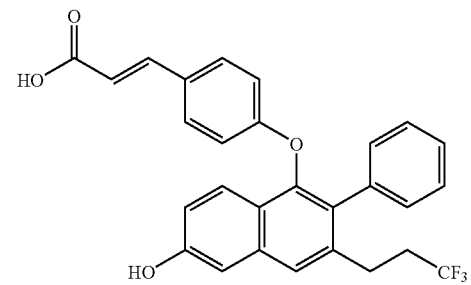

Step 1: 5,5,5-Trifluoro-1-[3-(methyloxy)phenyl]-2-pentanone (118)

Coupling of 3-methoxybenzyl bromide (2.5 g, 12.2 mmol) and 4,4,4-trifluorobutyryl chloride (1.96 g, 12.2 mmol) in DME with Pd(PPh$_3$)$_2$Cl$_2$ and Zn gave the crude product as a brown oil. The crude product was purified by flash chromatography over SiO$_2$ with hexanes:EtOAc (20:1) to give 1.75 g (58%) of the title compound (118) as a colorless glass-like solid. $^1$H NMR (400 MHz, CDCl$_3$): δ 2.30-2.45 (m, 2H), 2.65-2.75 (m, 2H), 3.69 (s, 2H), 3.80 (s, 3H), 6.70-6.75 (m, 1H), 6.78 (d, J=7.5 Hz, 1H), 6.82 (dd, J$_1$=8.2 Hz, J$_2$=2.4 Hz, 1H), 7.26 (t, J=8.0 Hz, 1H).

Step 2: Ethyl 6,6,6-trifluoro-3-{[3-(methyloxy)phenyl]methyl}hexanoate (119)

Peterson olefination of 5,5,5-trifluoro-1-[3-(methyloxy)phenyl]-2-pentanone (118) (1.75 g, 7.11 mmol) with ethyl (trimethylsilyl)acetate (2.30 g, 14.2 mmol) in the presence of dicyclohexylamine and nBuLi gave the α,β-unsaturated ester, which was purified and hydrogenated at room temperature with 10% Pd/C under a hydrogen balloon to yield 1.75 g (78% from the ketone) of the title compound (119) as a colorless oil. $^1$H NMR (400 MHz, CDCl$_3$): δ 1.24 (t, J=7.2 Hz, 3H), 1.55-1.65 (m, 2H), 2.00-2.35 (m, 5H), 2.55-2.65 (m, 2H), 3.79 (s, 3H), 4.11 (q, J=7.2 Hz, 2H), 6.70-6.73 (m, 1H), 6.74-6.80 (m, 2H), 7.20 (t, J=7.9 Hz, 1H).

Step 3: 6,6,6-Trifluoro-3-{[3-(methyloxy)phenyl]methyl}hexanoic acid (120)

Ethyl ester (119) (1.75 g, 5.50 mmol) was saponified with 1 N NaOH in THF and EtOH to give 1.56 g (98%) of the title compound (120) as a yellow oil. $^1$H NMR (400 MHz, CDCl$_3$): δ 1.60-1.70 (m, 2H), 2.05-2.40 (m, 5H), 2.55-2.70 (m, 2H), 3.80 (s, 3H), 6.70-6.74 (m, 1H), 6.74-6.80 (m, 2H), 7.21 (t, J=7.9 Hz, 1H).

Step 4: 6-(Methyloxy)-3-(3,3,3-trifluoropropyl)-3,4-dihydro-1(2H)-naphthalenone (121)

6,6,6-Trifluoro-3-{[3-(methyloxy)phenyl]methyl}hexanoic acid (120) (1.56 g, 5.38 mmol) was treated with oxalyl chloride followed by AlCl$_3$ in CH$_2$Cl to give 1.07 g (73%) of the title compound (121) as pale yellow solid. $^1$H NMR (400 MHz, CDCl$_3$): δ 1.65-1.75 (m, 2H), 2.10-2.35 (m, 4H), 2.65-2.80 (m, 2H), 2.90-3.05 (m, 1H), 3.85 (s, 3H), 6.70 (d, J=2.4 Hz, 1H), 6.84 (dd, J$_1$=8.8 Hz, J$_2$=2.5 Hz, 1H), 7.99 (d, J=8.8 Hz, 1H). LCMS (ESI): m/z 273 (M+H)$^+$.

Step 5: 2-Bromo-6-(methyloxy)-3-(3,3,3-trifluoropropyl)-1-naphthalenol (122)

Treatment of 6-(methyloxy)-3-(3,3,3-trifluoropropyl)-3,4-dihydro-1(2H-naphthalenone (121) (0.40 g, 1.47 mmol) with bromine followed by DBU in CH$_3$CN gave 0.47 g (92% from tetralone) of the title compound (122) as a white solid. $^1$H NMR (400 MHz, CDCl$_3$): δ 2.40-2.55 (m, 2H), 3.05-3.10 (m, 2H), 3.91 (s, 3H), 6.06 (s, 1H), 7.02 (d, J=2.5 Hz, 1H), 7.12 (dd, J$_1$=9.1 Hz, J$_2$=2.5 Hz, 1H), 7.20 (s, 1H), 8.10 (d, J=9.1 Hz, 1H). LCMS (ESI): m/z 347 (M−H)$^-$.

Step 6: 2-Bromo-6-(methyloxy)-1-{[(methyloxy)methyl]oxy}-3-(3,3,3-trifluoropropyl)naphthalene (123)

2-Bromo-6-(methyloxy)-3-(3,3,3-trifluoropropyl)-1-naphthalenol (122) (0.47 g, 1.35 mmol) was treated with chloromethyl methyl ether in the presence of diisopropylethylamine in THF to give 0.42 g (80%) of the title compound (123) as a colorless oil. $^1$H NMR (400 MHz, CDCl$_3$): δ 2.40-2.55 (m, 2H), 3.10-3.20 (m, 2H), 3.72 (s, 3H), 3.91 (s, 3H), 5.23 (s, 2H), 7.04 (d, J=2.6 Hz, 1H), 7.16 (dd, J$_1$=9.3 Hz, J$_2$=2.5 Hz, 1H), 7.43 (s, 1H), 8.03 (d, J=9.3 Hz, 1H).

Step 7: 6-(Methyloxy)-1-{[(methyloxy)methyl]oxy}-2-phenyl-3-(3,3,3-trifluoropropyl)naphthalene (124)

Suzuki coupling of 2-bromo-6-(methyloxy)-1-{[(methyloxy)methyl]oxy}-3-(3,3,3-trifluoropropyl)naphthalene (123) (0.42 g, 1.07 mmol) with phenyl boronic acid (0.27 g, 2.14 mmol) in the presence of Pd(PPh$_3$)$_4$ in DME using a sealed tube at 160° C. gave 0.40 g (97%) of the title compound (124) as a colorless oil. $^1$H NMR (300 MHz, CDCl$_3$): δ 2.05-2.25 (m, 2H), 2.80-2.90 (m, 2H), 3.10 (s, 3H), 3.96 (s, 3H), 4.76 (s, 2H), 7.14 (d, J=2.5 Hz, 1H), 7.19 (dd, J$_1$=9.1 Hz, J$_2$=2.5 Hz, 1H), 7.32-7.44 (m, 3H), 7.44-7.52 (m, 3H), 8.06 (d, J=9.1 Hz, 1H).

Step 8: 6-(Methyloxy)-2-phenyl-3-(3,3,3-trifluoropropyl)-1-naphthalenol (125)

6-(Methyloxy)-1-{[(methyloxy)methyl]oxy}-2-phenyl-3-(3,3,3-trifluoropropyl)naphthalene (124) (0.40 g, 1.03 mmol) was treated with 4 M HCl in dioxane at room temperature to give 0.35 g (96%) of the title compound (124) as a white solid. $^1$H NMR (400 MHz, CDCl$_3$): δ 2.05-2.25 (m, 2H), 2.70-2.80 (m, 2H), 3.93 (s, 3H), 5.21 (s, 1H), 7.06 (d, J=2.4 Hz, 1H), 7.12 (dd, J$_1$=9.1 Hz, J$_2$=2.5 Hz, 1H), 7.22 (s, 1H), 7.34 (d, J=6.7 Hz, 2H), 7.46-7.52 (m, 1H), 7.53-7.60 (m, 2H), 8.10 (d, J=9.2 Hz, 1H). LCMS (ESI): m/z 345 (M−H)$^-$.

Step 9: 4-{[6-(Methyloxy)-2-phenyl-3-(3,3,3-trifluoropropyl)-1-naphthalenyl]oxy}benzaldehyde (126)

6-(Methyloxy)-2-phenyl-3-(3,3,3-trifluoropropyl)-1-naphthalenol (125) (0.35 g, 1.00 mmol) was treated with NaH in DMF followed by addition of 4-fluorobenzaldehyde to give 0.32 g (71%) of the title compound (126) as a light yellow viscous oil. $^1$H NMR (400 MHz, CDCl$_3$): δ 2.10-2.25 (m, 2H), 2.80-2.90 (m, 2H), 3.94 (s, 3H), 6.67 (d, J=8.8 Hz, 2H), 7.07-7.14 (m, 3H), 7.18 (d, J=2.4 Hz, 1H), 7.22-7.30 (m, 3H), 7.60-7.64 (m, 3H), 7.70 (d, J=9.2 Hz, 1H), 9.80 (s, 1H). LCMS (ESI): m/z 451 (M+H)$^+$.

Step 10: Ethyl (2E)-3-(4-{[6-(methyloxy)-2-phenyl-3-(3,3,3-trifluoropropyl)-1-naphthalenyl]oxy}phenyl)-2-propenoate (127)

4-{[6-(Methyloxy)-2-phenyl-3-(3,3,3-trifluoropropyl)-1-naphthalenyl]oxy}benzaldehyde (126) (0.32 g, 0.70 mmol) was treated with a mixture of triethylphosphonoacetate and nBuLi to give 0.34 g (93%) of the title compound (127) as a colorless oil. $^1$H NMR (400 MHz, CDCl$_3$): δ 1.30 (t, J=7.1 Hz, 3H), 2.10-2.25 (m, 2H), 2.80-2.90 (m, 2H), 3.94 (s, 3H), 4.22 (q, J=7.1 Hz, 2H), 6.22 (d, J=15.9 Hz, 1H), 6.55 (d, J=8.6 Hz, 2H), 7.06-7.14 (m, 3H), 7.17 (d, J=2.3 Hz, 1H), 7.22-7.30 (m, 5H), 7.53 (d, J=15.9 Hz, 1H), 7.58 (s, 1H), 7.73 (d, J=9.2 Hz, 1H). LCMS (ESI): m/z 521 (M+H)$^+$.

Step 11: (2E)-3-(4-{[6-(methyloxy)-2-phenyl-3-(3,3,3-trifluoropropyl)-1-naphthalenyl]oxy}phenyl)-2-propenoic acid (128)

Ethyl ester (127) (0.34 g, 0.65 mmol) was saponified with 1 N NaOH in THF and EtOH to give 0.28 g (88%) of the title compound (128) as a white solid. $^1$H NMR (400 MHz, CDCl$_3$): δ 2.10-2.25 (m, 2H), 2.80-2.90 (m, 2H), 3.94 (s, 3H), 6.22 (d, J=15.9 Hz, 1H), 6.57 (d, J=8.6 Hz, 2H), 7.06-7.14 (m, 3H), 7.17 (d, J=2.4 Hz, 1H), 7.22-7.30 (m, 5H), 7.59 (s, 1H), 7.62 (d, J=15.9 Hz, 1H), 7.72 (d, J=9.1 Hz, 1H). LCMS (ESI): m/z 493 (M+H)$^+$, m/z 491 (M−H)$^-$.

Step 12: (2E)-3-(4-{[6-Hydroxy-2-phenyl-3-(3,3,3-trifluoropropyl)-1-naphthalenyl]oxy}phenyl)-2-propenoic acid (129)

Methyl ether (128) (0.15 g, 0.31 mmol) was treated with BBr$_3$ in CH$_2$Cl$_2$ to give the crude product as orange viscous oil, which was purified by reverse phase preparation HPLC on Agilent 1100 to afford 97 mg (67%) of the title compound (129) as a light yellow solid. mp 118-120° C. $^1$H NMR (400 MHz, CH$_3$OH-d$_4$): δ 2.15-2.30 (m, 2H), 2.80-2.90 (m, 2H), 6.26 (d, J=15.9 Hz, 1H), 6.57 (d, J=8.6 Hz, 2H), 7.00 (dd, J$_1$=9.0 Hz, J$_2$=2.3 Hz, 1H), 7.16-7.20 (m, 3H), 7.22-7.32 (m, 3H), 7.34 (d, J=8.8 Hz, 2H), 7.52 (d, J=15.9 Hz, 1H), 7.59 (s, 1H), 7.62 (d, J=9.1 Hz, 1H). LCMS (ESI): m/z 479 (M+H)$^+$, m/z 477 (M−H)$^-$. Anal. Calc for C$_{28}$H$_{21}$F$_3$O$_4$.0.25H$_2$O: C, 69.63; H, 4.49. Found: C, 69.63; H, 4.41.

Example 20 (141)

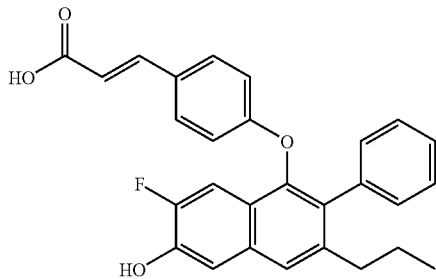

Step 1: 1-[4-Fluoro-3-(methyloxy)phenyl]-2-pentanone (130)

Coupling of 4-fluoro-3-methoxybenzyl bromide (3.39 g, 15.5 mmol) and butyryl chloride (1.69 g, 15.5 mmol) in DME with Pd(PPh$_3$)$_2$Cl$_2$ and Zn gave the crude product as a yellow oil. The crude product was purified by flash chromatography over SiO$_2$ eluted with a gradient from hexanes to 15% EtOAc in hexanes to give 1.83 g (56%) of compound 130 as a colorless oil. $^1$H NMR (400 MHz, CDCl$_3$): δ 0.87 (t, J=7.3 Hz, 3H), 1.55-1.65 (m, 2H), 2.43 (t, J=7.3 Hz, 2H), 3.62 (s, 2H), 3.87 (s, 3H), 6.67-6.73 (m, 1H), 6.78 (dd, J$_1$=8.2 Hz, J$_2$=2.0 Hz, 1H), 7.01 (dd, J$_1$=11.3 Hz, J$_2$=8.2 Hz, 1H). LCMS (ESI): m/z 211 (M+H)$^+$.

Step 2: Ethyl 3-{[4-fluoro-3-(methyloxy)phenyl]methyl}hexanoate (131)

Peterson olefination of 1-[4-fluoro-3-(methyloxy)phenyl]-2-pentanone (130) (1.83 g, 8.70 mmol) with ethyl (trimethylsilyl) acetate (2.82 g, 17.4 mmol) in the presence of dicyclohexylamine and nBuLi gave the α,β-unsaturated ester, which was purified and hydrogenated at room temperature with 10% Pd/C under a hydrogen balloon to yield 2.14 g (87% from the ketone) of compound 131 as a colorless oil. $^1$H NMR (400 MHz, CDCl$_3$): δ 0.88 (t, J=7.0 Hz, 3H), 1.24 (t, J=7.1 Hz, 3H), 1.24-1.40 (m, 4H), 2.10-2.25 (m, 3H), 2.45-2.55 (m, 1H), 2.55-2.65 (m, 1H), 3.87 (s, 3H), 4.09 (q, J=7.1 Hz, 2H), 6.64-6.70 (m, 1H), 6.76 (dd, J$_1$=8.2 Hz, J$_2$=2.0 Hz, 1H), 6.96 (dd, J$_1$=11.3 Hz, J$_2$=8.2 Hz, 1H). LCMS (ESI): m/z 305 (M+Na)$^+$.

Step 3: 3-{[4-Fluoro-3-(methyloxy)phenyl]methyl}hexanoic acid (132)

Ethyl ester (131) (2.14 g, 7.58 mmol) was saponified with 1 N NaOH in THF and EtOH to give 1.92 g (~100%) of the title compound (132) as a light yellow oil. $^1$H NMR (400 MHz, CDCl$_3$): δ 0.88 (t, J=7.0 Hz, 3H), 1.25-1.45 (m, 4H), 2.05-2.20 (m, 1H), 2.20-2.35 (m, 2H), 2.45-2.55 (m, 1H), 2.60-2.70 (m, 1H), 3.87 (s, 3H), 6.64-6.70 (m, 1H), 6.76 (dd, J$_1$=8.2 Hz, J$_2$=1.8 Hz, 1H), 6.96 (dd, J$_1$=11.3 Hz, J$_2$=8.2 Hz, 1H). LCMS (ESI): m/z 253 (M−H)$^-$.

Step 4: 7-Fluoro-6-(methyloxy)-3-propyl-3,4-dihydro-1(2H)-naphthalenone (133)

3-{[4-Fluoro-3-(methyloxy)phenyl]methyl}hexanoic acid (132) (1.92 g, 7.55 mmol) was treated with oxalyl chloride followed by AlCl$_3$ in CH$_2$Cl$_2$ to give 1.70 g (95%) of the title compound (133) as a white solid. $^1$H NMR (400 MHz, CDCl$_3$): δ 0.90-0.95 (m, 3H), 1.35-1.45 (m, 4H), 2.10-2.30 (m, 2H), 2.60-2.75 (m, 2H), 2.90-3.00 (m, 1H), 3.93 (s, 3H), 6.74 (d, J=7.7 Hz, 1H), 7.70 (d, J=11.5 Hz, 1H). LCMS (ESI): m/z 236 (M+H)$^+$.

Step 5: 2-Bromo-7-fluoro-6-(methyloxy)-3-propyl-1-naphthalenol (134)

Treatment of 7-fluoro-6-(methyloxy)-3-propyl-3,4-dihydro-1(2H)-naphthalenone (133) (0.40 g, 1.69 mmol) with bromine followed by DBU in CH$_3$CN gave 0.52 g (98% from tetralone) of the title compound (134) as a light yellow oil. $^1$H NMR (400 MHz, CDCl$_3$): δ 1.01 (t, J=7.3 Hz, 3H), 1.65-1.75 (m, 2H), 2.78 (t, J=7.7 Hz, 2H), 3.98 (s, 3H), 6.05 (s, 1H), 7.07 (d, J=8.2 Hz, 1H), 7.15 (s, 1H), 7.79 (d, J=12.3 Hz, 1H). LCMS (ESI): m/z 313 (M+H)$^+$, m/z 311 (M−H)$^-$.

Step 6: 2-Bromo-7-fluoro-6-(methyloxy)-1-{[(methyloxy)methyl]oxy}-3-propyl naphthalene (135)

2-Bromo-7-fluoro-6-(methyloxy)-3-propyl-1-naphthalenol (134) (0.52 g, 1.66 mmol) was treated with chloromethyl methyl ether in the presence of diisopropylethylamine in THF to give 0.49 g (83%) of the title compound (135) as a light yellow oil. $^1$H NMR (400 MHz, CDCl$_3$): δ 1.01 (t, J=7.3 Hz, 3H), 1.65-1.75 (m, 2H), 2.83 (t, J=7.8 Hz, 2H), 3.72 (s, 3H), 3.98 (s, 3H), 5.21 (s, 2H), 7.10 (d, J=8.3 Hz, 1H), 7.37 (s, 1H), 7.76 (d, J=12.4 Hz, 1H). LCMS (ESI): m/z 379 (M+Na)$^+$.

Step 7: 7-Fluoro-6-(methyloxy)-1-{[(methyloxy)methyl]oxy}-2-phenyl-3-propyl naphthalene (136)

Suzuki coupling of 2-bromo-7-fluoro-6-(methyloxy)-1-{[(methyloxy)methyl]oxy}-3-propyl naphthalene (135) (0.49 g, 1.38 mmol) with phenyl boronic acid (0.35 g, 2.76 mmol) in the presence of Pd(PPh$_3$)$_4$ in DME using a sealed tube at 160° C. gave 0.48 g (97%) of the title compound (136) as a colorless oil. $^1$H NMR (300 MHz, CDCl$_3$): δ 0.81 (t, J=7.4 Hz, 3H), 1.40-1.60 (m, 2H), 2.53 (t, J=7.8 Hz, 2H), 3.14 (s, 3H), 4.03 (s, 3H), 4.70 (s, 2H), 7.20 (d, J=8.3 Hz, 1H), 7.32-7.42 (m, 3H), 7.42-7.50 (m, 3H), 7.77 (d, J=12.7 Hz, 1H). LCMS (ESI): m/z 355 (M+H)$^+$.

Step 8: 7-Fluoro-6-(methyloxy)-2-phenyl-3-propyl-1-naphthalenol (137)

7-Fluoro-6-(methyloxy)-1-{[(methyloxy)methyl]oxy}-2-phenyl-3-propyl naphthalene (136) (0.48 g, 1.34 mmol) was treated with 4 M HCl in dioxane at room temperature to give 0.42 g (~100%) of the title compound (137) as a light yellow viscous oil. $^1$H NMR (400 MHz, CDCl$_3$): δ 0.79 (t, J=7.4 Hz, 3H), 1.40-1.60 (m, 2H), 2.44 (t, J=7.8 Hz, 2H), 4.00 (s, 3H), 5.13 (s, 1H), 7.13 (d, J=8.2 Hz, 1H), 7.21 (s, 1H), 7.30-7.36 (m, 2H), 7.42-7.49 (m, 1H), 7.50-7.56 (m, 2H), 7.79 (d, J=12.5 Hz, 1H). LCMS (ESI): m/z 311 (M+H)$^+$, m/z 309 (M−H)$^−$.

Step 9: 4-{[7-Fluoro-6-(methyloxy)-2-phenyl-3-propyl-1-naphthalenyl]oxy}benzaldehyde (138)

7-Fluoro-6-(methyloxy)-2-phenyl-3-propyl-1-naphthalenol (137) (0.42 g, 1.34 mmol) was dissolved in DMF (5 mL). To this solution was added 4-fluorobenzaldehyde (0.34 g, 2.68 mmol) followed by Cs$_2$CO$_3$ (0.57 g, 1.74 mmol). The mixture was heated at 100° C. for 36 h, poured into water (50 mL) and extracted with EtOAc (2×75 mL). The combined organic extract was washed with water, brine, dried over Na$_2$SO$_4$, filtered, and the filtrate was concentrated to give the crude product as reddish brown oil. The crude product was purified by flash chromatography over SiO$_2$ eluted with a gradient from hexanes to 15% EtOAc in hexanes to give 0.38 g (69%) of the title compound (138) as a yellow viscous oil. $^1$H NMR (400 MHz, CDCl$_3$): δ 0.81 (t, J=7.4 Hz, 3H), 1.40-1.60 (m, 2H), 2.53 (t, J=7.8 Hz, 2H), 4.02 (s, 3H), 6.66 (d, J=8.8 Hz, 2H), 7.06-7.12 (m, 2H), 7.18-7.25 (m, 4H), 7.40 (d, J=12.1 Hz, 1H), 7.56-7.64 (m, 3H), 9.80 (s, 1H). LCMS (ESI): m/z 415 (M+H)$^+$.

Step 10: Ethyl (2E)-3-(4-{[7-fluoro-6-(methyloxy)-2-phenyl-3-propyl-1-naphthalenyl]oxy}phenyl)-2-propenoate (139)

4-{[7-Fluoro-6-(methyloxy)-2-phenyl-3-propyl-1-naphthalenyl]oxy}benzaldehyde (138) (0.38 g, 0.92 mmol) was treated with a mixture of triethylphosphonoacetate and nBuLi to give 0.44 g (99%) of the title compound (139) as a yellow viscous oil. $^1$H NMR (400 MHz, CDCl$_3$): δ 0.80 (t, J=7.3 Hz, 3H), 1.30 (t, J=7.1 Hz, 3H), 1.40-1.60 (m, 2H), 2.51 (t, J=7.8 Hz, 2H), 4.01 (s, 3H), 4.22 (q, J=7.1 Hz, 2H), 6.22 (d, J=15.9 Hz, 1H), 6.53 (d, J=8.7 Hz, 2H), 7.06-7.12 (m, 2H), 7.18-7.25 (m, 6H), 7.43 (d, J=12.1 Hz, 1H), 7.50-7.58 (m, 2H). LCMS (ESI): m/z 485 (M+H)$^+$.

Step 11: (2E)-3-(4-{[7-Fluoro-6-(methyloxy)-2-phenyl-3-propyl-1-naphthalenyl]oxy}phenyl)-2-propenoic acid (140)

Ethyl ester (139) (0.44 g, 0.91 mmol) was saponified with 1 N NaOH in THF and EtOH to give 0.33 g (80%) of the title compound (140) as a white solid. $^1$H NMR (400 MHz, CDCl$_3$): δ 0.80 (t, J=7.3 Hz, 3H), 1.40-1.55 (m, 2H), 2.52 (t, J=7.8 Hz, 2H), 4.01 (s, 3H), 6.23 (d, J=15.9 Hz, 1H), 6.55 (d, J=8.8 Hz, 2H), 7.06-7.12 (m, 2H), 7.20-7.30 (m, 6H), 7.41 (d, J=12.1 Hz, 1H), 7.56 (s, 1H), 7.62 (d, J=15.9 Hz, 1H). LCMS (APCI): m/z 457 (M+H)$^+$, m/z 455 (M−H)$^−$.

Step 12: (2E)-3-{4-[(7-Fluoro-6-hydroxy-2-phenyl-3-propyl-1-naphthalenyl)oxy]phenyl}-2-propenoic acid (141)

Methyl ether (140) (0.15 g, 0.33 mmol) was treated with BBr$_3$ in CH$_2$Cl$_2$ to give the crude product as a brown viscous oil, which was purified by reverse phase preparation HPLC on Agilent 1100 to afford 122 mg (84%) of the title compound (141) as a light yellow solid. mp 118-120° C. $^1$H NMR (400 MHz, CH$_3$OH-d$_4$): δ 0.77 (t, J=7.3 Hz, 3H), 1.40-1.55 (m, 2H), 2.52 (t, J=7.6 Hz, 2H), 6.27 (d, J=15.9 Hz, 1H), 6.55 (d, J=8.4 Hz, 2H), 7.08-7.16 (m, 2H), 7.20-7.40 (m, 7H), 7.48-7.56 (m, 2H). LCMS (APCI): m/z 443 (M+H)$^+$, m/z 441 (M−H)$^−$. Anal. Calc for C$_{29}$H$_{25}$FO$_4$.0.4H$_2$O: C, 74.79; H, 5.33. Found: C, 74.71; H, 5.21.

Example 21 (148)

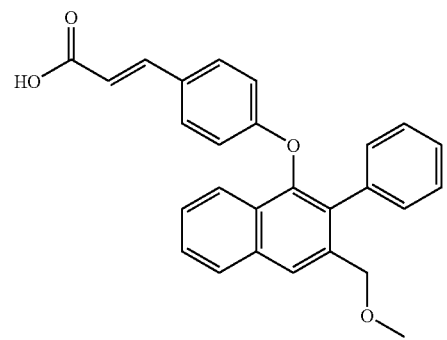

Step 1: Methyl 2-[3-(methyloxy)-1-propyn-1-yl]benzoate (142)

Coupling of methyl 2-bromo benzoate (1.0 g, 4.56 mmol) with methyl propargyl ether (0.80 mL, 9.11 mmol) using Pd(PPh$_3$)$_2$Cl$_2$ and CuI in DMF at 50° C. gave 0.64 g (69%) of the title compound (142) as a yellow oil. $^1$H NMR (400 MHz, CDCl$_3$): δ 3.49 (s, 3H), 3.92 (s, 3H), 4.39 (s, 2H), 7.32-7.40 (m, 1H), 7.40-7.50 (m, 1H), 7.56 (d, J=7.6 Hz, 1H), 7.93 (d, J=7.7 Hz, 1H). LCMS (ESI): m/z 205 (M+H)$^+$.

Step 2: N-Methyl-N-(methyloxy)-2-[3-(methyloxy)-1-propyn-1-yl]benzamide (143)

Treatment of methyl 2-[3-(methyloxy)-1-propyn-1-yl] benzoate (142) (0.64 g, 3.13 mmol) with a mixture of N,O-dimethylhydroxylamine hydrochloride and nBuLi gave 0.35 g (48%) of the title compound (143) as a yellow oil. $^1$H NMR (400 MHz, CDCl$_3$): δ 3.32 (br s, 3H), 3.43 (s, 3H), 3.50 (br s, 3H), 4.30 (s, 2H), 7.25-7.40 (m, 3H), 7.45-7.55 (m, 1H). LCMS (ESI): m/z 234 (M+H)$^+$.

Step 3: 1-{2-[3-(Methyloxy)-1-propyn-1-yl]phenyl}-2-phenylethanone (144)

N-Methyl-N-(methyloxy)-2-[3-(methyloxy)-1-propyn-1-yl]benzamide (143) (0.35 g, 1.50 mmol) was treated with benzylmagnesium chloride in THF to give 0.21 g (53%) of the title compound (144) as a light yellow oil. $^1$H NMR (400 MHz, CDCl$_3$): δ 3.44 (s, 3H), 4.34 (s, 2H), 4.38 (s, 2H), 7.20-7.26 (m, 3H), 7.27-7.38 (m, 3H), 7.38-7.44 (m, 1H), 7.54 (d, J=7.7 Hz, 1H), 7.57 (d, J=7.7 Hz, 1H). LCMS (ESI): m/z 265 (M+H)$^+$.

Step 4: 3-[(Methyloxy)methyl]-2-phenyl-1-naphthalenol (145)

A solution of 1-{2-[3-(methyloxy)-1-propyn-1-yl]phenyl}-2-phenylethanone (144) (0.21 g, 0.79 mmol) in toluene was treated with a KHMDS solution in toluene to give 46 mg (22%) of the title compound (145) as a light brown solid. $^1$H NMR (400 MHz, CDCl$_3$): δ 3.28 (s, 3H), 4.26 (s, 2H), 5.29 (s, 1H), 7.36-7.42 (m, 2H), 7.44-7.58 (m, 6H), 7.80-7.85 (m, 1H), 8.18-8.24 (m, 1H). LCMS (ESI): m/z 265 (M+H)$^+$, m/z 263 (M−H)−.

Step 5: 4-({3-[(Methyloxy)methyl]-2-phenyl-1-naphthalenyl}oxy)benzaldehyde (146)

3-[(Methyloxy)methyl]-2-phenyl-1-naphthalenol (145) (46 mg, 0.17 mmol) and 4-fluorobenzaldehyde was heated with Cs$_2$CO$_3$ in DMF at 100° C. to give 20 mg (30%) of the title compound (146) as a light yellow oil. $^1$H NMR (400 MHz, CDCl$_3$): δ 3.34 (s, 3H), 4.32 (s, 2H), 6.71 (d, J=8.8 Hz, 2H), 7.16-7.20 (m, 2H), 7.20-7.30 (m, 3H), 7.45 (t, J=7.5 Hz, 1H), 7.54 (t, J=7.4 Hz, 1H), 7.62 (d, J=8.6 Hz, 2H), 7.81 (d, J=8.4 Hz, 1H), 7.95 (d, J=9.0 Hz, 1H), 7.98 (s, 1H), 9.79 (s, 1H). LCMS (APCI): m/z 369 (M+H)$^+$.

Step 6: Ethyl (2E)-3-[4-({3-[(methyloxy)methyl]-2-phenyl-1-naphthalenyl}oxy)phenyl]-2-propenoate (147)

4-({3-[(Methyloxy)methyl]-2-phenyl-1-naphthalenyl}oxy)benzaldehyde (146) (20 mg, 0.05 mmol) was treated with a mixture of triethylphosphonoacetate and nBuLi to give 20 mg (86%) of the title compound (147) as a light yellow viscous oil. $^1$H NMR (400 MHz, CDCl$_3$): δ 1.30 (t, J=7.2 Hz, 3H), 3.33 (s, 3H), 4.22 (q, J=7.2 Hz, 2H), 4.31 (s, 2H), 6.22 (d, J=16.0 Hz, 1H), 6.59 (d, J=8.6 Hz, 2H), 7.15-7.20 (m, 2H), 7.20-7.30 (m, 5H), 7.43 (t, J=7.5 Hz, 1H), 7.48-7.57 (m, 2H), 7.85 (d, J=8.4 Hz, 1H), 7.93 (d, J=8.2 Hz, 1H), 7.95 (s, 1H). LCMS (APCI): m/z 461 (M+Na)$^+$.

Step 7: (2E)-3-[4-({3-[(Methyloxy)methyl]-2-phenyl-1-naphthalenyl}oxy)phenyl]-2-propenoic acid (148)

Ethyl ester (147) (20 mg, 0.046 mmol) was saponified with 1 N NaOH in THF and EtOH to give 18 mg (93%) of the title compound (148) as an off-white solid. mp 76-79° C. $^1$H NMR (400 MHz, CDCl$_3$): δ 3.33 (s, 3H), 4.31 (s, 2H), 6.22 (d, J=15.9 Hz, 1H), 6.60 (d, J=8.8 Hz, 2H), 7.15-7.20 (m, 2H), 7.20-7.30 (m, 5H), 7.44 (t, J=7.9 Hz, 1H), 7.52 (t, J=7.5 Hz, 1H), 7.62 (d, J=15.9 Hz, 1H), 7.83 (d, J=8.5 Hz, 1H), 7.93 (d, J=8.2 Hz, 1H), 7.95 (s, 1H). LCMS (ESI): m/z 433 (M+Na)$^+$, m/z 409 (M−H)$^-$. HRMS (EI) Calc for C$_{27}$H$_{22}$O$_4$: 411.1596 (M$^{+*}$). Found: 411.1606.

Example 22 (156)

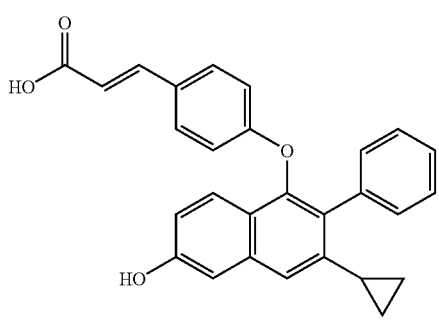

Step 1: Methyl 2-(cyclopropylethynyl)-4-(methyloxy)benzoate (149)

Coupling of methyl 4-(methyloxy)-2-{[(trifluoromethyl)sulfonyl]oxy}benzoate (77) (0.70 g, 2.23 mmol) with cyclopropylacetylene (0.30 g, 4.46 mmol) using Pd(PPh$_3$)$_2$Cl$_2$ and CuI in DMF at room temperature gave 0.49 g (96%) of the title compound (149) as a brown oil. $^1$H NMR (400 MHz, CDCl$_3$): δ 0.80-0.95 (m, 4H), 1.45-1.55 (m, 1H), 3.82 (s, 3H), 3.87 (s, 3H), 6.80 (dd, J$_1$=8.9 Hz, J$_2$=2.7 Hz, 1H), 6.96 (d, J=2.8 Hz, 1H), 7.88 (d, J=8.8 Hz, 1H). LCMS (ESI): m/z 231 (M+H)$^+$.

Step 2: 2-(Cyclopropylethynyl)-N-methyl-N,4-bis(methyloxy)benzamide (150)

Treatment of methyl 2-(cyclopropylethynyl)-4-(methyloxy)benzoate (149) (0.49 g, 2.13 mmol) with a mixture of N,O-dimethylhydroxylamine hydrochloride and nBuLi gave 0.47 g (86%) of the title compound (150) as a light yellow oil. $^1$H NMR (400 MHz, CDCl$_3$): δ 0.70-0.90 (m, 4H), 1.40-1.50 (m, 1H), 3.28 (br s, 3H), 3.63 (br s, 3H), 3.80 (s, 3H), 6.83 (dd, J$_1$=8.5 Hz, J$_2$=2.6 Hz, 1H), 6.91 (d, J=2.4 Hz, 1H), 7.24 (d, J=8.6 Hz, 1H). LCMS (ESI): m/z 260 (M+H)$^+$.

Step 3: 1-[2-(Cyclopropylethynyl)-4-(methyloxy)phenyl]-2-phenylethanone (151)

2-(Cyclopropylethynyl)-N-methyl-N,4-bis(methyloxy)benzamide (150) (0.47 g, 1.82 mmol) was treated with benzylmagnesium chloride in THF to give 0.47 g (89%) of the title compound (151) as a colorless oil. $^1$H NMR (400 MHz, CDCl$_3$): δ 0.80-0.95 (m, 4H), 1.45-1.55 (m, 1H), 3.82 (s, 3H), 4.41 (s, 2H), 6.80 (dd, J$_1$=8.8 Hz, J$_2$=2.6 Hz, 1H), 6.94 (d, J=2.5 Hz, 1H), 7.20-7.26 (m, 3H), 7.27-7.33 (m, 2H), 7.65 (d, J=8.8 Hz, 1H). LCMS (ESI): m/z 291 (M+H)$^+$.

Step 4: 3-Cyclopropyl-6-(methyloxy)-2-phenyl-1-naphthalenol (152)

A solution of 1-[2-(Cyclopropylethynyl)-4-(methyloxy)phenyl]-2-phenylethanone (151) (0.47 g, 1.62 mmol) in toluene was treated with a KHMDS solution in toluene to give 0.18 g (38%) of the title compound (152) as a light yellow viscous oil. $^1$H NMR (400 MHz, CDCl$_3$): δ 0.70-0.80 (m, 4H), 1.55-1.65 (m, 1H), 3.91 (s, 3H), 5.22 (s, 1H), 6.92 (s, 1H), 7.00-7.10 (m, 2H), 7.40-7.48 (m, 3H), 7.50-7.57 (m, 2H), 8.07 (d, J=8.9 Hz, 1H). LCMS (APCI): m/z 291 (M+H)$^+$, m/z 289 (M−H)$^+$.

Step 5: 4-{[3-Cyclopropyl-6-(methyloxy)-2-phenyl-1-naphthalenyl]oxy}benzaldehyde (153)

3-Cyclopropyl-6-(methyloxy)-2-phenyl-1-naphthalenol (152) (0.18 g, 0.62 mmol) was treated with NaH in DMF followed by addition of 4-fluorobenzaldehyde to give 0.21 g (86%) of the title compound (153) as a yellow viscous oil. $^1$H NMR (400 MHz, CDCl$_3$): δ 0.75-0.85 (m, 4H), 1.60-1.70 (m, 1H), 3.92 (s, 3H), 6.70 (d, J=8.6 Hz, 2H), 7.03 (dd, J$_1$=9.2 Hz, J$_2$=2.4 Hz, 1H), 7.14 (d, J=2.4 Hz, 1H), 7.18-7.28 (m, 6H), 7.62 (d, J=8.7 Hz, 2H), 7.66 (d, J=9.1 Hz, 1H), 9.79 (s, 1H). LCMS (ESI): m/z 395 (M+H)$^+$.

Step 6: Ethyl (2E)-3-(4-{[3-cyclopropyl-6-(methyloxy)-2-phenyl-1-naphthalenyl]oxy}phenyl)-2-propenoate (154)

4-{[3-Cyclopropyl-6-(methyloxy)-2-phenyl-1-naphthalenyl]oxy}benzaldehyde (153) (0.21 g, 0.53 mmol) was treated with a mixture of triethylphosphonoacetate and nBuLi to give 0.21 g (85%) of the title compound (154) as a light yellow solid. $^1$H NMR (400 MHz, CDCl$_3$): δ 0.75-0.85 (m, 4H), 1.30

(t, J=7.2 Hz, 3H), 1.60-1.70 (m, 1H), 3.92 (s, 3H), 4.22 (q, J=7.2 Hz, 2H), 6.21 (d, J=16.0 Hz, 1H), 6.58 (d, J=8.8 Hz, 2H), 7.02 (dd, $J_1$=9.2 Hz, $J_2$=2.4 Hz, 1H), 7.12 (d, J=2.4 Hz, 1H), 7.18-7.28 (m, 8H), 7.54 (d, J=15.9 Hz, 1H), 7.69 (d, J=9.2 Hz, 1H). LCMS (ESI): m/z 465 (M+H)$^+$.

Step 7: (2E)-3-(4-{[3-Cyclopropyl-6-(methyloxy)-2-phenyl-1-naphthalenyl]oxy}phenyl)-2-propenoic acid (155)

Ethyl ester (154) (0.21 g, 0.45 mmol) was saponified with 1 N NaOH in THF and EtOH to give 0.19 g (96%) of the title compound (155) as a white solid. $^1$H NMR (400 MHz, CDCl$_3$): δ 0.75-0.85 (m, 4H), 1.60-1.70 (m, 1H), 3.92 (s, 3H), 6.22 (d, J=15.9 Hz, 1H), 6.60 (d, J=8.6 Hz, 2H), 7.02 (dd, $J_1$=9.2 Hz, $J_2$=2.4 Hz, 1H), 7.13 (d, J=2.2 Hz, 1H), 7.18-7.30 (m, 8H), 7.62 (d, J=15.9 Hz, 1H), 7.68 (d, J=8.9 Hz, 1H). LCMS (APCI): m/z 437 (M+H)$^+$, m/z 435 (M–H)$^-$.

Step 8: (2E)-3-{4-[(3-Cyclopropyl-6-hydroxy-2-phenyl-1-naphthalenyl)oxy]phenyl}-2-propenoic acid (156)

Methyl ether (155) (0.14 g, 0.32 mmol) was treated with BBr$_3$ in CH$_2$Cl$_2$ to give the crude product as a yellow viscous oil, which was purified by reverse phase preparation HPLC on Agilent 1100 to afford 69 mg (51%) of the title compound (156) as an off-white solid. mp 242-243° C. $^1$H NMR (400 MHz, CH$_3$OH-d$_4$): δ 0.75-0.85 (m, 4H), 1.60-1.70 (m, 1H), 6.26 (d, J=15.9 Hz, 1H), 6.57 (d, J=8.6 Hz, 2H), 7.02 (dd, $J_1$=9.0 Hz, $J_2$=2.0 Hz, 1H), 7.12 (d, J=1.9 Hz, 1H), 7.16-7.28 (m, 6H), 7.34 (d, J=8.6 Hz, 2H), 7.52 (d, J=15.9 Hz, 1H), 7.58 (d, J=9.0 Hz, 1H). LCMS (APCI): m/z 423 (M+H)$^+$, m/z 421 (M–H)$^-$. Anal. Calc for $C_{28}H_{22}O_4 \cdot 1.25H_2O$: C, 75.58; H, 5.55. Found: C, 75.34; H, 5.34.

Example 23 (164)

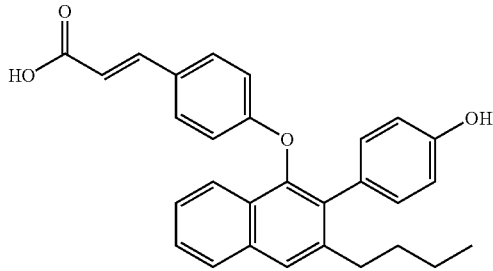

Step 1: Methyl 2-(1-hexyn-1-yl)benzoate (157)

Coupling of 2-iodobenzoate (3.0 g, 11.5 mmol) with 1-hexyne (2.71 mL, 22.9 mmol) using Pd(PPh$_3$)$_2$Cl$_2$ and CuI in DMF at room temperature gave 2.23 g (90%) of compound 157 as a brown oil. $^1$H NMR (400 MHz, CDCl$_3$): δ 0.95 (t, J=7.3 Hz, 3H), 1.45-1.55 (m, 2H), 1.55-1.65 (m, 2H), 2.47 (t, J=7.0 Hz, 2H), 3.91 (s, 3H), 7.26-7.33 (m, 1H), 7.37-7.44 (m, 1H), 7.50 (d, J=7.7 Hz, 1H), 7.87 (d, J=7.9 Hz, 1H). LCMS (APCI): m/z 217 (M+H)$^+$.

Step 2: 2-(1-Hexyn-1-yl)-N-methyl-N-(methyloxy)benzamide (158)

Treatment of methyl 2-(1-hexyn-1-yl)benzoate (157) (2.29 g, 10.6 mmol) with a mixture of N,O-dimethylhydroxylamine hydrochloride and nBuLi gave 2.0 g (77%) of the title compound (158) as a yellow oil. $^1$H NMR (400 MHz, CDCl$_3$): δ 0.92 (t, J=7.2 Hz, 3H), 1.40-1.60 (m, 4H), 2.39 (t, J=7.0 Hz, 2H), 3.32 (br s, 3H), 3.50 (br s, 3H), 7.26-7.35 (m, 3H), 7.37-7.45 (m, 1H). LCMS (APCI): m/z 246 (M+H)$^+$.

Step 3: 1-[2-(1-Hexyn-1-yl)phenyl]-2-[4-(methyloxy)phenyl]ethanone (159)

2-(1-Hexyn-1-yl)-N-methyl-N-(methyloxy)benzamide (158) (0.50 g, 2.04 mmol) was treated with 4-methoxy benzylmagnesium chloride in THF at 40° C. to give 0.43 g (69%) of the title compound (159) as a yellow oil. $^1$H NMR (400 MHz, CDCl$_3$): δ 0.93 (t, J=7.2 Hz, 3H), 1.40-1.53 (m, 2H), 1.56-1.65 (m, 2H), 2.45 (t, J=7.0 Hz, 2H), 3.78 (s, 3H), 4.36 (s, 2H), 6.83 (d, J=8.5 Hz, 2H), 7.14 (d, J=8.5 Hz, 2H), 7.26-7.30 (m, 1H), 7.33-7.39 (m, 1H), 7.44-7.50 (m, 2H). LCMS (ESI): m/z 307 (M+H)$^+$.

Step 4: 3-Butyl-2-[4-(methyloxy)phenyl]-1-naphthalenol (160)

A solution of 1-[2-(1-hexyn-1-yl)phenyl]-2-[4-(methyloxy)phenyl]ethanone (159) (0.43 g, 1.40 mmol) in toluene was treated with a KHMDS solution in toluene to give 0.25 g (58%) of the title compound (160) as a yellow solid. $^1$H NMR (400 MHz, CDCl$_3$): δ 0.78 (t, J=7.3 Hz, 3H), 1.15-1.30 (m, 2H), 1.40-1.50 (m, 2H), 2.49 (t, J=7.8 Hz, 2H), 3.89 (s, 3H), 5.24 (s, 1H), 7.07 (d, J=8.6 Hz, 2H), 7.26-7.32 (m, 3H), 7.38-7.48 (m, 2H), 7.74 (d, J=8.8 Hz, 1H), 8.17 (d, J=8.1 Hz, 1H). LCMS (ESI): m/z 307 (M+H)$^+$, m/z 305 (M–H)$^-$.

Step 5: 4-({3-Butyl-2-[4-(methyloxy)phenyl]-1-naphthalenyl}oxy)benzaldehyde (161)

3-Butyl-2-[4-(methyloxy)phenyl]-1-naphthalenol (160) (0.25 g, 0.82 mmol) and 4-fluorobenzaldehyde was heated with Cs$_2$CO$_3$ in DMSO at 100° C. to give 0.23 g (69%) of compound 161 as a light brown viscous oil. $^1$H NMR (400 MHz, CDCl$_3$): δ 0.80 (t, J=7.3 Hz, 3H), 1.20-1.30 (m, 2H), 1.40-1.50 (m, 2H), 2.60 (t, J=7.8 Hz, 2H), 3.78 (s, 3H), 6.71 (d, J=8.8 Hz, 2H), 6.79 (d, J=8.6 Hz, 2H), 7.05 (d, J=8.7 Hz, 2H), 7.39 (t, J=7.4 Hz, 1H), 7.50 (t, J=7.5 Hz, 1H), 7.64 (d, J=8.8 Hz, 2H), 7.70 (s, 1H), 7.77 (d, J=8.2 Hz, 1H), 7.87 (d, J=8.1 Hz, 1H), 9.81 (s, 1H). LCMS (ESI): m/z 411 (M+H)$^+$.

Step 6: Ethyl (2E)-3-[4-({3-butyl-2-[4-(methyloxy)phenyl]-1-naphthalenyl}oxy)phenyl]-2-propenoate (162)

4-({3-Butyl-2-[4-(methyloxy)phenyl]-1-naphthalenyl}oxy)benzaldehyde (161) (0.23 g, 0.56 mmol) was treated with a mixture of triethylphosphonoacetate and nBuLi to give 0.25 g (93%) of the title compound (162) as a colorless viscous oil. $^1$H NMR (400 MHz, CDCl$_3$): δ 0.79 (t, J=7.3 Hz, 3H), 1.15-1.29 (m, 2H), 1.30 (t, J=7.1 Hz, 3H), 1.40-1.50 (m, 2H), 2.58 (t, J=7.9 Hz, 2H), 3.78 (s, 3H), 4.22 (q, J=7.1 Hz, 2H), 6.22 (d, J=15.9 Hz, 1H), 6.58 (d, J=8.8 Hz, 2H), 6.79 (d, J=8.6 Hz, 2H), 7.04 (d, J=8.6 Hz, 2H), 7.25 (d, J=8.8 Hz, 2H), 7.36 (t, J=7.7 Hz, 1H), 7.45 (t, J=7.3 Hz, 1H), 7.54 (d, J=16.0 Hz, 1H), 7.66 (s, 1H), 7.79 (d, J=8.4 Hz, 1H), 7.85 (d, J=8.3 Hz, 1H). LCMS (ESI): m/z 481 (M+H)$^+$.

Step 7: (2E)-3-[4-({3-Butyl-2-[4-(methyloxy)phenyl]-1-naphthalenyl}oxy)phenyl]-2-propenoic acid (163)

Ethyl ester (162) (0.25 g, 0.52 mmol) was saponified with 1 N NaOH in THF and EtOH to give 0.21 g (88%) of compound 163 as a white solid. mp 186-187° C. $^1$H NMR (400 MHz, CH$_3$OH-d$_4$): δ 0.78 (t, J=7.3 Hz, 3H), 1.15-1.29 (m, 2H), 1.40-1.50 (m, 2H), 2.62 (t, J=7.3 Hz, 2H), 3.75 (s, 3H), 6.26 (d, J=15.9 Hz, 1H), 6.56 (d, J=8.8 Hz, 2H), 6.83 (d, J=8.6 Hz, 2H), 7.07 (d, J=8.6 Hz, 2H), 7.30-7.40 (m, 3H), 7.47 (t, J=7.5 Hz, 1H), 7.53 (d, J=16.0 Hz, 1H), 7.50-7.56 (m, 2H), 7.89 (d, J=8.2 Hz, 1H). LCMS (ESI): m/z 453 (M+H)$^+$, m/z 451 (M−H)$^-$.

Step 8: (2E)-3-(4-{[3-Butyl-2-(4-hydroxyphenyl)-1-naphthalenyl]oxy}phenyl)-2-propenoic acid (164)

Methyl ether (163) (0.12 g, 0.27 mmol) was treated with BBr$_3$ in CH$_2$Cl$_2$ to give the crude product as a yellow viscous oil, which was purified by reverse phase preparation HPLC on Agilent 1100 to afford 95 mg (82%) of the title compound (164) as a white solid. mp 107-109° C. $^1$H NMR (400 MHz, CH$_3$OH-d$_4$): δ 0.78 (t, J=7.4 Hz, 3H), 1.15-1.29 (m, 2H), 1.40-1.50 (m, 2H), 2.62 (t, J=7.9 Hz, 2H), 6.26 (d, J=15.9 Hz, 1H), 6.56 (d, J=8.8 Hz, 2H), 6.68 (d, J=8.4 Hz, 2H), 6.96 (d, J=8.6 Hz, 2H), 7.30-7.40 (m, 3H), 7.47 (t, J=7.9 Hz, 1H), 7.53 (d, J=15.9 Hz, 1H), 7.71 (s, 1H), 7.73 (d, J=8.5 Hz, 1H), 7.88 (d, J=8.2 Hz, 1H). LCMS (ESI): m/z 439 (M+H)$^+$, m/z 437 (M−H)$^-$. Anal. Calc for C$_{29}$H$_{26}$O$_4$·⅙H$_2$O: C, 78.89; H, 6.01. Found: C, 78.71; H, 5.91.

Example 24 (169)

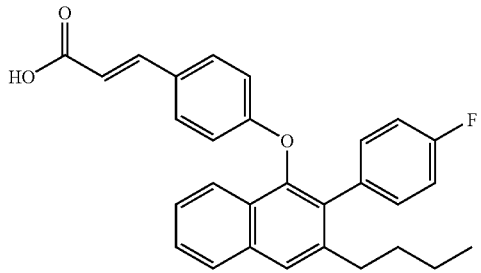

Step 1: 2-(4-Fluorophenyl)-1-[2-(1-hexyn-1-yl)phenyl]ethanone (165)

2-(1-Hexyn-1-yl)-N-methyl-N-(methyloxy)benzamide (158) (0.50 g, 2.04 mmol) was treated with 4-fluorobenzylmagnesium chloride in THF at room temperature to give 0.37 g (61%) of compound (165) as a yellow oil. $^1$H NMR (400 MHz, CDCl$_3$): δ 0.93 (t, J=7.2 Hz, 3H), 1.40-1.53 (m, 2H), 1.56-1.65 (m, 2H), 2.45 (t, J=7.1 Hz, 2H), 4.40 (s, 2H), 6.99 (t, J=8.6 Hz, 2H), 7.16-7.22 (m, 2H), 7.26-7.32 (m, 1H), 7.35-7.41 (m, 1H), 7.45-7.52 (m, 2H).

Step 2: 3-Butyl-2-(4-fluorophenyl)-1-naphthalenol (166)

A solution of 2-(4-fluorophenyl)-1-[2-(1-hexyn-1-yl)phenyl]ethanone (165) (0.37 g, 1.24 mmol) in toluene was treated with a KHMDS solution in toluene to give 0.25 g (69%) of the title compound (166) as a yellow solid upon standing. $^1$H NMR (400 MHz, CDCl$_3$): δ 0.77 (t, J=7.3 Hz, 3H), 1.15-1.30 (m, 2H), 1.35-1.50 (m, 2H), 2.47 (t, J=7.9 Hz, 2H), 5.10 (s, 1H), 7.20-7.28 (m, 2H), 7.30-7.37 (m, 3H), 7.40-7.50 (m, 2H), 7.75 (d, J=8.0 Hz, 1H), 8.17 (d, J=8.4 Hz, 1H). LCMS (APCI): m/z 295 (M+H) t.

Step 3: 4-{[3-Butyl-2-(4-fluorophenyl)-1-naphthalenyl]oxy}benzaldehyde (167)

3-Butyl-2-(4-fluorophenyl)-1-naphthalenol (166) (0.25 g, 0.83 mmol) and 4-fluorobenzaldehyde was heated with Cs$_2$CO$_3$ in DMSO at 100° C. to give 0.26 g (78%) of the title compound (167) as a colorless viscous oil. $^1$H NMR (400 MHz, CDCl$_3$): δ 0.78 (t, J=7.3 Hz, 3H), 1.20-1.30 (m, 2H), 1.40-1.50 (m, 2H), 2.56 (t, J=7.9 Hz, 2H), 6.68 (d, J=8.6 Hz, 2H), 6.95 (t, J=8.7 Hz, 2H), 7.06-7.14 (m, 2H), 7.40 (t, J=7.6 Hz, 1H), 7.51 (t, J=7.2 Hz, 1H), 7.63 (d, J=8.6 Hz, 2H), 7.71 (s, 1H), 7.77 (d, J=8.5 Hz, 1H), 7.87 (d, J=8.2 Hz, 1H), 9.81 (s, 1H). LCMS (ESI): m/z 399 (M+H)$^+$.

Step 4: Ethyl (2E)-3-(4-{[3-butyl-2-(4-fluorophenyl)-1-naphthalenyl]oxy}phenyl)-2-propenoate (168)

4-{[3-Butyl-2-(4-fluorophenyl)-1-naphthalenyl]oxy}benzaldehyde (167) (0.25 g, 0.63 mmol) was treated with a mixture of triethylphosphonoacetate and nBuLi to give 0.25 g (84%) of compound 168 as a colorless viscous oil. $^1$H NMR (400 MHz, CDCl$_3$): δ 0.78 (t, J=7.3 Hz, 3H), 1.15-1.28 (m, 2H), 1.30 (t, J=7.1 Hz, 3H), 1.40-1.50 (m, 2H), 2.55 (t, J=7.9 Hz, 2H), 4.22 (q, J=7.1 Hz, 2H), 6.22 (d, J=15.9 Hz, 1H), 6.56 (d, J=8.6 Hz, 2H), 6.95 (t, J=8.7 Hz, 2H), 7.06-7.14 (m, 2H), 7.26 (d, J=8.6 Hz, 2H), 7.38 (t, J=7.5 Hz, 1H), 7.49 (t, J=7.3 Hz, 1H), 7.54 (d, J=16.0 Hz, 1H), 7.68 (s, 1H), 7.81 (d, J=8.5 Hz, 1H), 7.86 (d, J=8.1 Hz, 1H). LCMS (ESI): m/z 469 (M+H)$^+$.

Step 5: (2E)-3-(4-{[3-Butyl-2-(4-fluorophenyl)-1-naphthalenyl]oxy}phenyl)-2-propenoic acid (169)

Ethyl ester (168) (0.25 g, 0.53 mmol) was saponified with 1 N NaOH in THF and EtOH to give 0.18 g (79%) of the title compound (169) as a white solid. mp 169-170° C. $^1$H NMR (400 MHz, CH$_3$OH-d$_4$): δ 0.78 (t, J=7.3 Hz, 3H), 1.15-1.28 (m, 2H), 1.40-1.50 (m, 2H), 2.60 (t, J=7.9 Hz, 2H), 6.27 (d, J=16.0 Hz, 1H), 6.56 (d, J=8.6 Hz, 2H), 7.01 (t, J=8.7 Hz, 2H), 7.12-7.22 (m, 2H), 7.32-7.42 (m, 3H), 7.46-7.56 (m, 2H), 7.70-7.80 (m, 2H), 7.90 (d, J=8.2 Hz, 1H). LCMS (ESI): m/z 441 (M+H)$^+$, m/z 439 (M−H)$^-$. Anal. Calc for C$_{29}$H$_{25}$FO$_3$·0.1H$_2$O: C, 78.75; H, 5.74. Found: C, 78.85; H, 5.64.

Example 25 (170)

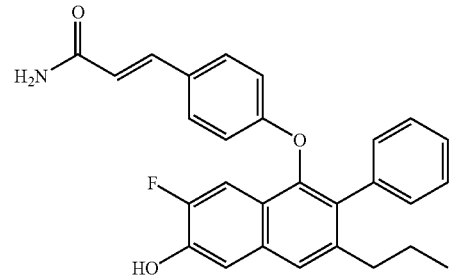

Step 1: (2E)-3-{4-[(7-Fluoro-6-hydroxy-2-phenyl-3-propyl-1-naphthalenyl)oxy]phenyl}-2-propenamide (170)

To a solution of (2E)-3-{4-[(7-fluoro-6-hydroxy-2-phenyl-3-propyl-1-naphthalenyl)oxy]phenyl}-2-propenoic acid (141) (60 mg, 0.14 mmol) in CH$_2$Cl$_2$ (2 mL) at room temperature was added oxalyl chloride (37 μL, 0.41 mmol) followed by one drop of DMF. The mixture was stirred at room temperature for 3 h. CH$_2$Cl$_2$ and excess of oxalyl chloride were removed under vacuum. The residue was dissolved in 1,4-dioxane (2 mL), cooled in an ice bath, concentrated aqueous NH$_4$OH (0.5 mL) was added. The resulting mixture was allowed to stir at room temperature for 30 min, acidified with 2 N HCl and extracted with EtOAc. The combined organic extract was washed with brine, dried over Na$_2$SO$_4$, filtered, and the filtrate was concentrated to give the crude product as a yellow viscous oil, which was purified by reverse phase preparation HPLC on Agilent 1100 to afford 35 mg (59%) of the title compound (170) as a white solid. mp 121-124° C. $^1$H NMR (400 MHz, CH$_3$OH-d$_4$): δ 0.77 (t, J=7.3 Hz, 3H), 1.40-1.55 (m, 2H), 2.52 (t, J=7.7 Hz, 2H), 6.42 (d, J=15.8 Hz, 1H), 6.54 (d, J=8.6 Hz, 2H), 7.08-7.16 (m, 2H), 7.20-7.35 (m, 7H), 7.40 (d, J=16.0 Hz, 1H), 7.53 (s, 1H). LCMS (ESI): m/z 442 (M+H)$^+$, m/z 440 (M−H)$^−$. HRMS (EI) Calc for C$_{28}$H$_{24}$FNO$_3$: 442.1818 (M$^{+•}$). Found: 442.1832.

Example 26 (174)

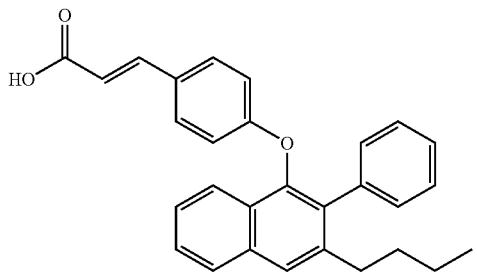

Step 1: 1-[2-(1-Hexyn-1-yl)phenyl]-2-phenylethanone (171)

2-(1-Hexyn-1-yl)-N-methyl-N-(methyloxy)benzamide (158) (1.0 g, 4.08 mmol) was treated with benzylmagnesium chloride in THF at 0° C. to give 0.88 g (78%) of compound 171 as a yellow oil. $^1$H NMR (400 MHz, CDCl$_3$): δ 0.93 (t, J=7.2 Hz, 3H), 1.40-1.53 (m, 2H), 1.56-1.65 (m, 2H), 2.45 (t, J=7.1 Hz, 2H), 4.43 (s, 2H), 7.20-7.26 (m, 4H), 7.27-7.36 (m, 2H), 7.34-7.39 (m, 1H), 7.45-7.52 (m, 2H). LCMS (ESI): m/z 277 (M+H)$^+$.

Step 2: 3-Butyl-2-phenyl-1-naphthalenol (172)

A solution of 1-[2-(1-hexyn-1-yl)phenyl]-2-phenylethanone (171) (0.88 g, 3.18 mmol) in toluene was treated with a KHMDS solution in toluene to give 0.60 g (68%) of the title compound (172) as a light yellow solid. $^1$H NMR (400 MHz, CDCl$_3$): δ 0.76 (t, J=7.3 Hz, 3H), 1.15-1.30 (m, 2H), 1.45-1.55 (m, 2H), 2.49 (t, J=7.8 Hz, 2H), 5.20 (s, 1H), 7.33 (s, 1H), 7.36 (d, J=7.0 Hz, 2H), 7.39-7.50 (m, 3H), 7.50-7.57 (m, 2H), 7.75 (d, J=7.9 Hz, 1H), 8.18 (d, J=8.0 Hz, 1H). LCMS (ESI): m/z 277 (M+H)$^+$, m/z 275 (M−H)$^−$.

Step 3: 4-[(3-Butyl-2-phenyl-1-naphthalenyl)oxy]benzaldehyde (173)

3-Butyl-2-phenyl-1-naphthalenol (172) (0.30 g, 1.09 mmol) and 4-fluorobenzaldehyde was heated with Cs$_2$CO$_3$ in DMSO at 100° C. to give 0.28 g (67%) of the title compound (173) as a light yellow viscous oil. $^1$H NMR (400 MHz, CDCl$_3$): δ 0.77 (t, J=7.3 Hz, 3H), 1.15-1.30 (m, 2H), 1.40-1.55 (m, 2H), 2.58 (t, J=7.8 Hz, 2H), 6.68 (d, J=8.6 Hz, 2H), 7.08-7.14 (m, 2H), 7.19-7.26 (m, 3H), 7.39 (t, J=7.4 Hz, 1H), 7.50 (1, J=7.3 Hz, 1H), 7.62 (d, J=8.8 Hz, 2H), 7.71 (s, 1H), 7.77 (d, J=8.4 Hz, 1H), 7.88 (d, J=8.3 Hz, 1H), 9.79 (s, 1H). LCMS (APCI): m/z 381 (M+H)$^+$.

Step 4: (2E)-3-{4-[(3-Butyl-2-phenyl-1-naphthalenyl)oxy]phenyl}-2-propenoic acid (174)

4-[(3-Butyl-2-phenyl-1-naphthalenyl)oxy]benzaldehyde (173) (0.14 g, 0.36 mmol) was heated with malonic acid (0.12 g, 1.09 mmol) and 1 drop of piperidine in pyridine at 85° C. overnight to give the crude product as a light yellow viscous oil, which upon trituration with 1% MeOH in hexanes, yielded 81 mg (53%) of the title compound (174) as a white solid. mp 160-161° C. $^1$H NMR (400 MHz, CH$_3$OH-d$_4$): δ 0.76 (t, J=7.3 Hz, 3H), 1.15-1.30 (m, 2H), 1.40-1.55 (m, 2H), 2.60 (t, J=7.9 Hz, 2H), 6.26 (d, J=16.0 Hz, 1H), 6.56 (d, J=8.6 Hz, 2H), 7.14-7.19 (m, 2H), 7.20-7.30 (m, 3H), 7.35 (d, J=8.6 Hz, 2H), 7.37-7.42 (m, 1H), 7.46-7.56 (m, 2H), 7.70-7.77 (m, 2H), 7.91 (d, J=8.2 Hz, 1H). LCMS (APCI): m/z 423 (M+H)$^+$, m/z 421 (M−H)$^−$. Anal. Calc for C$_{29}$H$_{26}$O$_3$·⅛H$_2$O: C, 81.86; H, 6.24. Found: C, 81.86; H, 6.25.

Example 27 (184)

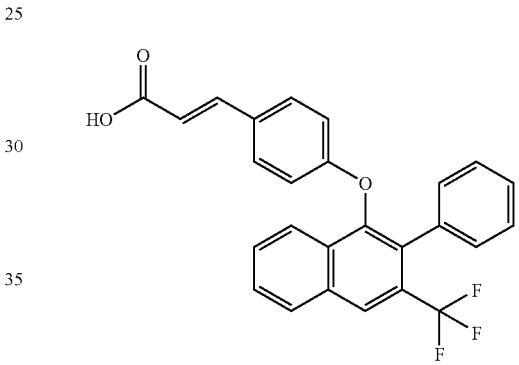

Step 1: Ethyl-4,4,4-trifluoro-3-(phenylmethyl)-2-butenoate (175)

1,1,1-Trifluoro-3-phenyl-2-propanone (1.0 g, 5.10 mmol) was dissolved in CH$_2$Cl$_2$ (20 mL). To this solution was added carbethoxymethylene triphosphorane (2.81 g, 7.65 mmol). The reaction mixture was stirred at room temperature overnight. CH$_2$Cl$_2$ was removed under reduced pressure. Upon adding hexanes to the residue, a white solid precipitated and was filtered and washed with hexanes. The filtrate was concentrated to give the crude product as a light yellow oil. The crude product was purified by flash chromatography over SiO$_2$ with hexanes:EtOAc (30:1 to 25:1) to give 0.85 g (65%) of (E) isomer of the title compound (175-E) as a colorless oil, along with 0.35 g (27%) of (Z) isomer (175-Z). For (E), $^1$H NMR (400 MHz, CDCl$_3$): δ 1.29 (t, J=7.1 Hz, 3H), 4.09 (s, 2H), 4.24 (q, J=7.1 Hz, 2H), 6.48 (s, 1H), 7.20-7.30 (m, 5H), $^{19}$F NMR (282.2 MHz, CDCl$_3$): δ 67.92. For (Z), $^1$H NMR (400 MHz, CDCl$_3$): δ 1.27 (t, J=7.1 Hz, 3H), 4.17 (s, 2H), 4.22 (q, J=7.1 Hz, 2H), 5.74 (s, 1H), 7.19 (d, J=7.1 Hz, 2H), 7.26-7.40 (m, 3H), $^{19}$F NMR (282.2 MHz, CDCl$_3$): δ 63.83.

Step 2: Ethyl 4,4,4-trifluoro-3-(phenylmethyl)butanoate (176)

Ethyl (2E)-4,4,4-trifluoro-3-(phenylmethyl)-2-butenoate (175-E) (0.85 g, 3.30 mmol) was hydrogenated at room temperature with 10% Pd/C under a hydrogen balloon to yield 0.77 g (90%) of the title compound (176) as a colorless oil. From ethyl (2Z)-4,4,4-trifluoro-3-(phenylmethyl)-2-butenoate (175-Z) (0.35 g, 1.36 mmol), 0.31 g (88%) of the title compound (176) was obtained as a colorless oil. $^1$H NMR (400 MHz, CDCl$_3$): δ 1.18 (t, J=7.2 Hz, 3H), 2.35 (dd, J$_1$=16.4 Hz, J$_2$=6.3 Hz, 1H), 2.55 (dd, J$_1$=16.5 Hz, J$_2$=6.2 Hz, 1H), 2.60-2.70 (m, 1H), 3.00-3.15 (m, 2H), 4.00 (q, J=7.2 Hz, 2H), 7.15-7.25 (m, 3H), 7.26-7.35 (m, 2H).

Step 3: 4,4,4-Trifluoro-3-(phenylmethyl)butanoic acid (177)

Ethyl ester (176) (1.08 g, 4.15 mmol) was saponified with 1 N NaOH in THF and EtOH to give 0.97 g (~100%) of the title compound (177) as a yellow oil. $^1$H NMR (400 MHz, CDCl$_3$): δ 2.41 (dd, J$_1$=16.9 Hz, J$_2$=5.8 Hz, 1H), 2.50-2.70 (m, 2H), 3.00-3.15 (m, 2H), 7.15-7.25 (m, 3H), 7.27-7.33 (m, 2H). LCMS (ESI): m/z 231 (M−H)$^-$.

Step 4: 3-(Trifluoromethyl)-3,4-dihydro-1(2H)-naphthalenone (178)

4,4,4-Trifluoro-3-(phenylmethyl)butanoic acid (177) (0.97 g, 4.18 mmol) was treated with oxalyl chloride followed by AlCl$_3$ in CH$_2$Cl$_2$ to give 0.74 g (82%) of the title compound (178) as an off-white solid. $^1$H NMR (400 MHz, CDCl$_3$): δ 2.60-2.75 (m, 1H), 2.85-3.00 (m, 2H), 3.05-3.25 (m, 2H), 7.30 (d, J=7.7 Hz, 1H), 7.37 (t, J=7.6 Hz, 1H), 7.50-7.57 (m, 1H), 8.05 (d, J=7.7 Hz, 1H). LCMS (ESI): m/z 215 (M−H)$^-$.

Step 5: 2-Bromo-3-(trifluoromethyl)-1-naphthalenol (179)

Treatment of 3-(trifluoromethyl)-3,4-dihydro-1(2H)-naphthalenone (178) (0.40 g, 1.87 mmol) with bromine followed by DBU in CH$_3$CN gave 0.23 g (43% from tetralone) of the title compound (179) as a colorless oil. $^1$H NMR (400 MHz, CDCl$_3$): δ 6.45 (s, 1H), 7.58-7.68 (m, 2H), 7.83 (s, 1H), 7.84-7.90 (m, 1H), 8.28 (d, J=7.5 Hz, 1H). LCMS (ESI): m/z 289 (M−H)$^-$.

Step 6: 2-Bromo-1-{[(methyloxy)methyl]oxy}-3-(trifluoromethyl)naphthalene (180)

2-Bromo-3-(trifluoromethyl)-1-naphthalenol (179) (0.23 g, 0.79 mmol) was treated with chloromethyl methyl ether in the presence of diisopropylethylamine in THF to give 0.24 g (91%) of the title compound (180) as a colorless oil. $^1$H NMR (400 MHz, CDCl$_3$): δ 3.75 (s, 3H), 5.29 (s, 2H), 7.59-7.65 (m, 1H), 7.65-7.71 (m, 1H), 7.91 (d, J=8.1 Hz, 1H), 8.05 (s, 1H), 8.22 (d, J=8.4 Hz, 1H). LCMS (ESI): m/z 335 (M+H)$^+$.

Step 7: 1-{[(Methyloxy)methyl]oxy}-2-phenyl-3-(trifluoromethyl)naphthalene (181)

Suzuki coupling of 2-bromo-1-{[(methyloxy)methyl]oxy}-3-(trifluoromethyl)naphthalene (180) (0.24 g, 0.72 mmol) with phenyl boronic acid (0.18 g, 1.43 mmol) in the presence of Pd(PPh$_3$)$_4$ in DME using a sealed tube at 160° C. gave 0.23 g (95%) of the title compound (181) as a white solid. $^1$H NMR (400 MHz, CDCl$_3$): δ 3.10 (s, 3H), 4.75 (s, 2H), 7.35-7.47 (m, 5H), 7.57-7.64 (m, 1H), 7.64-7.70 (m, 1H), 7.96 (d, J=8.0 Hz, 1H), 8.10 (s, 1H), 8.21 (d, J=8.2 Hz, 1H). LCMS (ESI): m/z 355 (M+Na)$^+$.

Step 8: 2-Phenyl-3-(trifluoromethyl)-1-naphthalenol (182)

1-{[(Methyloxy)methyl]oxy}-2-phenyl-3-(trifluoromethyl)naphthalene (181) (0.23 g, 0.68 mmol) was treated with 4.0M HCl in dioxane at room temperature to give 0.19 g (97%) of the title compound (182) as a colorless oil. $^1$H NMR (400 MHz, CDCl$_3$): δ 5.40 (s, 1H), 7.39 (d, J=7.1 Hz, 2H), 7.48-7.58 (m, 3H), 7.58-7.66 (m, 2H), 7.86 (s, 1H), 7.88-7.94 (m, 1H), 8.24-8.30 (m, 1H). LCMS (APCI): m/z 287 (M−H)$^-$.

Step 9: 4-{[2-Phenyl-3-(trifluoromethyl)-1-naphthalenyl]oxy}benzaldehyde (183)

2-Phenyl-3-(trifluoromethyl)-1-naphthalenol (182) (0.19 g, 0.66 mmol) and 4-fluorobenzaldehyde was heated with Cs$_2$CO$_3$ in DMSO at 100° C. to give 92 mg (36%) of the title compound (183) as a light brown solid. $^1$H NMR (400 MHz, CDCl$_3$): δ 6.67 (d, J=8.8 Hz, 2H), 7.14 (d, J=6.9 Hz, 2H), 7.18-7.27 (m, 3H), 7.58-7.70 (m, 4H), 7.89 (d, J=8.2 Hz, 1H), 8.05 (d, J=8.1 Hz, 1H), 8.27 (s, 1H), 9.82 (s, 1H). LCMS (ESI): m/z 415 (M+Na)$^+$.

Step 10: (2E)-3-(4-{[2-Phenyl-3-(trifluoromethyl)-1-naphthalenyl]oxy}phenyl)-2-propenoic acid (184)

4-{[2-Phenyl-3-(trifluoromethyl)-1-naphthalenyl]oxy}benzaldehyde (183) (92 mg, 0.24 mmol) was dissolved in pyridine (3 mL). To this solution was added malonic acid (74 mg, 0.70 mmol) and 1 drop of piperidine. The reaction mixture was heated at 85° C. overnight, cooled and poured into 5 N HCl (20 mL). The mixture was extracted with EtOAc. The combined organic extract was washed with 5 N HCl, water, brine, dried over Na$_2$SO$_4$, filtered, and the filtrate was concentrated to give the crude product as a light brown viscous oil, which upon trituration with 1% MeOH in hexanes, yielded 83 mg (81%) of the title compound (184) as a white solid. mp 210-211° C. $^1$H NMR (400 MHz, CH$_3$OH-d$_4$): δ 6.28 (d, J=15.9 Hz, 1H), 6.56 (d, J=8.8 Hz, 2H), 7.10-7.30 (m, 5H), 7.37 (d, J=8.7 Hz, 2H), 7.53 (d, J=16.0 Hz, 1H), 7.60-7.72 (m, 2H), 7.89 (d, J=8.1 Hz, 1H), 8.16 (d, J=8.1 Hz, 1H), 8.36 (s, 1H). LCMS (APCI): m/z 435 (M+H)$^+$, m/z 433 (M−H)$^-$. Anal. Calc for C$_{26}$H$_{17}$F$_3$O$_3$·⅛H$_2$O: C, 71.39; H, 3.99. Found: C, 71.50; H, 3.94.

Example 28 (190)

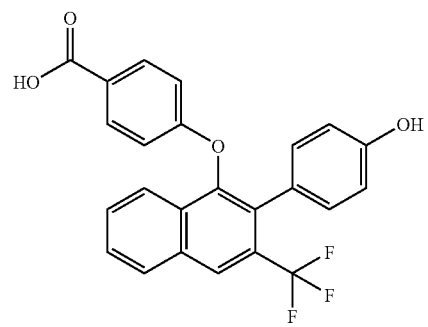

Step 1: 1-{[(Methyloxy)methyl]oxy}-2-{4-[(phenylmethyl)oxy]phenyl}-3-(trifluoro methyl)naphthalene (185)

Suzuki coupling of 2-bromo-1-{[(methyloxy)methyl]oxy}-3-(trifluoromethyl)naphthalene (180) (0.255 g, 0.76 mmol) with (4-benzoxyphenyl) boronic acid (0.36 g, 1.52 mmol) in the presence of Pd(PPh$_3$)$_4$ in DME using a sealed tube at 160° C. gave 0.32 g (95%) of compound 185 as a colorless viscous oil. $^1$H NMR (400 MHz, CDCl$_3$): δ 3.13 (s, 3H), 4.75 (s, 2H), 5.13 (s, 2H), 7.05 (d, J=8.8 Hz, 2H), 7.26-7.44 (m, 5H), 7.47 (d, J=7.3 Hz, 2H), 7.57-7.63 (m, 1H), 7.63-7.68 (m, 1H), 7.95 (d, J=8.1 Hz, 1H), 8.08 (s, 1H), 8.21 (d, J=8.2 Hz, 1H). LCMS (ESI): m/z 461 (M+Na)+.

Step 2: 2-{4-[(Phenylmethyl)oxy]phenyl}-3-(trifluoromethyl)-1-naphthalenol (186)

1-{[(Methyloxy)methyl]oxy}-2-{4-[(phenylmethyl)oxy] phenyl}-3-(trifluoromethyl)naphthalene (185) (0.32 g, 0.72 mmol) was treated with 4.0M HCl in dioxane at room temperature to give 0.28 g (99%) of the title compound (186) as a white solid. $^1$H NMR (400 MHz, CDCl$_3$): δ 5.14 (s, 2H), 5.48 (s, 1H), 7.14 (d, J=8.6 Hz, 2H), 7.31 (d, J=8.6 Hz, 2H), 7.34-7.40 (m, 1H), 7.40-7.50 (m, 2H), 7.49 (d, J=7.3 Hz, 2H), 7.57-7.65 (m, 2H), 7.85 (s, 1H), 7.88-7.94 (m, 1H), 8.24-8.29 (m, 1H). LCMS (ESI): m/z 417 (M+Na)+, m/z 393 (M–H)−.

Step 3: 4-{[2-{4-[(Phenylmethyl)oxy]phenyl}-3-(trifluoromethyl)-1-naphthalenyl]oxy} benzaldehyde (187)

2-{4-[(Phenylmethyl)oxy]phenyl}-3-(trifluoromethyl)-1-naphthalenol (186) (0.25 g, 0.64 mmol) and 4-fluorobenzaldehyde was heated with Cs$_2$CO$_3$ in DMSO at 100° C. for 5 h using microwave synthesizer to give 0.23 g (71%) of the title compound (187) as a light brown viscous oil. $^1$H NMR (400 MHz, CDCl$_3$): δ 5.01 (s, 2H), 6.67 (d, J=8.6 Hz, 2H), 6.83 (d, J=8.6 Hz, 2H), 7.06 (d, J=8.4 Hz, 2H), 7.30-7.44 (m, 5H), 7.57-7.68 (m, 4H), 7.88 (d, J=8.3 Hz, 1H), 8.04 (d, J=8.1 Hz, 1H), 8.25 (s, 1H), 9.82 (s, 1H). LCMS (ESI): m/z 521 (M+Na)+.

Step 4: Methyl 4-{[2-{4-[(phenylmethyl)oxy]phenyl}-3-(trifluoromethyl)-1-naphthalenyl] oxy}benzoate (188)

To a solution of 4-{[2-{4-[(phenylmethyl)oxy]phenyl}-3-(trifluoromethyl)-1-naphthalenyl]oxy}benzaldehyde (187) (0.23 g, 0.45 mmol) in MeOH (4 mL) and CH$_2$Cl$_2$ (2 mL) was added NaCN (0.12 g, 2.26 mmol) followed by MnO$_2$ (0.56 g, 5.42 mmol). The reaction mixture was stirred at room temperature overnight, diluted with EtOAc (50 mL) and filtered through a pad of celite on top of a layer of silica gel. The filtrate was washed with water, brine, dried over Na$_2$SO$_4$, filtered, and concentrated to give the crude product as a light yellow solid, which upon trituration with 1% MeOH in hexanes, gave 0.21 g (86%) of the title compound (188) as a white solid. mp 131-132° C. $^1$H NMR (400 MHz, CDCl$_3$): δ 3.85 (s, 3H), 5.01 (s, 2H), 6.58 (d, J=8.8 Hz, 2H), 6.83 (d, J=8.6 Hz, 2H), 7.05 (d, J=8.6 Hz, 2H), 7.30-7.44 (m, 5H), 7.55-7.66 (m, 2H), 7.79 (d, J=8.8 Hz, 2H), 7.89 (d, J=8.2 Hz, 1H), 8.03 (d, J=8.1 Hz, 1H), 8.24 (s, 1H). LCMS (ESI): m/z 551 (M+Na)+.

Step 5: Methyl 4-{[2-(4-hydroxyphenyl)-3-(trifluoromethyl)-1-naphthalenyl]oxy}benzoate (189)

Methyl 4-{[2-{4-[(phenylmethyl)oxy]phenyl}-3-(trifluoromethyl)-1-naphthalenyl]oxy}benzoate (188) (0.10 g, 0.19 mmol) was debenzylated in EtOAc and MeOH (1:1) at room temperature with 10% Pd/C under a hydrogen balloon to yield 78 mg (94%) of the title compound (189) as a white solid. mp 205-206° C. $^1$H NMR (400 MHz, CH$_3$OH-d$_4$): δ 3.82 (s, 3H), 6.62 (d, J=8.8 Hz, 2H), 6.63 (d, J=8.6 Hz, 2H), 6.96 (d, J=8.5 Hz, 2H), 7.60-7.72 (m, 2H), 7.80 (d, J=8.8 Hz, 2H), 7.88 (d, J=8.3 Hz, 1H), 8.15 (d, J=7.7 Hz, 1H), 8.35 (s, 1H). LCMS (ESI): m/z 461 (M+Na)+.

Step 6: 4-{[2-(4-Hydroxyphenyl)-3-(trifluoromethyl)-1-naphthalenyl]oxy}benzoic acid (190)

Methyl ester (189) (63 mg, 0.15 mmol) was saponified with 1 N NaOH in THF and EtOH to give 48 mg (79%) of the title compound (190) as a white solid. mp 244-245° C. $^1$H NMR (400 MHz, CH$_3$OH-d$_4$): δ 6.60 (d, J=8.8 Hz, 2H), 6.64 (d, J=8.6 Hz, 2H), 6.96 (d, J=8.4 Hz, 2H), 7.60-7.72 (m, 2H), 7.79 (d, J=9.0 Hz, 2H), 7.88 (d, J=8.1 Hz, 1H), 8.15 (d, J=7.9 Hz, 1H), 8.34 (s, 1H). LCMS (ESI): m/z 447 (M+Na)+, m/z 423 (M–H)−. Anal. Calc for C$_{24}$H$_{15}$F$_3$O$_4$.0.25H$_2$O: C, 67.21; H, 3.64. Found: C, 67.05; H, 3.47.

Example 29 (196)

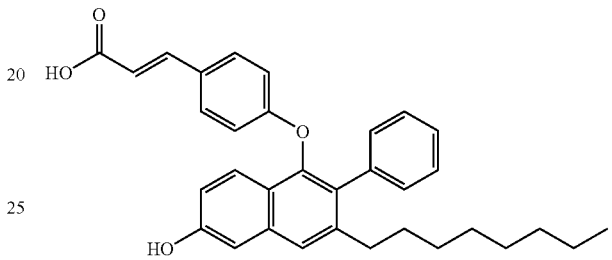

Step 1: Methyl 2-(1-decyn-1-yl)-4-(methyloxy)benzoate (191)

Coupling of methyl 4-(methyloxy)-2-{[(trifluoromethyl)sulfonyl]oxy}benzoate (77) (0.81 g, 2.58 mmol) with 1-decyne (0.95 mL, 5.16 mmol) using Pd(PPh$_3$)$_2$Cl$_2$ and CuI gave 0.78 g (~100%) of the title compound (191) as a dark brown oil. $^1$H NMR (400 MHz, CDCl$_3$): δ 0.85--0.90 (m, 3H), 1.20-1.40 (m, 8H), 1.40-1.55 (m, 2H), 1.60-1.70 (m, 2H), 2.47 (t, J=7.2 Hz, 2H), 3.83 (s, 3H), 3.87 (s, 3H), 6.82 (dd, J$_1$=8.8 Hz, J$_2$=2.6 Hz, 1H), 6.99 (d, J=2.3 Hz, 1H), 7.88 (d, J=8.7 Hz, 1H). LCMS (APCI): m/z 325 (M+Na)+.

Step 2: 2-(1-Decyn-1-yl)-N-methyl-N,4-bis(methyloxy)benzamide (192)

Treatment of methyl 2-(1-decyn-1-yl)-4-(methyloxy)benzoate (191) (0.78 g, 2.58 mmol) with a mixture of N,O-dimethylhydroxylamine hydrochloride and nBuLi gave 0.80 g (94%) of the title compound (192) as a light yellow oil. $^1$H NMR (400 MHz, CDCl$_3$): δ 0.85-0.90 (m, 3H), 1.20-1.37 (m, 8H), 1.37-1.50 (m, 2H), 1.55-1.65 (m, 2H), 2.38 (t, J=7.2 Hz, 2H), 3.28 (br s, 3H), 3.61 (br s, 3H), 3.80 (s, 3H), 6.84 (dd, J$_1$=8.5 Hz, J$_2$=2.5 Hz, 1H), 6.93 (d, J=2.4 Hz, 1H), 7.24 (d, J=8.6 Hz, 1H). LCMS (ESI): m/z 332 (M+H)+.

Step 3: 1-[2-(1-Decyn-1-yl)-4-(methyloxy)phenyl]-2-phenylethanone (193)

2-(1-Decyn-1-yl)-N-methyl-N,4-bis(methyloxy)benzamide (192) (0.80 g, 2.41 mmol) was treated with benzylmagnesium chloride in THF to give 0.80 g (91%) of compound 193 as a yellow oil. $^1$H NMR (400 MHz, CDCl$_3$): δ 0.85-0.90 (m, 3H), 1.20-1.37 (m, 8H), 1.40-1.50 (m, 2H), 1.55-1.65 (m, 2H), 2.45 (t, J=7.2 Hz, 2H), 3.83 (s, 3H), 4.45 (s, 2H), 6.83 (dd, J$_1$=8.7 Hz, J$_2$=2.7 Hz, 1H), 6.98 (d, J=2.8 Hz, 1H), 7.70-7.26 (m, 3H), 7.27-7.33 (m, 2H), 7.66 (d, J=8.8 Hz, 1H). LCMS (ESI): m/z 363 (M+H)+, m/z 361 (M–H)−.

Step 4: 6-(Methyloxy)-3-octyl-2-phenyl-1-naphthalenol (193)

A solution of 1-[2-(1-decyn-1-yl)-4-(methyloxy)phenyl]-2-phenylethanone (192) (0.80 g, 2.21 mmol) in toluene was treated with a KHMDS solution in toluene to give 0.60 g (75%) of the title compound (193) as a light brown oil. $^1$H NMR (400 MHz, CDCl$_3$): δ 0.85 (t, J=7.1 Hz, 3H), 1.10-1.30 (m, 10H), 1.35-1.50 (m, 2H), 2.46 (t, J=7.3 Hz, 2H), 3.93 (s, 3H), 5.16 (s, 1H), 7.06-7.10 (m, 2H), 7.22 (s, 1H), 7.32-7.37 (m, 2H), 7.42-7.48 (m, 1H), 7.50-7.56 (m, 2H), 8.08 (d, J=9.8 Hz, 1H). LCMS (ESI): m/z 363 (M+H)$^+$, m/z 361 (M−H)$^-$.

Step 5: 4-{[6-(Methyloxy)-3-octyl-2-phenyl-1-naphthalenyl]oxy}benzaldehyde (194)

6-(Methyloxy)-3-octyl-2-phenyl-1-naphthalenol (193) (0.60 g, 1.66 mmol) was treated with NaH in DMF followed by addition of 4-fluorobenzaldehyde to give 0.72 g (93%) of the title compound (194) as a yellow oil. $^1$H NMR (400 MHz, CDCl$_3$): δ 0.84 (t, J=7.0 Hz, 3H), 1.05-1.30 (m, 10H), 1.40-1.50 (m, 2H), 2.54 (t, J=7.9 Hz, 2H), 3.94 (s, 3H), 6.67 (d, J=8.4 Hz, 2H), 7.03-7.14 (m, 3H), 7.16-7.26 (m, 4H), 7.56-7.64 (m, 3H), 7.67 (d, J=9.1 Hz, 1H), 9.79 (s, 1H). LCMS (APCI): m/z 467 (M+H)$^+$.

Step 6: (2E)-3-(4-{[6-(Methyloxy)-3-octyl-2-phenyl-1-naphthalenyl]oxy}phenyl)-2-propenoic acid (191)

4-{[6-(Methyloxy)-3-octyl-2-phenyl-1-naphthalenyl]oxy}benzaldehyde (194) (0.20 g, 0.43 mmol) was heated with malonic acid (0.14 g, 1.29 mmol) and 1 drop of piperidine in pyridine at 85° C. overnight to give the crude product as a light yellow viscous oil, which was purified by flash chromatography over SiO$_2$ eluted with a gradient from hexanes to 35% EtOAc in hexanes to gave 0.20 g (92%) of the title compound (195) as a white solid upon standing in freezer. $^1$H NMR (400 MHz, CDCl$_3$): δ 0.85 (t, J=7.0 Hz, 3H), 1.10-1.30 (m, 10H), 1.40-1.50 (m, 2H), 2.54 (t, J=7.9 Hz, 2H), 3.93 (s, 3H), 6.22 (d, J=15.8 Hz, 1H), 6.58 (d, J=8.6 Hz, 2H), 7.04 (dd, J$_1$=9.2 Hz, J$_2$=2.5 Hz, 1H), 7.07-7.14 (m, 2H), 7.16 (d, J=2.4 Hz, 1H), 7.19-7.30 (m, 5H), 7.57 (s, 1H), 7.63 (d, J=16.0 Hz, 1H), 7.69 (d, J=9.2 Hz, 1H). LCMS (ESI): m/z 509 (M+H)$^+$, m/z 507 (M−H)$^-$.

Step 7: (2E)-3-{4-[(6-Hydroxy-3-octyl-2-phenyl-1-naphthalenyl)oxy]phenyl}-2-propenoic acid (196)

Methyl ether 195 (0.18 g, 0.35 mmol) was treated with BBr$_3$ in CH$_2$Cl$_2$ to give the crude product as an orange viscous oil, which was purified by reverse phase preparation HPLC on Agilent 1100 to afford 114 mg (65%) of the title compound (196) as a light beige solid. mp 163-164° C. $^1$H NMR (400 MHz, CH$_3$OH-d$_4$): δ 0.85 (t, J=7.2 Hz, 3H), 1.05-1.30 (m, 10H), 1.35-1.50 (m, 2H), 2.54 (t, J=7.9 Hz, 2H), 6.25 (d, J=16.0 Hz, 1H), 6.55 (d, J=8.7 Hz, 2H), 6.96 (dd, J$_1$=9.1 Hz, J$_2$=2.3 Hz, 1H), 7.10-7.16 (m, 3H), 7.18-7.28 (m, 3H), 7.34 (d, J=8.6 Hz, 2H), 7.48-7.56 (m, 2H), 7.59 (d, J=9.2 Hz, 1H). LCMS (ESI): m/z 495 (M+H)$^+$, m/z 493 (M−H)$^-$. Anal. Calc for C$_{33}$H$_{34}$O$_4$.0.2H$_2$O: C, 79.55; H, 6.96. Found: C, 79.59; H, 6.91.

Example 30 (198)

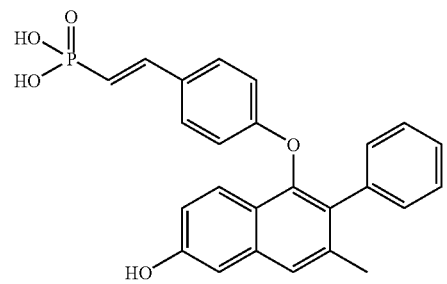

Step 1: {2-[4-(6-Methoxy-3-methyl-2-phenyl-naphthalen-1-yloxy)-phenyl]-vinyl}-phosphonic acid diethyl ester (197)

To a stirring solution of tetraethyl methylenediphosphonate (0.11 mL, 0.537 mmol) in hexanes (1 mL) was slowly added 1.6 M nBuLi (0.051 mL, 0.537 mmol) at 0° C. The reaction mixture was stirred at room temperature for 2 h under nitrogen. The reaction mixture was cooled to 0° C. then a solution of 4-[(6-methoxy-3-methyl-2-phenyl-1-naphthyl)oxy]benzaldehyde (8) (0.198 g, 0.537 mmol) in THF (1 mL) was added dropwise. After addition, reaction mixture was stirred at above temperature for 10 min then heated at 80° C. for 3 h. Reaction mixture was cooled to room temperature then diluted with water followed by EtOAc. The layers were separated and the aqueous layer was extracted with EtOAc. The combined organic layers were washed with water followed by brine, dried over MgSO$_4$, filtered and concentrated to give oil. The crude oil was chromatographed with 9% EtOAc in hexanes followed by straight MeOH to give 0.151 g (56%) of the title compound (197) as oil. $^1$H NMR (400 MHz, d-CDCl$_3$): δ 1.33 (t, J=7.1 Hz, 6H), 2.25 (s, 3H), 3.93 (s, 3H), 4.07-4.11 (m, 4H), 6.01 (t, J=17.6 Hz, 1H), 6.59 (d, J=8.8 Hz, 2H), 7.03 (dd, J$_1$=2.4, J$_2$=9.2 Hz, 1H), 7.12-7.14 (m, 3H), 7.22-7.28 (m, 5H), 7.30-7.36 (m, 1H), 7.40 (s, 1H), 7.69 (d, J=9.1 Hz, 1H).

Step 2: {2-[4-(6-Hydroxy-3-methyl-2-phenyl-naphthalen-1-yloxy)-phenyl]-vinyl}-phosphonic acid (198)

To a solution of {2-[4-(6-Methoxy-3-methyl-2-phenyl-naphthalen-1-yloxy)-phenyl]-vinyl}-phosphonic acid diethyl ester (197) (0.151 g, 0.301 mmol) in dry DCM (5 mL) was added dropwise bromotrimethylsilane (0.4 mL, 3.00 mmol). The reaction was stirred for 2 h at room temperature. Reaction mixture was concentrated to a white solid, then diluted with water. The aqueous layer was extracted with diethyl ether then the organic layer was dried over MgSO$_4$, filtered and concentrated to give 0.12 g of a white powder. BBr$_3$ (0.072 mL, 0.759 mmol) was added dropwise to the crude acid (0.113 g, 0.253 mmol) in reagent grade DCM (4 mL) at 0° C. The reaction mixture was stirred at 0° C. for 3 h, then concentrated to a solid. The solid was dissolved in DMSO (1 mL) and purified by reverse phase preparative HPLC using a C-18 column and a CH$_3$CN:H$_2$O gradient (5:95 to 95:5) with 0.05% TFA as a modifier to afford the title compound (198) as 75% pure by $^1$H NMR analysis. The impure compound was purified again using 90% water buffered to pH 3 with trace formic acid and 10% methanol to 100% methanol over 10 min, the gradient was held at 100% methanol for 5 min to afford 0.006 g (6%) of the title compound (19) as 80% pure by $^1$H NMR analysis. $^1$H NMR (400 MHz, d$_6$-DMSO): δ 2.14 (s, 3H), 6.21 (t, J=17.0 Hz, 1H), 6.56 (d, J=8.8 Hz, 2H), 6.95-7.05 (m, 2H), 7.12-7.16 (m, 4H), 7.22-7.24 (m, 1H), 7.28 (s, 1H), 7.36 (d, J=8.8 Hz, 2H), 7.49 (d, J=9.0 Hz, 1H), 7.57 (s, 1H), 9.84 (s, 1H). HRMS (ESI) Calcd for C$_{25}$H$_{22}$O$_5$P: 433.1205 (M+H)$^+$. Found: 433.1201

Example 31 (203)

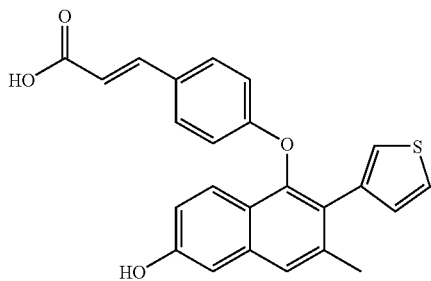

Step 1: 3-(6-Methoxy-1-(methoxymethoxy)-3-methyl-naphthalen-2-yl)-thiophene (199)

2-bromo-6-methoxy-1-(methoxymethoxy)-3-methyl-naphthalene (14) (0.35 g, 1.12 mmol), thiophene 3-boronic acid (0.359 g, 2.81 mmol), tetrakis(triphenylphosphino)palladium (0) (0.031 g, 0.027 mmol), 2 M sodium carbonate (4 mL) and ethylene glycol dimethyl ether (4 mL) were added in a sealed tube and heated at 160° C. for 20 min. Reaction mixture was cooled to room temperature then diluted with diethyl ether. The mixture was washed with water followed by brine, dried over Na$_2$SO$_4$, filtered and concentrated. The crude material purified with a gradient of 1% EtOAc to 4% EtOAc in hexanes over 45 min to afford the title compound (199) as oil, 0.347 g, (98%). $^1$H NMR (400 MHz, d-CDCl$_3$): δ 2.29 (s, 3H), 3.23 (s, 3H), 3.93 (s, 3H), 4.76 (s, 2H), 7.06-7.07 (m, 1H), 7.10-7.15 (m, 2H), 7.25-7.26 (m, 1H), 7.40-7.42 (m, 2H), 8.04 (d, J=9.2 Hz, 1H).

Step 2: 4-(6-Methoxy-3-methyl-2-thiophen-3-yl-naphthalen-1-yloxy)-benzaldehyde (200)

A solution of 3-(6-Methoxy-1-methoxymethoxy-3-methyl-naphthalen-2-yl)-thiophene (199) (0.347 g, 1.10 mmol) in 4 N HCl/Dioxane (5 mL) was stirred at room temperature for 30 min. The solvent was removed from the reaction mixture, then dissolved in DMSO (3 mL) followed by addition of Cs$_2$CO$_3$ (0.899 g, 2.76 mmol) and 4-fluorobenzaldehyde (0.142 mL, 1.32 mmol). The reaction mixture was irradiated with microwave at 80° C. for 4.5 h. Reaction mixture was diluted with water and EtOAc, separated the layers, then the aqueous layer was extracted with EtOAc. The combined organic layer was washed with water followed by brine, dried over Na$_2$SO$_4$, filtered and concentrated. The crude material was purified with a gradient of 5% EtOAc in hexanes over 50 min to afford 0.304 g (74%) of the title compound (200) as oil. $^1$H NMR (400 MHz, d-CDCl$_3$): δ 2.32 (s, 3H), 3.93 (s, 3H), 6.74 (d, J=8.6 Hz, 2H), 6.90-6.91 (m, 1H), 7.02-7.06 (m, 2H), 7.13 (m, 1H), 7.20-7.22 (m, 1H), 7.58 (s, 1H), 7.65 (d, J=8.7 Hz, 2H), 7.69 (d, J=9.2 Hz, 1H), 9.81 (s, 1H).

Step 3: 3-[4-(6-Methoxy-3-methyl-2-thiophen-3-yl-naphthalen-1-yloxy)-phenyl]-acrylic acid ethyl ester (201)

To a solution of triethylphosphonoacetate (0.242 mL, 1.22 mmol) in dry THF (4 mL) at −78° C. was slowly added 1.6 M nBuLi (0.812 mL, 1.30 mmol) then stirred for 30 min at above temperature. 4-(6-Methoxy-3-methyl-2-thiophen-3-yl-naphthalen-1-yloxy)-benzaldehyde (200) (0.304 g, 0.812 mmol) in dry THF (4 mL) was added to the reaction mixture slowly then stirred reaction mixture at above temperature for 1 h. The reaction was taken out of the acetone-dry ice bath and stirred at room temperature for 3 h. The reaction was quenched with 1 N HCl and extracted with EtOAc. The organic layer was washed with brine, dried over Na$_2$SO$_4$, filtered and concentrated. The crude material was purified with a gradient of 5% EtOAc in hexanes over 60 min to afford 0.27 g (75%) of compound (201) as a yellow solid. $^1$H NMR (400 MHz, d-CDCl$_3$): δ 1.28-1.32 (t, J=7.1, 7.2 Hz, 3H), 2.31 (s, 3H), 3.92 (s, 3H), 4.20-4.25 (m, 2H), 6.23 (d, J=15.9 Hz, 1H), 6.62 (d, J=8.8 Hz, 2H), 6.90-6.91 (m, 1H), 7.01-7.02 (m, 2H), 7.04-7.05 (m, 1H), 7.11-7.12 (m, 1H), 7.20-7.22 (m, 1H), 7.28 (d, J=8.8 Hz, 1H), 7.53-7.57 (m, 2H), 7.72 (d, J=9.2 Hz, 1H).

Step 4: 3-[4-(6-Methoxy-3-methyl-2-thiophen-3-yl-naphthalen-1-yloxy)-phenyl]-acrylic acid (202)

A solution containing 3-[4-(6-Methoxy-3-methyl-2-thiophen-3-yl-naphthalen-1-yloxy)-phenyl]-acrylic acid ethyl ester (201) (0.27 g, 0.61 mmol), 1 N NaOH (5 mL), EtOH (4 mL), THF (4 mL) was heated at 60° C. for 2.5 h. Reaction mixture was cooled to room temperature and quenched with 20% HCl then extracted with EtOAc. The organic layer was washed with brine, dried over Na$_2$SO$_4$, filtered and concentrated. The crude material was purified with 1.5% to 3.5% MeOH in DCM over 30 min to give 0.25 g (99%) of the title compound (202) as a white foam. $^1$H NMR (400 MHz, d-CDCl$_3$): δ 2.31 (s, 3H), 3.92 (s, 3H), 6.24 (d, J=16 Hz, 1H), 6.64 (d, J=8.8 Hz, 2H), 6.90-6.92 (m, 1H), 7.02-7.05 (m, 2H), 7.12 (m, 1H), 7.21-7.23 (m, 1H), 7.31 (d, J=8.6 Hz, 2H), 7.56 (m, 1H), 7.64 (d, J=15.9 Hz, 1H), 7.71 (d, J=9.2 Hz, 1H).

Step 5: 3-[4-(6-Hydroxy-3-methyl-2-thiophen-3-yl-naphthalen-1-yloxy)-phenyl]-acrylic acid (203)

Boron tribromide (0.183 mL, 1.93 mmol) was slowly added to a solution of 3-[4-(6-Methoxy-3-methyl-2-thiophen-3-yl-naphthalen-1-yloxy)-phenyl]-acrylic acid (202) (0.25 g, 0.600 mmol) in dry DCM (3 mL) at −5° C. The reaction mixture was stirred at 0° C. for 3 h. Reaction mixture was poured into ice water and extracted with EtOAc. The organic layer was washed with brine, dried over Na$_2$SO$_4$, filtered and concentrated. The crude material was purified by reverse phase preparative HPLC using a C-18 column and a CH$_3$CN:H$_2$O gradient (50:50 to 100:0) with 0.05% TFA as a modifier over 5 min to afford 0.0245 g, (10%) of the title compound (203). $^1$H NMR (400 MHz, d-CDCl$_3$): δ 2.30 (s, 3H), 6.24 (d, J=16 Hz, 1H), 6.64 (d, J=8.8 Hz, 2H), 6.91 (m, 1H), 7.00 (m, 2H), 7.13-7.14 (m, 1H), 7.21-7.23 (m, 1H), 7.31 (d, J=8.8 Hz, 2H), 7.5 (s, 1H), 7.64 (d, J=15.9 Hz, 1H), 7.73

(d, J=9.1 Hz, 1H). HRMS (ESI) Calcd for $C_{24}H_{19}O_4S$: 403.1004 (M+H)$^+$. Found: $C_{24}H_{19}O_4S$.

Example 32 (207)

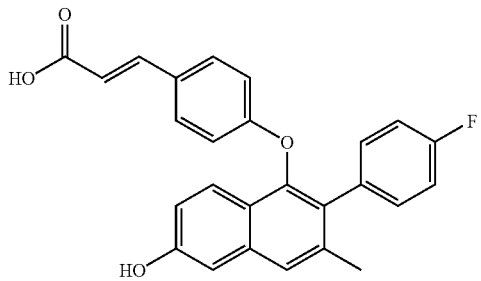

Step 1: 2-(4-Fluoro-phenyl)-6-methoxy-1-methoxymethoxy-3-methyl-naphthalene (203)

2-Bromo-6-methoxy-1-(methoxymethoxy)-3-methyl-naphthalene (14) (0.3 g, 0.964 mmol), 4-fluorobenzeneboronic acid (0.27 g, 1.93 mmol), tetrakis(triphenylphosphino)palladium (0) (0.11 g, 0.0964 mmol), 2 M sodium carbonate (5 mL) and ethylene glycol dimethyl ether (5 mL) were added in a sealed tube and reacted as described above to give 0.31 g (96%) of the title compound (203) as a white solid. $^1$H NMR (400 MHz, d-CDCl$_3$): δ 2.21 (s, 3H), 3.12 (s, 3H), 3.93 (s, 3H), 4.75 (s, 2H), 7.08-7.08 (m, 1H), 7.11-7.17 (m, 3H), 7.30-7.33 (m, 2H), 7.44 (s, 1H), 8.01 (d, J=9.2 Hz, 1H).

Step 2: 4-[2-(4-Fluoro-phenyl)-6-methoxy-3-methyl-naphthalen-1-yloxy]-benzaldehyde (204)

2-(4-Fluoro-phenyl)-6-methoxy-1-methoxymethoxy-3-methyl-naphthalene (203) (0.31 g, 0.95 mmol), 4 N HCl/Dioxane (5 mL), 4-fluorobenzaldehyde (0.132 mL, 1.23 mmol), Cs$_2$CO$_3$ (0.838 g, 2.57 mmol) and DMSO (3 mL) were reacted as described above to give 0.263 g (72%) of the title compound (204) as oil. $^1$H NMR (400 MHz, d-CDCl$_3$): δ 2.24 (s, 3H), 3.93 (s, 3H), 6.69 (d, J=8.8 Hz, 2H), 6.92-6.97 (m, 2H), 7.07-7.15 (m, 4H), 7.59-7.68 (m, 4H), 9.80 (s, 1H).

Step 3: 3-{4-[2-(4-Fluoro-phenyl)-6-methoxy-3-methyl-naphthalen-1-yloxy]-phenyl}-acrylic acid ethyl ester (205)

4-[2-(4-Fluoro-phenyl)-6-methoxy-3-methyl-naphthalen-1-yloxy]-benzaldehyde (204) (0.263 g, 0.681 mmol), triethylphosphonoacetate (0.195 mL, 0.985 mmol), 1.6 M nBuLi (0.66 mL, 1.05 mmol) and THF (8 mL) afforded 0.265 g (85%) of the title compound (205) as oil. $^1$H NMR (400 MHz, d-CDCl$_3$): δ 1.30 (t, J=7.1 Hz, 3H), 2.23 (s, 3H), 3.93 (s, 3H), 4.19-4.25 (m, 2H), 6.22 (d, J=16.1 Hz, 1H), 6.57 (d, J=8.6 Hz, 2H), 6.92-6.97 (m, 2H), 7.03-7.13 (m, 4H), 7.25-7.27 (m, 2H), 7.52-7.56 (m, 2H), 7.70 (d, J=9.2 Hz, 1H).

Step 4: 3-{4-[2-(4-Fluoro-phenyl)-6-methoxy-3-methyl-naphthalen-1-yloxy]-phenyl}-acrylic acid (206)

3-{4-[2-(4-Fluoro-phenyl)-6-methoxy-3-methyl-naphthalen-1-yloxy]-phenyl}-acrylic acid ethyl ester (205) (0.265 g, 0.58 mmol), 1 N NaOH (5 mL), EtOH (4 mL), THF (4 mL) afforded 0.213 g (86%) of title compound (206) as a white foam. $^1$H NMR (400 MHz, d-CDCl$_3$): δ 2.23 (s, 3H), 3.93 (s, 3H), 6.23 (d, J=16.0 Hz, 1H), 6.59 (d, J=8.8 Hz, 2H), 6.93-6.97 (m, 2H), 7.03-7.13 (m, 4H), 7.29 (d, J=8.8 Hz, 2H), 7.57 (s, 1H), 7.63 (d, J=15.9 Hz, 1H), 7.70 (d, J=9.2 Hz, 1H).

Step 5: 3-{4-[2-(4-Fluoro-phenyl)-6-hydroxy-3-methyl-naphthalen-1-yloxy]-phenyl}-acrylic acid (207)

3-{4-[2-(4-Fluoro-phenyl)-6-methoxy-3-methyl-naphthalen-1-yloxy]-phenyl}-acrylic acid (206) (0.213 g, 0.497 mmol), BBr$_3$ (0.141 mL, 1.49 mmol), DCM (3 mL) afforded 0.071 g (34%) of the title compound (207) as pink solid. $^1$H NMR (400 MHz, d-CDCl$_3$): δ 2.22 (s, 3H), 6.23 (d, J=15.9 Hz, 1H), 6.59 (d, J=8.7 Hz, 2H), 6.93-7.01 (m, 3H), 7.07-7.10 (m, 2H), 7.15 (d, J=2.5 Hz, 1H), 7.29 (d, J=8.8 Hz, 2H), 7.51 (s, 1H), 7.63 (d, J=15.9 Hz, 1H), 7.71 (d, J=9.0 Hz, 1H). HRMS (ESI) Calcd for $C_{26}H_{20}FO_4$: 415.1346 (M+H) t. Found: 415.1360.

Example 33 (212)

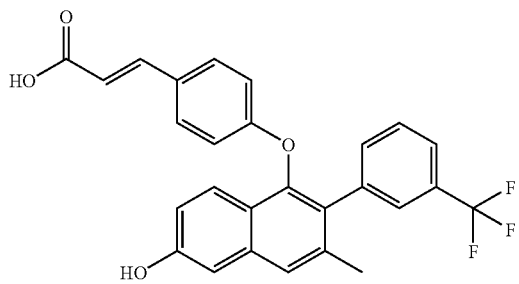

Step 1: 2-Bromo-6-methoxy-1-(methoxymethoxy)-3-methylnaphthalene (14)

Chloromethyl methyl ether (0.91 mL, 11.98 mmol) in dry THF (5 mL) was added dropwise via an addition funnel to a solution of 2-bromo-6-methoxy-3-methyl-naphthalen-1-ol (13) (2 g, 7.49 mmol) and DIEA (1.96 mL, 11.23 mmol) in dry THF (8 mL) at 0° C. The reaction mixture was stirred at RT for 18 h. Reaction mixture was diluted with Et$_2$O and water. The layers were separated and the organic layer was washed with 1 N HCl followed by brine. The organic layer was dried over MgSO$_4$, filtered and concentrated to give brown oil. The crude material was purified with a gradient of DCM (40%) in hexanes to afford 1.8 g (77%) of the title compound (14). $^1$H NMR (400 MHz, d-CDCl$_3$): δ 2.54 (s, 3H), 3.72 (s, 3H), 3.90 (s, 3H), 5.24 (s, 2H), 7.02-7.02 (m, 1H), 7.12 (dd, J$_1$=2.5 Hz, J$_2$=9.1 Hz, 1H), 7.42 (s, 1H), 8.03 (d, J=9.1 Hz, 1H).

Step 2: 6-Methoxy-1-methoxymethoxy-3-methyl-2-(3-trifluoromethyl-phenyl)-naphthalene (208)

2-Bromo-6-methoxy-1-(methoxymethoxy)-3-methyl-naphthalene (14) (0.5 g, 1.61 mmol), 3-trifluoromethylbenzeneboronic acid (0.61 g, 3.21 mmol), tetrakis(triphenylphosphino)palladium (0) (0.186 g, 0.161 mmol), 2 M sodium carbonate (15 mL) and ethylene glycol dimethyl ether (15 mL) were added in a sealed tube and reacted as described above to give 0.60 g (99%) of the title compound (208) as a white solid. $^1$H NMR (400 MHz, d-CDCl$_3$): δ 2.21 (s, 3H), 3.01 (s, 3H), 3.93 (s, 3H), 4.76 (s, 2H), 7.09 (m, 1H), 7.12-7.15 (dd, J$_1$=2.5 Hz, J$_2$=9.1 Hz, 1H), 7.45 (s, 1H), 7.55-7.65 (m, 4H), 7.98 (d, J=9.2 Hz, 1H).

Step 3: 4-[6-Methoxy-3-methyl-2-(3-trifluoromethyl-phenyl)-naphthalen-1-yloxy]-benzaldehyde (209)

6-Methoxy-1-methoxymethoxy-3-methyl-2-(3-trifluoromethyl-phenyl)-naphthalene (208) (0.35 g, 0.93 mmol), 4 N HCl/Dioxane (5 mL), 4-fluorobenzaldehyde (0.11 mL, 1.02 mmol), Cs$_2$CO$_3$ (0.364 g, 1.12 mmol) and DMF (3 mL) were reacted as described above to give 0.140 g (35%) of the title compound (209) as oil. $^1$H NMR (400 MHz, d-CDCl$_3$): δ 2.26 (s, 3H), 3.95 (s, 3H), 6.68 (d, J=8.8 Hz, 2H), 7.09 (dd, J$_1$=2.6 Hz, J$_2$=9.2 Hz, 1H), 7.17-7.17 (m, 1H), 7.31-7.39 (m, 2H), 7.44 (s, 1H), 7.48-7.50 (m, 1H), 7.61-7.64 (m, 3H), 7.73 (d, J=9.1 Hz, 1H), 9.80 (s, 1H).

Step 4: 3-{4-[6-Methoxy-3-methyl-2-(3-trifluoromethyl-phenyl)-naphthalen-1-yloxy]-phenyl}-acrylic acid ethyl ester (210)

4-[6-Methoxy-3-methyl-2-(3-trifluoromethyl-phenyl)-naphthalen-1-yloxy]-benzaldehyde (209) (0.14 g, 0.321 mmol), triethylphosphonoacetate (0.095 mL, 0.481 mmol), 1.6 M nBuLi (0.32 mL, 0.513 mmol) and THF (10 mL) afforded 0.122 g (75%) of the title compound (210) as a solid. $^1$H NMR (400 MHz, d-CDCl$_3$): δ 1.30 (t, J=7.1 Hz, 3H), 2.23 (s, 3H), 3.93 (s, 3H), 4.20-4.25 (m, 2H), 6.22 (d, J=15.9 Hz, 1H), 6.54 (d, J=8.8 Hz, 2H), 7.06 (dd, J$_1$=2.6 Hz, J$_2$=9.2 Hz, 1H), 7.14-7.15 (m, 1H), 7.24 (d, J=8.8 Hz, 2H), 7.29-7.38 (m, 2H), 7.42 (s, 1H), 7.46-7.48 (m, 1H), 7.53 (d, J=16.0 Hz, 1H), 7.58 (s, 1H), 7.75 (d, J=9.1 Hz, 1H).

Step 5: 3-{4-[6-Methoxy-3-methyl-2-(3-trifluoromethyl-phenyl)-naphthalen-1-yloxy]-phenyl}-acrylic acid (211)

3-{4-[6-Methoxy-3-methyl-2-(3-trifluoromethyl-phenyl)-naphthalen-1-yloxy]-phenyl}-acrylic acid ethyl ester (210) (0.122 g, 0.24 mmol), 1 N NaOH (2.5 mL), EtOH (2 mL) and THF (2 mL) afforded 0.09 g (78%) of title compound (211) as a white solid. $^1$H NMR (400 MHz, d-CDCl$_3$): δ 2.25 (s, 3H), 3.94 (s, 3H), 6.23 (d, J=16.0 Hz, 1H), 6.56 (d, J=8.8 Hz, 2H), 7.06 (dd, J$_1$=2.4 Hz, J$_2$=9.1 Hz, 1H), 7.15-7.16 (m, 1H), 7.27 (d, J=8.8 Hz, 2H), 7.30-7.32 (m, 1H), 7.35-7.39 (m, 1H), 7.43 (s, 1H), 7.48-7.50 (m, 1H), 7.60 (s, 1H), 7.63 (d, J=15.9 Hz, 1H), 7.75 (d, J=9.1 Hz, 1H).

Step 6: 3-{4-[6-Hydroxy-3-methyl-2-(3-trifluoromethyl-phenyl)-naphthalen-1-yloxy]-phenyl}-acrylic acid (212)

3-{4-[6-Methoxy-3-methyl-2-(3-trifluoromethyl-phenyl)-naphthalen-1-yloxy]-phenyl}-acrylic acid (211) (0.09 g, 0.188 mmol), BBr$_3$ (0.141 g, 0.564 mmol) and DCM (4 mL) afforded 0.03 g (34%) of the title compound (212) as a foam. $^1$H NMR (400 MHz, d-CDCl$_3$): δ 2.24 (s, 3H), 6.25 (d, J=16.0 Hz, 1H), 6.58 (d, J=8.3 Hz, 2H), 7.04 (dd, J$_1$=1.9 Hz, J$_2$=8.9 Hz, 1H), 7.18-7.18 (m, 1H), 7.27-7.32 (m, 3H), 7.37-7.40 (m, 1H), 7.43 (s, 1H), 7.49-7.50 (m, 1H), 7.55 (s, 1H), 7.64 (d, J=16.0 Hz, 1H), 7.78 (d, J=9.1 Hz, 1H). HRMS (ESI) Calcd for C$_{27}$H$_{18}$F$_3$O$_4$: 463.1157 (M–H)$^-$. Found: 463.1146.

Example 34 (216)

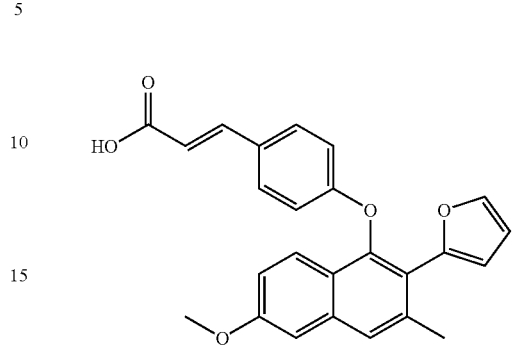

Step 1: 2-(6-Methoxy-1-methoxymethoxy-3-methyl-naphthalen-2-yl)-furan (213)

2-(Tributylstannyl)-furan (0.4 mL, 1.29 mmol)) was added slowly to a solution of 2-bromo-6-methoxy-1-(methoxymethoxy)-3-methylnaphthalene (14 (0.4 g, 1.29 mmol) in toluene (10 mL). Reaction mixture was heated at 105° C. A portion (0.01 g) of tetrakis(triphenylphosphino)palladium (0) (0.061 g, 0.053 mmol) was added every 1 h until reaction was complete. Reaction mixture was cooled to RT then diluted with Et$_2$O and water. The layers were separated and the organic layer was washed with brine, dried over MgSO$_4$, filtered and concentrated. The crude oil was purified with a gradient of 20% EtOAc in hexanes to give 0.29 g (76%) of the title compound (213) as oil. $^1$H NMR (400 MHz, d-CDCl$_3$): δ 2.36 (s, 3H), 3.37 (s, 3H), 3.93 (s, 3H), 4.85 (s, 2H), 6.49-6.50 (m, 1H), 6.53-6.55 (m, 1H), 7.05 (m, 1H), 7.11 (dd, J$_1$=2.4 Hz, J$_2$=9.2 Hz, 1H), 7.39 (s, 1H), 7.58-7.58 (m, 1H), 8.08 (d, J=9.2 Hz, 1H).

Step 2: 4-(2-Furan-2-yl-6-methoxy-3-methyl-naphthalen-1-yloxy)-benzaldehyde (214)

2-(6-Methoxy-1-methoxymethoxy-3-methyl-naphthalen-2-yl)-furan (213) (0.54, 1.8 mmol), 4 N HCl/Dioxane (6 mL), 4-fluorobenzaldehyde (0.23 mL, 2.17 mmol), Cs$_2$CO$_3$ (1.47 g, 4.53 mmol) and DMSO (8 mL) were reacted as described above to give 0.236 g (36%) of the title compound (214) as oil. $^1$H NMR (400 MHz, d-CDCl$_3$): δ 2.48 (s, 3H), 3.93 (s, 3H), 6.34 (s, 2H), 6.84 (d, J=8.6 Hz, 2H), 7.04 (dd, J$_1$=2.4 Hz, J$_2$=9.2 Hz, 1H), 7.11-7.12 (m, 1H), 7.39 (s, 1H), 7.57 (s, 1H), 7.69-7.73 (m, 3H), 9.84 (s, 1H).

Step 3: 3-[4-(2-Furan-2-yl-6-methoxy-3-methyl-naphthalen-1-yloxy)-phenyl]-acrylic acid ethyl ester (215)

4-(2-Furan-2-yl-6-methoxy-3-methyl-naphthalen-1-yloxy)-benzaldehyde (214) (0.23 g, 0.642 mmol), triethylphosphonoacetate (0.191 mL, 0.963 mmol), 1.6 M nBuLi (0.642 mL, 1.02 mmol) and THF (6 mL) reacted to afford 0.27 g (98%) of title compound (215). $^1$H NMR (400 MHz, d-CDCl$_3$): δ 1.31 (t, J=7.1 Hz, 3H), 2.47 (s, 3H), 3.92 (s, 3H), 4.20-4.25 (m, 2H), 6.25 (d, J=16.1 Hz, 1H), 6.34 (d, J=1.3 Hz, 2H), 6.72 (d, J=8.8 Hz, 2H), 7.02 (dd, J$_1$=2.5 Hz, J$_2$=9.2 Hz, 1H), 7.09-7.10 (m, 1H), 7.34 (d, J=8.8 Hz, 2H), 7.40 (s, 1H), 7.53 (s, 1H), 7.57 (d, J=16.0 Hz, 1H), 7.72 (d, J=9.1 Hz, 1H).

Step 4: 3-[4-(2-Furan-2-yl-6-methoxy-3-methyl-naphthalen-1-yloxy)-phenyl]-acrylic acid (216)

3-[4-(2-Furan-2-yl-6-methoxy-3-methyl-naphthalen-1-yloxy)-phenyl]-acrylic acid ethyl ester (215) (0.267 g, 0.623 mmol), 1 N NaOH (5 mL), EtOH (4 mL) and THF (4 mL) afforded 0.243 g (97%) of the title compound (216). $^1$H NMR (400 MHz, d-CDCl$_3$): δ 2.48 (s, 3H), 3.93 (s, 3H), 6.27 (d, J=15.8 Hz, 1H), 6.35-6.36 (m, 2H), 6.75 (d, J=8.8 Hz, 2H), 7.03 (dd, J$_1$=2.5 Hz, J$_2$=9.2 Hz, 1H), 7.10-7.11 (m, 1H), 7.37 (d, J=8.8 Hz, 2H), 7.41 (s, 1H), 7.55 (s, 1H), 7.66 (d, J=15.9 Hz, 1H), 7.72 (d, J=9.1 Hz, 1H).

Example 35 (218)

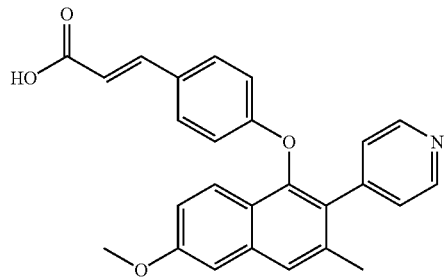

Step 1: 4-(6-Methoxy-3-methyl-2-pyridin-4-yl-naphthalen-1-yloxy)-benzaldehyde (217)

A solution of bromide 14 (1.43 g, 4.6 mmol) in anhydrous THF (15 mL) was cooled to −78° C. under N$_2$ and nBuLi (3.2 mL, 5.06 mmol, 1.6 M in hexanes) added dropwise. After stirring at −78° C. for 1 h a solution of B(OMe)$_3$ in THF (3 mL) was added and the resulting reaction stirred an additional 30 min at −78° C. then allowed to warm to RT and stirred overnight. After 20 h the reaction was quenched by addition of NH$_4$Cl (50 mL) and ether (50 mL) and the organic layer washed with diethyl ether (50 mL) and EtOAc (50 mL). The combined organics were washed water (20 mL) and brine (20 mL), dried (MgSO4) and concentrated to 1.27 g (~100%) of a solid. $^1$H NMR (400 MHz, d-CDCl$_3$): δ 2.59 (s, 3H), 3.51 (s, 3H), 3.91 (s, 3H), 5.19 (s, 2H), 7.03 (d, J=2.4 Hz, 1H), 7.08 (dd, J=2.4 Hz, J$_2$=9.1 Hz, 1H), 7.34 (s, 1H), 8.52 (d, J=9.1 Hz, 1H). The crude (3-methyl-6-(methyloxy)-1-{[(methyloxy)methyl]oxy}-2-naphthalenyl)boronic acid (0.25 g, 0.698 mmol), 4-bromopyridium chloride (0.149 g, 0.768 mmol), tetrakis(triphenylphosphino)palladium (0) (0.081 g, 0.0698 mmol), 2 M sodium carbonate (6 mL), DME (4 mL) were combined and heated for 30 min at 160° C. Reaction mixture was cooled to RT, diluted with Et$_2$O and water. The organic phase was washed with brine, dried over MgSO$_4$, filtered and concentrated. The crude material was flushed through a column with EtOAc to give the title compound along with ~10% of an uncharacterized impurity. This partially purified material (0.49 g, 1.61 mmol) was treated first with 4 N HCl/Dioxane (5 mL) and then 4-fluorobenzaldehyde (0.225 mL, 2.1 mmol), Cs$_2$CO$_3$ (1.3 g, 4.03 mmol) and DMSO (5 mL) using standard procedures previously describe to afford 0.14 g (23%) of title compound (217) as an oil. $^1$H NMR (400 MHz, d-CDCl$_1$): δ 2.25 (s, 3H), 3.93 (s, 3H), 6.70 (d, J=8.6 Hz, 2H), 7.09 (dd, J$_1$=2.5 Hz, J$_2$=9.2 Hz, 1H), 7.11-7.16 (m, 3H), 7.62-7.68 (m, 4H), 8.52 (d, J=5.9 Hz, 2H), 9.81 (s, 1H).

Step 2: 3-[4-(6-Methoxy-3-methyl-2-pyridin-4-yl-naphthalen-1-yloxy)-phenyl]-acrylic acid (218)

4-(6-Methoxy-3-methyl-2-pyridin-4-yl-naphthalen-1-yloxy)-benzaldehyde (217) (0.2 g, 0.619 mmol), triethylphosphonoacetate (0.184 g, 0.928 mmol), 1.6 M nBuLi (0.62 mL, 0.987) and THF (6 mL) afforded the crude ethyl ester that contained a minor impurity following silica gel column chromatography. The partially purified ester (0.26 g, 0.592 mmol) was treated with 1 N NaOH (5 mL), EtOH (4 mL) and THF (4 mL) to yield 0.2 g (91%) of title compound (218) as solid. $^1$H NMR (400 MHz, d-CDCl$_3$): δ 2.25 (s, 3H), 3.94 (s, 3H), 6.24 (d, J=16.0 Hz, 1H), 6.60 (d, J=8.8 Hz, 2H), 7.09 (dd, J$_1$=2.5 Hz, J$_2$=9.2 Hz, 1H), 7.15-7.19 (m, 3H), 7.30 (d, J=8.8 Hz, 2H), 7.60-7.64 (m, 2H), 7.70 (d, J=9.2 Hz, 1H), 8.55 (d, J=5.7 Hz, 2H).

Example 36 (221)

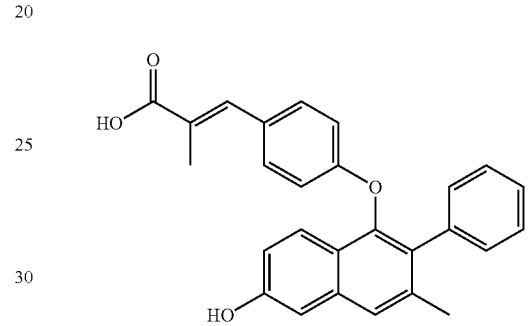

Step 1: 3-[4-(6-Methoxy-3-methyl-2-phenyl-naphthalen-1-yloxy)-phenyl]-2-methyl-acrylic acid ethyl ester (219)

As described above, 4-(6-Methoxy-3-methyl-2-phenyl-naphthalen-1-yloxy)-benzaldehyde (8) (0.21 g, 0.570 mmol), triethyl 2-phosphonopropionate (0.183 mL, 0.855 mmol), 1.6 M nBuLi (0.57 mL, 0.912 mmol) in dry THF (8 mL) afforded 0.2 g (78%) of the title compound (219) as oil. $^1$H NMR (400 MHz, d-CDCl$_3$): δ 1.31 (t, J=7.1 Hz, 3H), 2.04 (s, 3H), 2.24 (s, 3H), 3.93 (s, 3H), 4.20-4.25 (m, 2H), 6.59 (d, J=8.8 Hz, 2H), 7.03-7.06 (m, 1H), 7.11-7.16 (m, 5H), 7.21-7.25 (m, 3H), 7.55 (d, J=9.7 Hz, 2H), 7.75 (d, J=9.1 Hz, 1H).

Step 2: 3-[4-(6-Methoxy-3-methyl-2-phenyl-naphthalen-1-yloxy)-phenyl]-2-methyl-acrylic acid (220)

As described above, 3-[4-(6-Methoxy-3-methyl-2-phenyl-naphthalen-1-yloxy)-phenyl]-2-methylacrylic acid ethyl ester (219) (0.189 g, 0.418 mmol), THF (3 mL), EtOH (3 mL) and 1 N NaOH (4 mL) afforded 0.156 g (88%) of title compound (220) as a solid. $^1$H NMR (400 MHz, d-CDCl$_3$): δ 2.07 (s, 3H), 2.24 (s, 3H), 3.93 (s, 3H), 6.61 (d, J=8.8 Hz, 2H), 7.04 (dd, J$_1$=2.5 Hz, J$_2$=9.2 Hz, 1H), 7.12-7.14 (m, 3H), 7.17-7.21 (m, 2H), 7.23-7.27 (m, 3H), 7.56 (s, 1H), 7.64 (s, 1H), 7.74 (d, J=9.1 Hz, 1H).

Step 3: 3-[4-(6-Hydroxy-3-methyl-2-phenyl-naphthalen-1-yloxy)-phenyl]-2-methyl-acrylic acid (221)

As previously described, 3-[4-(6-Methoxy-3-methyl-2-phenyl-naphthalen-1-yloxy)-phenyl]-2-methylacrylic acid (220) (1.56 g, 0.367 mmol), BBr$_3$ (0.104 mL, 1.10 mmol) and DCM (5 mL) afforded 0.0356 g (24%) of the title compound (221) as a white powder. $^1$H NMR (400 MHz, d-CDCl$_3$): δ 2.07 (s, 3H), 2.22 (s, 3H), 6.61 (d, J=8.8 Hz, 2H), 7.04 (dd, J$_1$=2.5 Hz, J$_2$=9.2 Hz, 1H), 7.11-7.15 (m, 3H), 7.18-7.21 (m, 2H), 7.23-7.27 (m, 3H), 7.51 (s, 1H), 7.65 (s, 1H), 7.75 (d, J=9.1 Hz, 1H). HRMS (ESI) Calcd for C$_{27}$H$_{22}$O$_4$Na: 433.1416 (M+Na)$^+$. Found: 433.1418.

Example 37 (224)

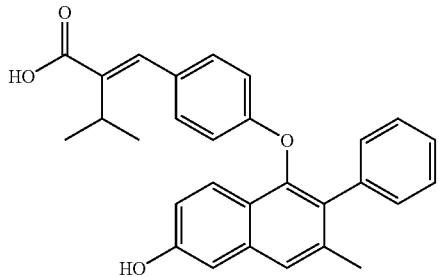

Step 1: 2-[4-(6-Methoxy-3-methyl-2-phenyl-naphthalen-1-yloxy)-benzylidene]-3-methyl-butyric acid ethyl ester (222)

* synthesis of ethyl ester described below.

Using the procedure described in Example 31 (Step 3), reaction of 4-(6-Methoxy-3-methyl-2-phenyl-naphthalen-1-yloxy)-benzaldehyde (8) (0.507 g, 1.38 mmol), 2-(diethoxyphosphoryl)-3-methyl-butyric acid ethyl ester (1.1 g, 4.13 mmol) and 1.6 M nBuLi (2.8 mL, 4.41 mmol) in dry THF (14 mL) afforded 2 isomeric products (222) as oils. Yield: (222-1) Isomer (1) 0.177 (27%); (222-2) Isomer (2) 0.195 g (30%). Isomer (1): $^1$H NMR (400 MHz, d-CDCl$_3$): δ 1.20 (d, J=6.9 Hz, 6H), 1.32 (t, J=7.1 Hz, 3H), 2.24 (s, 3H), 3.06-3.10 (m, 1H), 3.94 (s, 3H), 4.20-4.25 (m, 2H), 6.58 (d, J=8.8 Hz, 2H), 7.03-7.07 (m, 3H), 7.12-7.14 (m, 3H), 7.22-7.26 (m, 3H), 7.39 (s, 1H), 7.56 (s, 1H), 7.78 (d, J=9.1 Hz, 1H).
Isomer (2): $^1$H NMR (400 MHz, d-CDCl$_3$): δ 1.08 (t, J=7.1 Hz, 3H), 1.13 (d, J=6.9 Hz, 6H), 2.24 (s, 3H), 2.68-2.72 (m, 1H), 3.93 (s, 3H), 4.06-4.11 (m, 2H), 6.38 (s, 1H), 6.52 (d, J=8.8 Hz, 2H), 6.95-7.02 (m, 3H), 7.12-7.15 (m, 3H), 7.22-7.26 (m, 3H), 7.56 (s, 1H), 7.69 (d, J=9.1 Hz, 1H).

Step 2: 2-[4-(6-Methoxy-3-methyl-2-phenyl-naphthalen-1-yloxy)-benzylidene]-3-methyl-butyric acid (223)

Using the procedure described in Example 31 (Step 4), isomer (1) of 2-[4-(6-Methoxy-3-methyl-2-phenyl-naphthalen-1-yloxy)-benzylidene]-3-methyl-butyric acid ethyl ester (222-1) (0.159 g, 0.331 mmol), 1 N NaOH (4 mL), EtOH (3 mL) and THF (3 mL) afforded isomer (1) (223-1) 0.139 g (93%) of the title compound. $^1$H NMR (400 MHz, d-CDCl$_3$): δ 1.22 (d, J=7.0 Hz, 6H), 2.23 (s, 3H), 3.08-3.15 (m, 1H), 3.93 (s, 3H), 6.58 (d, J=8.6 Hz, 2H), 7.04-7.07 (m, 3H), 7.12-7.13 (m, 3H), 7.20-7.28 (m, 4H), 7.54 (d, J=13.4, 2H), 7.76 (d, J=9.1 Hz, 1H).
Similarly isomer (2) of 2-[4-(6-Methoxy-3-methyl-2-phenyl-naphthalen-1-yloxy)-benzylidene]-3-methyl-butyric acid ethyl ester (222-1) (0.191 g, 0.397 mmol) afforded 0.114 g (63%) of isomer (2) (223-2) of the title compound as solid. $^1$H NMR (400 MHz, d-CDCl$_3$): δ 1.15 (d, J=7.0 Hz, 6H), 2.22 (s, 3H), 2.70-2.77 (m, 1H), 3.91 (s, 3H), 6.47-6.51 (m, 3H), 7.00-7.04 (m, 3H), 7.09-7.13 (m, 3H), 7.18-7.25 (m, 4H), 7.54 (s, 1H), 7.73 (d, J=9.2 Hz, 1H).

Step 3: 2-[4-(6-Hydroxy-3-methyl-2-phenyl-naphthalen-1-yloxy)-benzylidene]-3-methyl-butyric acid (224)

Using the procedure described in Example 31 (Step 54), isomer (1) of 2-[4-(6-Methoxy-3-methyl-2-phenyl-naphthalen-1-yloxy)-benzylidene]-3-methyl-butyric acid (223-1) (0.139 g, 0.307 mmol), BBr$_3$ (0.0871 mL, 0.921 mmol), DCM (4 mL) afforded 0.0427 g (32%) of title compound (224-1). $^1$H NMR (400 MHz, d-CDCl$_3$): δ 1.23 (d, J=7.0 Hz, 6H), 2.23 (s, 3H), 3.09-3.14 (m, H), 6.60 (d, J=8.8 Hz, 2H), 7.00-7.01 (dd, J$_1$=2.0 Hz, J$_2$=9.0 Hz, 1H), 7.07 (d, J=8.6 Hz, 2H), 7.12-7.16 (m, 3H), 7.22-7.29 (m, 3H), 7.54 (d, J=14.3, 2H), 7.78 (d, J=8.0 Hz, 1H). HRMS (ESI) Calcd for C$_{29}$H$_{25}$O$_4$: 437.1753 (M–H). Found: 437.1756.
Similarly Isomer (2) of 2-[4-(6-Methoxy-3-methyl-2-phenyl-naphthalen-1-yloxy)-benzylidene]-3-methyl-butyric acid (223-2) (0.092 g, 0.203 mmol) was treated as described above to afford 0.0254 g (29%) of the title compound (224-1) with ~33% of 224-1 of the title compound as solid.

Example 38 (228)

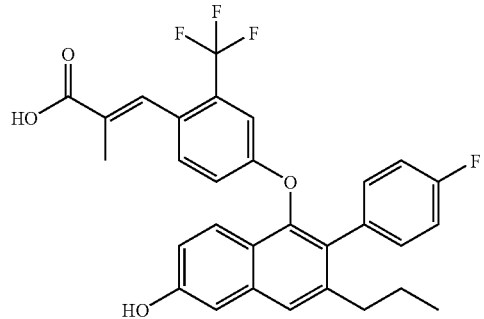

Step 1:
2-Bromo-6-methoxy-3-propyl-naphthalen-1-ol (94)

To a solution of 6-Methoxy-3-propyl-3,4-dihydro-2H-naphthalen-1-one (93) (1.6 g, 7.33 mmol) in dry chloroform (65 mL) was added dropwise via an addition funnel bromine (2.35 g, 14.7 mmol) in chloroform (20 mL). The reaction mixture was stirred at ambient temperature for 20 h. The reaction mixture was concentrated to afford the title compound as oil, 2.76 g. The crude material (2.76 g, 7.33 mmol) in dry acetonitrile (64 mL) was cooled to −10° C., 1,8-diazabicyclo[5.4.0]undec-7-ene (1.64 mL, 10.99 mmol) in dry acetonitrile (8 mL) was added dropwise via an addition funnel. The reaction mixture was quenched with 1 N HCl (50 mL) after stirring for 1 h at 6° C. The aqueous layer was extracted with EtOAc, the organic layer was washed with brine, dried over MgSO$_4$, filtered and concentrated. The crude product was purified with 1:9 EtOAc:hexanes over 40 min to obtain 1.41 g (65%) of the title compound (94). $^1$H NMR (400 MHz, d-CDCl$_3$): δ 1.01 (t, J=7.3 Hz, 3H), 1.68-1.74 (m, 2H), 2.79 (t, J=7.7 Hz, 2H), 3.90 (s, 3H), 6.06 (s, 1H), 7.00-7.01 (m, 1H), 7.08 (dd, J$_1$=2.6 Hz, J$_2$=9.1 Hz, 1H), 7.17 (s, 1H), 8.07 (d, J=9.1 Hz, 1H).

Step 2: 2-Bromo-6-methoxy-1-methoxymethoxy-3-propyl-naphthalene (95)

To a solution of 2-Bromo-6-methoxy-3-propyl-naphthalen-1-ol (94) (1.41 g, 4.78 mmol) in dry THF (23 mL) at 0° C. was added diisopropylethylamine (3.3 mL, 19.1 mmol) followed by chloromethyl methyl ether (1.1 mL, 14.3 mmol) slowly. Reaction mixture was stirred at ambient temperature for 24 h. Reaction mixture was diluted with water and the aqueous layer was extracted with DCM, washed organic layer with brine, dried over $Na_2SO_4$, filtered and concentrated. The crude material was purified using 1:9 EtOAc:hexanes to provide 1.26 g (78%) of the title compound (95) as a solid. $^1$H NMR (400 MHz, d-CDCl$_3$): δ 1.01 (t, J=7.4 Hz, 3H), 1.70-1.75 (m, 2H), 2.85 (t, J=7.7 Hz, 2H), 3.72 (s, 3H), 3.91 (s, 3H), 5.23 (s, 2H), 7.04 (s, 1H), 7.12 (dd, J$_1$=2.6 Hz, J$_2$=9.1 Hz, 1H), 7.39 (s, 1H), 8.03 (d, J=9.1 Hz, 1H).

Step 3: 2-(4-Fluoro-phenyl)-6-methoxy-1-methoxymethoxy-3-propyl-naphthalene (225)

2-Bromo-6-methoxy-1-methoxymethoxy-3-propyl-naphthalene (95) (1.26 g, 3.71 mmol), 4-fluorobenzeneboronic acid (1.04 g, 7.43 mmol), tetrakis(triphenylphosphino)palladium (0) (0.43 g, 0.371 mmol), 2 M sodium carbonate (20 mL) and ethylene glycol dimethyl ether (20 mL) were added in a sealed tube and reacted as described above to give 1.26 g (95%) of the title compound (225) as oil. $^1$H NMR (400 MHz, d-CDCl$_3$): δ 0.80 (t, J=7.3 Hz, 3H), 1.43-1.45 (m, 2H), 2.50 (t, J=7.8 Hz, 2H), 3.11 (s, 3H), 3.93 (s, 3H), 4.73 (s, 2H), 7.10-7.15 (m, 4H), 7.29-7.32 (m, 2H), 7.43 (s, 1H), 8.00 (d, J=8.9 Hz, 1H).

Step 4: 4-[2-(4-Fluoro-phenyl)-6-methoxy-3-propyl-naphthalen-1-yloxy]-2-trifluoromethyl-benzaldehyde (226)

2-(4-Fluoro-phenyl)-6-methoxy-1-methoxymethoxy-3-propyl-naphthalene (225) (0.6 g, 1.69 mmol), 4 N HCl/Dioxane (12 mL), 4-fluoro-2-trifluoromethyl-benzaldehyde (0.277 mL, 2.03 mmol), Cs$_2$CO$_3$ (1.38 g, 4.23 mmol) and DMSO (12 mL) were reacted as described above to give 0.80 g (98%) of the title compound (226) as oil. $^1$H NMR (400 MHz, d-CDCl$_3$): δ 0.83 (t, J=7.3 Hz, 3H), 1.47-1.55 (m, 2H), 2.54 (t, J=7.8 Hz, 2H), 3.95 (s, 3H), 6.75 (dd, J=2.3, 8.7 Hz, 1H), 6.94-6.99 (m, 3H), 7.06-7.10 (m, 3H), 7.19 (m, 1H), 7.63-7.66 (m, 2H), 7.89 (d, J=8.8 Hz, 1H), 10.18-10.19 (m, 1H).

Step 5: 3-{4-[2-(4-Fluoro-phenyl)-6-hydroxy-3-propyl-naphthalen-1-yloxy]-2-trifluoromethyl-phenyl}-2-methyl-acrylic acid (228)

4-[2-(4-Fluoro-phenyl)-6-methoxy-3-propyl-naphthalen-1-yloxy]-2-trifluoromethyl-benzaldehyde (226) (0.425 g, 0.881 mmol), triethyl-2-phosphonopropionate (0.26 mL, 1.32 mmol), 1.6 M nBuLi (0.88 mL, 1.41 mmol) and THF (12 mL) afforded 0.38 g of a mixture of isomers (30:70) of ethyl esters as an oil. The ester mixture (0.38 g, 0.67 mmol) was treated with 1 N NaOH (8 mL), EtOH (7 mL) and THF (7 mL) to afford a mixture of isomeric acrylic acids. Yields: Isomer (1) (227-1) 0.08 g with ~31% contamination with isomer (2) (227-2); Isomer (2) (227-2) 0.246 g compound with ~20% contamination with isomer (1) (227-1). Treatment of (227-2) (0.24 g, 0.446 mmol) with 1 M BBr$_3$ (1.34 mL, 1.34 mmol) and DCM (12 mL) afforded 0.122 g (52%) of the title compound (228) as a white powder. $^1$H NMR (400 MHz, d-CDCl$_3$): δ 0.82 (t, J=7.3 Hz, 3H), 1.46-1.51 (m, 2H), 1.87-1.88 (m, 3H), 2.52 (t, J=7.8 Hz, 2H), 6.75 (dd, J=2.4, 8.6 Hz, 1H), 6.91-6.97 (m, 3H), 7.04-7.08 (m, 4H), 7.19-7.20 (m, 1H), 7.53 (s, 1H), 7.78 (d, J=8.9 Hz, 1H), 7.84 (br s, 1H). HRMS (ESI) Calcd for $C_{30}H_{23}F_4O_4$: 523.1532 (M–H)$^-$. Found: 523.1522.

Example 39 (229)

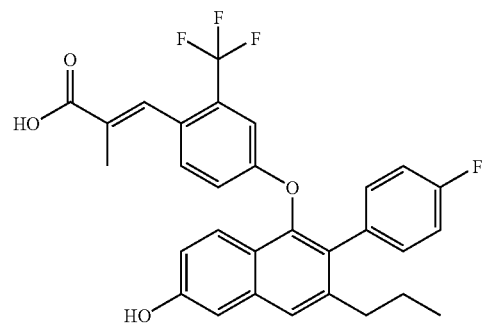

Step 1: 3-{4-[2-(4-Fluoro-phenyl)-6-hydroxy-3-propyl-naphthalen-1-yloxy]-2-trifluoromethyl-phenyl}-2-methyl-acrylamide (229)

To a solution of 3-{4-[2-(4-fluoro-phenyl)-6-hydroxy-3-propyl-naphthalen-1-yloxy]-2-trifluoromethyl-phenyl}-2-methyl-acrylic acid (228) (0.06 g, 0.114 mmol) in DCM (5 mL) was added dropwise oxalyl chloride (0.0199 mL, 0.229 mmol), followed by 2 drops of DMF. Reaction mixture was stirred for 2 h at room temperature. Reaction mixture was concentrated then 30% aqueous NH$_3$ (5 mL) was added and stirred for 20 h. Reaction mixture was extracted with EtOAc, organic phase was washed with brine, dried over Na$_2$SO$_4$, filtered and concentrated. Crude material was purified by reverse phase preparative HPLC using a C-18 column and a CH$_3$CN:H$_2$O gradient (50:50 to 100:0) with 0.05% TFA as a modifier over 5 min to afford 0.014 g (23%) of the title compound (229) as a white foam. $^1$H NMR (400 MHz, d-CDCl$_3$): δ 0.82 (t, J=7.3 Hz, 3H), 1.46-1.51 (m, 2H), 1.85 (s, 3H), 2.51 (t, J=7.8 Hz, 2H), 5.65 (br s, 1H), 6.67 (dd, J$_1$=2.5 Hz, J$_2$=8.6 Hz, 1H), 6.89-7.00 (m, 4H), 7.04-7.08 (m, 3H), 7.19-7.20 (m, 1H), 7.36 (s, 1H), 7.53 (s, 1H), 7.79 (d, J=8.9 Hz, 1H). HRMS (ESI) Calcd for $C_{30}H_{26}F_4NO_3$: 524.1849 (M+H)$^+$. Found: 524.1857.

Example 40 (232)

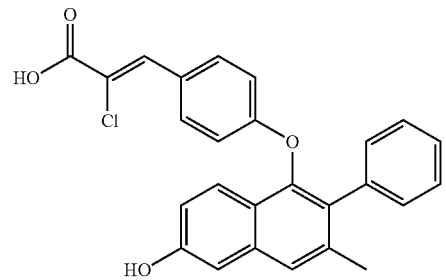

Step 1: 2-Chloro-3-[4-(6-methoxy-3-methyl-2-phenyl-naphthalen-1-yloxy)-phenyl]-acrylic acid ethyl ester (230)

A 1.6 M solution of nBuLi in hexanes (2.98 mL, 4.77 mmol), triethyl-2-chloro-2-phosphonoacetate (0.96 mL, 4.48 mmol), 4-(6-Methoxy-3-methyl-2-phenyl-naphthalen-1-yloxy)-benzaldehyde (8) (0.55 g, 1.49 mmol) and THF (16 mL) afforded 0.296 g (42%) of isomer (1) (230-1) and 0.325 g (46%) of isomer (2) (230-2) of the title compound.

(230-1): $^1$H NMR (400 MHz, d-CDCl$_3$): δ 1.16 (t, J=7.2 Hz, 3H), 2.24 (s, 3H), 3.93 (s, 3H), 4.15-4.20 (m, 2H), 6.54 (d, J=8.8 Hz, 2H), 7.01-7.04 (m, 2H), 7.08 (d, J=8.8 Hz, 2H), 7.12-7.14 (m, 3H), 7.22-7.26 (m, 3H), 7.57 (s, 1H), 7.70 (d, J=9.1 Hz, 1H).

(230-2): $^1$H NMR (400 MHz, d-CDCl$_3$): δ 1.35 (t, J=7.2 Hz, 3H), 2.25 (s, 3H), 3.93 (s, 3H), 4.29-4.34 (m, 2H), 6.64 (d, J=8.8 Hz, 2H), 7.05 (dd, J$_1$=2.4 Hz, J$_2$=9.1 Hz, 1H), 7.13-7.15 (m, 3H), 7.22-7.28 (m, 2H), 7.58 (s, 1H), 7.65 (d, J=8.8 Hz, 2H), 7.71 (d, J=9.1 Hz, 1H), 7.76 (s, 1H).

Step 2: 2-Chloro-3-[4-(6-methoxy-3-methyl-2-phenyl-naphthalen-1-yloxy)-phenyl]-acrylic acid (231)

Treatment of 2-chloro-3-[4-(6-methoxy-3-methyl-2-phenyl-naphthalen-1-yloxy)-phenyl]-acrylic acid ethyl ester (230-1) (0.23 g, 0.486 mmol) with 1 N NaOH (5 mL), EtOH (4 mL) and THF (4 mL) afforded 0.177 g (82%) of the title compound, isomer (1) (231-1) as oil. $^1$H NMR (400 MHz, d-CDCl$_3$): δ 2.23 (s, 3H), 3.93 (s, 3H), 6.54 (d, J=8.7 Hz, 2H), 7.04 (dd, J$_1$=2.4 Hz, J$_2$=9.1 Hz, 1H), 7.10-7.14 (m, 3H), 7.18-7.26 (m, 6H), 7.56 (s, 1H), 7.73 (d, J=9.1 Hz, 1H).

Similarly, treatment of 2-chloro-3-[4-(6-methoxy-3-methyl-2-phenyl-naphthalen-1-yloxy)-phenyl]-acrylic acid ethyl ester (230-2) (0.24 g, 0.507 mmol) with 1 N NaOH (5 mL), EtOH (4 mL) and THF (4 mL) afforded 0.2 g (89%) of the title compound, isomer (2) (231-2) of as oil. $^1$H NMR (400 MHz, d-CDCl$_3$): δ 2.25 (s, 3H), 3.94 (s, 3H), 6.65 (d, J=8.8 Hz, 2H), 7.05 (dd, J$_1$=2.4 Hz, J$_2$=9.1 Hz, 1H), 7.13-7.15 (m, 3H), 7.23-7.27 (m, 3H), 7.59 (s, 1H), 7.67-7.71 (m, 3H), 7.86 (s, 1H).

Step 3: 2-Chloro-3-[4-(6-hydroxy-3-methyl-2-phenyl-naphthalen-1-yloxy)-phenyl]-acrylic acid (232)

Treatment of 2-Chloro-3-[4-(6-methoxy-3-methyl-2-phenyl-naphthalen-1-yloxy)-phenyl]-acrylic acid (231-1) (0.17 g, 0.382 mmol) with BBr$_3$ (0.11 mL, 1.15 mmol) and DCM (5 mL) afforded 0.053 g (32%) of the title compound (232) as powder. $^1$H NMR (400 MHz, d-CDCl$_3$): δ 2.24 (s, 3H), 6.65 (d, J=8.9 Hz, 2H), 7.00 (dd, J$_1$=2.4 Hz, J$_2$=9.1 Hz, 1H), 7.12-7.17 (m, 3H), 7.23-7.29 (m, 3H), 7.53 (s, 1H), 7.68-7.73 (m, 3H), 7.87 (s, 1H). HRMS (ESI) Calcd for C$_{26}$H$_{18}$ClO$_4$: 429.0894 (M−H)$^-$. Found: 429.0888.

Treatment of 2-Chloro-3-[4-(6-methoxy-3-methyl-2-phenyl-naphthalen-1-yloxy)-phenyl]-acrylic acid (231-2) (0.177 g, 0.398 mmol) with BBr$_3$ (0.113 mL, 1.19 mmol) and DCM (5 mL) afforded 0.044 g (26%) of the title compound (232 as pink powder. $^1$H NMR (400 MHz, d-CDCl$_3$): δ 2.24 (s, 3H), 6.65 (d, J=8.9 Hz, 2H), 7.00 (dd, J$_1$=2.4 Hz, J$_2$=9.1 Hz, 1H), 7.12 J 7.17 (m, 3H), 7.23-7.29 (m, 3H), 7.53 (s, 1H), 7.68-7.73 (m, 3H), 7.87 (s, 1H).

2-(Diethoxy-phosphoryl)-3-methyl-butyric acid ethyl ester (233)

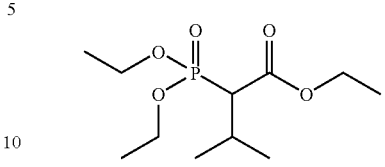

Triethyl phosphonoacetate (1 g, 4.46 mmol) was slowly added to a solution of NaH (0.18 g, 4.46 mmol) in DMSO (5 mL) at 0° C. After stirring for 20 min, 2-iodopropane (0.49 mL, 4.9 mmol) was added and reaction left to stir at room temperature for 20 h. The reaction mixture was quenched with saturated NH$_4$Cl and extracted with EtOAc. The organic layer was washed with brine, dried over MgSO$_4$, filtered and concentrated to give an oil.

Example 41 (236)

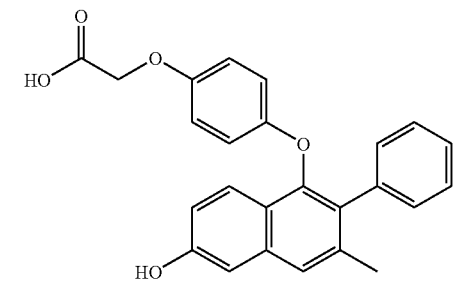

Step 1: 4-{[3-Methyl-6-(methyloxy)-2-phenyl-1-naphthalenyl]oxy}phenol (233)

To a solution of 4-{[3-methyl-6-(methyloxy)-2-phenyl-1-naphthalenyl]oxy}benzaldehyde (8) (0.740 g, 2 mmol) in MeOH (20 mL) were added an aqueous solution of 30-40%, by weight, H$_2$O$_2$ (0.60 mL) and 2-3 drops of conc. H$_2$SO$_4$. The resultant mixture was stirred for over night. The reaction mixture was neutralized with sat. NaHCO$_3$ and then diluted with EtOAc (100 mL). The organic layer was washed with water, brine, dried (Na$_2$SO$_4$) and concentrated under reduced pressure to afford the crude product. The product was purified by SiO$_2$ column chromatography using hexanes:EtOAc (9:1 to 4:1) as an eluent to give 0.570 g (80%) of the title compound (233) as a white foam. IR (film) 3415, 1633, 1599, 1503, 1198 cm-1. $^1$H NMR (400 MHz, CDCl$_3$): δ 7.80 (d, J=9.2 Hz, 1H), 7.53 (s, 1H), 7.29-7.22 (m, 3H), 7.14-7.11 (m, 3H), 7.08 and 7.03 (dd, J$_1$=9.2 Hz, J$_2$=2.4 Hz, 1H), 6.53-6.50 (m, 2H), 6.45-6.42 (m, 2H), 3.93 (s, 3H), 2.23 (s, 3H). LCMS (ES) m/z 357.01 (M+H)$^+$.

Step 2: Ethyl [(4-{[3-methyl-6-(methyloxy)-2-phenyl-1-naphthalenyl]oxy}phenyl)oxy]acetate (234)

A round-bottomed flask was charged with 4-{[3-methyl-6-(methyloxy)-2-phenyl-1-naphthalenyl]oxy}phenol (233) (0.150 g, 0.421 mmol), K$_2$CO$_3$ (0.116 g, 0.842 mol), acetone, and ethylbromoacetate (0.105 g, 0.632 mmol) under N$_2$. The reaction mixture was refluxed for 5 h and cooled at room temperature. Reaction mixture was filtered and concentrated under reduced pressure to afford the crude product. The product was purified by SiO$_2$ column chromatography using hexanes:EtOAc (19:1 to 9:1) as an eluent to give 0.177 g (95%) of the title compound (234) as a white foam. $^1$H NMR (400 MHz, CDCl$_3$): δ 7.80 (d, J=9.2 Hz, 1H), 7.54 (s, 1H), 7.29-7.22 (m, 3H), 7.13-7.11 (m, 3H), 7.05 and 7.03 (dd, J$_1$=9.2 Hz, J$_2$=2.4 Hz, 1H), 6.63 (d, J$_1$=9.2 Hz, 2H), 6.50 (d, J$_1$=9.2 m, 2H), 4.48 (s, 2H), 4.24 (q, J=3.8 Hz, 2H), 3.93 (s, 3H), 2.23 (s, 3H), 1.27 (t, J=3.00 Hz, 3H).

Step 3: [(4-{[3-methyl-6-(methyloxy)-2-phenyl-1-naphthalenyl]oxy}phenyl)oxy]acetic acid (235)

Ethyl [(4-{[3-methyl-6-(methyloxy)-2-phenyl-1-naphthalenyl]oxy}phenyl)oxy]acetate (234) (0.170 g, 0.39 mmol) was dissolved in 1:1 THF:EtOH (6 mL). To the above mixture was added 1 N NaOH (0.5 mL) at room temperature and heated to 50° C. The reaction mixture was kept at that temperature for 0.5 h and cooled at RT. Reaction mixture was acidified with 25% aqueous HCl, and then extracted with EtOAc. The organic layer was washed with brine, dried (Na$_2$SO$_4$), and concentrated under reduced pressure to afford 0.155 g (97%) the crude product (235). $^1$H NMR (400 MHz, CDCl$_3$): δ 7.78 (d, J=10.0 Hz, 1H), 7.54 (s, 1H), 7.28-7.03 (m, 4H), 6.64 (d, J=9.0 Hz, 2H), 6.50 (d, J=8.9 Hz, 2H), 4.54 (s, 2H), 3.93 (s, 3H), 2.23 (s, 3H).

Step 4: ({4-[(6-hydroxy-3-methyl-2-phenyl-1-naphthalenyl)oxy]phenyl}oxy)acetic acid (236)

To a cold (5° C.) solution of ([(4-{[3-methyl-6-(methyloxy)-2-phenyl-1-naphthalenyl]oxy}phenyl)oxy]acetic acid (235) (0.150 g, 0.36 mmol) in CH$_2$Cl$_2$ (5 mL) was added BBr$_3$ (0.1 mL, 1.1 mmol) slowly. The reaction mixture was stirred between 5° C. and 20° C. for 2 h and poured into 10% aqueous NaHCO$_3$ (60 mL) slowly. The reaction mixture was extracted with EtOAc (3×75 mL). The combined organic layer was washed with brine (1×50 mL), dried (Na$_2$SO$_4$), and concentrated to afford the crude product. Purification by flash column chromatography using CHCl$_3$ and MeOH as an eluent gave 0.028 g (19%) of the title compound (236) as an off-white solid. A 0.058 g of 5-[(4-hydroxyphenyl)oxy]-7-methyl-6-phenyl-2-naphthalenol was also isolated. $^1$H NMR (400 MHz, CDCl$_3$): δ 7.62 (d, J=8.8 Hz, 1H), 7.46 (s, 1H), 7.26-7.18 (m, 3H), 7.12-7.09 (m, 2H), 6.92 and 6.90 (dd, J$_1$=8.8 Hz, J$_2$=2.4 Hz, 1H), 6.65 (d, J=9.2 Hz, 2H), 6.50 (d, J=8.8 Hz, 2H), 4.29 (s, 2H), 2.17 (s, 3H). LCMS (ESI) m/z 401.35 (M+H)$^+$.

Example 43 (238)

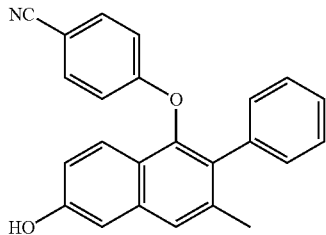

Step 1: 4-{[3-methyl-6-(methyloxy)-2-phenyl-1-naphthalenyl]oxy}benzonitrile (237)

To a solution of 4-{[3-methyl-6-(methyloxy)-2-phenyl-1-naphthalenyl]oxy}benzaldehyde (8) (0.920 g, 2.5 mmol) in MeOH (25 mL) was added N,N-dimethylhydrazine (0.341 mL, 4.5 mmol). The resultant mixture was stirred at room temperature for 12 h under N$_2$. Reaction mixture was concentrated under reduced pressure and the residue was re-dissolved in CH$_3$CN (25 mL) to which were added dimethylsulfate (0.378 mL, 3 mmol) and K$_2$CO$_3$ (0.415 g, 3 mmol) under N$_2$. The reaction mixture was refluxed for 24 h. Reaction mixture was cooled at room temperature and poured into water (100 mL). Reaction mixture was extracted with EtOAc (3×100 mL). The combined organic layer was washed with brine, dried (Na$_2$SO$_4$) and concentrated under reduced pressure to afford the crude product. The product was purified by column chromatography using hexanes:EtOAc (19:1 to 9:1) as an eluent to afford 0.560 g (62%) of the title compound (237) as an off-white solid. IR (film) 2958, 2225, 1602, 1501, 1235 cm$^{-1}$. $^1$H NMR (400 MHz, CDCl$_3$): δ 7.66 (d, J=9.2 Hz, 1H), 7.60 (s, 1H), 7.37 (d, J=6.4 Hz, 2H), 7.29-7.23 (m, 3H), 7.15 (d, J=2.4 Hz, 1H), 7.11 (d, J=1.6 Hz, 1H), 7.09 (d, J=1.6 Hz, 1H), 7.08 and 7.05 (dd, J$_1$=9.2 Hz, J$_2$=2.4 Hz, 1H), 6.64 (d, J=6.8 Hz, 2H), 3.94 (s, 3H), 2.25 (s, 3H). LCMS (ESI) m/z 366.11 (M+H)$^+$.

Step 2: 4-[(6-hydroxy-3-methyl-2-phenyl-1-naphthalenyl)oxy]benzonitrile (238) The demethylation procedure described in Example 1 (Step 11) was followed. To a cold solution of 4-{[3-methyl-6-(methyloxy)-2-phenyl-1-naphthalenyl]oxy}benzonitrile (237) (0.074 g, 0.207 mmol) in CH$_2$Cl$_2$ (5 mL) was added BBr$_3$ (0.059 mL, 0.62 mmol). The reaction mixture was stirred between 5° C. and 20° C. for 3 h. Upon normal work-up followed by chromatographic purification gave 0.049 g (69%) of the title compound (238) as an off-white solid. IR (film) 3382, 3050, 2229, 1602, 1500, 1240 cm$^{-1}$. $^1$H NMR (300 MHz, CD$_3$OD): δ 7.57 (d, J=8.8 Hz, 1H), 7.54 (s, 1H), 7.45 (d, J=7.2 Hz, 2H), 7.28-7.21 (m, 3H), 7.14 (d, J=2.0 Hz, 2H), 7.11 (br s, 1H), 6.99 and 6.97 (dd, J$_1$=9.2 Hz, J$_2$=2.4 Hz, 1H), 6.68 (d, J=8.8 Hz, 2H), 2.20 (s, 3H). LCMS (ESI) m/z 352.04 (M+H)$^+$.

Example 44 (242)

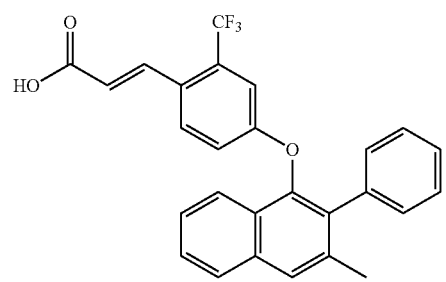

Step 1: 5-hydroxy-7-methyl-6-phenyl-2-naphthalenyl 4-methylbenzenesulfonate (239)

A round-bottomed flask was charged with 3-methyl-6-(methyloxy)-2-phenyl-1-naphthalenyl acetate (6) (5.00 g, 16.34 mmol), acetic acid (100 mL) and 48% aqueous HBr (50 mL). The resultant mixture was stirred between 90° C. and 100° C. for 4 h. The reaction mixture was concentrated under reduced pressure and the residue was neutralized with sat. NaHCO$_3$ (100 mL). The aqueous reaction mixture was extracted with CH$_2$Cl$_2$ (4×150 mL). The combined organic layer was dried (Na$_2$SO$_4$) and concentrated under reduced pressure to afford ~4.10 g (86%) the crude title product. To a solution of the above obtained crude product (~1.00 g) in CHCl₃ (50 mL) were added pyridine (1 mL), p-toluene sulfonic acid (2 equiv). The resultant mixture was stirred at RT for 36 h. Reaction mixture was diluted with CH₂Cl₂ (250 mL), washed with 10% aqueous HCl, brine (1×50 mL), and dried (Na₂SO₄). The organic layer was concentrated under reduced pressure to afford the crude product. The product was purified by SiO₂ column chromatography to afford 850 mg (89%) of the title compound (239). $^1$H NMR (400 MHz, CDCl₃): δ 8.08 (d, J=9.2 Hz, 1H), 7.73 (d, J=8.4 Hz, 2H), 7.54 (dd, J₁=7.6 Hz, 2H), 7.47 (d, J=7.2 Hz, 1H), 7.39 (d, J=2.0 Hz, 1H), 7.30 (dd, J₁=6.4 Hz, J₂=6.4 Hz, 4H), 7.22 (br s, 1H), 6.98 and 6.96 (dd, J₁=9.2 Hz, J₂=2.0 Hz, 1H), 5.25 (s, 1H), 2.44 (s, 3H), 2.16 (s, 3H). LCMS (ESI) m/z 405.22 (M+H)⁺.

Step 2: 3-methyl-2-phenyl-1-naphthalenol (86)

To a cold (5° C.) solution of 5-hydroxy-7-methyl-6-phenyl-2-naphthalenyl 4-methylbenzenesulfonate (239) (0.250 g, 0.62 mmol) in CHCl₃ (5 mL) and MeOH (5 mL) was added nickel chloride hexahydrate (0.238 g, 1.24 mmol). To the above mixture sodium borohydrate (0.471 g, 12.4 mmol) was added portion-wise. The resulting black mixture was stirred at that temperature for 15 min. Reaction mixture was filtered through a pad of celite (washings were done with CHCl₃). The filtrate was concentrated under reduced pressure to afford the crude product. The product was purified by column chromatography to afford 0.064 g (44%) of the title compound (86) as an oil. $^1$H NMR (400 MHz, CDCl₃): δ 8.22 (d, J=8.0 Hz, 1H), 7.77 (d, J=8.0 Hz, 1H), 7.59-7.55 (m, 2H), 7.52-7.46 (m, 3H), 7.40-7.36 (m, 3H), 5.28 (s, 1H), 2.22 (s, 3H). LCMS (ESI) m/z (M+H)⁺.

Step 3: 4-[(3-methyl-2-phenyl-1-naphthalenyl)oxy]-2-(trifluoromethyl)benzaldehyde The nucleophilic substitution procedure described in Example 1 (Step 8) was followed. A round-bottomed flask was charged with 3-methyl-2-phenyl-1-naphthalenol (86) (0.063 g, 0.27 mmol), 4-fluoro-2-(trifluoromethyl)benzaldehyde (0.044 mL, 0.32 mmol), Cs₂CO₃ (0.115 g, 0.35 mmol), and anhydrous DMF (1 mL) under N₂. The reaction mixture was refluxed for 3 h. Reaction mixture was cooled at room temperature and purified by SiO₂ column chromatography using hexanes:EtOAc (19:1 to 4:1) as an eluent to afford 0.71 g (65%) of the title compound (240) as a white foam. $^1$H NMR (400 MHz, CDCl₃): δ 10.18 (s, 1H), 7.87 (d, J=8.8 Hz, 2H), 7.77 (d, J=8.8 Hz, 1H), 7.74 (s, 1H), 7.53 (dd, J₁=7.2 Hz, J₂=7.2 Hz, 1H), 7.43 (dd, J₁=7.2 Hz, J₂=7.2 Hz, 1H), 7.30-7.23 (m, 3H), 7.13 (d, J=2.0 Hz, 1H), 7.11 (s, 1H), 7.03 (d, J=2.4 Hz, 1H), 6.79 and 6.77 (dd, J₁=8.8 Hz, J₂=2.0 Hz, 1H). 2.29 (s, 3H). LCMS (ESI) m/z 235.11 (M+H)⁺.

Step 4: Ethyl (2E)-3-[4-[(3-methyl-2-phenyl-1-naphthalenyl)oxy]-2-(trifluoromethyl) phenyl]-2-propenoate (241)

The Witting reaction procedure described in Example 1 (Step 9) was employed. To a cold (−78° C.) solution of triethyl phosphonoacetate (0.052 mL, 0.26 mmol) in anhydrous THF (3 mL) was added nBuLi (0.110 mL, 0.28 mmol, 2.5 M solution in hexanes). The reaction mixture was stirred for 0.5 h under N₂. A solution of 4-[(3-methyl-2-phenyl-1-naphthalenyl)oxy]-2-(trifluoromethyl)benzaldehyde (240) (0.070 g, 0.172 mmol) in THF (2 mL) was added to the above reaction mixture and stirred for 20 min at that temperature under N₂. The reaction mixture was allowed to warm to room temperature and stirred for 2 h. Upon normal work-up followed by purification gave 0.072 g (88%) of the title compound (241) as a white foam. $^1$H NMR (400 MHz, CDCl₃): δ 7.89 (br d, J=16.0 Hz, 1H), 7.85 (d, J=8.4 Hz, 1H), 7.80 (d, J=8.4 Hz, 1H), 7.71 (s, 1H), 7.51 (dd, J₁=7.2 Hz, J₂=7.2 Hz, 1H), 7.42 and 7.40 (dd, J₁=7.6 Hz, J₂=3.6 Hz, 1H), 7.28-7.23 (m, 3H), 7.11 (d, J=1.6 Hz, 1H), 7.1 (s, 1H), 6.94 (d, J=2.4 Hz, 1H), 6.70 and 6.68 (dd, J=8.80 Hz, J₂=2.4 Hz, 1H), 6.22 (d, J=16.0 Hz, 1H), 4.24 (q, J=7.2 Hz, 2H), 2.27 (s, 3H), 1.27 (t, J=7.2 Hz, 3H). LCMS (ESI) m/z 499.53 (M+Na)⁺.

Step 5: (2E)-3-[4-[(3-methyl-2-phenyl-1-naphthalenyl)oxy]-2-(trifluoromethyl)phenyl]-2-propenoic acid (242)

The saponification procedure described in Example 1 (Step 10) was followed. Ethyl (2E)-3-[4-[(3-methyl-2-phenyl-1-naphthalenyl)oxy]-2-(trifluoromethyl)phenyl]-2-propenoate (241) (0.070 g, 0.147 mmol) was dissolved in 1:1 THF:EtOH (6 mL). To the above mixture was added 1 N NaOH (1 mL, excess) at room temperature followed by heating at 70° C., with stirring, for 30 min. The reaction mixture was cooled at RT, subjected to standard work up and purification to afford 0.065 g (99%) of the title compound (242) as a white foam. IR (film) 3058, 1693, 1606, 1491, 1313, 1165, 1128 cm⁻¹. $^{19}$F NMR (282.2 MHz, CD₃OD): δ −60.98. $^1$H NMR (400 MHz, CD₃OD): δ 7.91 (br d, J=8.0 Hz, 1H), 7.84 (d, J=16.0 Hz, 1H), 7.79 (s, 1H), 7.77 (d, J=8.8 Hz, 1H), 7.64 (d, J=7.6 Hz, 1H), 7.52 (dd, J₁=7.2 Hz, J₂=7.2 Hz, 1H), 7.43 (dd, J₁=7.6 Hz, J₂=7.6 Hz, 1H), 7.28 (m, 3H), 7.15 (br s, 1H), 7.14 (s, 1H), 6.90 (s, 1H), 6.76 (d, J=8.4 Hz, 1H), 6.33 (d, J=16.0 Hz, 1H), 2.26 (s, 3H).

LCMS (ESI) m/z 447.27 (M−H)⁻.

Example 45 (244)

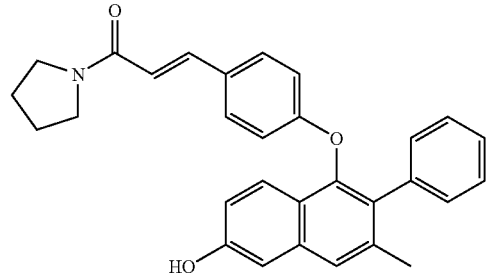

Step 1: 1-[(2E)-3-(4-{[3-methyl-6-(methyloxy)-2-phenyl-1-naphthalenyl]oxy}phenyl)-2-propenoyl]pyrrolidine (243)

To a solution of (2E)-3-(4-{[3-methyl-6-(methyloxy)-2-phenyl-1-naphthalenyl]oxy}phenyl)-2-propenoic acid (10) (0.135 g, 0.33 mmol) in CH₂Cl₂ (2 mL) was added oxalyl chloride (0.043 mL, 0.49 mmol) under N₂. The resultant mixture was stirred at room temperature for 2 h. Reaction mixture was concentrated under reduced pressure to afford the crude acid chloride. The acid chloride was dried (Na₂SO₄) and re-dissolved in CH₂Cl₂ (5 mL) at room temperature. To the above solution pyrrolidine (0.055 ml, 0.66 mmol) was introduced slowly and the mixture was stirred for 12 h. Reaction mixture was concentrated under reduced pressure to afford the crude amide. The product was purified by SiO₂ column chromatography using hexanes:EtOAc (9:1 to 3:2) as an eluent to afford 0.146 g (96%) of the title compound (243) as a white foam. $^1$H NMR (400 MHz, CDCl$_3$): δ 7.71 (d, J=9.2 Hz, 1H), 7.55 (s, 1H), 7.54 d, J=15.6 Hz, 1H), 7.27-7.20 (m, 5H), 7.13-7.11 (m, 3H), 7.03 and 7.01 (dd, J$_1$=9.2 Hz, J$_2$=2.4 Hz, 1H), 6.57 (d, J=8.8 Hz, 2H), 6.51 (d, J=15.2 Hz, 1H), 3.91 (s, 3H), 3.55 (t, J=6.8 Hz, 4H), 2.22 (s, 3H), 1.94 (quintet, J=6.4 Hz, 2H), 1.85 (quintet, J=6.8 Hz, 2H), 2.26 (s, 3H). LCMS (ESI) m/z 464.15 (M+H)$^+$.

Step 2: 7-methyl-5-({4-[(1E)-3-oxo-3-(1-piperidinyl)-1-propen-1-yl]phenyl}oxy)-6-phenyl-2-naphthalenol (4)

To a cold (5° C.) solution 1-[(2E)-3-(4-{[3-methyl-6-(methyloxy)-2-phenyl-1-naphthalenyl]oxy}phenyl)-2-propenoyl]pyrrolidine (243) (0.140 g, 0.30 mmol) in CH$_2$Cl$_2$ (2 mL) was added BBr$_3$ (0.071 mL, 0.75 mmol) slowly. The reaction mixture was stirred between 5° C. and 20° C. for 1.5 h and poured into water (25 mL) slowly. The layers were separated and the aqueous layer was further extracted with EtOAc (3×50 mL). The combined organic layer was washed with brine (1×100 mL), dried (Na$_2$SO$_4$), and concentrated to afford the crude product. Regular purification by flash column chromatography using CHCl$_3$ and MeOH as an eluent gave 0.104 g (77%) of the title compound (244) as an off-white solid. $^1$H NMR (400 MHz, DMSO-d$_6$): δ 9.86 (s, 1H), 7.58 (s, 1H), 7.48 (d, J=15.6 Hz, 1H), 7.47 (d, J=6.4 Hz, 1H), 7.44 (s, 1H), 7.32-7.27 (m, 3H), 7.24 (d, J=7.2 Hz, 1 h), 7.17 (d, J=6.8 Hz, 2H), 7.13 9d, J=2.0 Hz, 1H), 6.97 and 6.95 (dd, J$_1$=8.8 Hz, J$_2$=2.0 Hz, 1H), 6.74 (d, J=15.6 Hz, 1H), 6.51 (d, J=15.2 Hz, 1H), 3.91 (s, 3H), 3.55 (t, J=6.8 Hz, 4H), 2.22 (s, 3H), 1.94 (quintet, J=6.4 Hz, 2H), 1.85 (quintet, J=6.8 Hz, 2H), 2.26 (s, 3H). LCMS (ESI) m/z 464.15 (M+H)$^+$.

Example 46 (251)

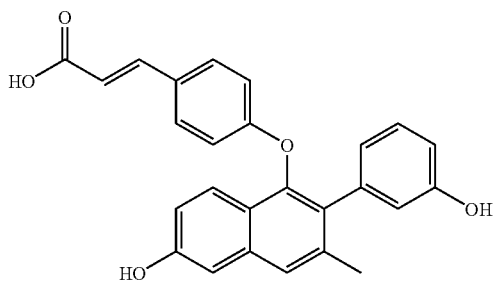

Step 1: 2-Methyl-4,4-bis(methyloxy)-3-[3-(methyloxy)phenyl]-2-cyclobuten-1-one (245)

A THF solution (12 mL) of known 2-methyl-3,4,4-tris(methyloxy)-2-cyclobuten-1-one (0.500 g, 2.91 mmol, 1 equiv) was cooled to ca. −78° C. 3-Methoxyphenyl magnesium bromide (4.36 mL, 1.0 M, 1.5 equiv) was added. After 5 min, TFAA (0.657 mL, 4.66 mmol, 1.6 equiv) was added. The reaction was quenched with saturated NaHCO$_3$ (5 mL) after an additional 5 min. Extraction with EtOAc was followed by drying (Na$_2$SO$_4$), filtration, and concentration to a bright yellow oil. Radial chromatography (SiO$_2$, 4 mm plate, 80:20; hexanes/EtOAc) afforded the title compound (245) as a bright yellow oil (0.540 g, 75%). $^1$H NMR (CDCl$_3$, 300 MHz) δ 7.44-7.33 (m, 3H), 7.15-7.09 (m, 1H), 3.89 (s, 3H), 3.54 (s, 6H), 2.13 (s, 3H). TLC (60:40; hexanes/EtOAc): R$_f$=0.45.

Step 2: 4-Hydroxy-3-methyl-2,4-bis[3-(methyloxy)phenyl]-2-cyclobuten-1-one (246)

A THF solution (12 mL) of 2-methyl-4,4-bis(methyloxy)-3-[3-(methyloxy)phenyl]-2-cyclobuten-1-one (245) (0.500 g, 2.02 mmol, 1 equiv) was cooled to ca. −78° C. 3-Methoxyphenylmagnesium bromide (3.02 mL, 1.0 M, 1.5 equiv) was added. After 5 min, aqueous HCl (3 N, 20 mL) was added. Extraction with EtOAc (3×20 mL) was followed by washing with 50% aqueous NaHCO$_3$, drying (Na$_2$SO$_4$), filtration, and concentration to a bright yellow oil. Radial chromatography (SiO$_2$, 4 mm plate, 80:20; hexanes/EtOAc) afforded the title compound (246) as a bright yellow oil (0.515 g, 82%). $^1$H NMR (CDCl$_3$, 300 MHz) δ 7.39-7.29 (m, 4H), 7.10-6.88 (m, 4H), 3.88 (s, 3H), 3.85 (s, 3H), 2.47 (s, 3H); TLC (60:40; hexanes/EtOAc): R$_f$=0.23.

Step 3: 3-Methyl-2,4-bis[3-(methyloxy)phenyl]-2-cyclobuten-1-one (247)

A CH$_2$Cl$_2$ solution (15 mL) of 4-hydroxy-3-methyl-2,4-bis[3-(methyloxy)phenyl]-2-cyclobuten-1-one (246) (0.464 g, 1.50 mmol, 1 equiv) was cooled to ca. 0° C. Triethylsilane (3.02 mL, 1.0 M, 1.5 equiv) was added followed by TFA. After 5 min, the ice bath was removed and the reaction was allowed to warm to ambient temperature. After an additional 2 h, the reaction was quenched with 50% saturated aqueous NaHCO$_3$. The organic portion was separated and pooled with those extracted using EtOAc (3×20 mL). The organic portions were dried (Na$_2$SO$_4$), filtered, and concentrated. Radial chromatography (SiO$_2$, 2 mm plate, 80:20; hexanes/EtOAc) afforded the title compound as a yellow oil (0.374 g, 85%). $^1$H NMR (CDCl$_3$, 300 MHz) δ 7.38-7.30 (m, 4H), 6.96-6.80 (m, 4H), 4.69 (s, 1H), 3.89 (s, 3H), 3.83 (s, 3H), 2.49 (s, 3H). TLC (80:20; hexanes/EtOAc): R$_f$=0.46.

Step 4: 3-Methyl-6-(methyloxy)-2-[3-(methyloxy)phenyl]-1-naphthalenol (247)

A toluene solution (15 mL) of 3-methyl-2,4-bis[3-(methyloxy)phenyl]-2-cyclobuten-1-one (246) (0.337 g, 1.15 mmol, 1 equiv) was heated to gentle reflux under a blanket of N$_2$. After 3 h, the mixture was concentrated and chromatographed radially (SiO$_2$, 1 mm plate, 90:10; hexanes/EtOAc) to afford the title compound (247) s a pale yellow oil (0.225 g, 67%). $^1$H NMR (CDCl$_3$, 400 MHz) δ 8.01 (d, J=9.0 Hz, 1H), 7.45 (dd, J=7.9, 7.9 Hz, 1H), 7.22 (s, 1H), 7.08 (dd, J=9.0, 2.4 Hz, 1H), 7.05 (d, J=2.3 Hz, 1H), 6.99 (dd, J=10.8, 2.4 Hz, 1H), 6.93 (d, J=7.5 Hz, 1H), 6.89 (d, J=2.1 Hz, 1H), 5.29 (s, 1H), 3.93 (s, 3H), 3.84 (s, 3H), 2.20 (s, 3H). TLC (80:20; hexanes/EtOAc): R$_f$=0.50.

Step 5: 4-({3-Methyl-6-(methyloxy)-2-[3-(methyloxy)phenyl]-1-naphthalenyl}oxy)benzaldehyde (248)

A dimethylacetamide solution (2 mL) of 3-methyl-6-(methyloxy)-2-[3-(methyloxy)phenyl]-1-naphthalenol (247) (0.072 g, 0.25 mmol, 1 equiv) was treated with 4-fluorobenzaldehyde (0.030 mL, 0.27 mmol, 1.1 equiv) followed by cesium carbonate (0.096 g, 0.29 mmol, 1.2 equiv). After 10 min at gentle reflux, the mixture was diluted with H$_2$O (2 mL) and extracted with EtOAc (3×5 mL). The pooled organic portions were dried (Na$_2$SO$_4$) and concentrated. Radial chromatography (SiO$_2$, 1 mm plate, 80:20; hexanes/EtOAc) afforded the title compound (248) as a pale yellow oil (0.060 g, 61%). $^1$H NMR (CDCl$_3$, 300 MHz) δ 9.80 (s, 1H), 7.68-

7.59 (m, 4H), 7.19-7.14 (m, 2H), 7.05 (dd, J=9.2, 2.4 Hz, 1H), 6.78-6.65 (m, 5H), 3.93 (s, 3H), 3.64 (s, 3H), 2.26 (s, 3H). TLC (75:25; hexanes/EtOAc): $R_f$=0.55.

Step 6: Ethyl (2E)-3-[4-({3-methyl-6-(methyloxy)-2-[3-(methyloxy)phenyl]-1-naphthalenyl}oxy)phenyl]-2-propenoate (249)

A THF solution (2 mL) of 4-({3-Methyl-6-(methyloxy)-2-[3-(methyloxy)phenyl]-1-naphthalenyl}oxy)benzaldehyde (248) (0.030 g, 0.08 mmol, 1 equiv) was cooled to ca. −78° C. and treated with the ylide generated from triethyl phosphonoacetate (0.030 mL, 0.15 mmol, 2.0 equiv) and nBuLi (0.094 mL, 1.6 M, 2.0 equiv). The cold bath was removed and the reaction was allowed to warm to ambient temperature. After 30 min at ambient temperature, the mixture was quenched with saturated aqueous ammonium chloride (2 mL) and extracted with EtOAc (3×5 mL). The pooled organic portions were dried ($Na_2SO_4$) and concentrated. Radial chromatography ($SiO_2$, 1 mm plate, 80:20; hexanes/EtOAc) afforded the title compound (249) as a pale yellow oil (0.032 g, 91%). $^1$H NMR ($CDCl_3$, 300 MHz) δ 7.71 (d, J=9.2 Hz, 1H), 7.58-7.53 (m, 2H), 7.28 (d, J=8.7 Hz, 2H), 7.20-7.13 (m, 2H), 7.04 (dd, J=9.2, 2.5 Hz, 1H), 6.79-6.70 (m, 2H), 6.64-6.60 (m, 3H), 6.23 (d, J=15.9 Hz, 1H), 4.23 (q, J=7.0 Hz, 2H), 3.93 (s, 3H), 3.62 (s, 3H), 2.26 (s, 3H), 1.31 (t, J=7.1 Hz, 3H). TLC (80:20; hexanes/EtOAc): $R_f$=0.53.

Step 7: (2E)-3-[4-({3-Methyl-6-(methyloxy)-2-[3-(methyloxy)phenyl]-1-naphthalenyl}oxy)phenyl]-2-propenoic acid (250)

A THF solution (2 mL) of ethyl (2E)-3-[4-({3-methyl-6-(methyloxy)-2-[3-(methyloxy)phenyl]-1-naphthalenyl}oxy)phenyl]-2-propenoate (249) (0.030 g, 0.06 mmol, 1 equiv) was treated with 1 M aqueous LiOH (0.260 mL). After 2 h at 50° C., the mixture was acidified with 3M aqueous HCl to pH ca. 1 and extracted with EtOAc (3×5 mL). The pooled organic portions were dried ($Na_2SO_4$) and concentrated. Radial chromatography ($SiO_2$, 1 mm plate, 80:20; hexanes/EtOAc) afforded the title compound (250) as a white foam (0.024 g, 85%). $^1$H NMR ($CDCl_3$, 400 MHz) δ 7.69 (d, J=9.2 Hz, 1H), 7.63 (d, J=15.9 Hz, 1H), 7.55 (s, 1H), 7.27 (d, J=8.3 Hz, 2H), 7.16 (dd, J=7.9, 7.9 Hz, 1H), 7.13 (d, J=2.0 Hz, 1H), 7.03 (dd, J=9.1, 2.2 Hz, 1H), 6.77 (dd, J=8.1, 1.9 Hz, 1H), 6.71 (d, J=7.4 Hz, 1H), 6.64-6.60 (m, 3H), 6.22 (d, J=15.9 Hz, 1H), 3.92 (s, 3H), 3.62 (s, 3H), 2.25 (s, 3H). TLC (98:2; $CHCl_3$/MeOH): $R_f$=0.05.

Step 8: (2E)-3-(4-{[6-Hydroxy-2-(3-hydroxyphenyl)-3-methyl-1-naphthalenyl]oxy}phenyl)-2-propenoic acid (251)

To a solution of (2E)-3-[4-({3-methyl-6-(methyloxy)-2-[3-(methyloxy)phenyl]-1-naphthalenyl}oxy)phenyl]-2-propenoic acid (250) (0.032 g, 0.07 mmol, 1 equiv) in $CH_2Cl_2$ (3 mL) at 0° C. was added boron tribromide (0.66 mL, 1.0 M, 9.0 equiv). After 2.5 h, the mixture was treated with saturated aqueous $NaHCO_3$, reacidified to a pH of 2 with 1 M HCl, and extracted with EtOAc (3×5 mL). The pooled organic portions were dried ($MgSO_4$) and concentrated. Radial chromatography ($SiO_2$, 1 mm plate, 70:30; $CHCl_3$/MeOH) furnished the title compound (251) as a pale yellow foam (0.017 g, 57%). $^1$H NMR ($CD_3OD$, 400 MHz) δ 7.59 (d, J=9.0 Hz, 1H), 7.48 (s, 1H), 7.44-7.36 (m, 1H), 7.29 (d, J=8.2 Hz, 2H), 7.10 (d, J=2.2 Hz, 1H), 7.04 (dd, J=7.5, 7.5 Hz, 1H), 6.94 (dd, J=9.0, 2.2 Hz, 1H), 6.64-6.62 (m, 1H), 6.57-6.55 (m, 4H), 6.39-6.24 (m, 1H), 2.20 (s, 3H). TLC (90:10; $CHCl_3$/MeOH): $R_f$=0.54.

Example 47 (252)

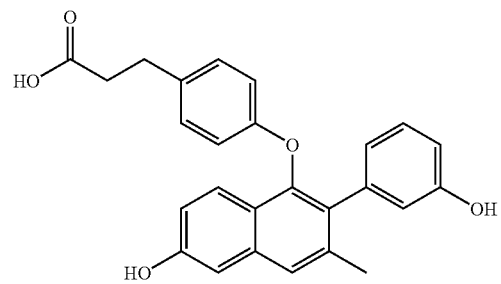

Step 1: 3-(4-{[6-Hydroxy-2-(3-hydroxyphenyl)-3-methyl-1-naphthalenyl]oxy}phenyl)propanoic acid (252)

A 1:1 EtOAc/EtOH solution (4 mL) of (2E)-3-(4-{[6-hydroxy-2-(3-hydroxyphenyl)-3-methyl-1-naphthalenyl]oxy}phenyl)-2-propenoic acid (251) (0.041 g, 0.01 mmol, 1 equiv) was treated with 5% Pd—C (0.027 g, 0.02 mmol, 0.1 equiv) and the reaction vessel was equipped with an $H_2$-filled balloon. After 14 h at ambient temperature, the crude mixture was filtered through a pad of Celite. Concentration gave a light pink solid that was purified by radial chromatography ($SiO_2$, 1 mm plate, 90:10; $CHCl_3$/MeOH) to afford the title compound (252) as a pink solid (0.018 g, 44%). $^1$H NMR ($CD_3OD$, 400 MHz) δ 7.58 (d, J=9.0 Hz, 1H), 7.40 (s, 1H), 7.07-7.03 (m, 2H), 6.95-6.89 (m, 3H), 6.62 (dd, J=8.1, 2.3 Hz, 1H), 6.55-6.52 (m, 2H), 6.43 (d, J=8.5 Hz, 2H), 2.75 (t, J=7.7 Hz, 2H), 2.34 (t, J=7.3 Hz, 2H), 2.17 (s, 3H).

LRMS (ESI) m/z 413 (M−1)⁻. TLC (90:10; $CHCl_3$/MeOH): $R_f$=0.14.

Example 48 (259)

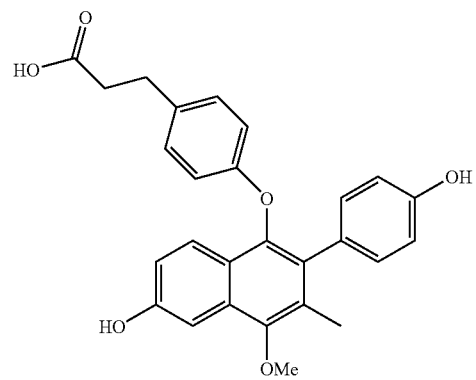

Step 1: 2-Methyl-4,4-bis(methyloxy)-3-{4-[(phenylmethyl)oxy]phenyl}-2-cyclobuten-1-one (253)

Synthesized in a manner similar to that employed for Example 46 (Step 1) using 1-bromo-4-[(phenylmethyl)oxy]benzene. TLC (70:30; hexanes/EtOAc): $R_f$=0.39

Step 2: 3-Methyl-4-(methyloxy)-4-{3-[(phenylmethyl)oxy]phenyl}-2-{4-[(phenylmethyl)oxy]phenyl}-2-cyclobuten-1-one (254)

Synthesized in a manner similar to that employed for Example 46 (Step 2) using 2-methyl-4,4-bis(methyloxy)-3-{4-[(phenylmethyl)oxy]phenyl}-2-cyclobuten-1-one (253) and 1-bromo-3-[(phenylmethyl)oxy]benzene and quenching with methyl triflate. TLC (70:30; hexanes/EtOAc): $R_f$=0.27.

Step 3: 3-Methyl-4-(methyloxy)-6-[(phenylmethyl)oxy]-2-{4-[(phenylmethyl)oxy]phenyl}-1-naphthalenol (255)

Synthesized in a manner similar to that employed for Example 46 (Step 4) using 3-methyl-4-(methyloxy)-4-{3-[(phenylmethyl)oxy]phenyl}-2-{4-[(phenylmethyl)oxy]phenyl}-2-cyclobuten-1-one (254). TLC (90:10; hexanes/EtOAc): $R_f$=0.38.

Step 4: 4-[(3-Methyl-4-(methyloxy)-6-[(phenylmethyl)oxy]-2-{4-[(phenylmethyl)oxy]phenyl}-1-naphthalenyl)oxy]benzaldehyde (256)

Synthesized in a manner similar to that employed for Example 46 (Step 5) using 3-methyl-4-(methyloxy)-6-[(phenylmethyl)oxy]-2-{4-[(phenylmethyl)oxy]phenyl}-1-naphthalenol (255). TLC (75:25; hexanes/EtOAc): $R_f$=0.46.

Step 5: Ethyl (2E)-3-{4-[(3-methyl-4-(methyloxy)-6-[(phenylmethyl)oxy]-2-{4-[(phenylmethyl)oxy]phenyl}-1-naphthalenyl)oxy]phenyl}-2-propenoate (257)

Synthesized in a manner similar to Example 46 (Step 6) using 4-[(3-methyl-4-(methyloxy)-6-[(phenylmethyl)oxy]-2-{4-[(phenylmethyl)oxy]phenyl}-1-naphthalenyl)oxy]benzaldehyde (256). $^1$H NMR (CDCl$_3$, 300 MHz) δ 7.73 (d, J=9.1 Hz, 1H), 7.58-7.23 (m, 14H), 7.14 (dd, J=9.0, 2.5 Hz, 1H), 7.03 (d, J=8.6 Hz, 2H), 6.87 (d, J=8.7 Hz, 2H), 6.58 (d, J=8.7 Hz, 2H), 6.23 (d, J=15.9 Hz, 1H), 5.24 (s, 2H), 5.02 (s, 2H), 4.23 (q, J=7.1 Hz, 2H), 3.88 (s, 3H), 2.19 (s, 3H), 1.31 (t, J=7.1 Hz, 3H). TLC (75:25; hexanes/EtOAc): $R_f$=0.37.

Step 6: (2E)-3-{4-[(3-Methyl-4-(methyloxy)-6-[(phenylmethyl)oxy]-2-{4-[(phenylmethyl)oxy]phenyl}-1-naphthalenyl)oxy]phenyl}-2-propenoic acid (258)

Synthesized in a manner similar to Example 46 (Step 7) using ethyl (2E)-3-{4-[(3-methyl-4-(methyloxy)-6-[(phenylmethyl)oxy]-2-{4-[(phenylmethyl)oxy]phenyl}-1-naphthalenyl)oxy]phenyl}-2-propenoate (257). $^1$H NMR (CDCl$_3$, 300 MHz) δ 7.65 (d, J=9.1 Hz, 1H), 7.57 (d, J=16.0 Hz, 1H), 7.45-7.18 (m, 1H), 7.07 (dd, J=9.0, 2.5 Hz, 1H), 6.96 (d, J=8.5 Hz, 2H), 6.80 (d, J=8.7 Hz, 2H) 6.53 (d, J=8.6 Hz, 2H), 6.53 (d, J=8.6 Hz, 2H), 6.16 (d, J=16.0 Hz, 1H), 5.16 (s, 2H), 4.95 (s, 2H), 3.81 (s, 3H), 2.12 (s, 3H). LRMS (ESI) m/z 621 (M−1)$^−$. TLC (90:10; CHCl$_3$/MeOH): $R_f$=0.44.

Step 7: 3-(4-{[6-Hydroxy-2-(4-hydroxyphenyl)-3-methyl-4-(methyloxy)-1-naphthalenyl]oxy}phenyl)propanoic acid (259)

Synthesized in manner similar to that employed for Example 46 (Step 8) using (2E)-3-{4-[(3-methyl-4-(methyloxy)-6-[(phenylmethyl)oxy]-2-{4-[(phenylmethyl)oxy]phenyl}-1-naphthalenyl)oxy]phenyl}-2-propenoic acid (258). $^1$H NMR (CD$_3$OD, 400 MHz) δ 7.61 (d, J=9.1 Hz, 1H), 7.35 (d, J=2.4 Hz, 1H), 6.94-6.89 (m, 5H), 6.66 (d, J=8.4 Hz, 2H), 6.42 (d, J=8.4 Hz, 2H), 3.88 (s, 3H), 2.77-2.73 (m, 2H), 2.38 (bs, 2H), 2.12 (s, 3H). LRMS (ES$^−$) m/z 443 (M−1)$^−$. TLC (90:10; CHCl$_3$/MeOH): $R_f$=0.07.

Example 49 (267)

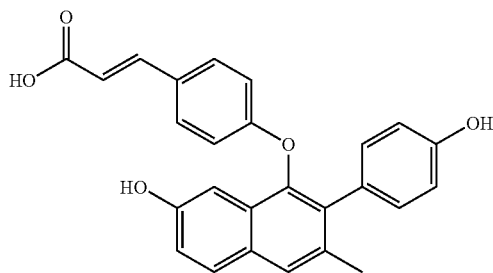

Step 1: 2-Methyl-4,4-bis(methyloxy)-3-[4-(methyloxy)phenyl]-2-cyclobuten-1-one (260)

Synthesized according to the procedure utilized for Example 46 (Step 1) using 4-methoxyphenylmagnesium bromide. $^1$H NMR (CDCl$_3$, 400 MHz) δ 7.50 (d, J=8.9 Hz, 2H), 6.98 (d, J=8.8 Hz, 2H), 3.86 (s, 3H), 3.49 (s, 6H), 2.07 (s, 3H). TLC (75:25; hexanes/EtOAc): $R_f$=0.29.

Step 2: 4-Hydroxy-3-methyl-2,4-bis[4-(methyloxy)phenyl]-2-cyclobuten-1-one (261)

Synthesized according to the procedure utilized for Example 46 (Step 2) using 2-methyl-4,4-bis(methyloxy)-3-[4-(methyloxy)phenyl]-2-cyclobuten-1-one (260) and 4-methoxyphenylmagnesium bromide. $^1$H NMR (CDCl$_3$, 300 MHz) δ 7.39-7.29 (m, 4H), 7.10-6.88 (m, 4H), 3.88 (s, 3H), 3.85 (s, 3H), 2.47 (s, 3H). TLC (60:40; hexanes/EtOAc): $R_f$=0.23.

Step 3: 3-Methyl-2,4-bis[4-(methyloxy)phenyl]-2-cyclobuten-1-one (262)

Synthesized according to the procedure utilized for Example 46 (Step 3) using 4-hydroxy-3-methyl-2,4-bis[4-(methyloxy)phenyl]-2-cyclobuten-1-one (261). $^1$H NMR (CDCl$_3$, 300 MHz) δ 7.74 (d, J=8.8 Hz, 2H), 7.18 (d, J=8.8 Hz, 2H), 6.98 (d, J=8.7 Hz, 2H), 6.92 (d, J=8.8 Hz, 2H), 4.64 (s, 1H), 3.88 (s, 3H), 3.83 (s, 3H), 2.44 (s, 3H). LSMS (ESI) m/z 293 (M$^−$)$^−$. TLC (80:20; hexanes/EtOAc): $R_f$=0.45.

Step 4: 3-Methyl-7-(methyloxy)-2-[4-(methyloxy)phenyl]-1-naphthalenol (263)

Synthesized according to the procedure utilized for Example 46 (Step 4) using 3-methyl-2,4-bis[4-(methyloxy)phenyl]-2-cyclobuten-1-one (262). $^1$H NMR (CDCl$_3$, 300 MHz) δ 7.67 (d, J=8.8 Hz, 1H), 7.49 (d, J=2.7 Hz, 1H), 7.32-7.29 (m, 4H), 7.17 (dd, J=8.9, 2.4 Hz, 1H), 7.11 (d, J=8.8 Hz, 1H), 5.27 (s, 1H), 3.97 (s, 3H), 3.93 (s, 3H), 2.20 (s, 3H). LRMS (ESI) m/z 293 (M$^−$)$^−$. TLC (75:25; hexanes/EtOAc): $R_f$=0.39.

Step 5: 4-({3-Methyl-7-(methyloxy)-2-[4-(methyloxy)phenyl]-1-naphthalenyl}oxy)benzaldehyde (264)

Synthesized according to the procedure utilized for Example 46 (Step 5) using 3-methyl-7-(methyloxy)-2-[4-(methyloxy)phenyl]-1-naphthalenol (263). $^1$H NMR (CDCl$_3$, 300 MHz) δ 9.84 (s, 1H), 7.78 (d, J=9.0 Hz, 1H), 7.67 (d, J=8.8 Hz, 2H), 7.66 (s, 1H), 7.19 (dd, J=8.7, 2.3 Hz, 1H), 7.08 (d, J=6.7 Hz, 2H), 7.06 (s, 1H), 6.83 (d, J=9.0 Hz, 2H), 6.76 (d, J=8.5 Hz, 2H), 3.80 (s, 3H), 3.77 (s, 3H), 2.28 (s, 3H). TLC (75:25; hexanes/EtOAc): $R_f$=0.46.

Step 6: Ethyl (2E)-3-[4-({3-methyl-7-(methyloxy)-2-[4-(methyloxy)phenyl]-1-naphthalenyl}oxy)phenyl]-2-propenoate (265)

Synthesized in a manner similar to Example 46 (Step 6) using 4-({3-methyl-7-(methyloxy)-2-[4-(methyloxy)phenyl]-1-naphthalenyl}oxy)benzaldehyde (264). $^1$H NMR (CDCl$_3$, 400 MHz) δ 7.73 (d, J=8.9 Hz, 1H), 7.59 (s, 1H), 7.55 (d, J=16.0 Hz, 1H), 7.26 (d, J=8.6 Hz, 2H), 7.14 (dd, J=9.0, 2.6 Hz, 1H), 7.07 (d, J=2.4 Hz, 1H), 7.04 (d, J=8.6 Hz, 2H), 6.80 (d, J=8.7 Hz, 2H), 6.61 (d, J=8.7 Hz, 2H), 6.63 (d, J=15.9 Hz, 1H), 4.23 (q, J=7.1 Hz, 2H), 3.78 (s, 3H), 3.73 (s, 3H), 2.23 (s, 3H), 1.31 (t, J=7.0 Hz, 3H). TLC (80:20; hexanes/EtOAc): $R_f$=0.52.

Step 7: (2E)-3-[4-({3-Methyl-7-(methyloxy)-2-[4-(methyloxy)phenyl]-1-naphthalenyl}oxy)phenyl]-2-propenoic acid (266)

Synthesized in a manner similar to Example 46 (Step 7) using ethyl (2E)-3-[4-({3-methyl-7-(methyloxy)-2-[4-(methyloxy)phenyl]-1-naphthalenyl}oxy)phenyl]-2-propenoate (265). $^1$H NMR (CDCl$_3$, 400 MHz) δ 7.74 (d, J=9.0 Hz, 1H), 7.64 (d, J=15.9 Hz, 1H), 7.60 (s, 1H), 7.29 (d, J=8.8 Hz, 2H), 7.14 (dd, J=8.7, 2.4 Hz, 1H), 7.06-7.04 (m, 3H), 6.81 (d, J=8.7 Hz, 2H), 6.63 (d, J=8.7 Hz, 2H), 6.24 (d, J=15.9 Hz, 1H), 3.78 (s, 3H), 3.74 (s, 3H), 2.24 (s, 3H). TLC (90:10; CHCl$_3$/MeOH): $R_f$=0.26.

Step 8: (2E)-3-(4-{[7-Hydroxy-2-(4-hydroxyphenyl)-3-methyl-1-naphthalenyl]oxy}phenyl)-2-propenoic acid (267)

Synthesized in a manner similar to Example 46 (Step 8) using (2E)-3-[4-({3-methyl-7-(methyloxy)-2-[4-(methyloxy)phenyl]-1-naphthalenyl}oxy)phenyl]-2-propenoic acid (266). $^1$H NMR (CD$_3$OD, 400 MHz) δ 7.71 (d, J=8.6 Hz, 1H), 7.58 (s, 1H), 7.49 (d, J=15.5 Hz, 1H), 7.34 (d, J=8.4 Hz, 2H), 7.04 (dd, J=8.7, 2.0 Hz, 1H), 7.00 (s, 1H), 6.94 (d, J=8.5 Hz, 2H), 6.68 (d, J=8.4 Hz, 2H), 6.58 (d, J=8.4 Hz, 2H), 6.27 (d, J=15.2 Hz, 1H), 2.19 (s, 3H). TLC (90:10; CHCl$_3$/MeOH): $R_f$=0.19.

Example 50 (268)

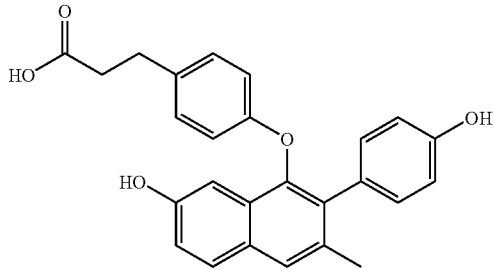

3-(4-{[7-Hydroxy-2-(4-hydroxyphenyl)-3-methyl-1-naphthalenyl]oxy}phenyl)propanoic acid (268)

Synthesized in a manner similar to Example 47 using (2E)-3-(4-{[7-hydroxy-2-(4-hydroxyphenyl)-3-methyl-1-naphthalenyl]oxy}phenyl)-2-propenoic acid (267). $^1$H NMR (CD$_3$OD, 400 MHz) δ 7.68 (d, J=9.5 Hz, 1H), 7.54 (s, 1H), 7.03-7.00 (m, 2H), 6.95-6.91 (m, 4H), 6.67 (d, J=8.4 Hz, 2H), 6.45 (d, J=8.4 Hz, 2H), 2.78-2.74 (m, 2H), 2.49-2.47 (m, 2H), 2.18 (s, 3H). LRMS (ESI) m/z 413 (M−1)$^-$. TLC (90:10; CHCl$_3$/MeOH): $R_f$=0.21.

Example 51 (270)

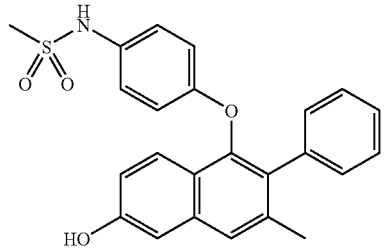

Step 1: N-{4-[(6-methoxy-3-methyl-2-phenyl-1-naphthalenyl)oxy]phenyl}methanesulfonamide (269)

To a flask containing a solution of 29, Et$_3$N (0.26 g, 2.55 mmol) and DMAP (0.032, 0.26 mmol) in CH$_2$Cl$_2$ (5 mL) was added methanesulfonyl chloride (0.24 g, 2.13 mmol), dropwise at RT and the reaction allowed to stir overnight. After 18 h the reaction was diluted with CH$_2$Cl$_2$ (15 mL) and the reaction rinsed with 10% aqueous HCl (25 mL). The CH$_2$Cl$_2$ layer was dried (MgSO$_4$) and concentrated to a dark amber oil. The crude product was purified by silica gel column chromatography to afford 170 mg (46%) of the title compound (269) as a colorless oil. An additional 90 mg of a mixture of 269 and N,N-bissulfonylated product was also isolated. $^1$H NMR (400 MHz, DMSO-d$_6$): δ 2.15 (s, 3H), 2.82 (s, 3H), 3.85 (s, 3H), 6.54 (d, J=8.9 Hz, 2H), 6.94 (d, J=8.8 Hz, 2H), 6.97 (dd, J$_1$=2.4 Hz, J$_2$=9.1 Hz, 1H), 6.96 (d, J=6.6 Hz, 1H), 7.15-7.32 (m, 5H), 7.58 (d, J=9.1 Hz, 1H), 7.67 (s, 1H), 9.32 (s, 1H).

Step 2: N-{4-[(6-hydroxy-3-methyl-2-phenyl-1-naphthalenyl)oxy]phenyl}methanesulfonamide (270)

A stirring solution of 269 (0.27 g, 0.62 mmol) in CH$_2$Cl$_2$ (10 mL) chilled to −20° C. under N$_2$ was added BBr$_3$ (0.47 g, 1.86 mmol), dropwise, via syringe, over 1 minute. The resulting yellow/orange rxn was stirred for 2 h at −20° C. and then poured over 50 g ice followed by addition of EtOAc (50 mL). The resulting slurry was transferred to a separatory funnel and the organic layer washed with brine (50 mL), dried (Na$_2$SO$_4$) and concentrated to a pale yellow foam. The crude product was purified by silica gel column chromatography with 2% MeOH: CH$_2$Cl$_2$ to yield 162 mg (63%) of the title compound 270, as a white solid. $^1$H NMR (400 MHz, DMSO-d$_6$): δ 2.13 (s, 3H), 2.83 (s, 3H), 6.55 (d, J=9.0 Hz, 2H), 6.97 (d, J=8.3 Hz, 2H), 6.96 (dd, J$_1$=2.3 Hz, J$_2$=9.1 Hz, 1H), 7.12 (d, J=2.3 Hz, 1H), 7.16 (d, J=7.0 Hz, 1H), 7.21-7.30 (m, 4H), 7.54 (d, J=8.5 Hz, 1H), 7.55 (s, 1H), 9.33 (s, 1H), 9.84 (s, 1H). Anal. Calc for C$_{29}$H$_{26}$O$_3$.0.5H$_2$O: C, 67.27; H, 5.18; N, 3.27. Found: C, 67.13; H, 5.04; N, 3.27.

Example 52 (272)

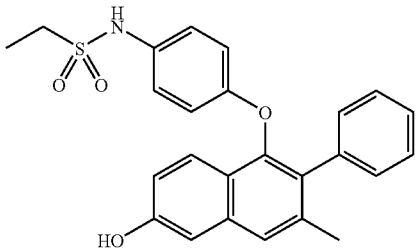

Step 1: N-{4-[(6-methoxy-3-methyl-2-phenyl-1-naphthalenyl)oxy]phenyl}ethanesulfonamide (271)

A flask containing a solution of 29 (0.21 g, 0.59 mmol), Et$_3$N (0.18 g, 1.78 mmol) and DMAP (0.034 g, 0.28 mmol) in CH$_2$Cl$_2$ (5 mL) was added ethanesulfonyl chloride (0.19 g, 1.48 mmol), dropwise, at RT and the reaction allowed to stir overnight at RT.

After 18 hr the reaction was diluted with 15 mL CH$_2$Cl$_2$ and rinsed with 10% aq. HCl (25 mL). The CH$_2$Cl$_2$ layer was dried (MgSO$_4$), concentrated to a dark amber oil, and purified by silica gel column chromatography with 20% EtOAc/hexanes to afford 170 mg (64%) of the title compound, 271, as a light yellow solid. $^1$H NMR (400 MHz, DMSO-d$_6$): δ 1.11 (t, J=7.3 Hz, 3H), 2.15 (s, 3H), 3.85 (s, 3H), 4.00 (q, J=7.3 Hz, 2H), 6.52 (d, J=9.0 Hz, 2H), 6.93 (d, J=9.0 Hz, 2H), 7.05 (dd, J$_1$=2.6 Hz, J$_2$=9.2 Hz, 1H), 7.14-7.32 (m, 5H), 7.59 (d, J=8.8 Hz, 1H), 7.66 (s, 1H), 9.39 (s, 1H).

Step 2: N-{4-[(6-hydroxy-3-methyl-2-phenyl-1-naphthalenyl)oxy]phenyl}ethanesulfonamide (272)

To a stirring solution of 271 (0.14 g, 0.31 mmol) in 6 mL CH$_2$Cl$_2$ (6 mL), chilled to −20° C. under N$_2$, was added BBr$_3$ (0.24 g, 0.94 mmol) dropwise, via syringe, over 1 minute. After 90 min at −20° C. the rxn was poured over 50 g ice followed by EtOAc (50 mL). The EtOAC layer was washed with brine (50 mL), dried (Na$_2$SO$_4$) and concentrated to a viscous yellow oil that was purified by column chromatography using a gradient of 100% DCM to 1% MeOH: CH$_2$Cl$_2$ to yield a foam. The foam is crystallized from EtOAc/hexanes to yield the title compound 272, as a light yellow solid (72 mg, 55%). $^1$H NMR (400 MHz, DMSO-d$_6$): δ 1.13 (t, J=7.3 Hz, 3H), 2.13 (s, 3H), 4.01 (q, J=7.3 Hz, 2H), 6.53 (d, J=8.9 Hz, 2H), 6.94 (d, J=8.9 Hz, 2H), 6.97 (dd, J$_1$=2.3 Hz, J$_2$=9.1 Hz, 1H), 7.11-7.30 (m, 5H), 7.54 (s, 1H), 7.55 (d, J=8.8 Hz, 1H), 9.40 (s, 1H), 9.81 (s, 1H).

Example 53 (274)

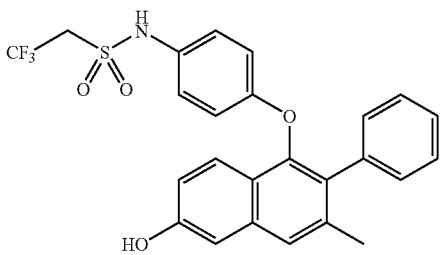

Step 1: 2,2,2-trifluoro-N-{4-[(6-methoxy-3-methyl-2-phenyl-1-naphthalenyl)oxy]phenyl}ethanesulfonamide (273)

A flask containing a solution of 29 (0.30 g, 0.85 mmol), Et$_3$N (0.26 g, 2.55 mmol) and DMAP (0.032 g, 0.26 mmol) in CH$_2$Cl$_2$ (5 mL) was added trifluoroethanesulfonyl chloride (0.39 g, 2.13 mmol), dropwise, at RT and the reaction allowed to stir overnight at RT. After 18 h the reaction was diluted with 15 mL CH$_2$Cl$_2$ and rinsed with 10% aq. HCl (25 mL). The CH$_2$CO$_2$ layer was dried (MgSO$_4$), concentrated to a dark amber oil, and purified by silica gel column chromatography with 10% EtOAc/hexanes to afford 270 mg (64%) of the title compound, 273, as a white foam. $^1$H NMR (400 MHz, DMSO-d$_6$): δ 2.18 (s, 3H), 3.88 (s, 3H), 4.33 (q, J=9.8 Hz, 2H), 6.58 (d, J=9.0 Hz, 2H), 6.98 (d, J=9.0 Hz, 2H), 7.08 (dd, J$_1$=2.4 Hz, J$_2$=9.1 Hz, 1H), 7.18-7.36 (m, 5H), 7.61 (d, J=9.1 Hz, 1H), 7.70 (s, 1H), 10.07 (s, 1H).

Step 2: 2,2,2-trifluoro-N-{4-[(6-hydroxy-3-methyl-2-phenyl-1-naphthalenyl)oxy]phenyl}ethanesulfonamide (274)

To a stirring solution of 273 (0.14 g, 0.31 mmol) in CH$_2$Cl$_2$ (6 mL), chilled to −20° C. under N$_2$, was added BBr$_3$ (0.24 g, 0.94 mmol) dropwise, via syringe, over 1 minute. After 90 min at −20° C. the rxn was poured over 50 g ice followed by EtOAc (50 mL). The EtOAC layer was washed with brine (50 mL), dried (Na$_2$SO$_4$) and concentrated to a viscous yellow oil that was purified by column chromatography using a gradient of 100% CH$_2$Cl$_2$ to 1% MeOH: CH$_2$Cl$_2$ to yield a foam. The foam was crystallized from EtOAc/hexanes to yield the title compound 274, as a light yellow solid (72 mg, 55%). $^1$H NMR (400 MHz, DMSO-d$_6$): δ 2.13 (s, 3H), 4.33 (q, J=9.8 Hz, 2H), 6.57 (d, J=9.0 Hz, 2H), 6.96 (d, J=9.0 Hz, 2H), 6.97 (dd, J$_1$=2.4 Hz, J$_2$=9.1 Hz, 1H), 7.12-7.30 (m, 5H), 7.53 (s, 1H), 7.55 (d, J=9.8 Hz, 1H), 9.40 (s, 1H), 9.84 (s, 1H), 10.06 (s, 1H).

Example 54 (275)

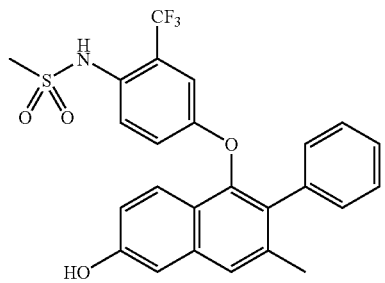

Compound 275, N-[4-[(6-hydroxy-3-methyl-2-phenyl-1-naphthalenyl)oxy]-2-(trifluoromethyl)phenyl]methanesulfonamide, was prepared from 7 and 1-fluoro-3-trifluoromethyl-4-nitrobenzene using procedures analogous to those described in Example 6. $^1$H NMR (400 MHz, DMSO-d$_6$): δ 2.14 (s, 3H), 2.96 (s, 3H), 6.80 (dd, J$_1$=2.9 Hz, J$_2$=8.8 Hz, 1H), 6.85 (d, J=2.9 Hz, 1H), 7.01 (dd, J$_1$=2.3 Hz, J$_2$=9.0 Hz, 1H), 7.13-7.30 (m, 7H), 7.56 (d, J=9.0 Hz, 1H), 7.60 (s, 1H), 9.17 (s, 1H), 9.90 (s, 1H). HRMS (ESI) Calcd for C$_{25}$H$_{20}$F$_3$NO$_4$S: 488.1143 (M+H)$^+$. Found: 488.1145.

Example 55 (276)

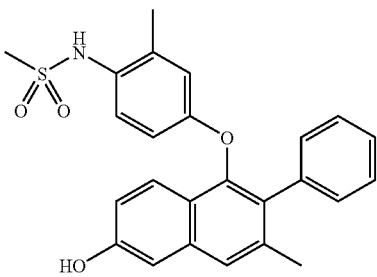

Compound 276, N-{4-[(6-hydroxy-3-methyl-2-phenyl-1-naphthalenyl)oxy]-2-methylphenyl}methanesulfonamide, was obtained from 7 and 1-fluoro-3-methyl-4-nitrobenzene using procedures analogous to those described in Example 6. BBr$_3$ demethylation gave the title compound, 276, in 22% yield as an off-white solid. $^1$H NMR (400 MHz, DMSO-d$_6$): δ 2.11 (s, 3H), 2.13 (s, 3H), 2.85 (s, 3H), 6.35 (dd, J$_1$=3.0 Hz, J$_2$=8.8 Hz, 1H), 6.52 (d, J=2.8 Hz, 1H), 6.96 (d, J=9.0 Hz, 2H), 7.11-7.36 (m, 7H), 7.51 (d, J=9.0 Hz, 1H), 7.54 (s, 1H), 8.77 (s, 1H), 9.82 (s, 1H). HRMS (ESI) Calcd for C$_{25}$H$_{23}$NO$_4$S: 434.1426 (M+H)$^+$. Found: 434.1417.

Example 56 (277)

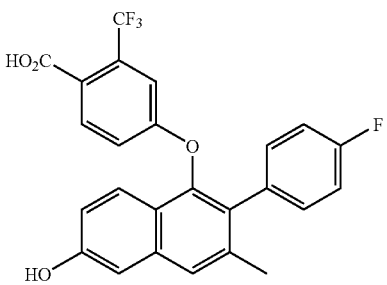

Compound 278, 4-{[2-(4-fluorophenyl)-6-hydroxy-3-methyl-1-naphthalenyl]oxy}-2-(trifluoromethyl)benzoic acid, was prepared from the corresponding benzaldehyde using the oxidation and demethylation procedure described for compound 19 (Example 3). BBr$_3$ demethylation afforded the title compound, 278, in 35% yield as a solid. $^1$H NMR (400 MHz, d-CDCl$_3$): δ 2.24 (s, 3H), 6.72 (dd, J$_1$=2.4 Hz, J$_2$=8.6 Hz, 1H), 6.96-7.11 (m, 5H), 7.18 (d, J=2.4 Hz, 1H), 7.26 (s, 1H), 7.56 (s, 1H), 7.67 (d, J=9.0 Hz, 1H), 7.80 (d, J=8.7 Hz, 1H). HRMS (ESI) Calcd for C$_{25}$H$_{16}$F$_4$O$_4$: 455.0906 (M−H)$^-$. Found: 455.0897.

Example 57 (278)

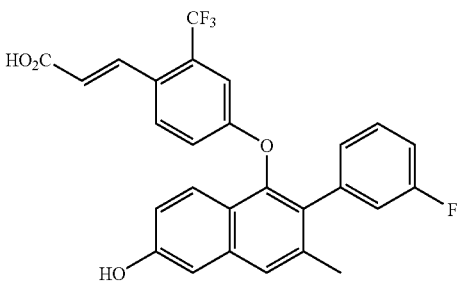

Compound 278, (2E)-3-[4-{[2-(3-fluorophenyl)-6-hydroxy-3-methyl-1-naphthalenyl]oxy}-2-(trifluoromethyl)phenyl]-2-propenoic acid, was prepared using the procedures analogous to those described in Example 32. 3-Fluorobenzeneboronic acid was used in place of 4-fluorobenzeneboronic acid (Step 1) and 2-trifluoromethyl-4-fluorobenzaldehyde was used in place of 4-fluorobenzaldehyde (Step 2). BBr$_3$ demethylation afforded the title compound, 278, in 44% yield as a solid. $^1$H NMR (400 MHz, d-CDCl$_3$): δ 2.25 (s, 3H), 6.25 (d, J=15.7 Hz, 1H), 6.72 (dd, J$_1$=2.4 Hz, J$_2$=8.6 Hz, 1H), 6.85-6.97 (m, 3H), 7.04 (dd, J$_1$=2.4 Hz, J$_2$=8.6 Hz, 1H), 7.18 (d, J=2.4 Hz, 1H), 7.20-7.24 (m, 1H), 7.26 (s, 1H), 7.48 (d, J=8.8 Hz, 1H), 7.55 (s, 1H), 7.71 (d, J=9.1 Hz, 1H), 8.00 (d, J=15.7 Hz, 1H). LCMS (ESI) m/z 986 (2M+Na)$^+$.

Example 58 (279)

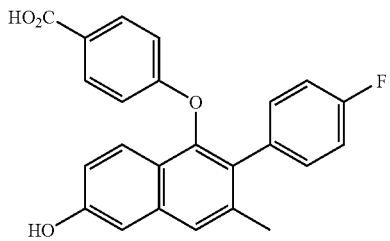

Compound 279, 4-{[2-(4-fluorophenyl)-6-hydroxy-3-methyl-1-naphthalenyl]oxy}benzoic acid, was prepared from 4-[2-(4-fluoro-phenyl)-6-methoxy-3-methyl-naphthalen-1-yloxy]-benzaldehyde 204 using the oxidation procedure described for compound 19 (Example 3). BBr$_3$ demethylation afforded the title compound, 279, in 41% yield as a solid. $^1$H NMR (400 MHz, d-CDCl$_3$): δ 2.23 (s, 3H), 6.63 (d, J=8.8 Hz, 2H), 6.65-7.11 (m, 4H), 7.16 (d, J=2.4 Hz), 7.26 (s, 1H), 7.53 (s, 1H), 7.70 (d, J=9.1 Hz, 1H), 7.85 (d, J=8.7 Hz, 1H).

Example 59 (280)

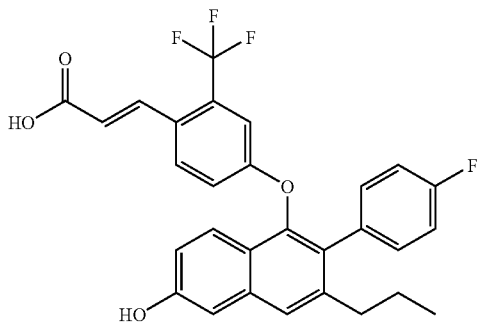

Compound 280, (2E)-3-[4-{[2-(4-fluorophenyl)-6-hydroxy-3-propyl-1-naphthalenyl]oxy}-2-(trifluoromethyl)phenyl]-2-propenoic acid, was prepared using the procedures analogous to those described in Example 38. BBr$_3$ demethylation afforded the title compound, 280, in 50% yield as a solid. $^1$H NMR (400 MHz, d-CDCl$_3$): δ 0.82 (t, J=7.4 Hz, 3H), 1.44-1.53 (m, 2H), 2.48-2.54 (m, 2H), 6.25 (d, J=15.7 Hz, 1H), 6.70 (dd, J=2.6 Hz, J$_2$=8.6 Hz, 1H), 6.93-7.09 (m, 5H), 7.20 (d, J=2.4 Hz, 1H), 7.26 (s, 1H), 7.54 (d, J=7.2 Hz, 1H), 7.55 (s, 1H), 7.71 (d, J=9.1 Hz, 1H), 8.00 (dd, J$_1$=15.7 Hz, J$_2$=1.9 Hz, 1H). HRMS (ESI) Calcd for C$_{29}$H$_{22}$F$_4$O$_4$: 509.1376 (M−H)$^-$. Found: 509.1389.

Example 60 (281)

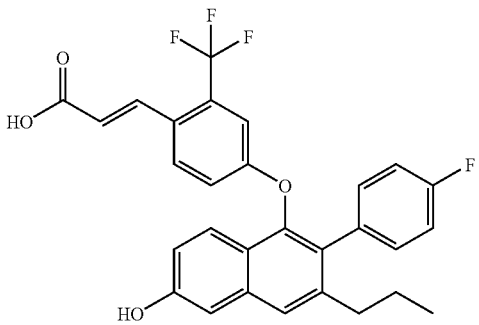

Compound 281, (2E)-3-[4-{[2-(4-fluorophenyl)-6-hydroxy-3-propyl-1-naphthalenyl]oxy}-2-(trifluoromethyl)phenyl]-2-propenamide, was prepared using the procedures analogous to those described in Example 39. BBr$_3$ demethylation afforded the title compound, 281, in 57% yield as a solid. $^1$H NMR (400 MHz, d-CDCl$_3$): δ 0.81 (t, J=7.5 Hz, 3H), 1.44-1.53 (m, 2H), 2.49-2.53 (m, 2H), 5.46 (br, 2H), 6.24 (d, J=15.5 Hz, 1H), 6.67 (dd, J$_1$=2.4 Hz, J$_2$=8.8 Hz, 1H), 6.66-7.08 (m, 5H), 7.20 (d, J=2.4 Hz, 1H), 7.26 (s, 1H), 7.40 (d, J=8.8 Hz, 1H), 7.54 (s, 1H), 7.71 (d, J=8.9 Hz, 1H), 7.80 (d, J=15.4 Hz, 1H). HRMS (ESI) Calcd for C$_{29}$H$_{23}$NF$_4$O$_3$: 510.1692 (M+H)$^+$. Found: 510.1707.

Example 61 (282)

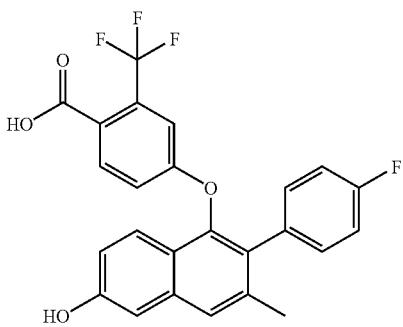

Compound 282, 4-{[2-(4-fluorophenyl)-6-hydroxy-3-methyl-1-naphthalenyl]oxy}-2-(trifluoromethyl)benzamide, was prepared using the procedures analogous to those described in Example 39. BBr$_3$ demethylation afforded the title compound, 282, in 50% yield as a solid. $^1$H NMR (400 MHz, d-CDCl$_3$): δ2.24 (s, 3H), 5.71 (br, 2H), 6.72 (dd, J$_1$=2.4 Hz, J$_2$=8.6 Hz, 1H), 6.97-7.12 (m, 5H), 7.17 (d, J=2.4 Hz, 1H), 7.26 (s, 1H), 7.37 (d, J=7.5 Hz, 1H), 7.54 (s, 1H), 7.64 (d, J=9.0 Hz, 1H). HRMS (EI) Calcd for C$_{26}$H$_{20}$FO$_4$: 455.1145 (M$^+$). Found: 45.1155.

Example 62 (287)

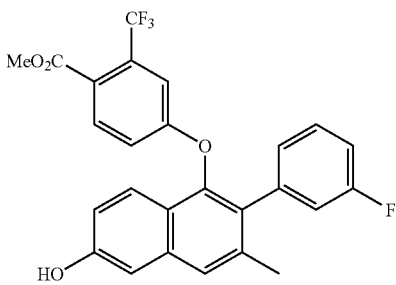

Step 1: 2-(4-Fluoro-phenyl)-6-methoxy-1-methoxymethoxy-3-methyl-naphthalene (283)

2-Bromo-6-methoxy-1-(methoxymethoxy)-3-methyl-naphthalene (14) (2.00 g, 6.44 mmol), 3-fluorobenzeneboronic acid (1.80 g, 12.88 mmol), tetrakis(triphenylphosphino) palladium (0) (0.74 g, 0.64 mmol), 2 M sodium carbonate (60 mL) and ethylene glycol dimethyl ether (60 mL) were combined and heated in a sealed tube at 160° C. for 75 min. The reaction was cooled to room temperature and filtered through a celite pad with 100 mL each diethyl ether and water. The organic layer was washed with brine (100 mL), dried (Na$_2$SO$_4$) and concentrated to an orange viscous oil. The crude product was purified by column chromatography with 10% EtOAc/hexane to afford 1.77 g (84%) of the title compound, 283 as a yellow oil. $^1$H NMR (400 MHz, DMSO-d$_6$): δ 2.14 (s, 3H), 3.02 (s, 3H), 3.86 (s, 3H), 4.71 (s, 3H), 7.12-7.23 (m, 4H), 7.25 (d, J=2.5 Hz, 1H), 7.46-7.52 (m, 1H), 7.53 (s, 1H), 7.93 (d, J=9.2 Hz, 1H).

Step 2: 4-[(6-Hydroxy-3-methyl-2(3-fluorophenyl)-1-naphthalenyl)oxy]-2-(trifluoromethyl)benzaldehyde (285)

Compound (283) (1.77 g, 5.43 mmol) was dissolved in HCl (4 N in 1,4-dioxane) (15 mL) and the solution was stirred at RT under N$_2$ for 30 min. The reaction mixture was concentrated to give crude 2-(3-fluorophenyl)-3-methyl-6-(methyloxy)-1-naphthalenol (284) as a gold-yellow oil. $^1$H NMR (400 MHz, DMSO-d$_6$): δ 2.07 (s, 3H), 3.84 (s, 3H), 6.99-7.44 (m, 6H), 8.04 (d, J=9.3 Hz, 1H), 8.75 (s, 1H). Compound 284 (~1.50 g, 5.32 mmol) was immediately treated with 4-fluoro-2-trifluoromethylbenzaldehyde (1.53 g, 7.96 mmol) and Cs$_2$CO$_3$ (2.59 g, 7.98 mmol) in DMF (5 mL). The mixture was heated at 110° C. for 16 h, cooled to RT and diluted with 100 mL each H$_2$O and EtOAc. The organic layer was washed with 100 mL each water and brine, dried (Na$_2$SO$_4$) and concentrated to 2.92 g of an amber oil. The oil was purified by column chromatography with 10% EtOAc/hexanes to yield 1.57 g (65%) of the title compound 285 as a white foam. $^1$H NMR (400 MHz, DMSO-d$_6$): δ 2.20 (s, 3H), 3.88 (s, 3H), 6.96 (dd, J$_1$=2.3 Hz, J$_2$=8.6 Hz, 1H), 7.01-7.14 (m, 4H), 7.17 (d, J=2.5 Hz, 1H), 7.23-7.38 (m, 1H), 7.39 (d, J=2.5 Hz, 1H), 7.93 (d, J=9.1 Hz, 1H), 7.79 (s, 1H), 7.90 (d, J=8.7 Hz, 1H), 10.02 (s, 1H).

Step 3: 4-{[2-(3-Fluorophenyl)-6-hydroxy-3-methyl-1-naphthalenyl]oxy}-2-(trifluoromethyl)benzaldehyde (286)

To a stirring solution of 285 in MeOH (8 mL) and CH$_2$Cl$_2$ (4 mL) was added NaCN (0.19 g, 3.95 mmol) followed by MnO$_2$ (0.96 g, 11.06 mmol) and the resulting mixture stirred at RT for 16 h. The reaction was diluted with 75 mL EtOAc and filtered through a pad of 20 g celite layered on top of 10 g of silica gel. The pad was rinsed with an additional 25 mL EtOAc and the colorless filtrated washed with water and brine (100 mL each), dried (Na$_2$SO$_4$) and concentrated to a colorless oil. The oil was purified by column chromatography using a gradient of 100% hexanes to 10% EtOAc:hexanes to afford 300 mg (78%) of the title compound (286) as a white foam.

$^1$H NMR (400 MHz, DMSO-d$_6$): δ 2.20 (s, 3H), 3.77 (s, 3H), 3.87 (s, 3H), 6.87 (dd, J$_1$=2.5 Hz, J$_2$=8.6 Hz, 1H), 7.00-7.35 (m, 6H), 7.39 (d, J=2.5 Hz, 1H), 7.61 (d, J=9.3 Hz, 1H), 7.67 (d, J=8.5 Hz, 1H), 7.77 (s, 1H). LCMS (APCI): m/z 484 (M+H)$^+$.

Step 4: Methyl 4-{[2-(3-fluorophenyl)-6-hydroxy-3-methyl-1-naphthalenyl]oxy}-2-(trifluoromethyl) benzoate (287)

A stirring solution of 286 (0.30 g, 0.62 mmol) in CH$_2$Cl$_2$ (10 mL) was chilled to −20° C. under N$_2$ and BBr$_3$, 1 M in CH$_2$Cl$_2$ (2.86, 2.86 mmol, 1 M), was added drop wise. The resulting orange-brown reaction was stirred at −20° C. for 3 h and the reaction then poured onto ice followed by 1 N HCl (20 mL) and EtOAc (100 mL).

The organic layer was washed with brine (100 mL), dried (Na$_2$SO$_4$) and concentrated to an amber oil. The oil was purified by column chromatography with 20% EtOAc/hexanes to afford 200 mg (69%) of the title compound 287 as a white foam. $^1$H NMR (400 MHz, DMSO-d$_6$): δ 2.17 (s, 3H), 3.77 (s, 3H), 6.87 (dd, J$_1$=2.5 Hz, J$_2$=8.6 Hz, 1H), 6.98-7.09 (m, 5H), 7.17 (d, J=2.3 Hz, 1H), 7.33 (dd, J$_1$=7.8 Hz, J$_2$=14.1 Hz, 1H), 7.55 (d, J=9.1 Hz, 1H), 7.64 (s, 1H), 7.65 (d, J=8.7 Hz, 1H), 9.97 (s, 1H). LCMS (APCI): m/z 468.89 (M−H)$^-$.

Example 63 (289)

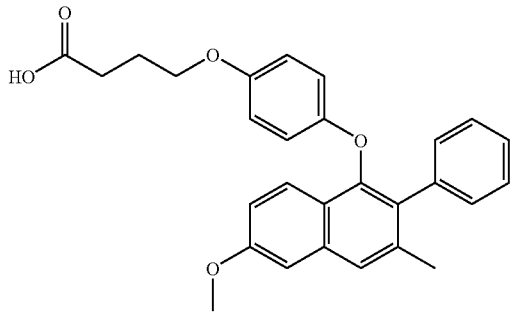

Step 1: 4-{[3-Methyl-6-(methyloxy)-2-phenyl-1-naphthalenyl]oxy}phenol (233)

To a solution of 4-{[3-methyl-6-(methyloxy)-2-phenyl-1-naphthalenyl]oxy}benzaldehyde (8) (2.00 g, 5.43 mmol) in MeOH (40 mL) were added an aqueous solution of, 30-40% by weight, H$_2$O$_2$ (5.0 mL) and a few drops (10-12) of conc. H$_2$SO$_4$. The resultant mixture was stirred for 24 h. Reaction mixture was neutralized with saturated aqueous NaHCO$_3$ and then diluted with EtOAc (200 mL). Reaction mixture was washed with water (2×30 mL), brine (1×30 mL), dried (Na$_2$SO$_4$), and concentrated under reduced pressure to afford the crude product. The product was purified by SiO$_2$ column chromatography using hexanes:EtOAc (9:1 to 4:1) as an eluent to give 1.180 g (61%) of the title compound (233) as a white foam. The $^1$H NMR and mass spectral data are consistent with the data reported in Example 41 (Step 1).

Step 2: Ethyl 4-[(4-{[3-methyl-6-(methyloxy)-2-phenyl-1-naphthalenyl]oxy}phenyl)oxy]butanoate (288)

A round-bottomed flask was charged with 4-{[3-methyl-6-(methyloxy)-2-phenyl-1-naphthalenyl]oxy}phenol (233) (0.300 g, 0.842 mmol), Cs$_2$CO$_3$ (0.824 g, 2.53 mmol), DMF (4 mL), and ethyl 4-bromobutanoate (0.602 mL, 4.21 mmol) under N$_2$. The reaction mixture was refluxed for 15 h and cooled at room temperature. Reaction mixture was partitioned between water and EtOAC (1:1, 100 mL) and the layers were separated. The aqueous phase was further extracted with EtOAc (2×30 mL). The combined organic layer was washed with brine (1×25 mL), dried (Na$_2$SO$_4$), and then concentrated under reduced pressure to afford the crude product. The product was purified by SiO$_2$ column chromatography using hexanes:EtOAc (19:1 to 9:1) as an eluent to give 0.356 g (90%) of the title compound (288) as a colorless oil. LCMS (ESI) m/z 493.27 (M+Na)$^+$.

Step 3: 4-[(4-{[3-Methyl-6-(methyloxy)-2-phenyl-1-naphthalenyl]oxy}phenyl)oxy]butanoic acid (289)

ethyl 4-[(4-{[3-methyl-6-(methyloxy)-2-phenyl-1 naphthalenyl]oxy}phenyl)oxy]butanoate (288) (0.300 g, 0.638 mmol) was dissolved in a 1:1 THF:EtOH (1:1, 30 mL) mixture. To the above mixture was added 1 N NaOH (6.4 mL) at room temperature and heated to 70° C. The reaction mixture was kept at that temperature for 2 h and cooled at RT. Reaction mixture was concentrated under reduced pressure to afford the residue and the residue was acidified with 25% aqueous HCl (30 mL), and then extracted with EtOAc (3×50 mL). The combined organic layer was washed with brine (1×30 mL), dried (Na$_2$SO$_4$), and concentrated under reduced pressure to afford the crude product which was purified by flash SiO$_2$ column chromatography using hexanes:EtOAc (19:1 to 1:1) as an eluent to afford 0.247 g (88%) of the title product (289) as a white solid. $^1$H NMR (400 MHz, DMSO-d$_6$): δ 12.10 (s, 1H), 7.65 (s, 1H), 7.57 (d, J=9.2 Hz, 1H), 7.30 (d, J=2.4 Hz, 1H), 7.29 (d, J=7.6 Hz, 2H), 7.24 (m, 1H), 7.16 (d, J=8.4 Hz, 2H), 7.05 and 7.03 (dd, J$_1$=9.2 Hz, J$_2$=2.4 Hz, 1H), 6.66 (d, J=9.2 Hz, 2H), 6.47 (d, J=9.2 Hz, 2H), 3.85 (s, 3H), 3.79 (t, J=6.4 Hz, 2H), 2.30 (t, J=7.2 Hz, 2H), 2.16 (s, 3H), 1.83 (quintet, J=6.8 Hz, 2H). LCMS (ESI) m/z 443.18 (M+H)$^+$.

Example 64 (290)

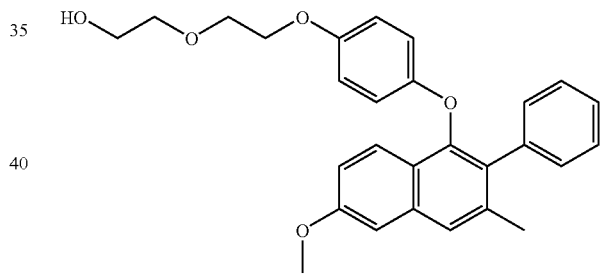

Step 1: 2-({2-[(4-{[3-Methyl-6-(methyloxy)-2-phenyl-1-naphthalenyl]oxy}phenyl)oxy]ethyl}oxy)ethanol (290)

The O-alkylation procedure described for Example 63 (Step 2) was employed with 4-{[3-methyl-6-(methyloxy)-2-phenyl-1-naphthalenyl]oxy}phenol (233) (0.605 g, 1.697 mmol), Cs$_2$CO$_3$ (1.658 g, 5.09 mmol), anhydrous DMF (8 mL), and 2-[(2-chloroethyl)oxy]ethanol (0.604 mL, 8.49 mmol) under N$_2$. The reaction mixture was refluxed for 15 h and then cooled to room temperature. Standard work-up followed by column chromatography gave 0.754 g (~100%) of the title compound (290) as a colorless oil. $^1$H NMR (400 MHz, DMSO-d$_6$): δ 7.65 (s, 1H), 7.58 (d, J=8.8 Hz, 1H), 7.31 (d, J=2.4 Hz, 1H), 7.29 (d, J=7.6 Hz, 2H), 7.24 (m, 1H), 7.16 (d, J=8.4 Hz, 2H), 7.05 and 7.03 (dd, J$_1$=9.2 Hz, J$_2$=2.4 Hz, 1H), 6.67 (d, J=9.2 Hz, 2H), 6.47 (d, J=9.2 Hz, 2H), 4.58 (t, J=5.6 Hz, 1H), 3.91 (t, J=4.8 Hz, 2H), 3.85 (s, 3H), 3.63 (t, J=4.8 Hz, 2H), 3.45 (t, J=5.2 Hz, 2H), 3.43 (t, J=4.4 Hz, 2H), 2.17 (s, 3H). LCMS (ESI) m/z 445.27 (M+H)$^+$.

PROPHETIC EXAMPLES

The following compounds can be prepared analogously using the descriptions of synthesis herein provided. Although slight variations in synthetic procedure may be necessary, all should be within the ordinary skill of the art.

Prophetic Example 65

5-{[4-({2-[(2-hydroxyethyl)oxy]ethyl}oxy)phenyl]oxy}-7-methyl-6-phenyl-2-naphthalenol

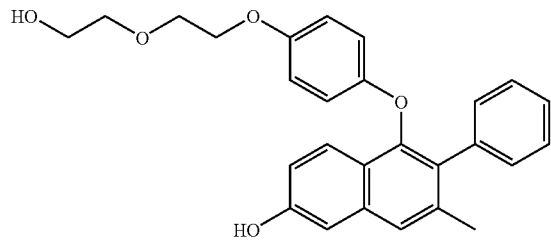

Prophetic Example 66

6-(3-fluorophenyl)-5-{[4-({2-[(2-hydroxyethyl)oxy]ethyl}oxy)-3-(trifluoromethyl)phenyl]oxy}-7-methyl-2-naphthalenol

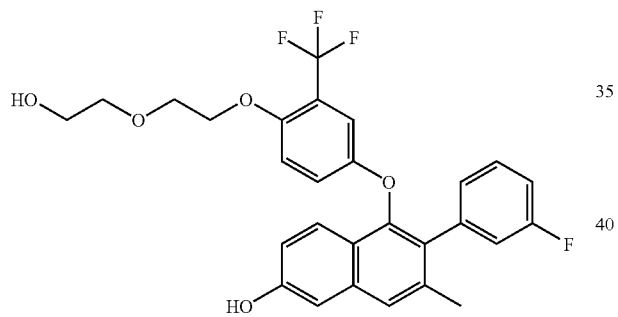

Prophetic Example 67

{[4-{[2-(3-fluorophenyl)-6-hydroxy-3-methyl-1-naphthalenyl]oxy}-2-(trifluoromethyl)phenyl]oxy}acetic acid

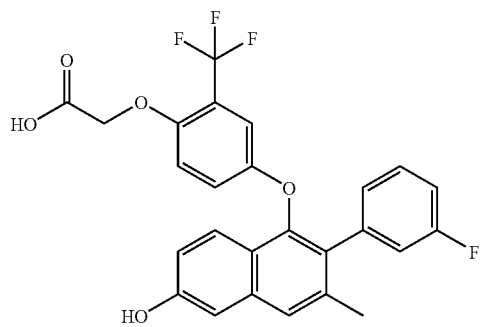

Prophetic Example 68

6-(3-fluorophenyl)-5-{[4-[(2-hydroxyethyl)oxy]-3-(trifluoromethyl)phenyl]oxy}-7-methyl-2-naphthalenol

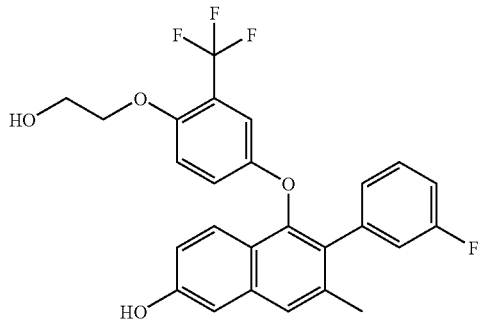

Prophetic Example 69

4-({4-[(6-hydroxy-3-methyl-2-phenyl-1-naphthalenyl)oxy]phenyl}oxy)butanoic acid

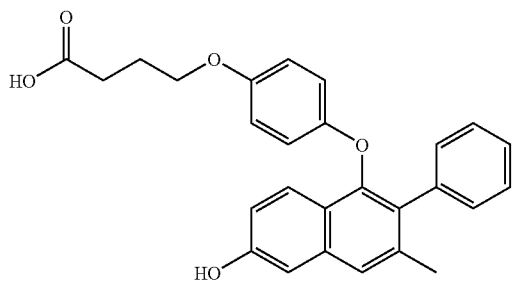

Prophetic Example 70

4-{[4-[(6-hydroxy-3-methyl-2-phenyl-1-naphthalenyl)oxy]-2-(trifluoromethyl)phenyl]oxy}butanoic acid

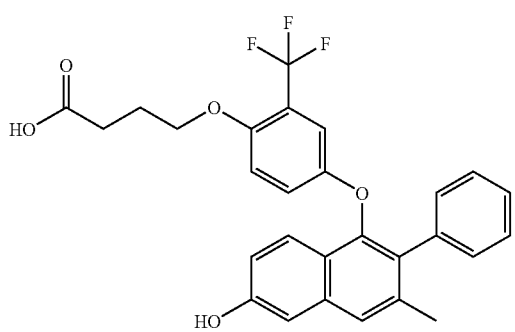

BIOLOGICAL DATA

Competition Binding Assay:

Recombinant full length human ERα and ERβ protein was purchased from PanVera (PanVera-Invitrogen Discovery Screening, Discovery Center, 501 Charmany Drive, Madison, Wis. 53719, USA). Polylysine coated Yttrium Silicate SPA beads (Amersham #RPNQ 0010) are re-suspended in assay buffer [10 mM potassium phosphate buffer pH 7.0 containing 2 mM EDTA, 50 mM NaCl, 1 mM DTT, 2 mM CHAPS, 10% glycerol] to a concentration of 1 g/60 ml. 30 μl (0.5 mg) of the SPA beads are then added to each well of a Packard OptiPlate (Packard 6005190, Packard Instruments, Meriden, Conn.). The ERα or ERβ protein is diluted to the appropriate concentration (empirically determined for each protein prep by generating a protein curve using 0.5 to 10 μg total protein and 1 nM [3H] Estradiol and selecting a protein concentration that does not deplete the radioligand) and added as 30 μl aliquots to each well. [2,4,6,7,16,17-3H(N)]-Estradiol is added as a 30 μl aliquot to give a final assay concentration of 1 nM. To give a final volume of 100 μl, either 10 μl of a test compound solution (typically in 10% DMSO as solvent), solvent containing no test compound (to determine total binding, T), or solvent containing 17-b-estradiol at 100 μM (to determine non-specific binding, NS) are finally added to the plate. The plates are shaken vigorously for two hours then counted on a Packard TopCount using the protocol for counting tritium yttrium silicate SPA beads. Data analysis was done by standard methods.

% Bound was Calcd for each concentration of each test compound using the equation % Bound=100*((Test−NS)/(T−NS)).

% Bound was plotted vs concentration and curve fitting was accomplished using non-linear regression.

At least two binding curves were generated for each compound.

The compounds of the present invention tested exhibited $pIC_{50}$ values ranging from 10 μM to 1 nM.

Test compounds were employed in free or salt form.

All research complied with the principles of laboratory animal care (NIH publication No. 85-23, revised 1985) and GlaxoSmithKline policy on animal use.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of formula (I):

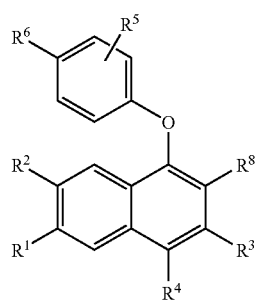

including salts thereof wherein:
$R^1$ is H, OH, alkoxy, or halogen;
$R^2$ is H, OH, or halogen;
$R^3$ is alkyl, haloalkyl, cycloalkyl, alkoxy, or alkoxyalkyl;
$R_4$ is H or alkoxy;
$R_5$ is halogen or haloalkyl;
$R_6$ is —(Y)z-R7;
z is 0 or 1;
Y is —C≡C— or —$CR^e$=$CR^f$—;
when z is 0, then $R^7$ is —CO-piperidinyl, —$CO_2H$, —$NHSO_2$-phenyl, $NHCOCH_2CO_2NHSO_2$alkyl optionally substituted with halogen, alkyl substituted with $CO_2H$, —$CO_2$-alkyl, —O-alkyl-$CO_2H$, or —O-alkyl-O-alkyl-OH;
when z is 1, then $R^7$ is —$CO_2H$, —CO-piperazinyl, —CO-pyrrolidinyl, —$CONH_2$ or —$PO_2H_2$;
$R^8$ is phenyl, optionally substituted with OH, halogen, or haloalkyl; and
$R^e$ and $R^f$ each independently are selected from H, alkyl, halogen, and haloalkyl.

2. A compound of formula (I):

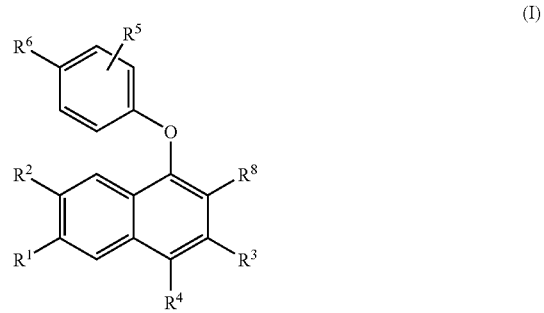

including salts thereof wherein:
$R^1$ is H, OH, alkoxy, or halogen;
$R^2$ is H, OH, or halogen;
$R^3$ is alkyl, haloalkyl, cycloalkyl, alkoxy, or alkoxyalkyl;
$R^4$ is H or alkoxy;
$R^5$ is halogen or haloalkyl;
$R^6$ is —(Y)z-R7;
z is 0 or 1;
Y is —C≡O— or —$CR^e$=$CR^f$;
when z is 0, then $R^7$ is —CO-piperidinyl, —$CO_2H$, —$NHSO_2$-phenyl, $NHCOCH_2CO_2H$, —$NHSO_2$alkyl optionally substituted with halogen, alkyl substituted with —$CO_2H$, $CO_2$-alkyl, —O-alkyl-$CO_2H$, or —O-alkyl-O-alkyl-OH
when z is 1, then $R^7$ is —$CO_2H$, —CO-piperazinyl, —CO-pyrrolidinyl, —$CONH_2$ or —$PO_2H_2$;
$R^8$ is phenyl, optionally substituted with OH, halogen, or haloalkyl; and
Re and Rf each independently are selected from H, alkyl, halogen, and haloalkyl.

3. The compound of claim 2 wherein alkyl is $C_{1-9}$alkyl.

4. The compound of claim 2 wherein $R^1$ is H or OH.

5. The compound of claim 4 wherein $R^1$ is OH.

6. The compound of claim 2 wherein $R^2$ is H, OH, or F.

7. The compound of claim 2 wherein $R^3$ is alkyl or haloalkyl.

8. The compound of claim 2 wherein $R^4$ is H.

9. The compound of claim 2 wherein $R^5$ is haloalkyl.

10. The compound of claim 2 wherein z is 1, Y is —$CR^e$=$CR^f$, $R^e$ and $R^f$ each are H, and $R^7$ is —$CO_2H$.

11. The compound of claim 2 wherein z is 0 and $R^7$ is —$CO_2H$.

12. The compound of claim 2 wherein $R^8$ is phenyl, or phenyl monosubstituted with halogen.

13. The compound of claim 12 wherein $R^8$ is phenyl, 3-fluorophenyl, or 4-fluorophenyl.

14. A compound selected from
(2E)-3-[4-[(6-hydroxy-3-methyl-2-phenyl-1-naphthalenyl)oxy]-2-(trifluoromethyl)phenyl]-2-propenoic acid;
(2E)-3-[4-[(6-hydroxy-3-methyl-2-phenyl-1-naphthalenyl)oxy]-3-(trifluoromethyl)phenyl]-2-propenoic acid;
3-{4-[2-(4-Fluoro-phenyl)-6-hydroxy-3-propyl-naphthalen-1-yloxy]-2-trifluoromethyl-phenyl}-2-methyl-acrylic acid;
3-{4-[2-(4-Fluoro-phenyl)-6-hydroxy-3-propyl-naphthalen-1-yloxy]-2-trifluoromethyl-phenyl}-2-methyl-acrylamide;
(2E)-3-[4-[(3-methyl-2-phenyl-1-naphthalenyl)oxy]-2-(trifluoromethyl)phenyl]-2-propenoic acid;
N-[4-[(6-hydroxy-3-methyl-2-phenyl-1-naphthalenyl)oxy]-2-(trifluoromethyl)phenyl]methanesulfonamide;
4-{[2-(4-fluorophenyl)-6-hydroxy-3-methyl-1-naphthalenyl]oxy}-2-(trifluoromethyl)benzoic acid;
(2E)-3-[4-{[2-(3-fluorophenyl)-6-hydroxy-3-methyl-1-naphthalenyl]oxy}-2-(trifluoromethyl)phenyl]-2-propenoic acid;
(2E)-3-[4-{[2-(4-fluorophenyl)-6-hydroxy-3-propyl-1-naphthalenyl]oxy}-2-(trifluoromethyl)phenyl-2-propenoic acid;
(2E)-3-[4-{[2-(4-fluorophenyl)-6-hydroxy-3-propyl-1-naphthalenyl]oxy}-2-(trifluoromethyl)phenyl-2-propenamide;
4-{[2-(4-fluorophenyl)-6-hydroxy-3-methyl-1-naphthalenyl]oxy}-2-(trifluoromethyl)benzamide;
Methyl 4-{[2-(3-fluorophenyl)-6-hydroxy-3-methyl-1-naphthalenyl]oxy}-2-(trifluoromethyl)benzoate;
6-(3-fluorophenyl)-5-{[4-({2-[(2-hydroxyethyl)oxy]ethyl}oxy)-3-(trifluoromethyl)phenyl]oxy}-7-methyl-2-naphthalenol;
{[4-{[2-(3-fluorophenyl)-6-hydroxy-3-methyl-1-naphthalenyl]oxy}-2-(trifluoromethyl)phenyl]oxy}acetic acid; and
6-(3-fluorophenul)-5-{[4-[(2-hydroxyethyl)oxy-3-(trifluoromethyl)phenyl]oxy}-7-methyl-2-naphthslenol,
including pharmaceutically acceptable salts thereof.

15. (2E)-3-[4-{[2-(3-fluorophenyl)-6-hydroxy-3-methyl-1-naphthaleneyl]oxy}-2-(trifluoromethyl)phenyl]-2-propenoic acid, including pharmaceutically acceptable salts thereof.

16. A pharmaceutical composition comprising a compound according to claim 2, and a pharmaceutically acceptable carrier.

17. A compound according to claim 2 for use as an active therapeutic substance.

* * * * *